United States Patent
Hatakeyama et al.

(10) Patent No.: US 11,435,665 B2
(45) Date of Patent: Sep. 6, 2022

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP); Takayuki Fujiwara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 404 days.

(21) Appl. No.: 16/426,673

(22) Filed: May 30, 2019

(65) Prior Publication Data

US 2019/0369491 A1    Dec. 5, 2019

(30) Foreign Application Priority Data

May 31, 2018  (JP) .............................. JP2018-104855
Feb. 20, 2019  (JP) .............................. JP2019-028583

(51) Int. Cl.

| | | |
|---|---|---|
| G03F 7/004 | (2006.01) | |
| G03F 7/039 | (2006.01) | |
| G03F 7/038 | (2006.01) | |
| C07C 311/51 | (2006.01) | |
| C07C 321/28 | (2006.01) | |
| G03F 7/32 | (2006.01) | |
| G03F 7/16 | (2006.01) | |
| G03F 7/20 | (2006.01) | |

(52) U.S. Cl.
CPC .......... *G03F 7/0045* (2013.01); *C07C 311/51* (2013.01); *C07C 321/28* (2013.01); *G03F 7/0382* (2013.01); *G03F 7/0392* (2013.01); *C07C 2601/16* (2017.05); *G03F 7/162* (2013.01); *G03F 7/168* (2013.01); *G03F 7/2053* (2013.01); *G03F 7/322* (2013.01)

(58) Field of Classification Search
CPC ... C07C 311/51; C07C 311/12; C07C 311/14; C07C 311/15; C07C 311/00
See application file for complete search history.

(56) References Cited

U.S. PATENT DOCUMENTS

| | | |
|---|---|---|
| 6,551,758 B2 | 4/2003 | Ohsawa et al. |
| 6,692,893 B2 | 2/2004 | Ohsawa et al. |
| 6,749,988 B2 | 6/2004 | Hatakeyama et al. |
| 6,916,593 B2 | 7/2005 | Hatakeyama et al. |

(Continued)

FOREIGN PATENT DOCUMENTS

| | | |
|---|---|---|
| CN | 102289149 A | 12/2011 |
| JP | 5-204157 A | 8/1993 |

(Continued)

OTHER PUBLICATIONS

Office Action dated Nov. 24, 2020, issued in counterpart KR Application No. 10-2019-0063603, with English translation (10 pages).

(Continued)

*Primary Examiner* — Amanda C. Walke
(74) *Attorney, Agent, or Firm* — WHDA, LLP

(57) ABSTRACT

A resist composition comprising a base polymer and an onium salt of N-carbonylsulfonamide having iodized benzene ring offers a high sensitivity, minimal LWR and improved CDU, independent of whether it is of positive or negative tone.

14 Claims, 2 Drawing Sheets

(56) References Cited

U.S. PATENT DOCUMENTS

| | | | |
|---|---|---|---|
| 8,026,390 B2 | 9/2011 | Oh et al. | |
| 8,148,044 B2 | 4/2012 | Yamaguchi et al. | |
| 9,250,518 B2 | 2/2016 | Hatakeyama et al. | |
| 9,523,912 B2* | 12/2016 | Kataoka | C07D 411/06 |
| 10,054,853 B2* | 8/2018 | Fujiwara | G03F 7/38 |
| 10,451,968 B2* | 10/2019 | Fujii | C08F 12/24 |
| 2009/0274978 A1 | 11/2009 | Ohashi et al. | |
| 2010/0233629 A1* | 9/2010 | Wada | C07C 311/48 |
| | | | 430/286.1 |
| 2011/0008731 A1* | 1/2011 | Yamaguchi | C07D 333/46 |
| | | | 430/270.1 |
| 2011/0269072 A1* | 11/2011 | Shibuya | G03F 7/0045 |
| | | | 430/270.1 |
| 2013/0017377 A1* | 1/2013 | Kataoka | G03F 7/0045 |
| | | | 428/195.1 |
| 2013/0089819 A1 | 4/2013 | Kawaue et al. | |
| 2015/0212417 A1 | 7/2015 | Hatakeyama et al. | |
| 2016/0070167 A1* | 3/2016 | Kataoka | C07D 333/76 |
| | | | 428/195.1 |
| 2017/0351177 A1 | 12/2017 | Hatakeyama et al. | |
| 2017/0369616 A1 | 12/2017 | Hatakeyama et al. | |

FOREIGN PATENT DOCUMENTS

| | | |
|---|---|---|
| JP | 2001-194776 A | 7/2001 |
| JP | 2002-226470 A | 8/2002 |
| JP | 2002-363148 A | 12/2002 |
| JP | 2010265226 A * | 11/2010 |
| JP | 2011-252147 A | 12/2011 |
| JP | H5572739 B2 * | 8/2014 |
| JP | 2015-25789 A | 2/2015 |
| JP | 2015-90382 A | 5/2015 |
| JP | 2015-161823 A | 9/2015 |
| JP | 2018-5224 A | 1/2018 |
| KR | 10-2013-0044239 A | 5/2013 |
| KR | 10-2017-0138355 A | 12/2017 |
| TW | 201009493 A | 3/2010 |
| TW | 201533528 A | 9/2015 |
| WO | 2013/024777 A1 | 2/2013 |

OTHER PUBLICATIONS

Yamamoto et al., "Polymer-Structure Dependence of Acid Generation in Chemically Amplified Extreme Ultraviolet Resists", Japanese Journal of Applied Physics, (2007), vol. 46, No. 7, pp. L142-L144, Cited in Specification. (3 pages).

Office Action dated Feb. 26, 2018, issued in counterpart TW Application No. 106121402. (12 pages).

Non-Final Office Action dated May 7, 2020, issued in counterpart U.S. Appl. No. 16/130,271 (11 pages).

Non-Final Office Action dated Jun. 27, 2019, issued in counterpart U.S. Appl. No. 15/920,641 (10 pages).

Non-Final Office Action dated Aug. 9, 2018, issued in counterpart U.S. Appl. No. 15/623,561 (8 pages).

Wang et al., "Photobase generator and photo decomposable quencher for high-resolution photoresist applications," SPIE vol. 7639, 2010, p. 76390W1-15.

Lio, "EUV Resists: What's Next?," SPIE vol. 9776, 2016, p. 97760V-1-14.

* cited by examiner

RESIST COMPOSITION AND PATTERNING PROCESS

CROSS-REFERENCE TO RELATED APPLICATION

This non-provisional application claims priority under 35 U.S.C. § 119(a) on Patent Application Nos. 2018-104855 and 2019-028583 filed in Japan on May 31, 2018 and Feb. 20, 2019, respectively, the entire contents of which are hereby incorporated by reference.

TECHNICAL FIELD

This invention relates to a resist composition and a pattern forming process.

BACKGROUND ART

While a higher integration density, higher operating speed and lower power consumption of LSIs are demanded to comply with the expanding IoT market, the effort to reduce the pattern rule is in rapid progress. The wide-spreading logic device market drives forward the miniaturization technology. As the advanced miniaturization technology, microelectronic devices of 10-nm node are manufactured in a mass scale by the double, triple or quadro-patterning version of the immersion ArF lithography. Active research efforts have been made on the manufacture of 7-nm node devices by the next generation EUV lithography of wavelength 13.5 nm.

In the EUV lithography, line patterns can be formed to a line width of 20 nm or less and chemically amplified resist compositions are applicable. Since the influence of image blur due to acid diffusion becomes more significant, the EUV lithography needs more acid diffusion control than the ArF lithography.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 to 3.

As the pattern feature size is reduced, approaching to the diffraction limit of light, light contrast lowers. In the case of positive resist film, a lowering of light contrast leads to reductions of resolution and focus margin of hole and trench patterns. For mitigating the influence of reduced resolution of resist pattern due to a lowering of light contrast, an attempt is made to enhance the dissolution contrast of resist film.

One such attempt is a chemically amplified resist material utilizing an acid amplifying mechanism that a compound is decomposed with an acid to generate another acid. In general, the concentration of acid creeps up linearly with an increase of exposure dose. In the case of the acid amplifying mechanism, the concentration of acid jumps up non-linearly as the exposure dose increases. The acid amplifying system is beneficial for further enhancing the advantages of chemically amplified resist film including high contrast and high sensitivity, but worsens the drawbacks of chemically amplified resist film that environmental resistance is degraded by amine contamination and maximum resolution is reduced by an increase of acid diffusion distance. The acid amplifying system is very difficult to control when implemented in practice.

Another approach for enhanced contrast is by reducing the concentration of amine with an increasing exposure dose. This may be achieved by applying a compound which loses the quencher function upon light exposure.

With respect to the acid labile group used in methacrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher.

Further, the sulfonium or iodonium salt capable of generating an α-non-fluorinated sulfonic acid also functions as a photodegradable quencher since it loses the quencher function by photodegradation. Non-Patent Document 1 points out that the addition of a photodegradable quencher expands the margin of a trench pattern although the structural formula is not illustrated. However, it has only a little influence on performance improvement. There is a desire to have a quencher for further improving contrast.

Patent Document 4 discloses a quencher of onium salt type which reduces its basicity through a mechanism that it generates an amino-containing carboxylic acid upon light exposure, which in turn forms a lactam in the presence of acid. Due to the mechanism that basicity is reduced under the action of acid, acid diffusion is controlled by high basicity in the unexposed region where the amount of acid generated is minimal, whereas acid diffusion is promoted due to reduced basicity of the quencher in the overexposed region where the amount of acid generated is large. This expands the difference in acid amount between the exposed and unexposed regions, from which an improvement in contrast is expected. Despite the advantage of improved contrast, the acid diffusion controlling effect is rather reduced.

As the pattern feature size is reduced, the the edge roughness (LWR) of line patterns or the critical dimension uniformity (CDU) of hole patterns is regarded significant. It is pointed out that LWR is affected by the segregation or agglomeration of a base polymer and acid generator and the diffusion of generated acid. There is a tendency that as the resist film becomes thinner, LWR becomes greater. A film thickness reduction to comply with the progress of size reduction causes a degradation of LWR, which becomes a serious problem.

The EUV lithography resist material must meet high sensitivity, high resolution, low LWR and good CDU at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR or CDU. For EB which is high-energy radiation like EUV, there is a tradeoff relation between sensitivity and LWR or CDU.

The energy of EUV is extremely higher than that of ArF excimer laser. The number of photons available with EUV exposure is 1/14 of the number by ArF exposure. The size of pattern features formed by the EUV lithography is less than half the size by the ArF lithography. Therefore, the EUV lithography is quite sensitive to a variation of photon number. Since a variation in number of photons in the radiation region of extremely short wavelength is shot noise as a physical phenomenon, it is impossible to eliminate the influence of a variation in number of photons.

Attention is paid to stochastics. While it is impossible to eliminate the influence of shot noise, discussions are held how to reduce the influence. There is observed a phenomenon that under the influence of shot noise, CDU and LWR are increased and holes are blocked at a probability of one several millionth. The blockage of holes leads to electric conduction failure and non-operation of transistors, adversely affecting the performance of an overall device. As the means for reducing the influence of shot noise on the resist side, several approaches are taken, for example, the modification of the resist more absorptive so as to absorb more photons and the development of a single-component low molecular weight resist from the standpoint that variations are concomitant with polymeric materials.

As the acid generator for making the resist more absorptive, Patent Documents 5 and 6 disclose an acid generator in the form of an onium salt having iodine on the anion side, which is added to a resist material. The resist material is then improved in sensitivity and LWR or CDU.

CITATION LIST

Patent Document 1: JP-A 2001-194776
Patent Document 2: JP-A 2002-226470
Patent Document 3: JP-A 2002-363148
Patent Document 4: JP-A 2015-090382
Patent Document 5: JP-A 2018-005224
Patent Document 6: JP-A 2015-025789
Non-Patent Document 1: SPIE Vol. 7639 p76390W (2010)
Non-Patent Document 2: SPIE Vol. 9776 p97760V-1 (2016)

DISCLOSURE OF INVENTION

For the acid-catalyzed chemically amplified resist, it is desired to develop a quencher or acid generator capable of providing a high sensitivity and reducing LWR or CDU as well as a resist material which contributes to shot noise reduction.

An object of the invention is to provide a resist composition which exhibits a high sensitivity and a reduced LWR or improved CDU, independent of whether it is of positive tone or negative tone; and a pattern forming process using the same.

The inventors have found that using an onium salt of N-carbonylsulfonamide having iodized benzene ring as the quencher or acid generator, a resist material having a high sensitivity, reduced LWR, improved CDU, high contrast, improved resolution, and wide process margin is obtainable.

In one aspect, the invention provides a resist composition comprising a base polymer and an onium salt having the formula (A).

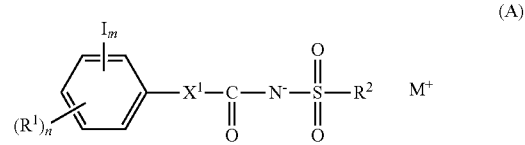

Herein $R^1$ is hydrogen, hydroxyl, $C_1$-$C_6$ alkyl group, $C_1$-$C_6$ alkoxy group, $C_2$-$C_7$ acyloxy group, $C_2$-$C_7$ alkoxycarbonyl group, $C_1$-$C_4$ alkylsulfonyloxy group, fluorine, chlorine, bromine, amino, nitro, cyano, —$NR^{1A}$—C(=O)—$R^{1B}$, or —$NR^{1A}$—C(=O)—O—$R^{1B}$, some or all of the hydrogen atoms on the alkyl, alkoxy, acyloxy, alkoxycarbonyl and alkylsulfonyloxy groups may be substituted by halogen, $R^{1A}$ is hydrogen or a $C_1$-$C_6$ alkyl group, $R^{1B}$ is a $C_1$-$C_6$ alkyl group or $C_2$-$C_8$ alkenyl group; $R^2$ is a $C_1$-$C_{10}$ alkyl or $C_6$-$C_{10}$ aryl group in which some or all hydrogen may be substituted by amino, nitro, cyano, $C_1$-$C_{12}$ alkyl, $C_1$-$C_{12}$ alkoxy, $C_2$-$C_{12}$ alkoxycarbonyl, $C_2$-$C_{12}$ acyl, $C_2$-$C_{12}$ alkylcarbonyloxy, hydroxyl, or halogen; $X^1$ is a single bond or a $C_1$-$C_{20}$ divalent linking group which may contain an ether bond, carbonyl moiety, ester bond, amide bond, sultone ring, lactam ring, carbonate bond, halogen, hydroxyl moiety or carboxyl moiety; m and n are integers satisfying $1 \le m \le 5$, $0 \le n \le 4$, and $1 \le m+n \le 5$.

$M^+$ is a sulfonium cation having the formula (Aa), an iodonium cation having the formula (Ab), or an ammonium cation having the formula (Ac).

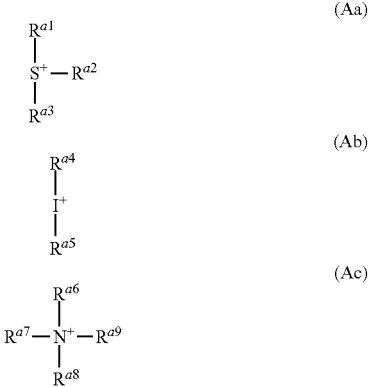

Herein $R^{a1}$ to $R^{a3}$ are each independently halogen or a $C_1$-$C_{20}$ monovalent hydrocarbon group which may contain a heteroatom, or any two of $R^{a1}$, $R^{a2}$ and $R^3$ may bond together to form a ring with the sulfur atom to which they are attached; $R^{a4}$ and $R^{a5}$ are each independently halogen or a $C_1$-$C_{20}$ monovalent hydrocarbon group which may contain a heteroatom; $R^{a6}$ to $R^{a9}$ are each independently hydrogen or a $C_1$-$C_{24}$ monovalent hydrocarbon group which may contain halogen, hydroxyl, carboxyl, ether bond, ester bond, thiol, thioester bond, thionoester bond, dithioester bond, amino moiety, nitro moiety, sulfone moiety, or ferrocenyl moiety, $R^{a6}$ and $R^{a7}$ may bond together to form a ring with the nitrogen atom to which they are attached, a pair of $R^{a6}$ and $R^{a7}$ and a pair of $R^{a8}$ and $R^{a9}$ may bond together to form a spiro-ring with the nitrogen atom to which they are attached, $R^{a8}$ and $R^{a9}$, taken together, may form =C($R^{a10}$)($R^{a11}$), $R^{a10}$ and $R^{a11}$ are each independently hydrogen or a $C_1$-$C_{16}$ monovalent hydrocarbon group, $R^{a10}$ and $R^{a11}$ may bond together to form a ring with the carbon and nitrogen atoms to which they are attached, the ring may contain a double bond, oxygen, sulfur or nitrogen atom therein.

Preferably, m is an integer satisfying 2≤m≤4.

The resist composition may further comprise an acid generator capable of generating a sulfonic acid, imide acid or methide acid and/or an organic solvent.

In one preferred embodiment, the base polymer comprises recurring units having the formula (a1) or recurring units having the formula (a2).

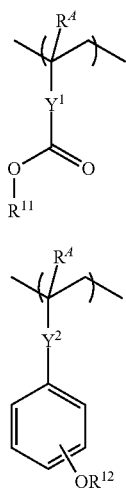

(a1)

(a2)

wherein $R^A$ is each independently hydrogen or methyl, $Y^1$ is a single bond, phenylene group, naphthylene group, or $C_1$-$C_{12}$ linking group containing ester bond or lactone ring, $Y^2$ is a single bond or ester bond, $R^{11}$ and $R^{12}$ each are an acid labile group.

In one embodiment, the resist composition is a chemically amplified positive resist composition.

The base polymer may be free of an acid labile group.

In one preferred embodiment, the resist composition may further comprise a crosslinker. Typically, the resist composition is a chemically amplified negative resist composition.

In one preferred embodiment, the base polymer further comprises recurring units of at least one type selected from recurring units having the formulae (f1) to (f3).

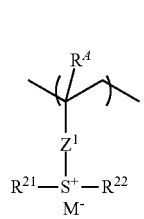

(f1)

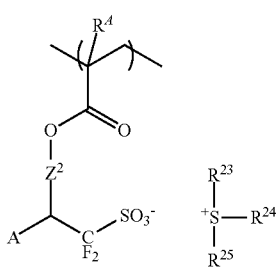

(f2)

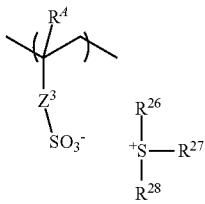

(f3)

Herein $R^A$ is each independently hydrogen or methyl; $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain a carbonyl, ester bond, ether bond or hydroxyl moiety; $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain a carbonyl moiety, ester bond or ether bond; $Z^3$ is a single bond, methylene, ethylene, phenylene, fluorinated phenylene, —C(=O)—O—$Z^{31}$—, or —C(=O)—NH—$Z^{31}$—, $Z^{31}$ is a $C_1$-$C_6$ alkanediyl group, phenylene group, fluorinated phenylene group, trifluoromethyl-substituted phenylene group, or $C_2$-$C_6$ alkenediyl group, which may contain a carbonyl moiety, ester bond, ether bond or hydroxy moiety; A is hydrogen or trifluoromethyl; $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached; and $M^-$ is a non-nucleophilic counter ion.

The resist composition may further comprise a surfactant.

In another aspect the invention provides a process for forming a pattern comprising the steps of applying the resist composition defined herein onto a substrate, baking to form a resist film, exposing the resist film to high-energy radiation, and developing the exposed resist film in a developer.

Most often, the high-energy radiation is ArF excimer laser radiation of wavelength 193 nm, KrF excimer laser radiation of wavelength 248 nm, EB or EUV of wavelength 3 to 15 nm.

In a further aspect, the invention provides a sulfonium salt having the formula (B):

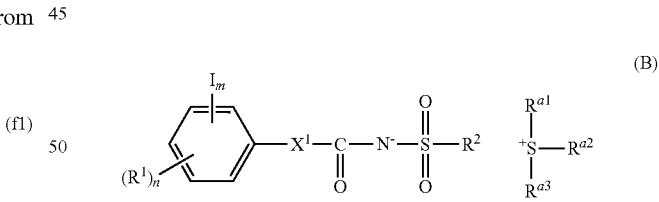

(B)

Herein $R^1$, $R^2$, $X^1$, m, n, $R^{a1}$ to $R^{a3}$ are as defined above.

Advantageous Effects of Invention

A resist film containing an onium salt of N-carbonylsulfonamide having iodized benzene ring has the advantage of high sensitivity because the sulfonamide having iodized benzene ring is fully absorptive to EB and EUV so that more secondary electrons are generated in the film. Since the bond distance between the anion and the cation of the onium salt is long owing to the steric hindrance of substituents on both sides of the amide bond, the inventive onium salt is liable to ion exchange with sulfonic acid as compared with the quencher in the form of carboxylic acid onium salt. That is, the inventive onium salt has a higher quencher ability enough to provide a high contrast. Where a fluorinated alkyl or aryl group is positioned forward of the sulfonamide group, the onium salt functions as an acid generator because the acid generated therefrom has a higher strength. In this case, the onium salt functions as an acid generator with controlled acid diffusion.

DESCRIPTION OF EMBODIMENTS

Figure 1:
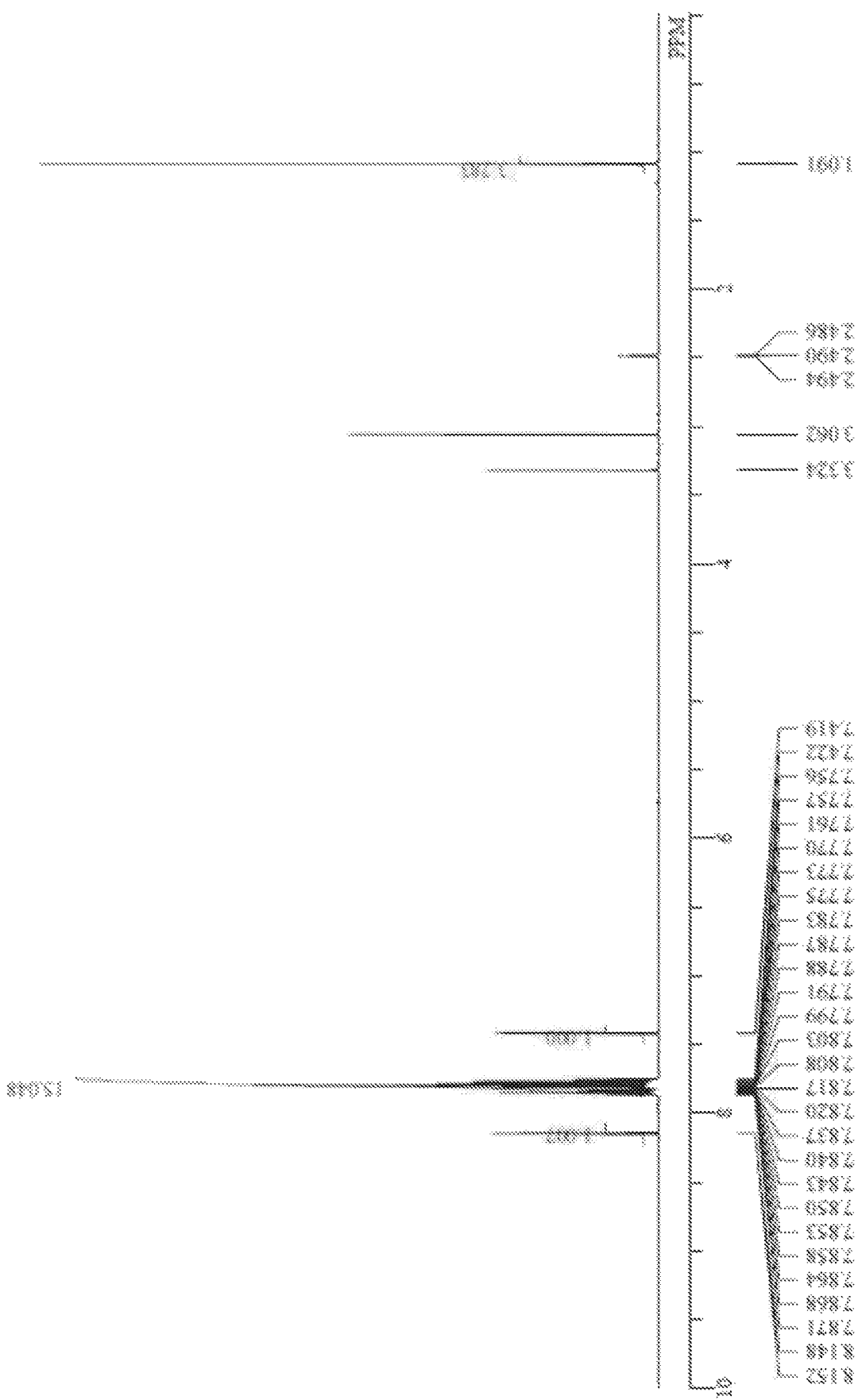
FIG. 1 is a diagram showing the $^1$H-NMR spectrum of Sulfonium Salt 1 in Synthesis Example 1-1.

As used herein, the singular forms "a," "an" and "the" include plural referents unless the context clearly dictates otherwise. The notation ($C_n$-$C_m$) means a group containing from n to m carbon atoms per group. As used herein, the term "iodized" compound means an iodine-containing compound. In chemical formulae, Me stands for methyl, and Ac for acetyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and an onium salt of N-carbonylsulfonamide having iodized benzene ring (referred to as iodized benzene ring-containing sulfonamide, hereinafter). In the embodiment wherein the onium salt is a sulfonium or iodonium salt, the salt is an acid generator capable of generating iodized benzene ring-containing sulfonamide upon light exposure, and it also functions as a quencher because it has a strongly basic sulfonium or iodonium salt form. When the iodized benzene ring-containing sulfonamide has a fluorinated alkyl or aryl group bonded thereto, it functions as an acid generator because it generates a strong acid. When the iodized benzene ring-containing sulfonamide is fluorine-free, it does not possess a sufficient acidity to induce deprotection reaction of an acid labile group, and it is recommended to separately add an acid generator capable of generating a strong acid such as sulfonic acid, imide acid or methide acid, as will be described later, in order to induce deprotection reaction of an acid labile group. Notably, the acid generator capable of generating sulfonic acid, imide acid or methide acid may be either of separate type which is added to the base polymer or of bound type which is bound in the base polymer.

When a resist composition containing the sulfonium or iodonium salt of iodized benzene ring-containing sulfonamide in admixture with an acid generator capable of generating a perfluoroalkylsulfonic acid or superstrong acid is exposed to radiation, iodized benzene ring-containing sulfonamide and perfluoroalkylsulfonic acid generate. Since the acid generator is not entirely decomposed, the undecomposed acid generator is present nearby. When the sulfonium or iodonium salt of iodized benzene ring-containing sulfonamide co-exists with the perfluoroalkylsulfonic acid, first the perfluoroalkylsulfonic acid undergoes ion exchange with the sulfonium or iodonium salt of iodized benzene ring-containing sulfonamide, whereby a sulfonium or iodonium salt of perfluoroalkylsulfonic acid is created and iodized benzene ring-containing sulfonamide is released. This is because the salt of perfluoroalkylsulfonic acid having a high acid strength is more stable. In contrast, when a sulfonium or iodonium salt of perfluoroalkylsulfonic acid co-exists with iodized benzene ring-containing sulfonamide, no ion exchange takes place. The ion exchange takes place not only with the perfluoroalkylsulfonic acid, but also similarly with arylsulfonic acid, alkylsulfonic acid, imide acid and methide acid having a higher acid strength than the iodized benzene ring-containing sulfonamide.

The sulfonium, iodonium or ammonium salt of iodized benzene ring-containing sulfonamide is not only effective for suppressing acid diffusion, but is also highly absorptive to EUV so that it generates more secondary electrons, thereby providing the resist with a higher sensitivity and reducing shot noise. The sulfonium, iodonium or ammonium salt of iodized benzene ring-containing sulfonamide functions not only as an acid generator or quencher for controlling acid diffusion, but also as a sensitizer.

While the resist composition of the invention should essentially contain the sulfonium, iodonium or ammonium salt of iodized benzene ring-containing sulfonamide, another sulfonium or iodonium salt may be separately added as the quencher. Examples of the sulfonium or iodonium salt to be added as the quencher include sulfonium or iodonium salts of carboxylic acid, sulfonic acid, imide acid and saccharin. The carboxylic acid used herein may or may not be fluorinated at α-position.

In the resist composition, an acid generator in the form of a sulfonium or iodonium salt of fluorosulfonamide having a fluorinated alkyl or aryl group bonded thereto may be used in combination with a quencher in the form of a sulfonium salt of fluorosulfonamide having a non-fluorinated alkyl or aryl group bonded thereto.

For the LWR improving purpose, it is effective to prevent a polymer and/or acid generator from agglomeration as indicated above. Effective means for preventing agglomeration of a polymer is by reducing the difference between hydrophobic and hydrophilic properties or by lowering the glass transition temperature (Tg) thereof. Specifically, it is effective to reduce the polarity difference between a hydrophobic acid labile group and a hydrophilic adhesive group or to lower the Tg by using a compact adhesive group like monocyclic lactone. One effective means for preventing agglomeration of an acid generator is by introducing a substituent into the triphenylsulfonium cation. In particular, with respect to a methacrylate polymer containing an alicyclic protective group and a lactone adhesive group for ArF lithography, a triphenylsulfonium composed solely of aromatic groups has a heterogeneous structure and low compatibility. As the substituent to be introduced into triphenylsulfonium, an alicyclic group or lactone similar to those used in the base polymer is regarded adequate. When lactone is introduced in a sulfonium salt which is hydrophilic, the resulting sulfonium salt becomes too hydrophilic and thus less compatible with a polymer, with a likelihood that the sulfonium salt will agglomerate. When a hydrophobic alkyl group is introduced, the sulfonium salt may be uniformly dispersed within the resist film WO 2011/048919 discloses the technique for improving LWR by introducing an alkyl group into a sulfonium salt capable of generating an α-fluorinated sulfone imide acid.

Another factor to be taken into account for the LWR improving purpose is the dispersibility of a quencher. Even when the dispersibility of an acid generator in a resist film is improved, the uneven distribution of a quencher can cause a degradation of LWR. For those quenchers of sulfonium salt type, the introduction of an alkyl or similar substituent into the triphenylsulfonium cation moiety is effective for LWR improvement. Further, the introduction of halogen atoms into the quencher of sulfonium salt type efficiently enhances hydrophobicity and improves dispersibility. The introduction of bulky halogen atoms such as iodine is effective not only in the cation moiety, but also in the anion moiety of the sulfonium salt. The sulfonium salt of iodized benzene ring-containing sulfonamide according to the invention has iodine introduced in the anion moiety, whereby the dispersibility of the quencher within the resist film is enhanced and LWR is reduced.

The sulfonium, iodonium or ammonium salt of iodized benzene ring-containing sulfonamide exerts a LWR reducing effect, which may stand good either in positive and negative tone pattern formation by alkaline development or in negative tone pattern formation by organic solvent development.

Onium Salt of Iodized Benzene Ring-Containing Sulfonamide

The inventive resist composition contains the onium salt of iodized benzene ring-containing sulfonamide which has the formula (A).

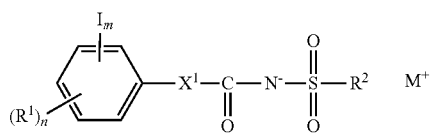

(A)

In formula (A), $R^1$ is hydrogen, hydroxyl, a $C_1$-$C_6$ alkyl group, $C_1$-$C_6$ alkoxy group, $C_2$-$C_7$ acyloxy group, $C_2$-$C_7$ alkoxy carbonyl group, $C_1$-$C_4$ alkylsulfonyloxy group, fluorine, chlorine, bromine, amino, nitro, cyano, —$NR^{1A}$—C(=O)—$R^{1B}$, or —$NR^{1A}$—C(=O)—O—$R^{1B}$. Some or all of the hydrogen atoms on the alkyl, alkoxy, acyloxy, alkoxy carbonyl and alkylsulfonyloxy groups may be substituted by halogen. $R^{1A}$ is hydrogen or a $C_1$-$C_6$ alkyl group. $R^{1B}$ is a $C_1$-$C_6$ alkyl group or $C_2$-$C_8$ alkenyl group.

The $C_1$-$C_6$ alkyl group may be straight, branched or cyclic, and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, and cyclohexyl. Examples of the alkyl moiety in the $C_1$-$C_6$ alkoxy, $C_2$-$C_7$ acyloxy, and $C_2$-$C_7$ alkoxycarbonyl groups are as exemplified above for the alkyl group. Examples of the alkyl moiety in the $C_1$-$C_4$ alkylsulfonyloxy group include exemplary groups of 1 to 4 carbon atoms as described above for the alkyl group. The $C_2$-$C_8$ alkenyl group may be straight, branched or cyclic, and examples thereof include vinyl, 1-propenyl, and 2-propenyl. Examples of the aralkyl group include benzyl and phenethyl. Inter alia, $R^1$ is preferably fluorine, chlorine, bromine, hydroxyl, amino, $C_1$-$C_3$ alkyl, $C_1$-$C_3$ alkoxy, $C_2$-$C_4$ acyloxy, —$NR^{1A}$—C(=O)—$R^{1B}$, or —$NR^{1A}$—C(=O)—O—$R^{1B}$.

In formula (A), $R^2$ is a $C_1$-$C_{10}$ alkyl or $C_6$-$C_{10}$ aryl group in which some or all hydrogen may be substituted by amino, nitro, cyano, $C_1$-$C_{12}$ alkyl, $C_1$-$C_{12}$ alkoxy, $C_2$-$C_{12}$ alkoxy carbonyl, $C_2$-$C_{12}$ acyl, $C_2$-$C_{12}$ alkylcarbonyloxy, hydroxyl, or halogen.

The $C_1$-$C_{10}$ alkyl group may be straight, branched or cyclic, and examples thereof include n-heptyl, n-octyl, n-nonyl, n-decyl, adamantyl as well as the above-mentioned examples of $C_1$-$C_6$ alkyl group. Examples of the $C_6$-$C_{10}$ aryl group include phenyl and naphthyl.

In formula (A), $X^1$ is a single bond or a $C_1$-$C_{20}$ divalent linking group which may contain an ether bond, carbonyl moiety, ester bond, amide bond, sultone ring, lactam ring, carbonate bond, halogen, hydroxyl moiety or carboxyl moiety. Preferably, $X^1$ is a single bond.

In formula (A), m and n are integers satisfying 1≤m≤5, 0≤n≤4, and 1≤m+n≤5, preferably m is an integer of 2 to 4 and n is 0 or 1.

Examples of the anion in the onium salt having formula (A) are shown below, but not limited thereto.

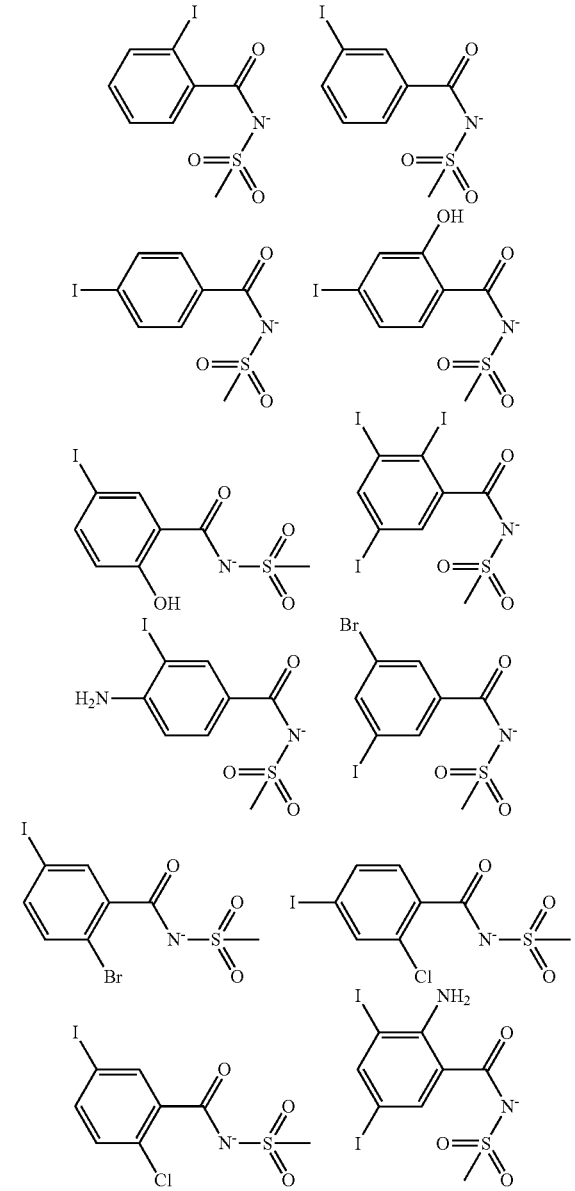

-continued
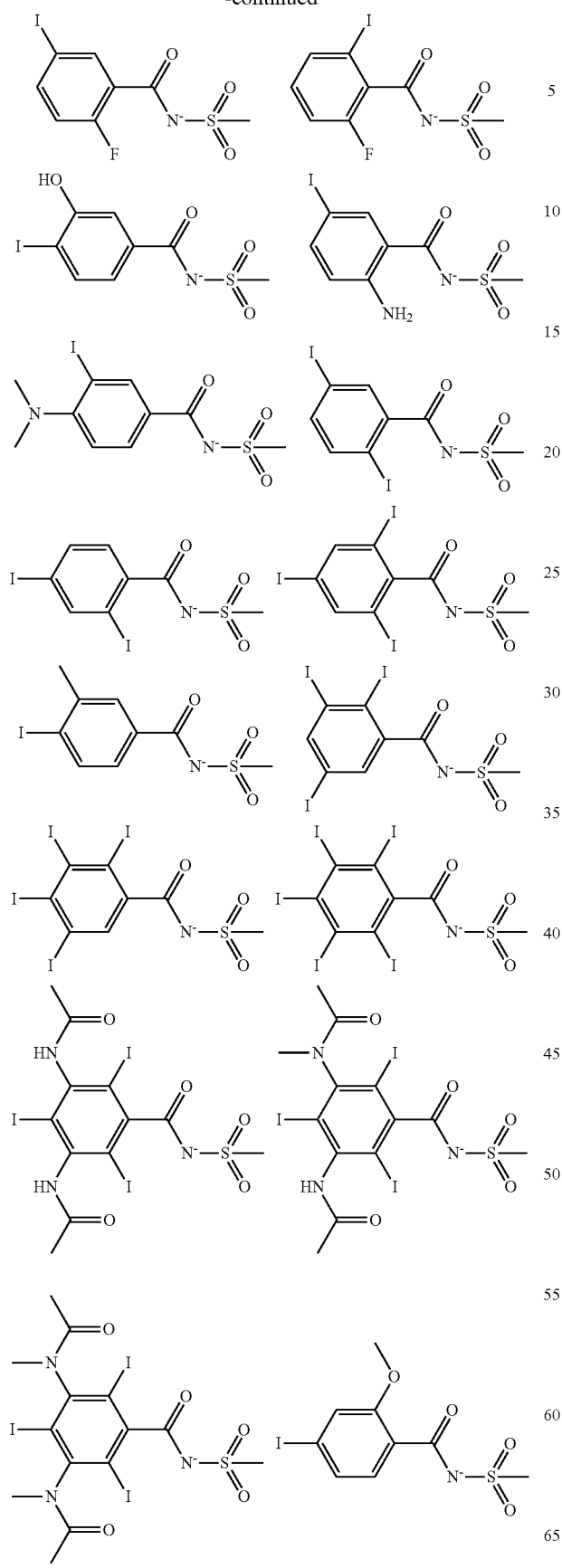
-continued
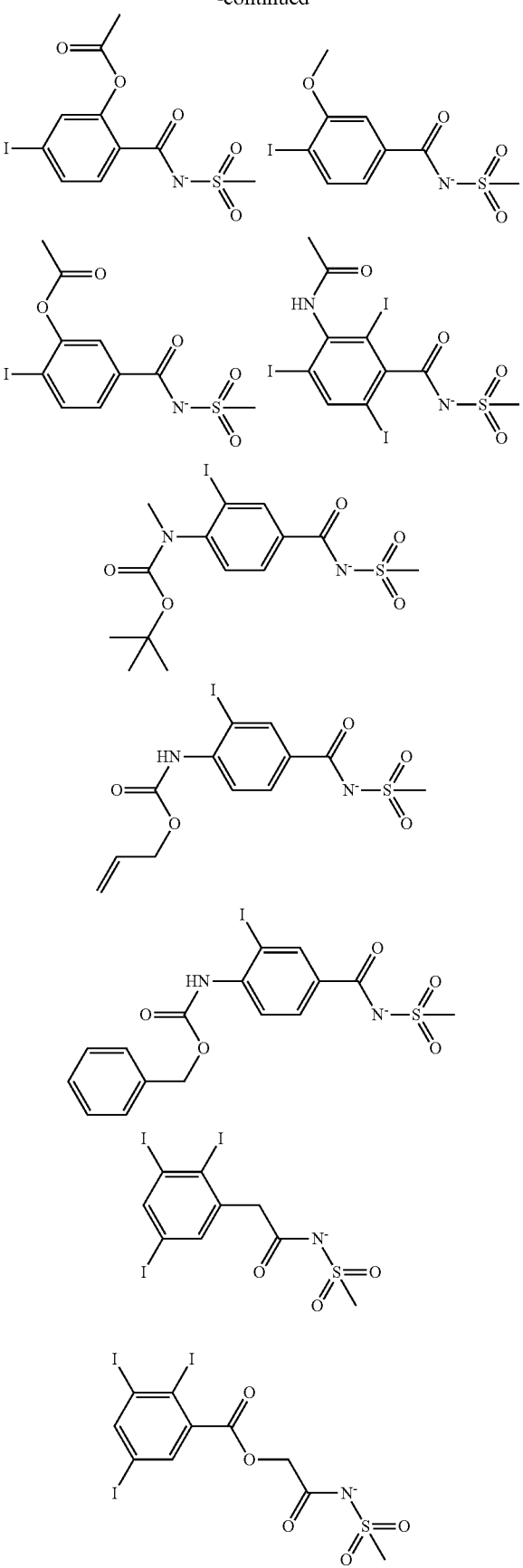

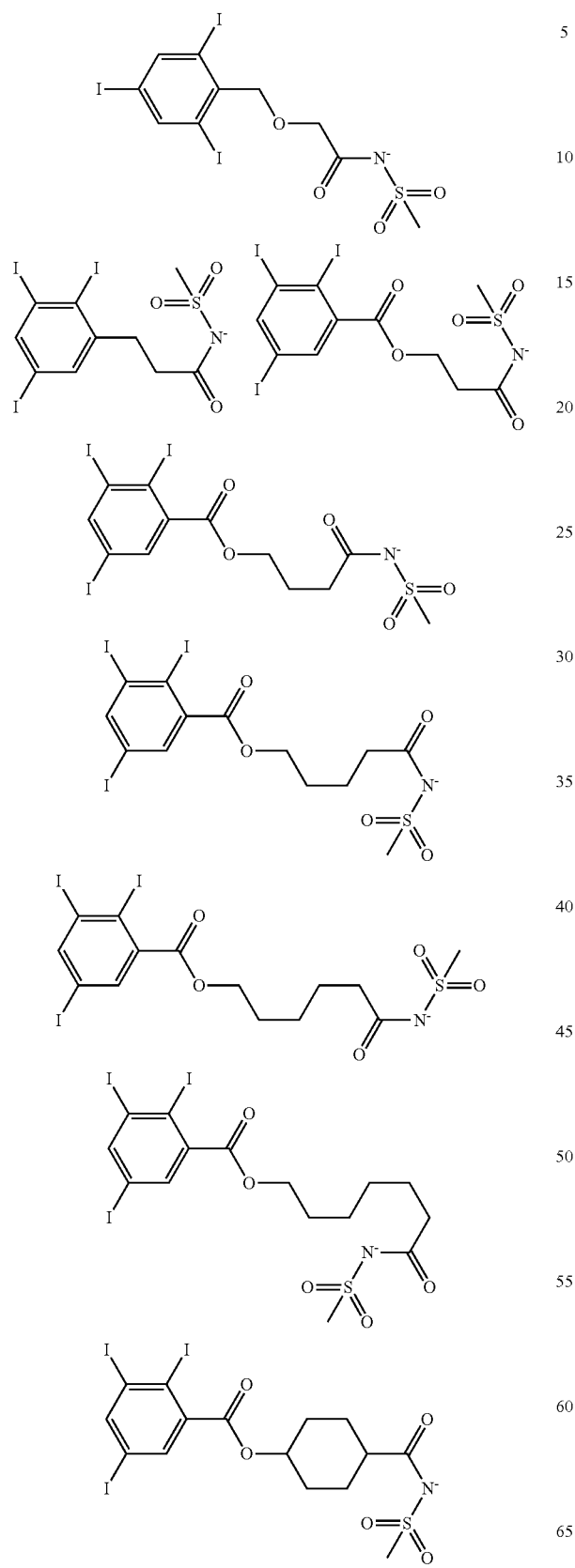
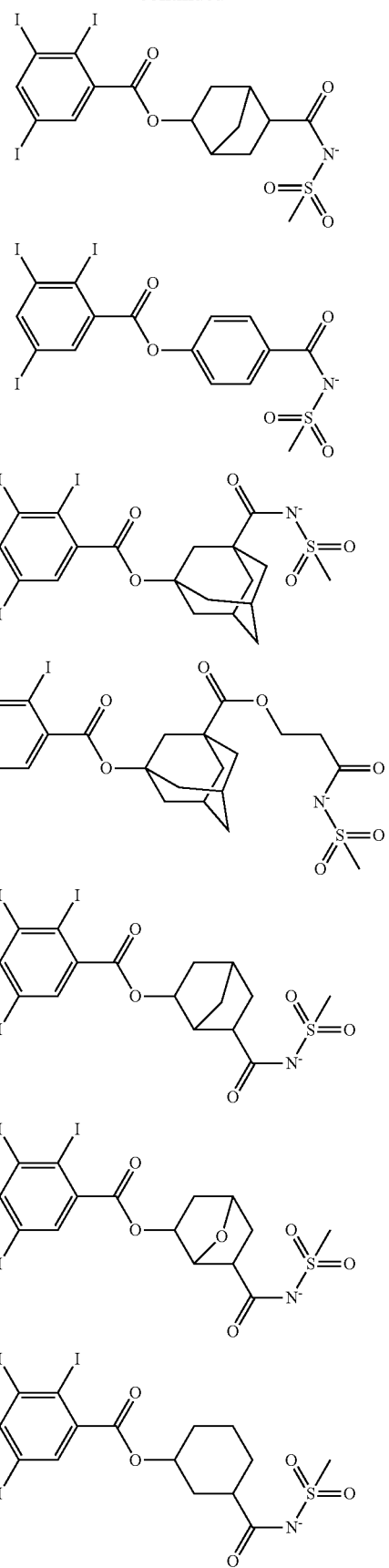

-continued

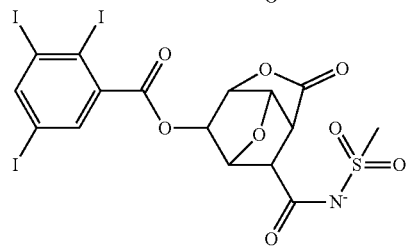
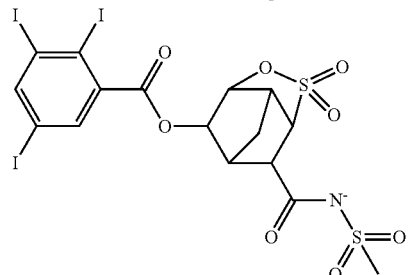
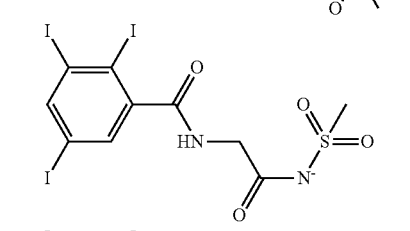
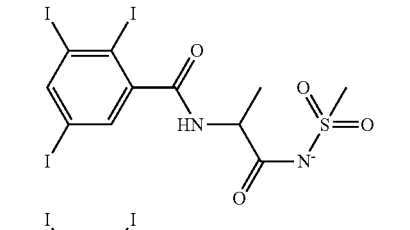
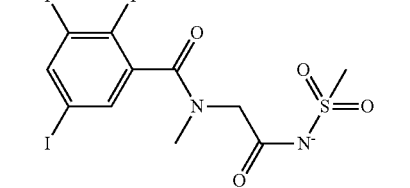
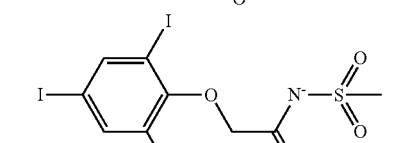
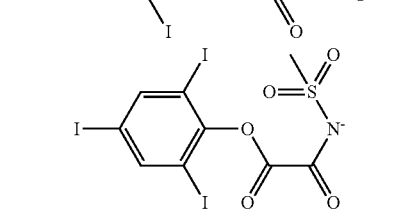
-continued
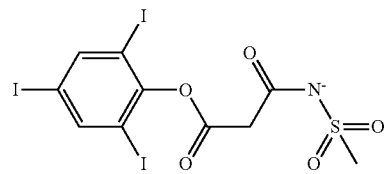
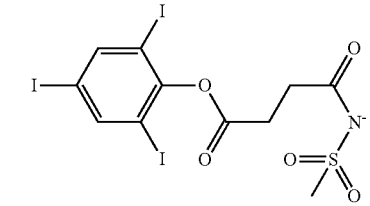
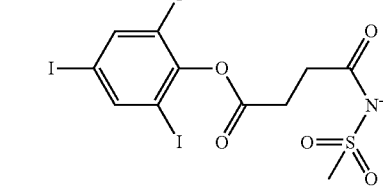
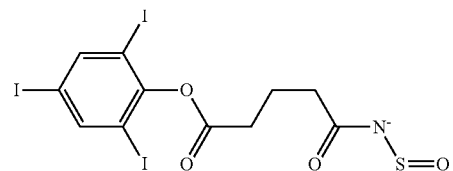
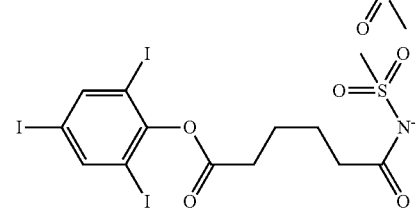
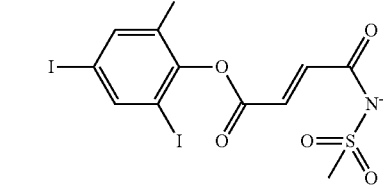
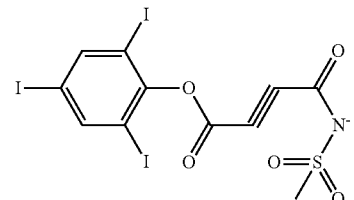
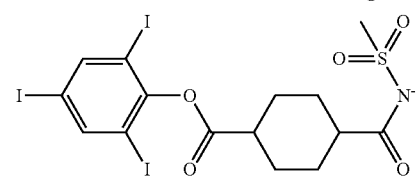
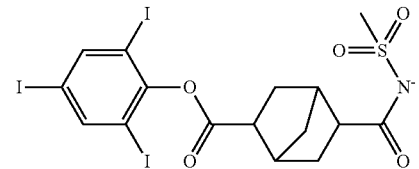

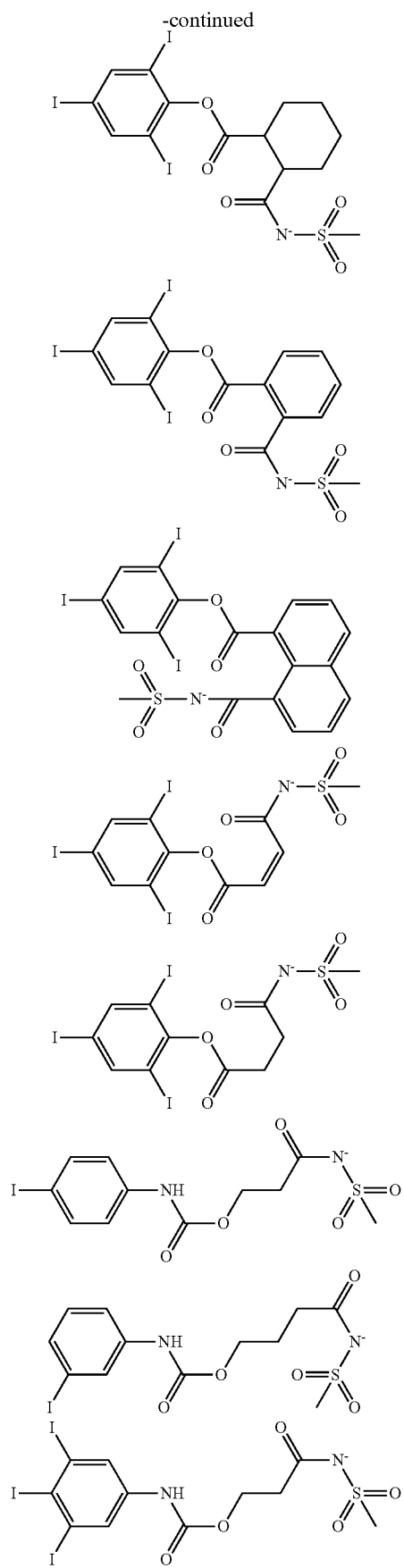

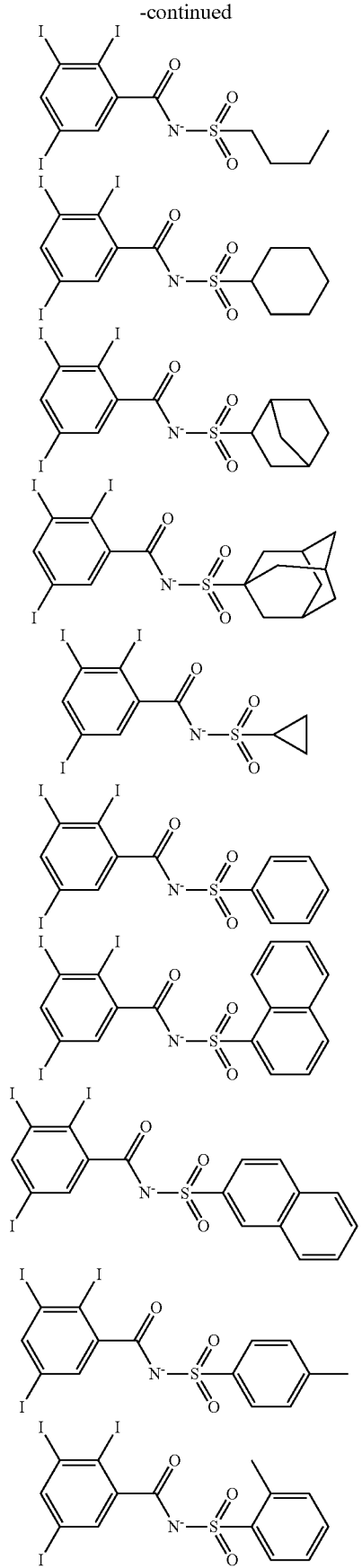
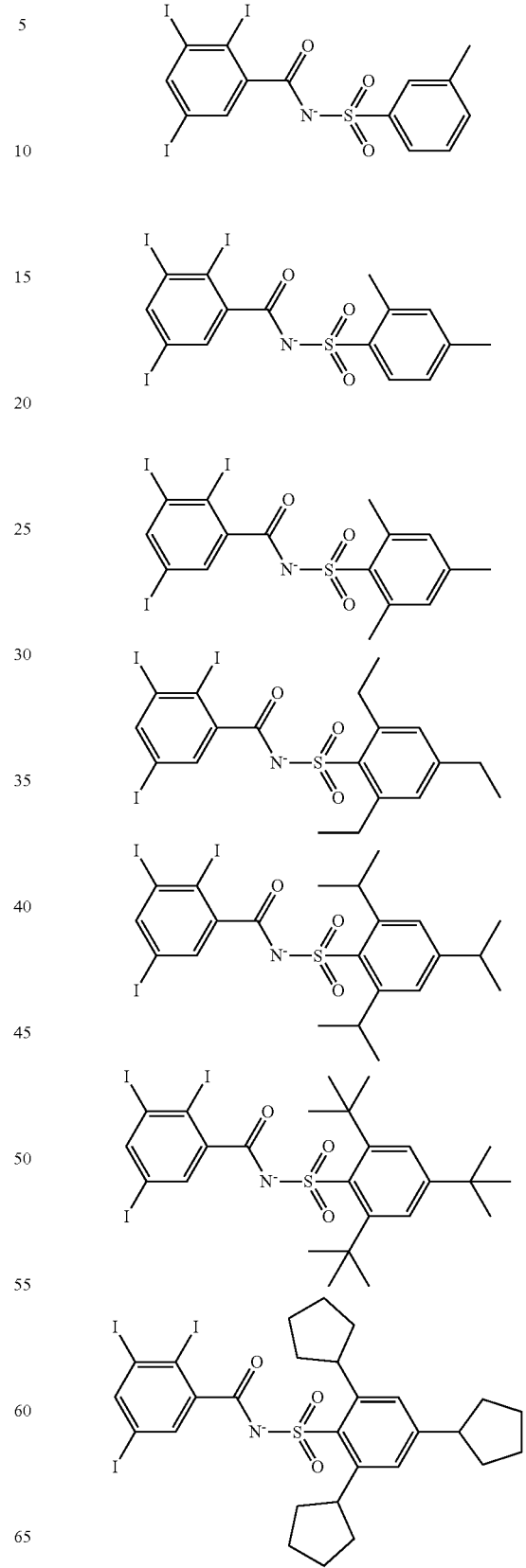

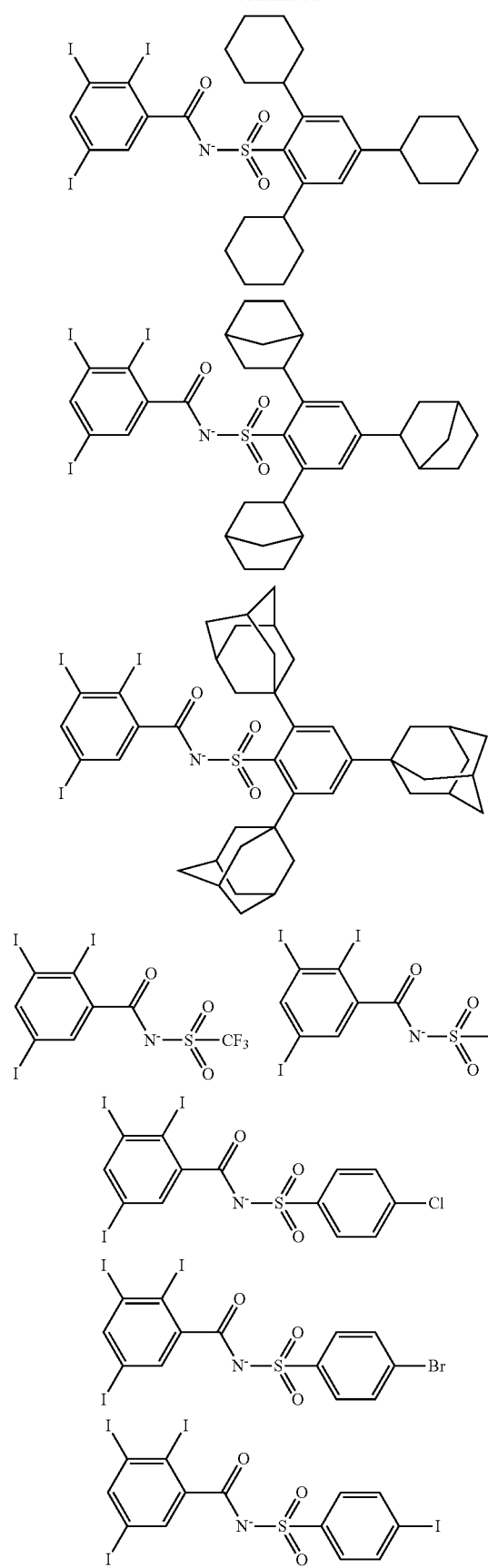
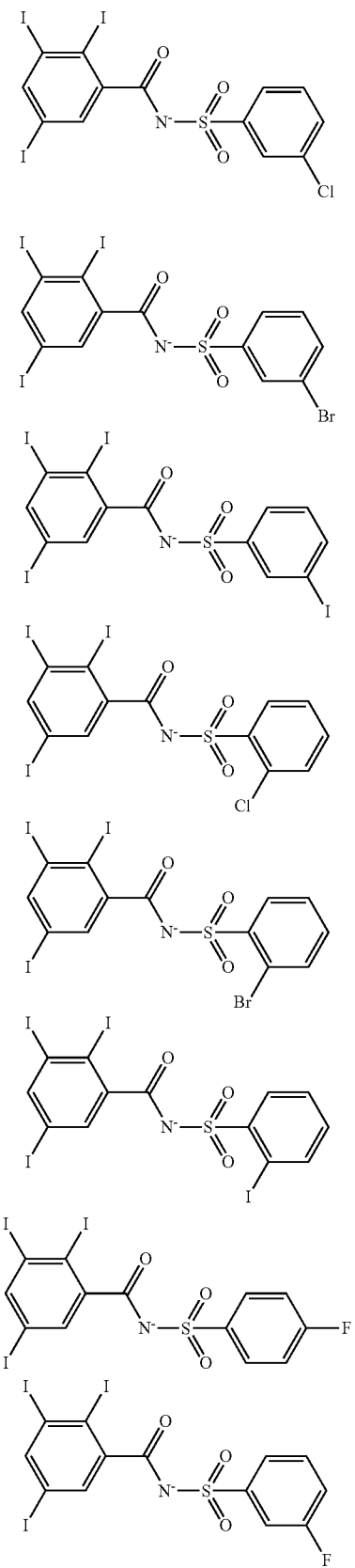

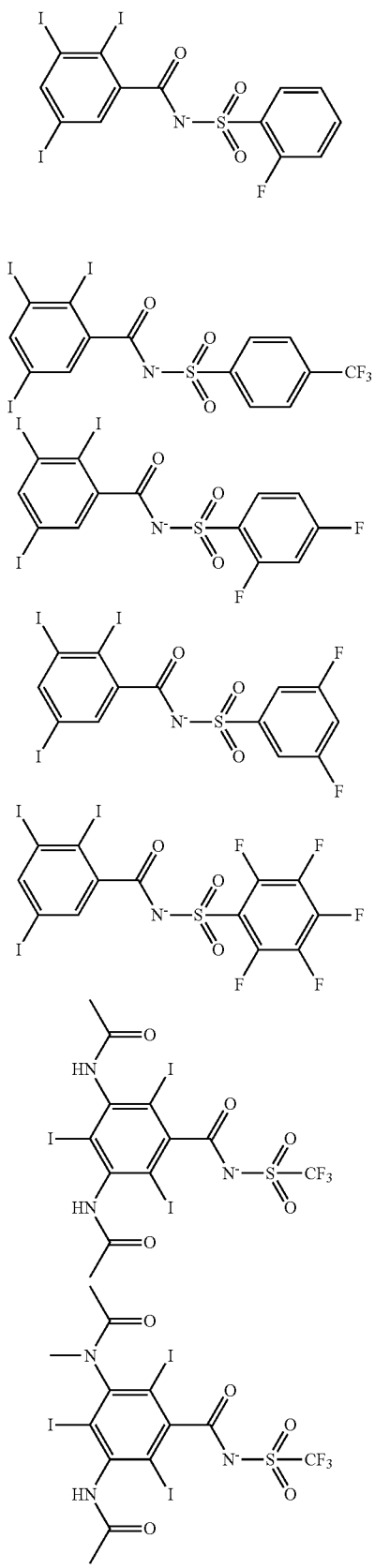
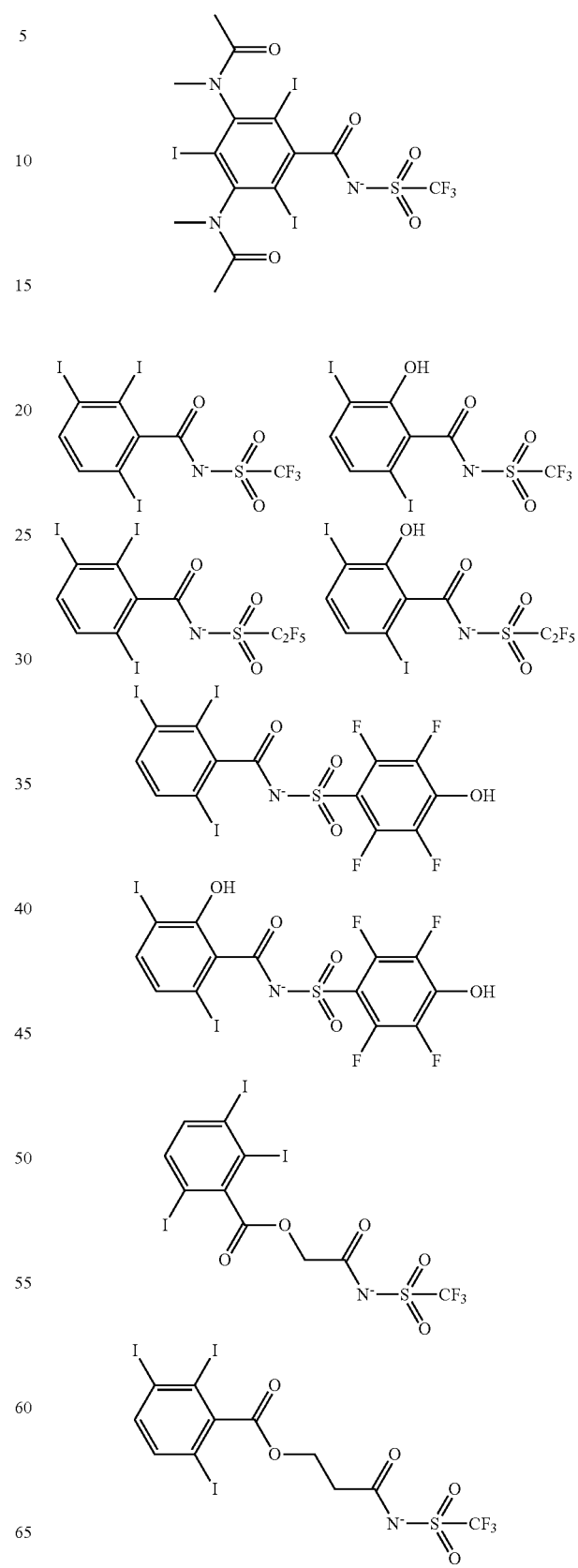

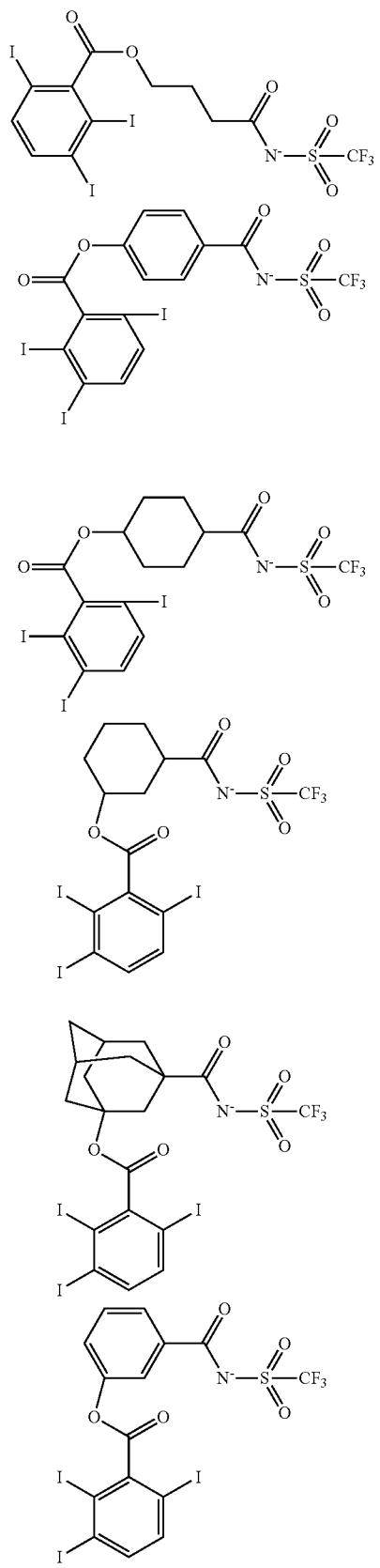
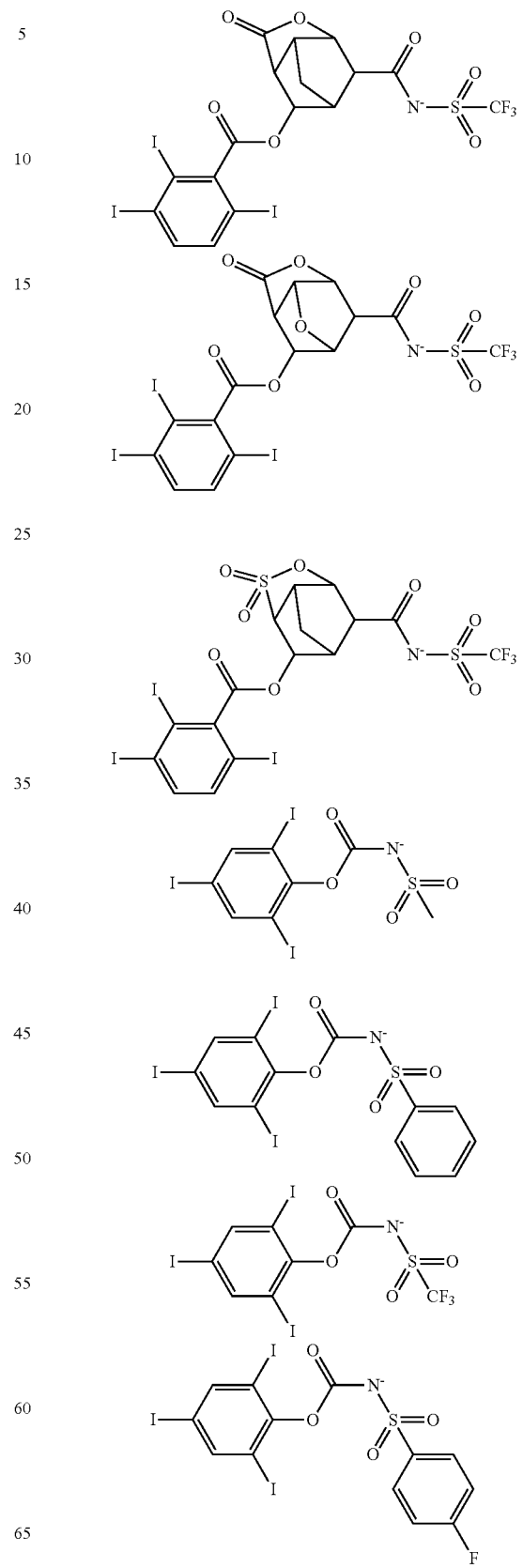

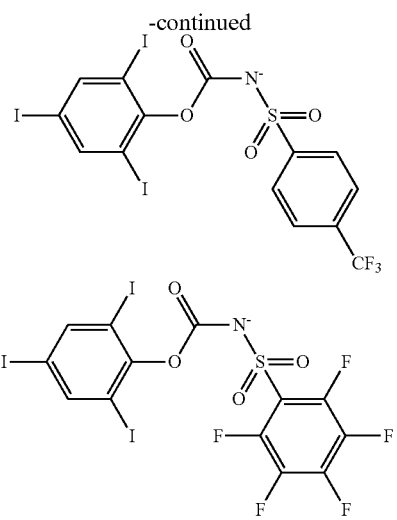

In formula (A), M⁺ is a sulfonium cation having the formula (Aa), an iodonium cation having the formula (Ab), or an ammonium cation having the formula (Ac).

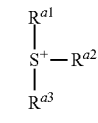 (Aa)

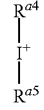 (Ab)

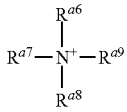 (Ac)

When M⁺ is a sulfonium cation having formula (Aa), for example, the onium salt having formula (A) is a sulfonium salt having the formula (B).

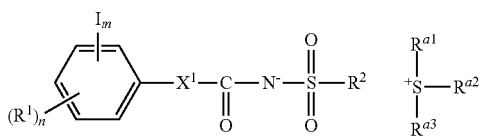 (B)

Herein $R^1$, $R^2$, $X^1$, m, n, $R^{a1}$ to $R^{a3}$ are as defined above.

In formulae (Aa) and (Ab), $R^{a1}$ to $R^{a3}$ are each independently halogen or a $C_1$-$C_{20}$ monovalent hydrocarbon group which may contain a heteroatom. Any two of $R^{a1}$, $R^{a2}$ and $R^{a3}$ may bond together to form a ring with the sulfur atom to which they are attached. $R^{a4}$ and $R^{a5}$ are each independently halogen or a $C_1$-$C_{20}$ monovalent hydrocarbon group which may contain a heteroatom.

The monovalent hydrocarbon groups may be straight, branched or cyclic and include $C_1$-$C_{20}$ alkyl, $C_2$-$C_{12}$ alkenyl, $C_2$-$C_{12}$ alkynyl, $C_6$-$C_{20}$ aryl, $C_7$-$C_{12}$ aralkyl and $C_7$-$C_{12}$ aryloxyalkyl groups. Some or all of the hydrogen atoms on these groups may be substituted by hydroxyl, carboxyl, halogen, oxo, cyano, amide bond, nitro, sultone, sulfone or sulfonium salt-containing moiety, or some carbon may be replaced by an ether bond, ester bond, carbonyl moiety, carbonate bond or sulfonic acid ester bond.

In formula (Ac), $R^{a6}$ to $R^{a9}$ are each independently hydrogen or a $C_1$-$C_{24}$ monovalent hydrocarbon group which may contain halogen, hydroxyl, carboxyl, ether bond, ester bond, thiol, thioester bond, thionoester bond, dithioester bond, amino moiety, nitro moiety, sulfone moiety, or ferrocenyl moiety. $R^{a6}$ and $R^{a7}$ may bond together to form a ring with the nitrogen atom to which they are attached, a pair of $R^{a6}$ and $R^{a7}$ and a pair of $R^{a8}$ and $R^{a9}$ may bond together to form a spiro-ring with the nitrogen atom to which they are attached, $R^{a8}$ and $R^{a9}$, taken together, may form =C($R^{a10}$)($R^{a11}$), wherein $R^{a10}$ and $R^{a11}$ are each independently hydrogen or a $C_1$-$C_{16}$ monovalent hydrocarbon group, $R^{a10}$ and $R^{a11}$ may bond together to form a ring with the carbon and nitrogen atoms to which they are attached, the ring may contain a double bond, oxygen, sulfur or nitrogen atom therein.

The $C_1$-$C_{24}$ monovalent hydrocarbon groups may be straight, branched or cyclic and include $C_1$-$C_{24}$ alkyl, $C_2$-$C_{24}$ alkenyl, $C_2$-$C_{24}$ alkynyl, $C_6$-$C_{20}$ aryl, and $C_7$-$C_{20}$ aralkyl groups, and combinations thereof.

Examples of the sulfonium cation having formula (Aa) are shown below, but not limited thereto.

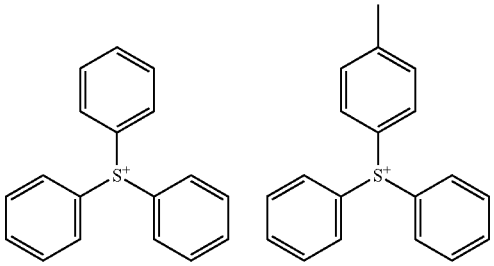

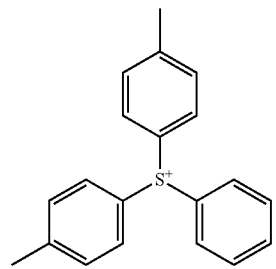

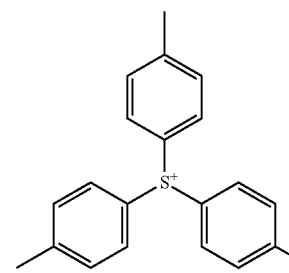

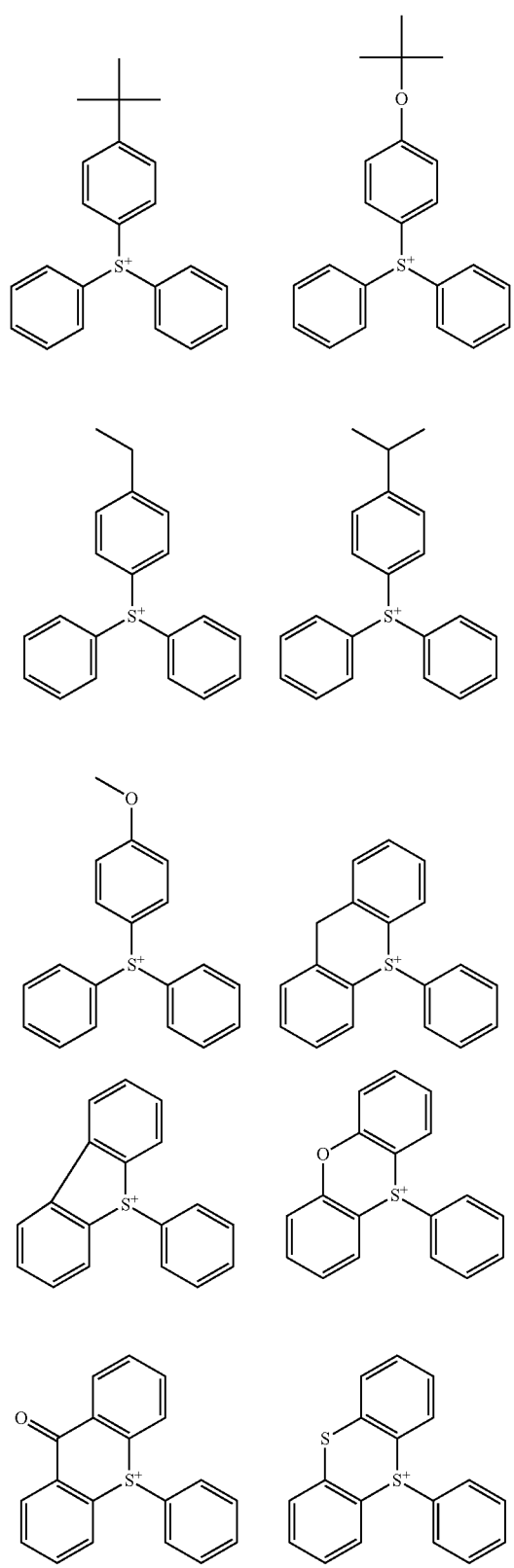
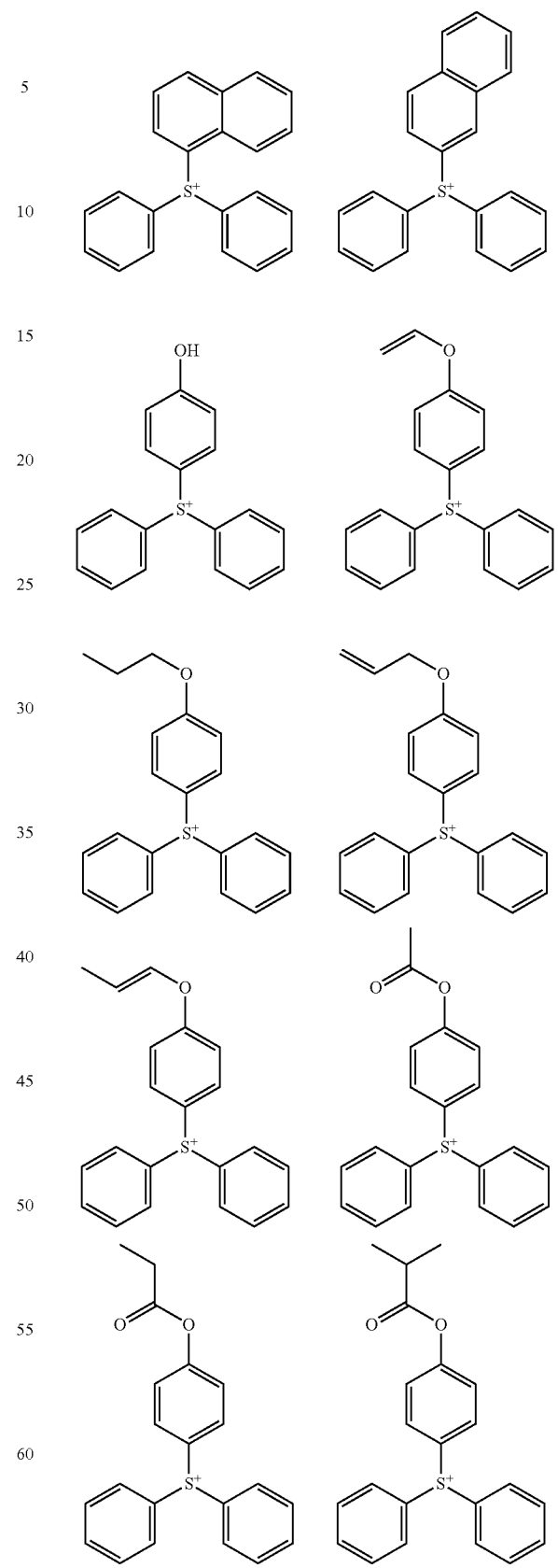

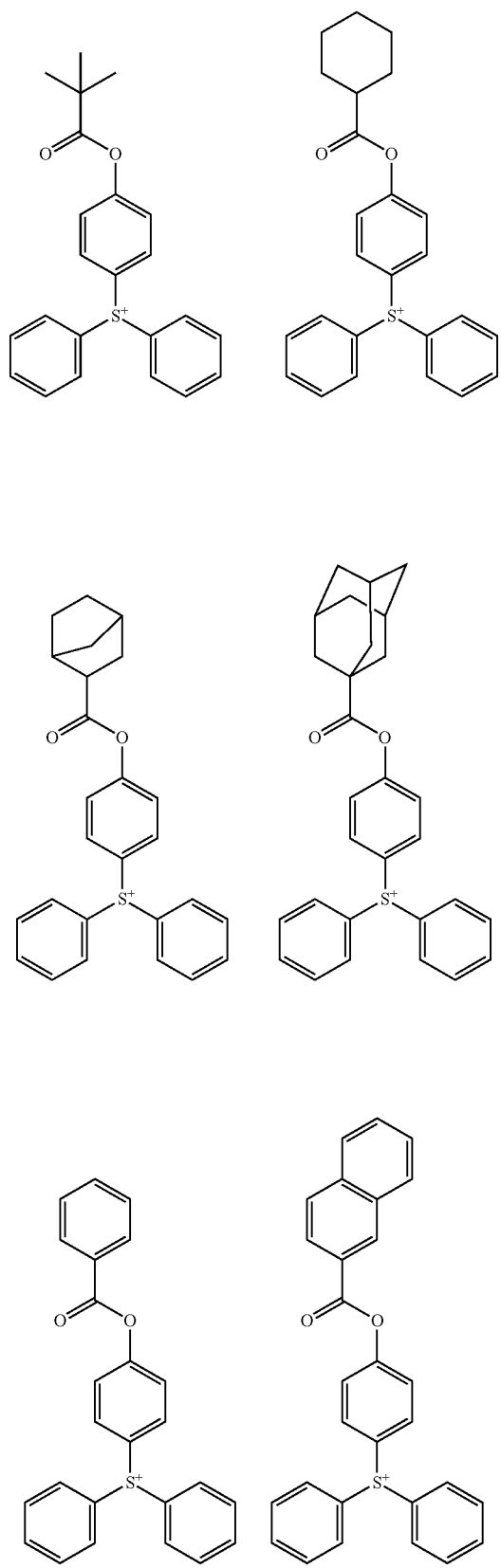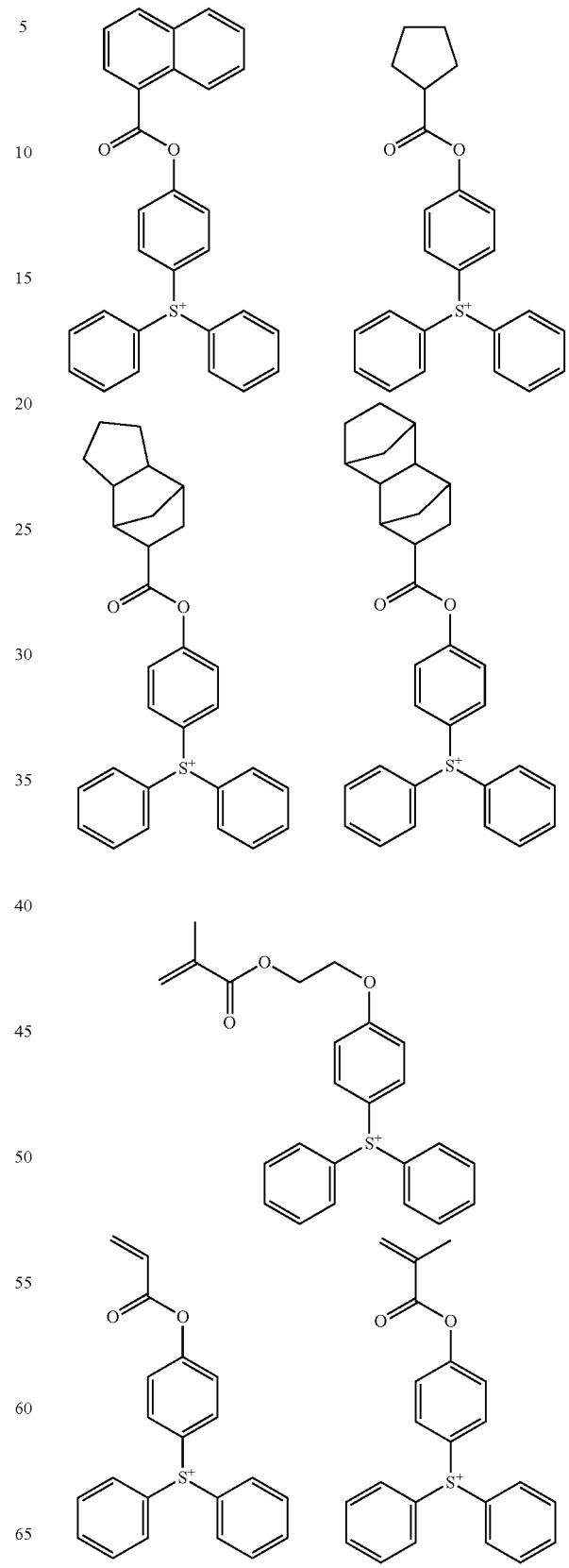

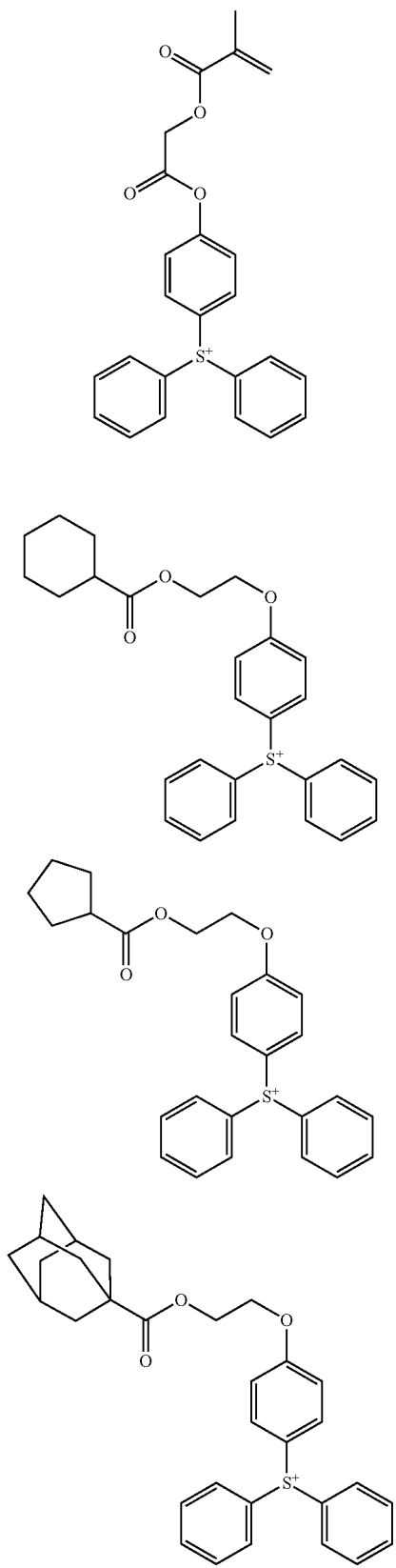
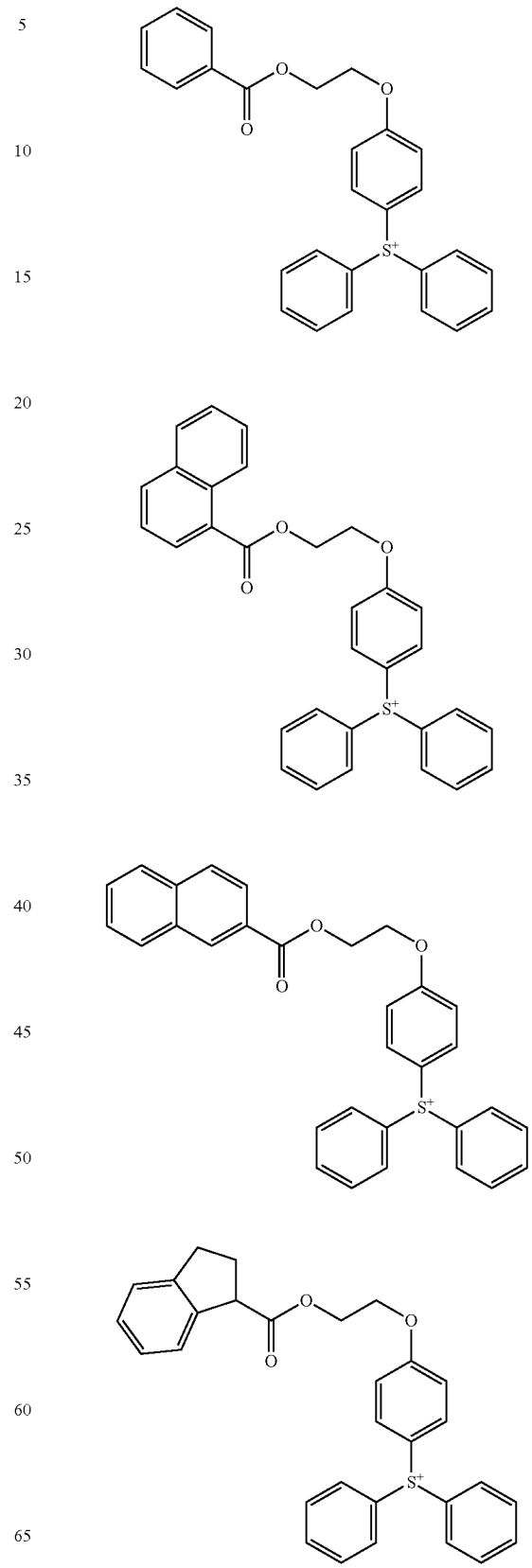

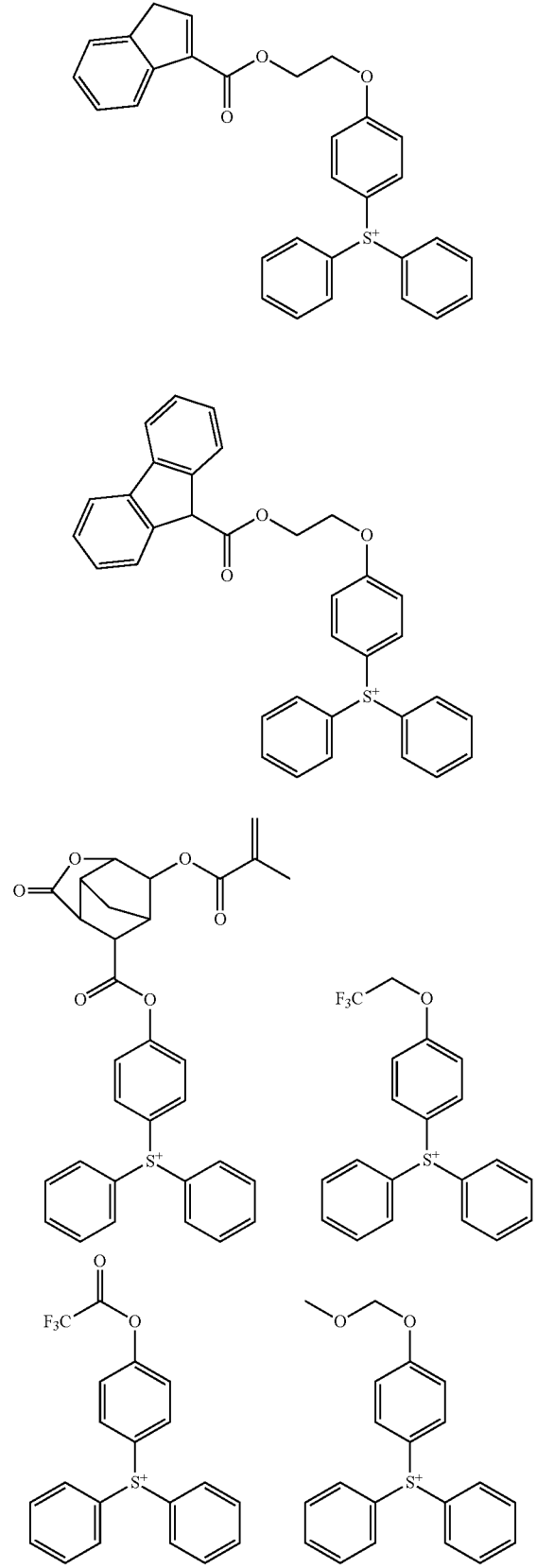
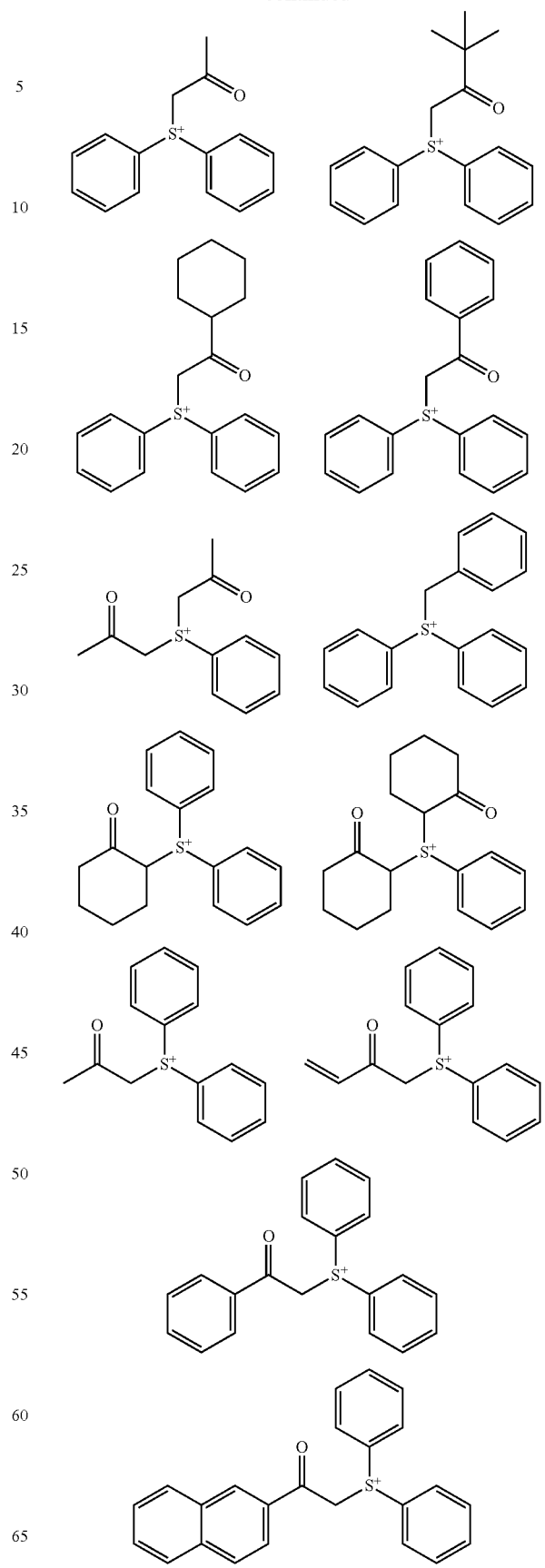

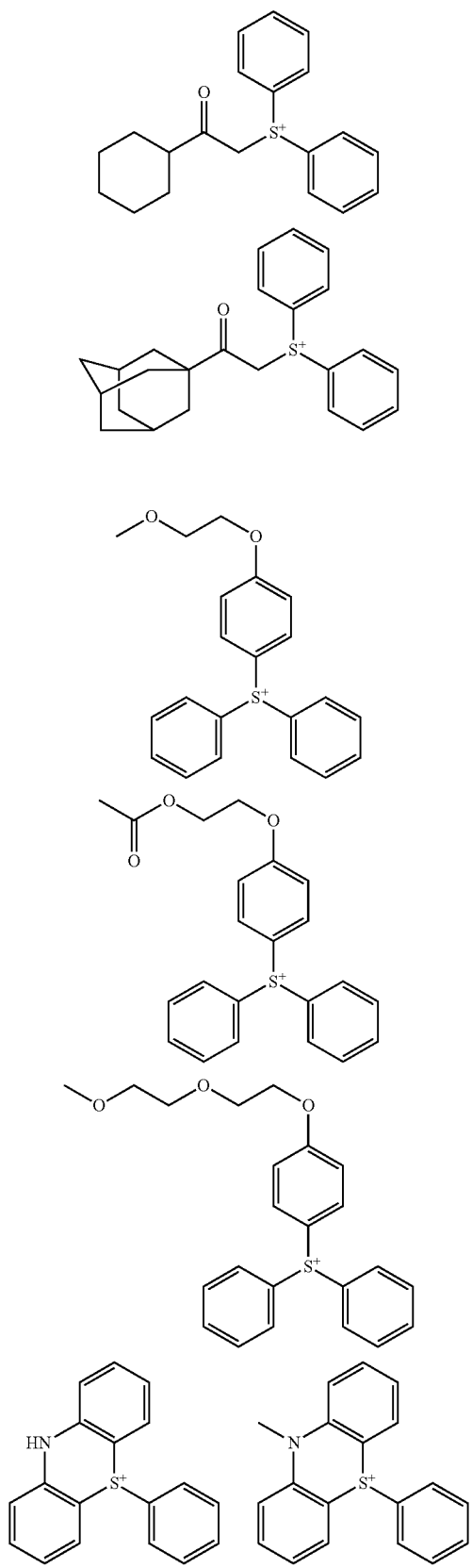
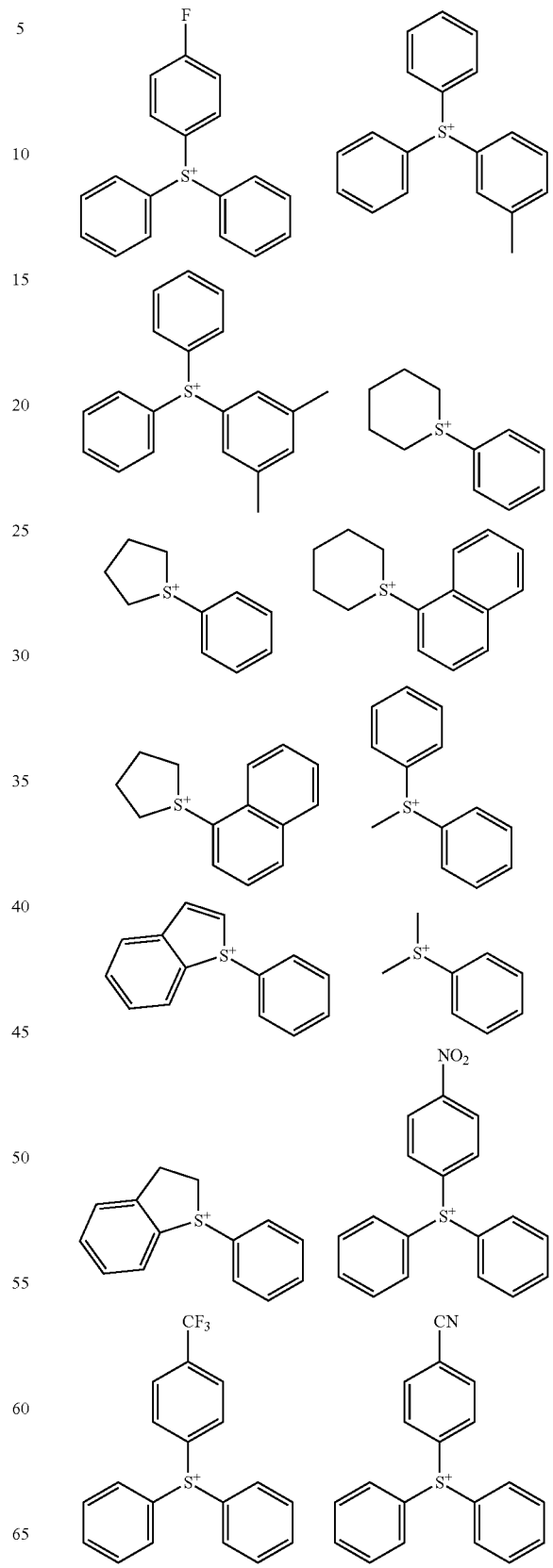

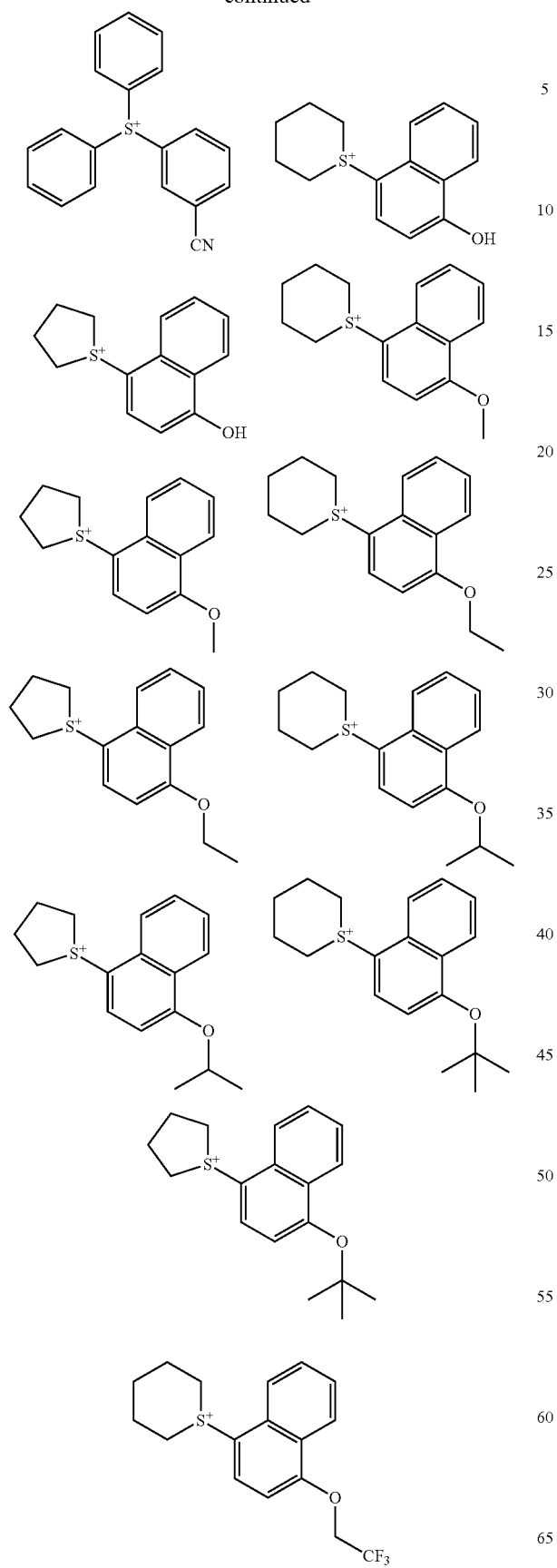
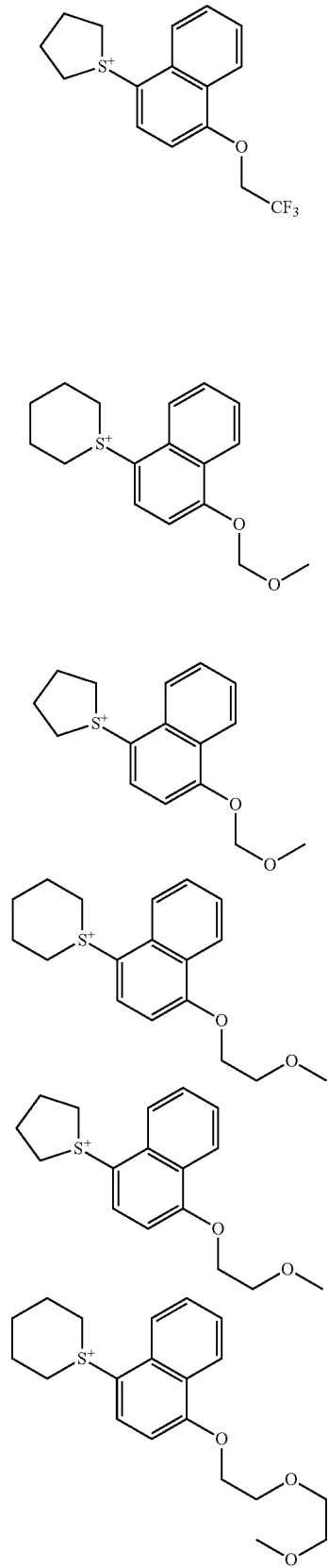

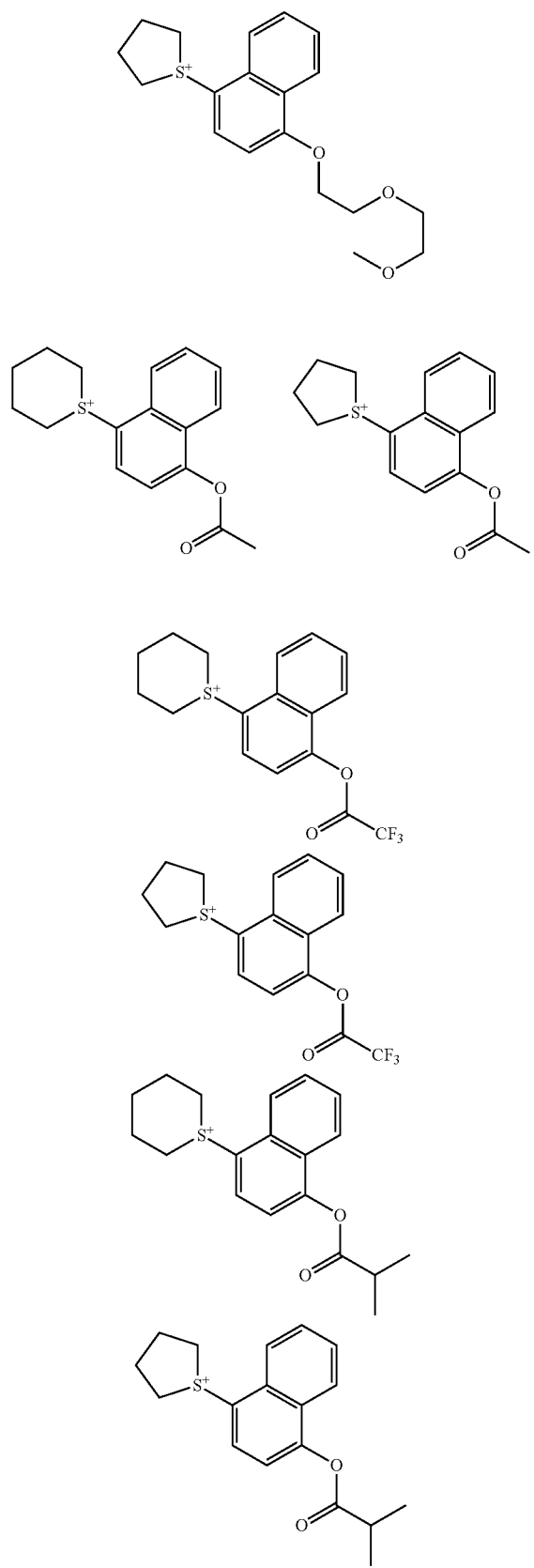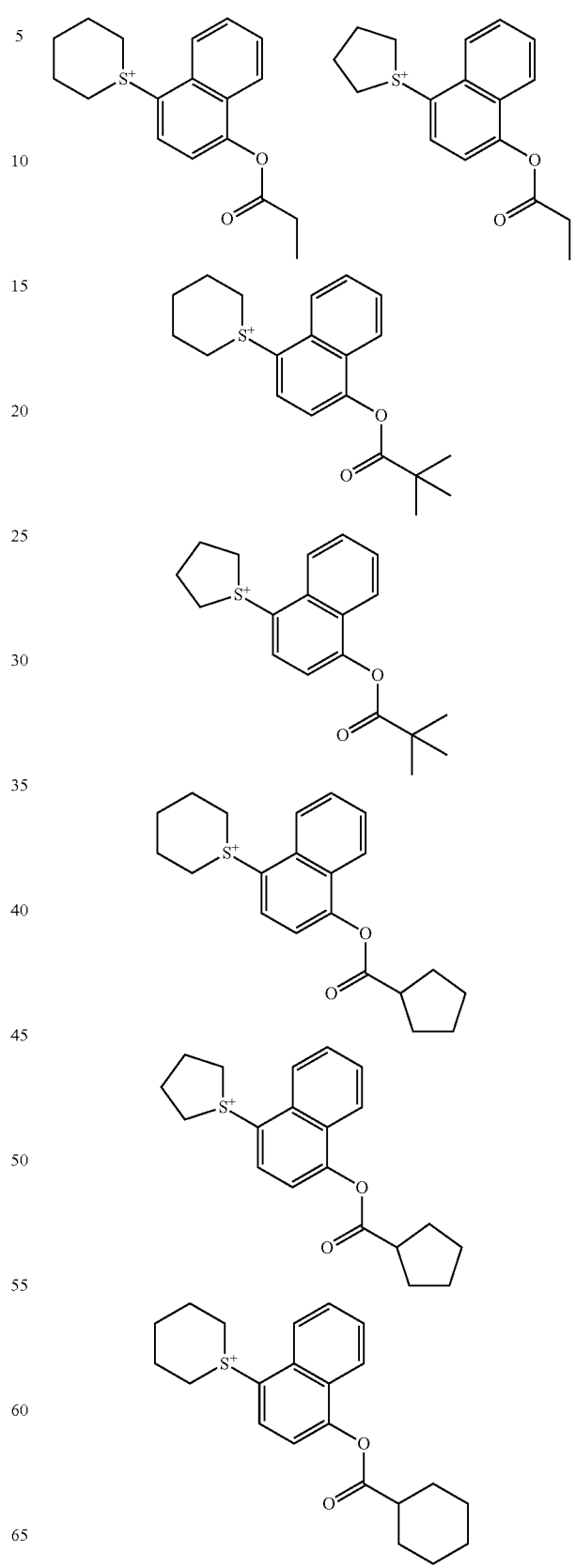

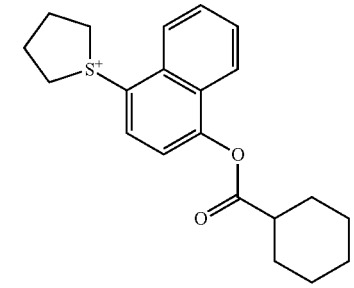
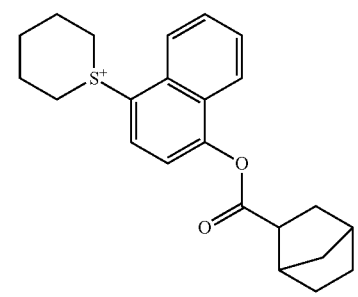
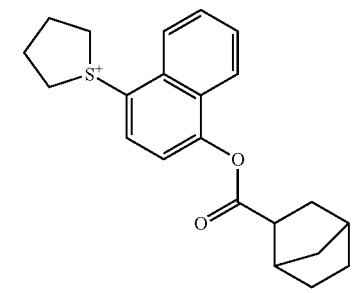
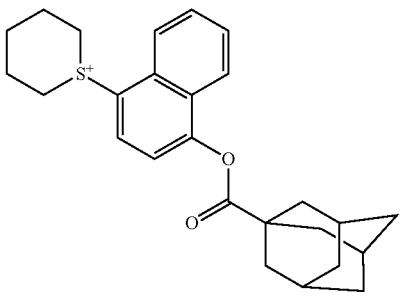
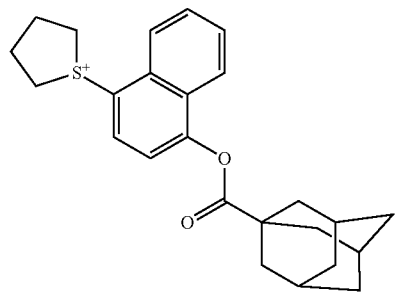
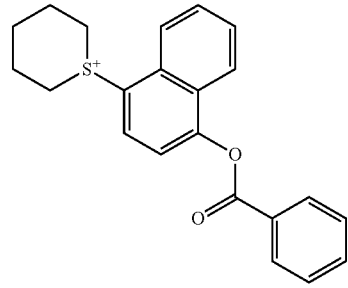
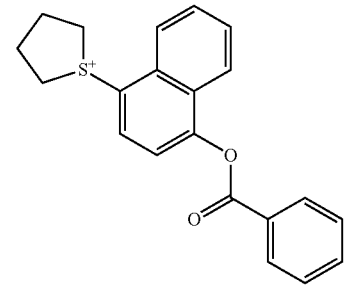
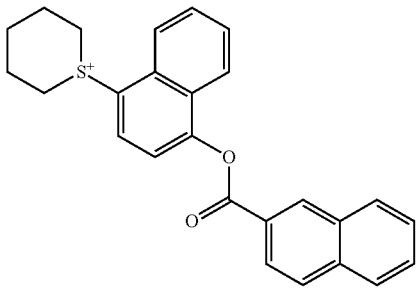
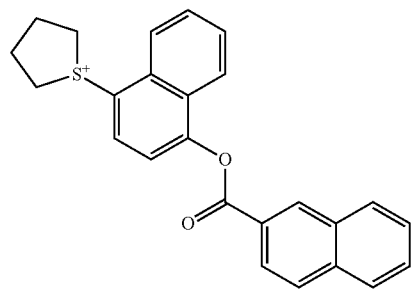
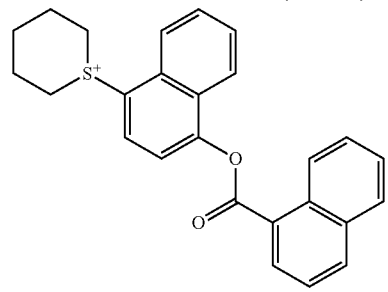
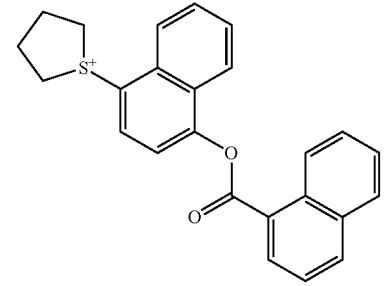

-continued
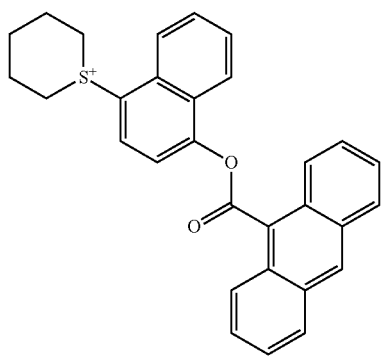
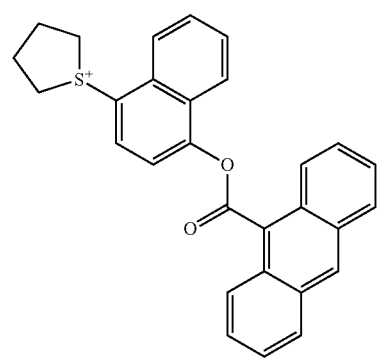
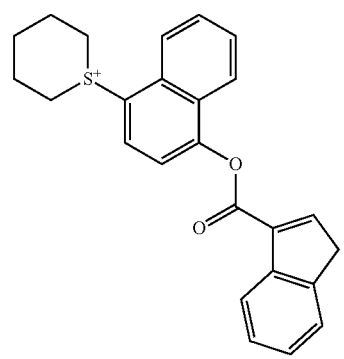
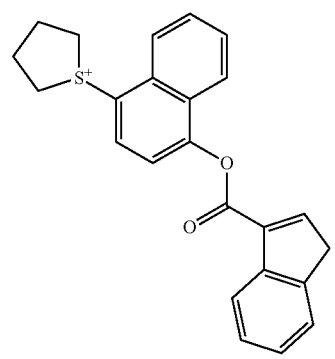
-continued
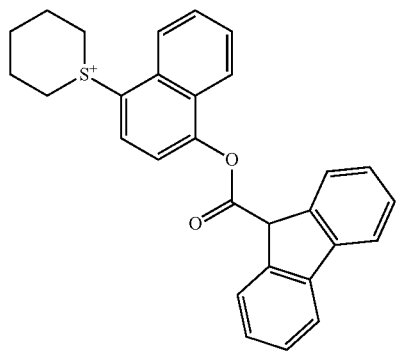
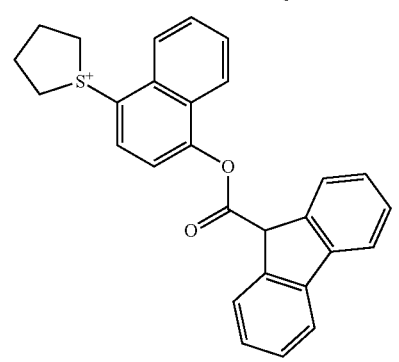
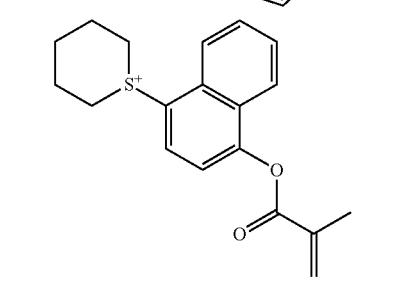
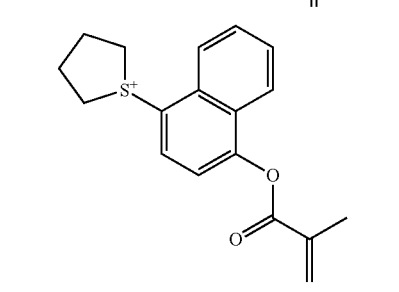
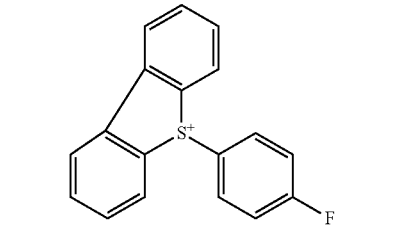
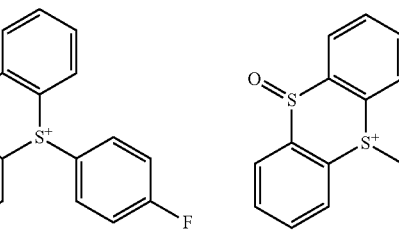

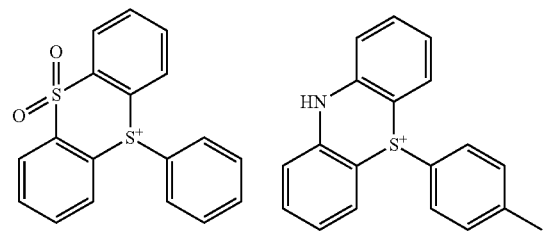
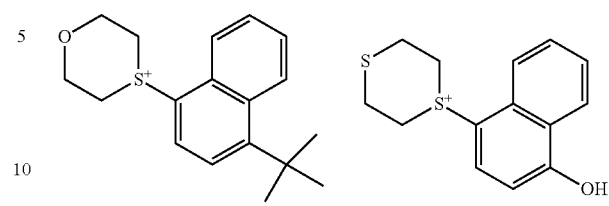
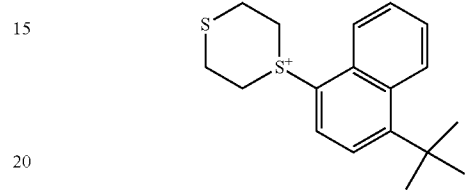
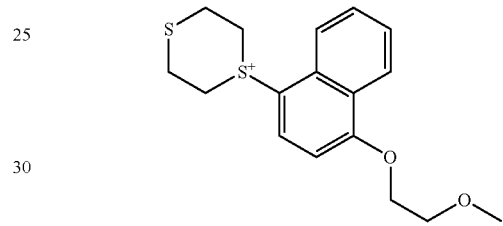
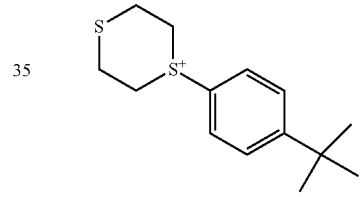
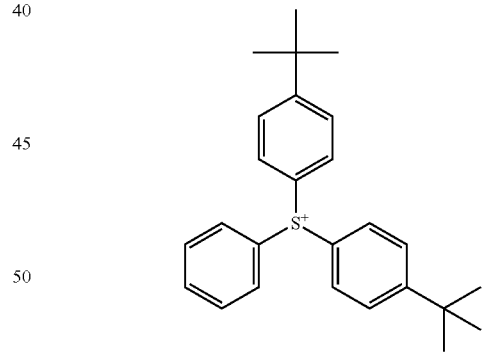
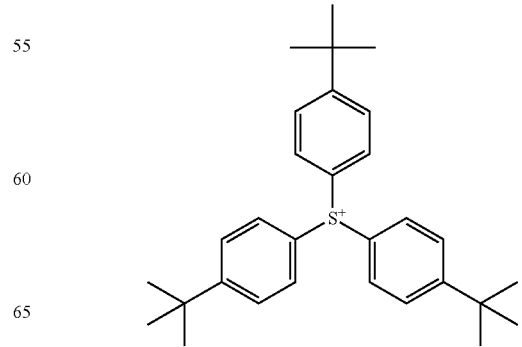

49
-continued
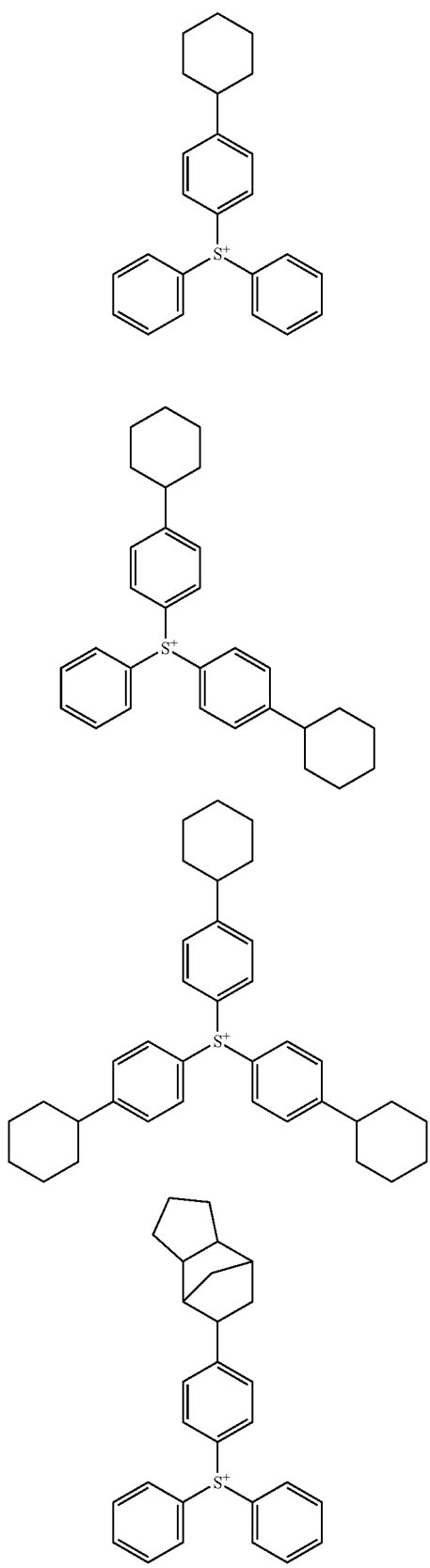
50
-continued
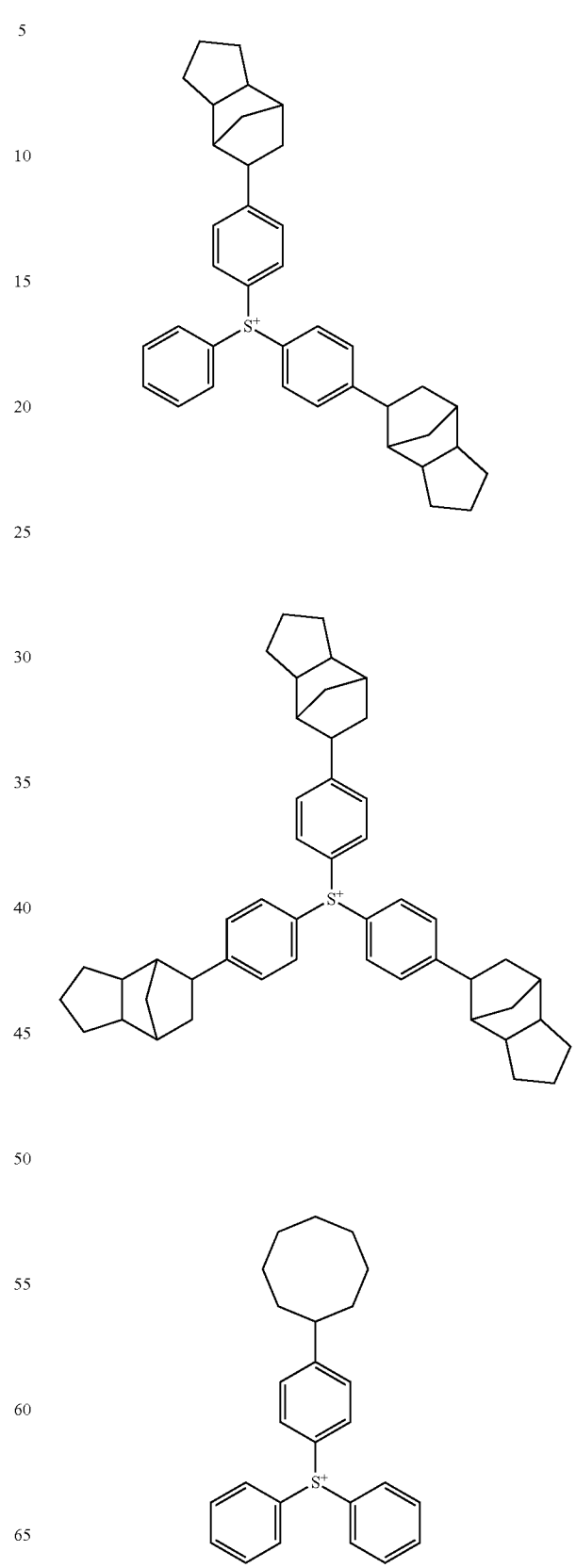

51
-continued
52
-continued
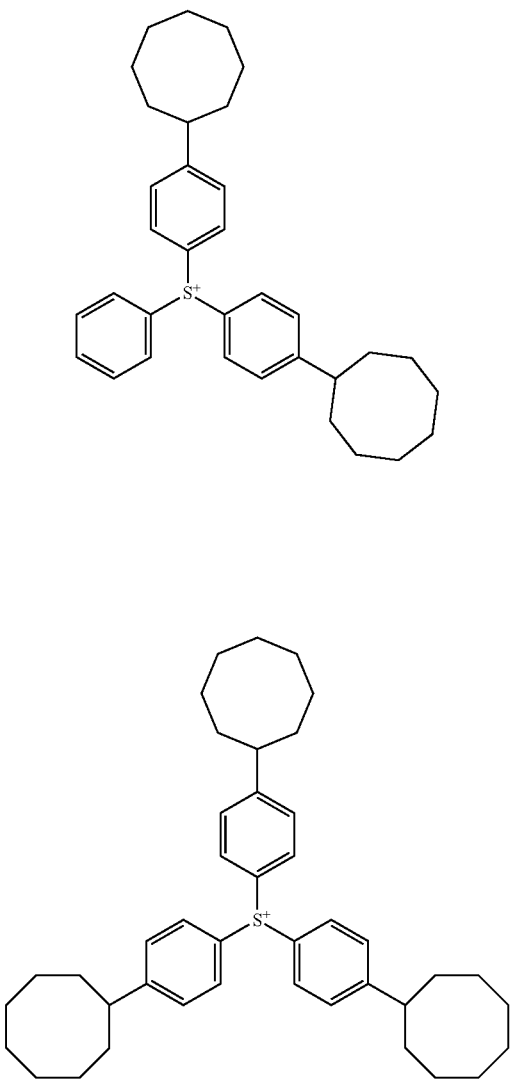
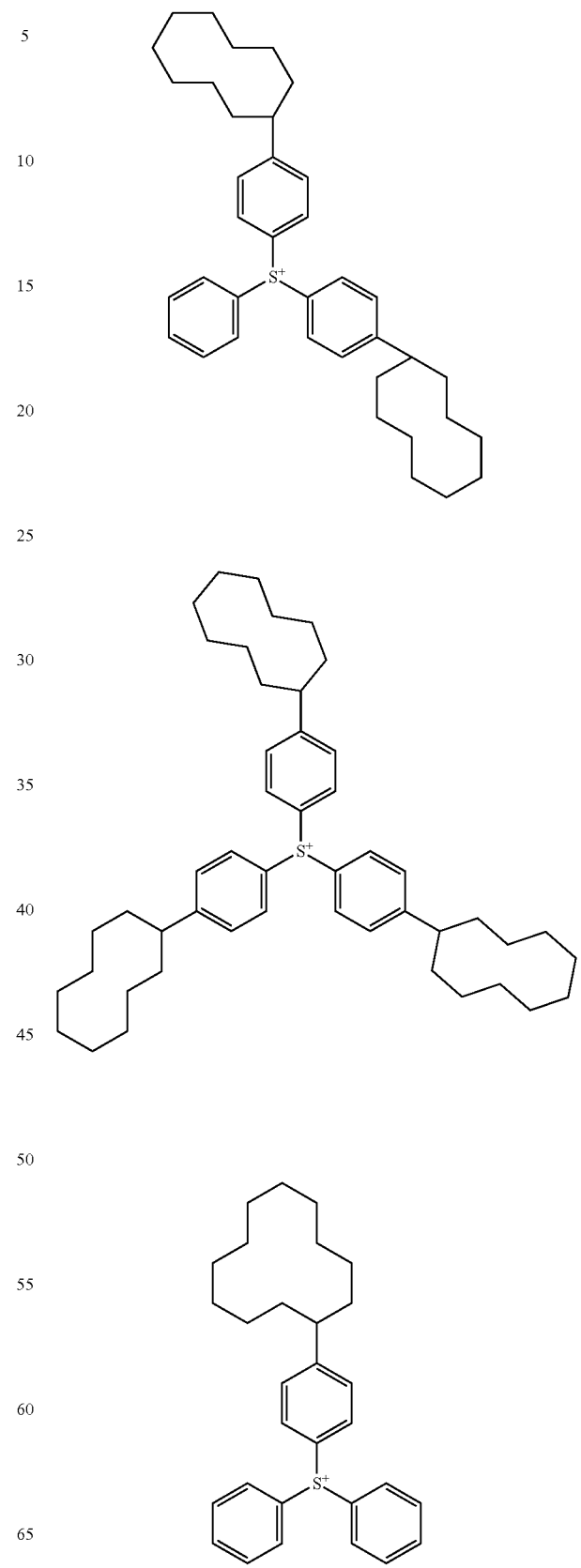

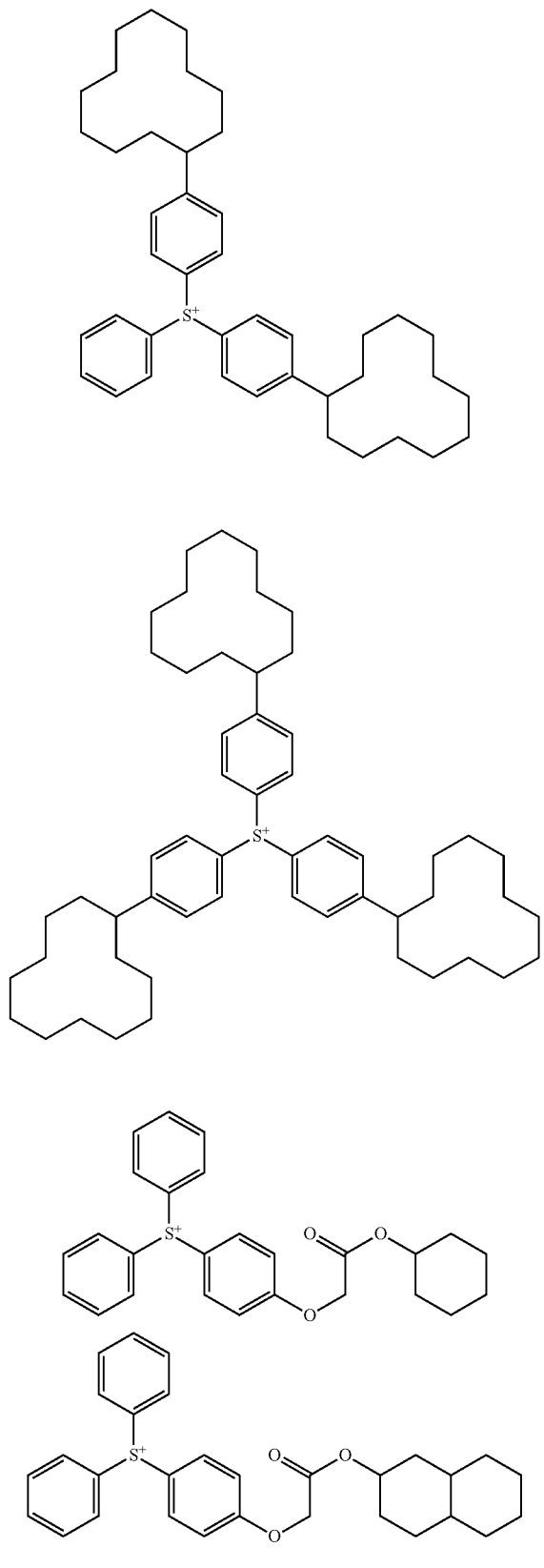
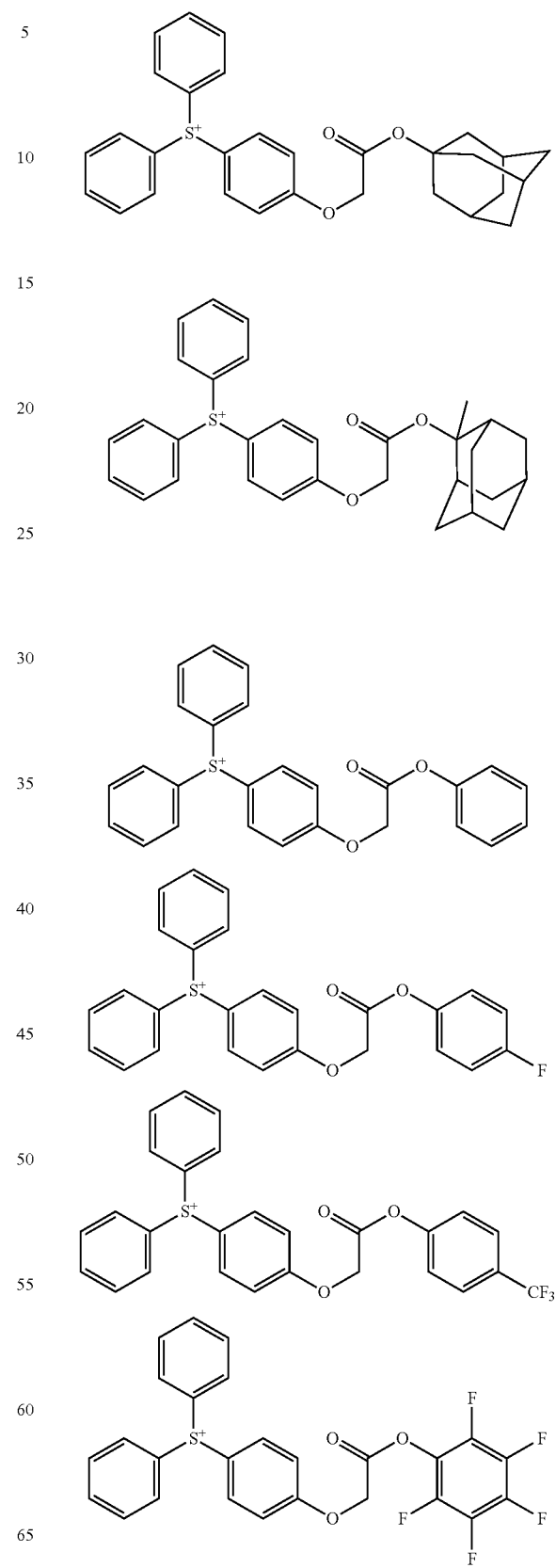

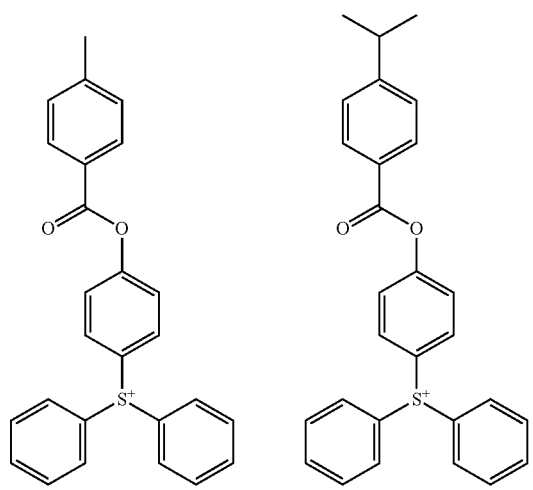
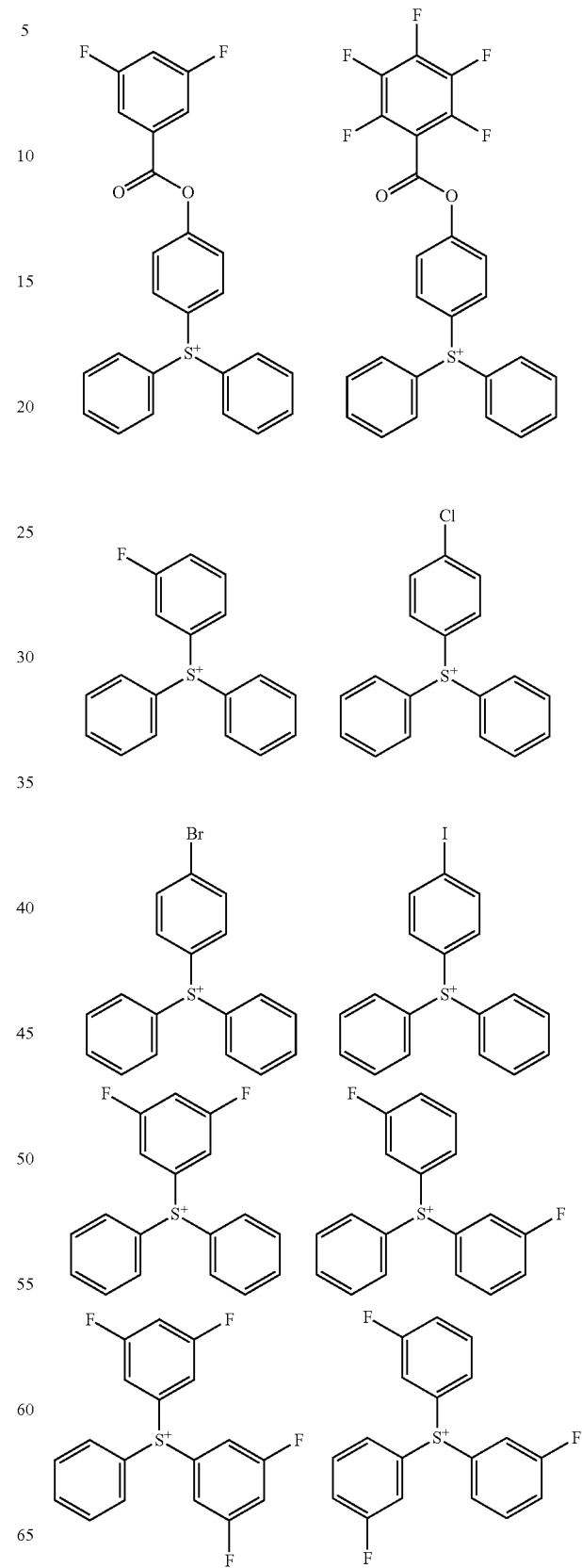

-continued
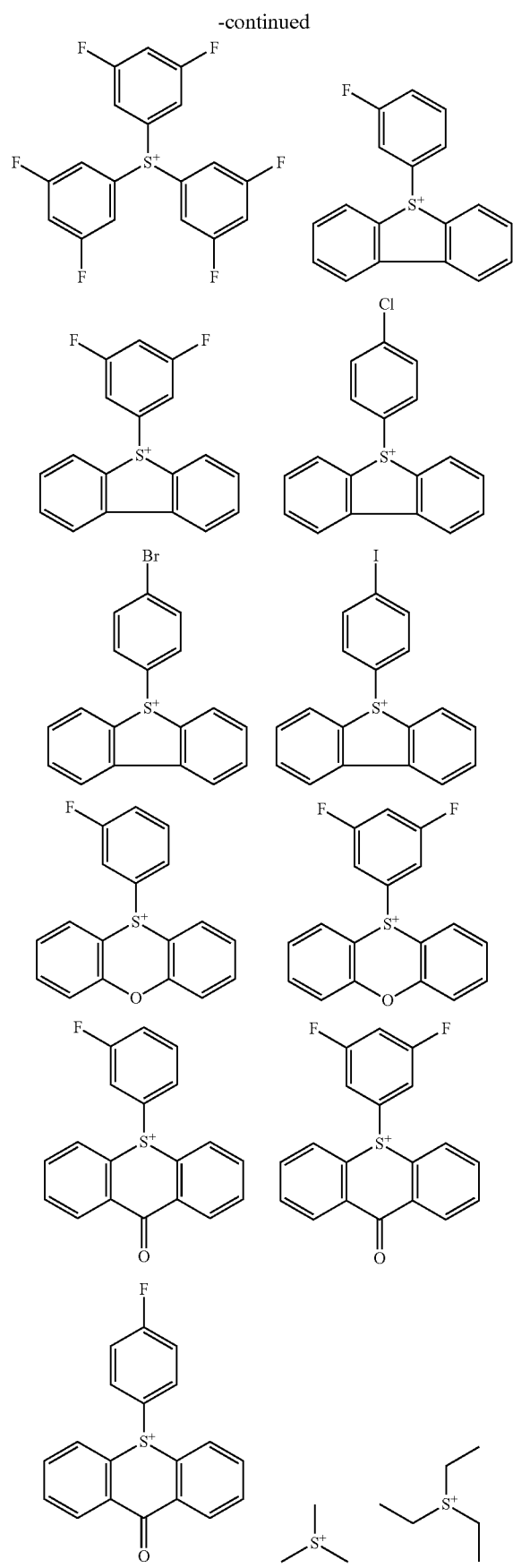
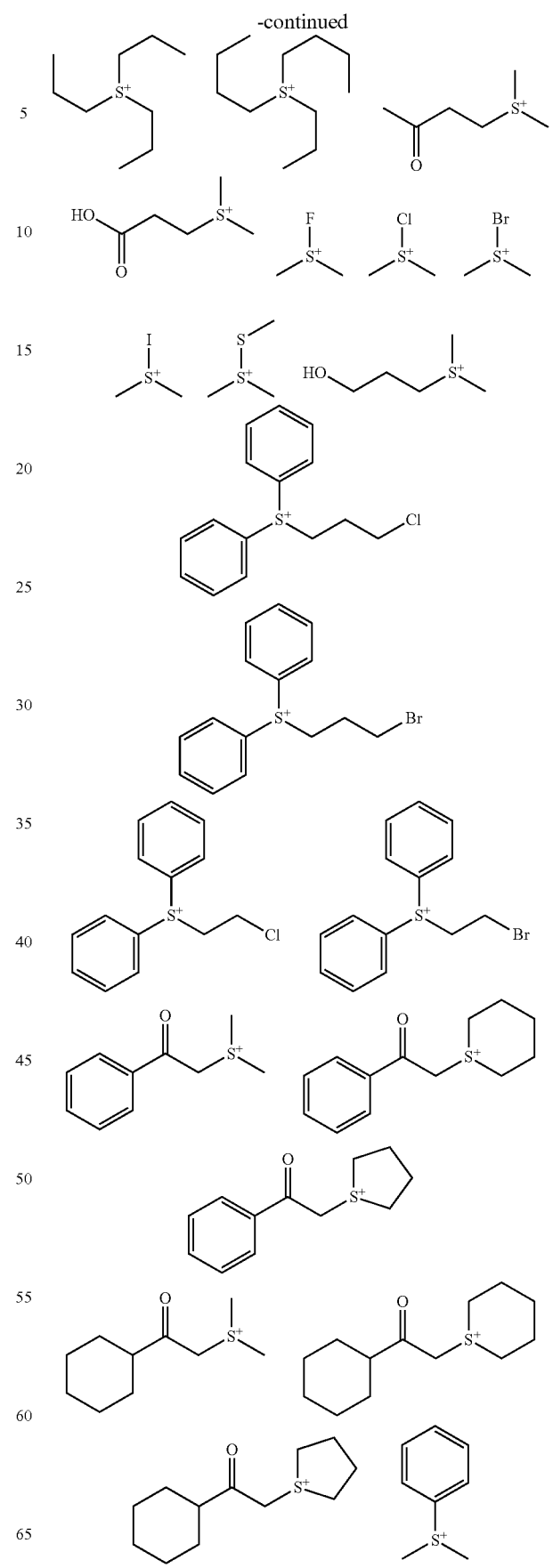

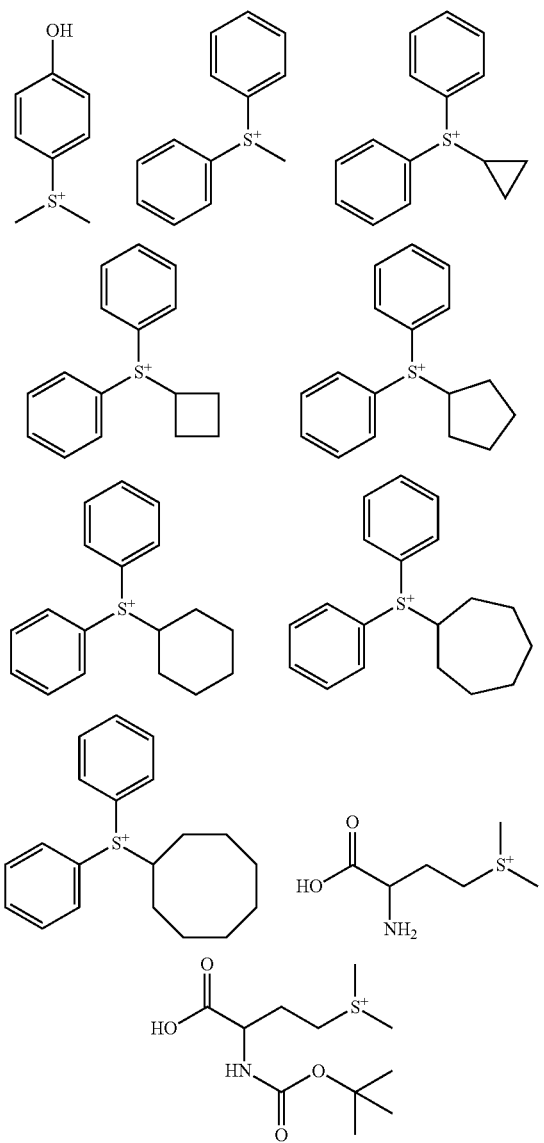
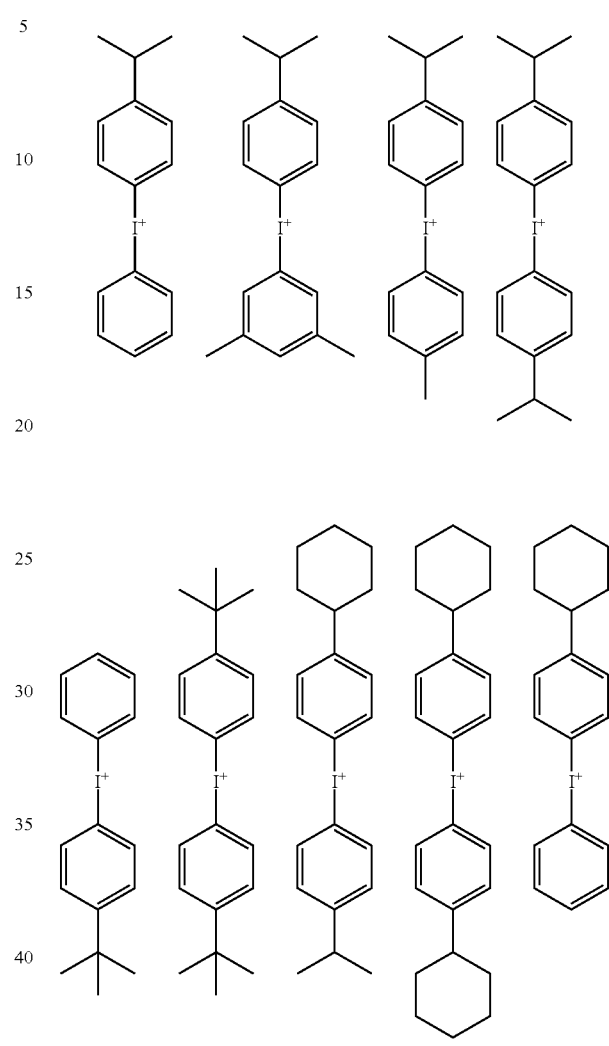
Examples of the iodonium cation having formula (Ab) are shown below, but not limited thereto.
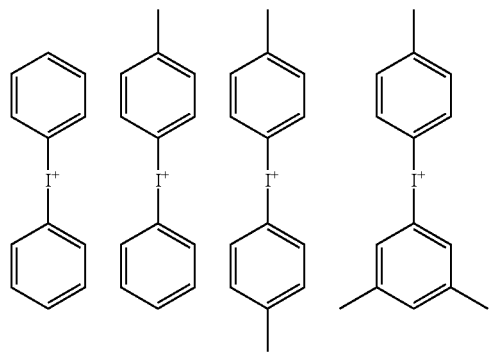
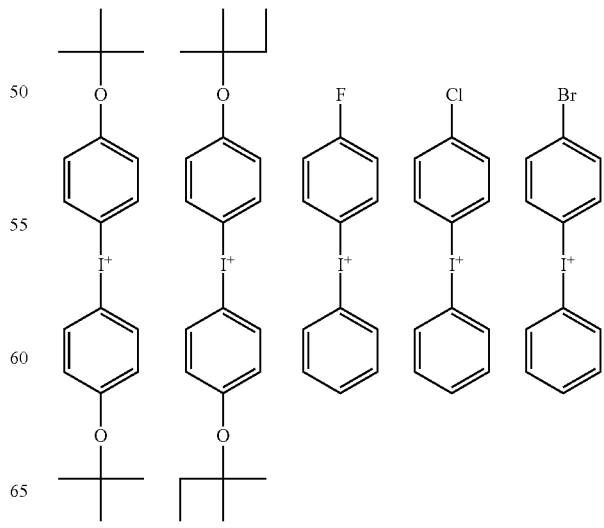

-continued
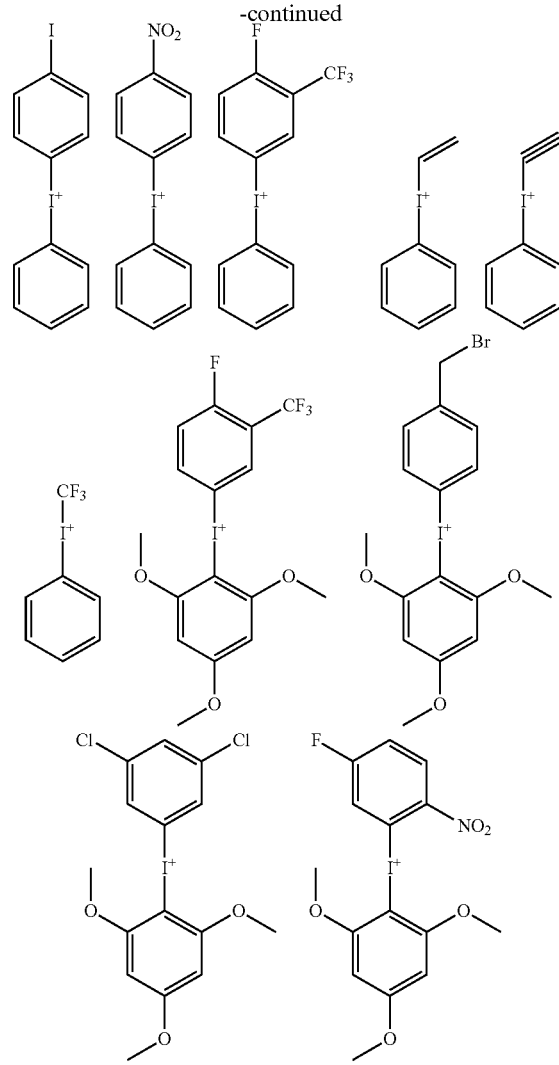
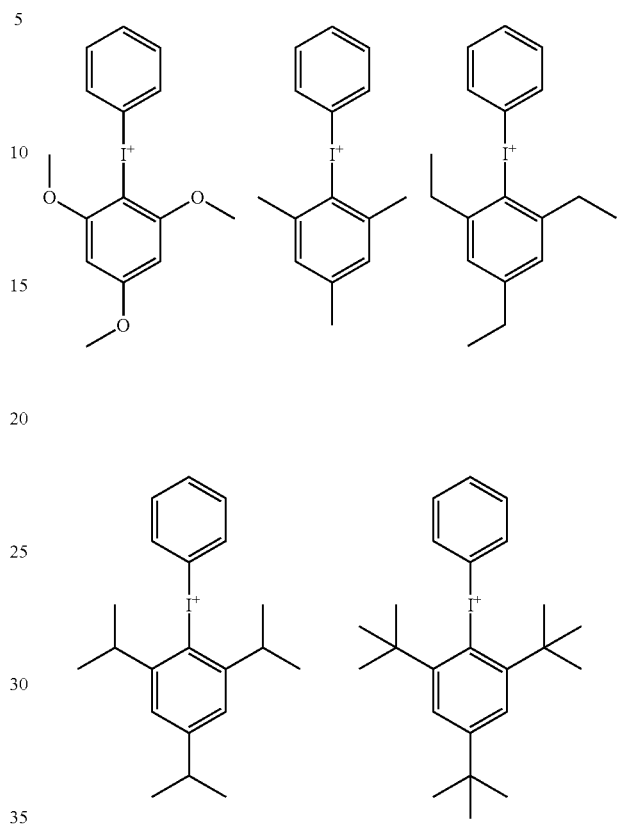
Examples of the ammonium cation having formula (Ac) are shown below, but not limited thereto.
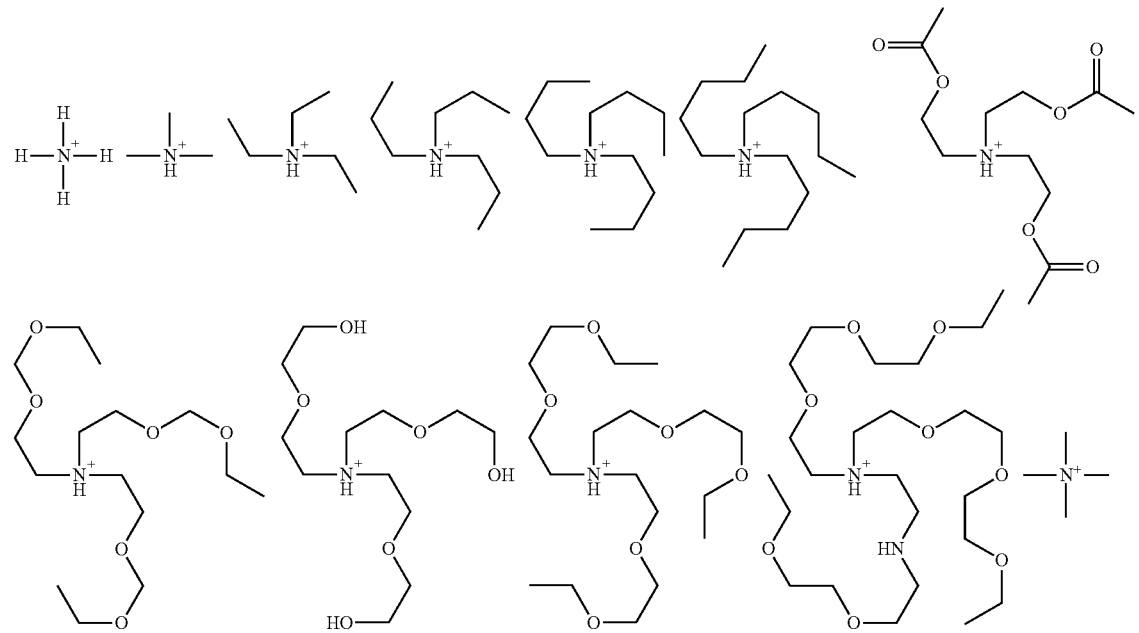

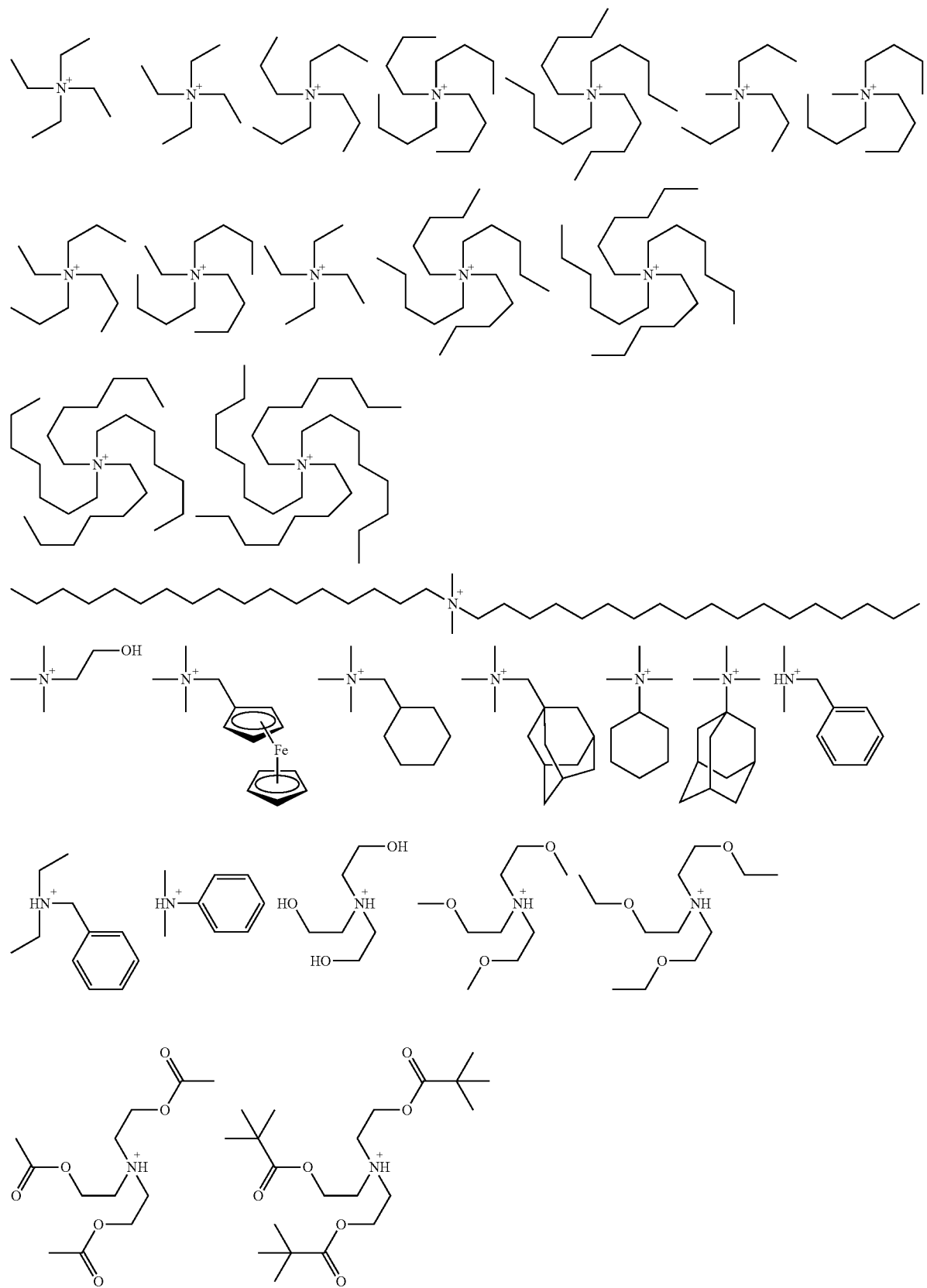

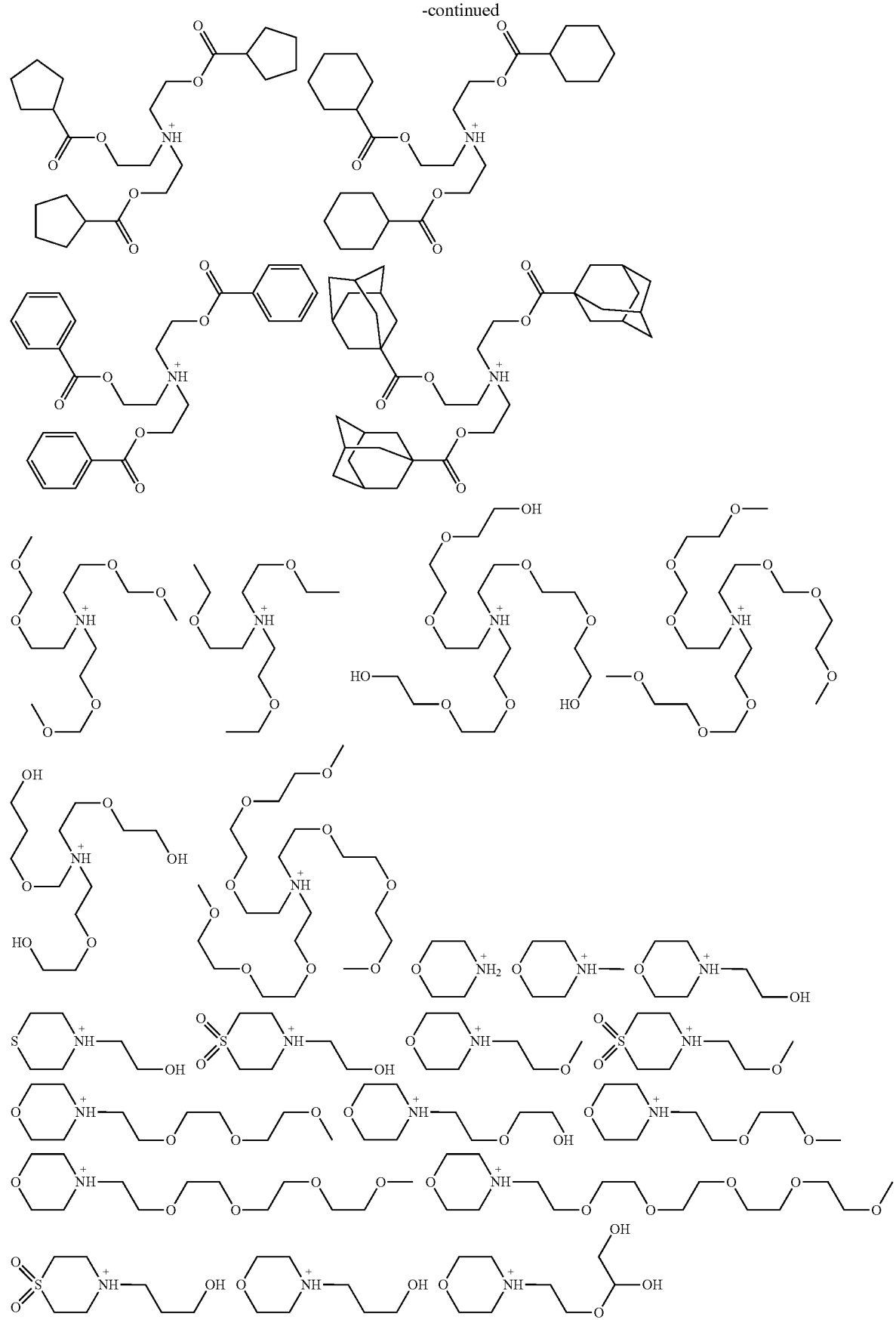

-continued
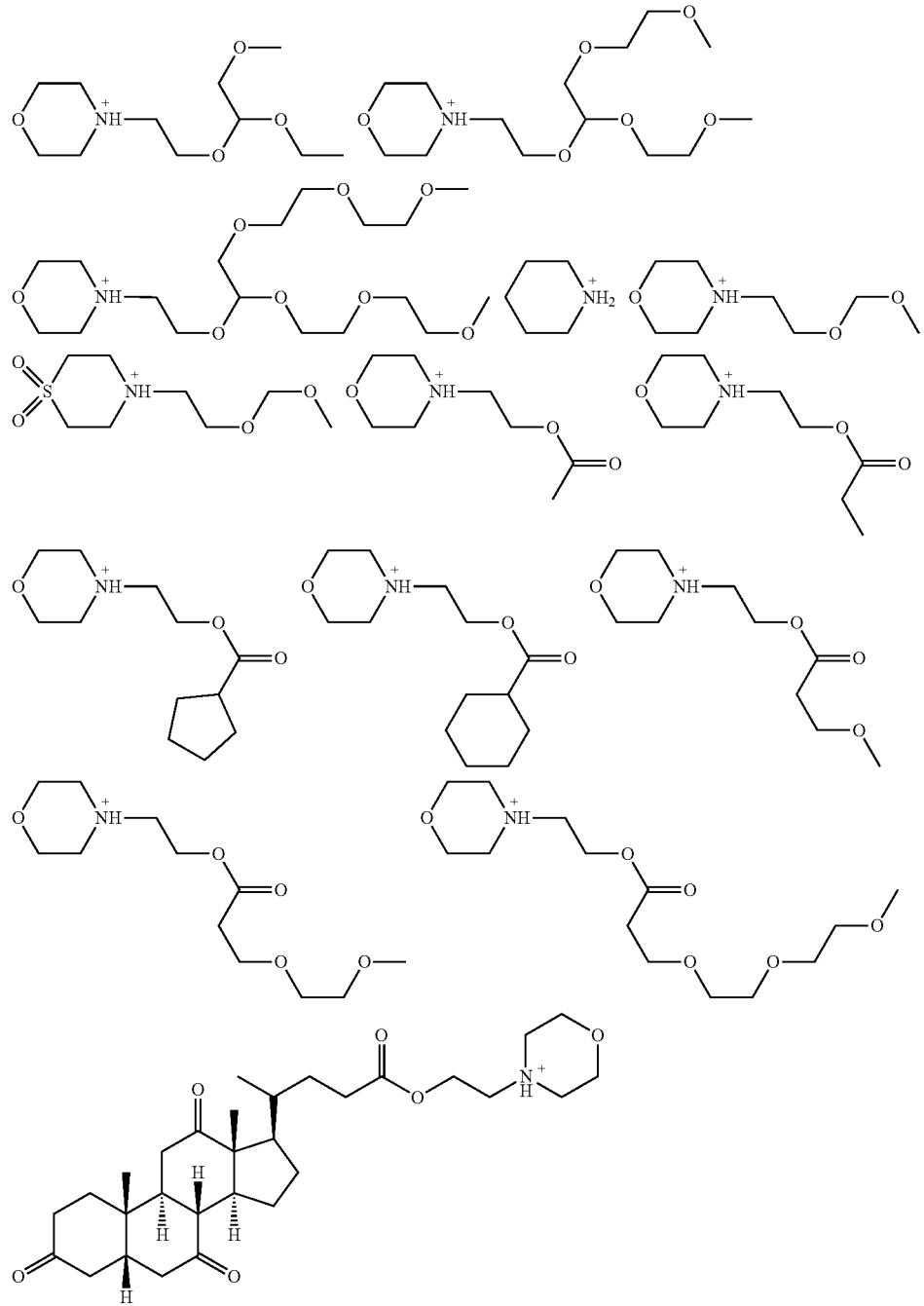
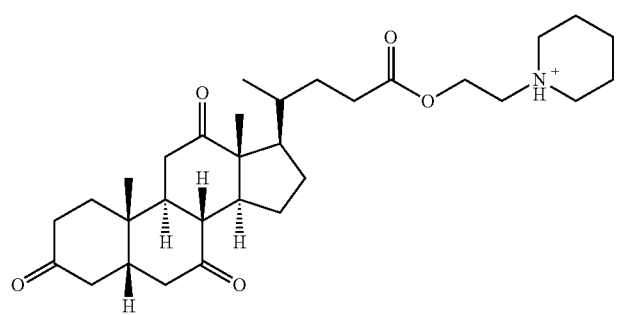

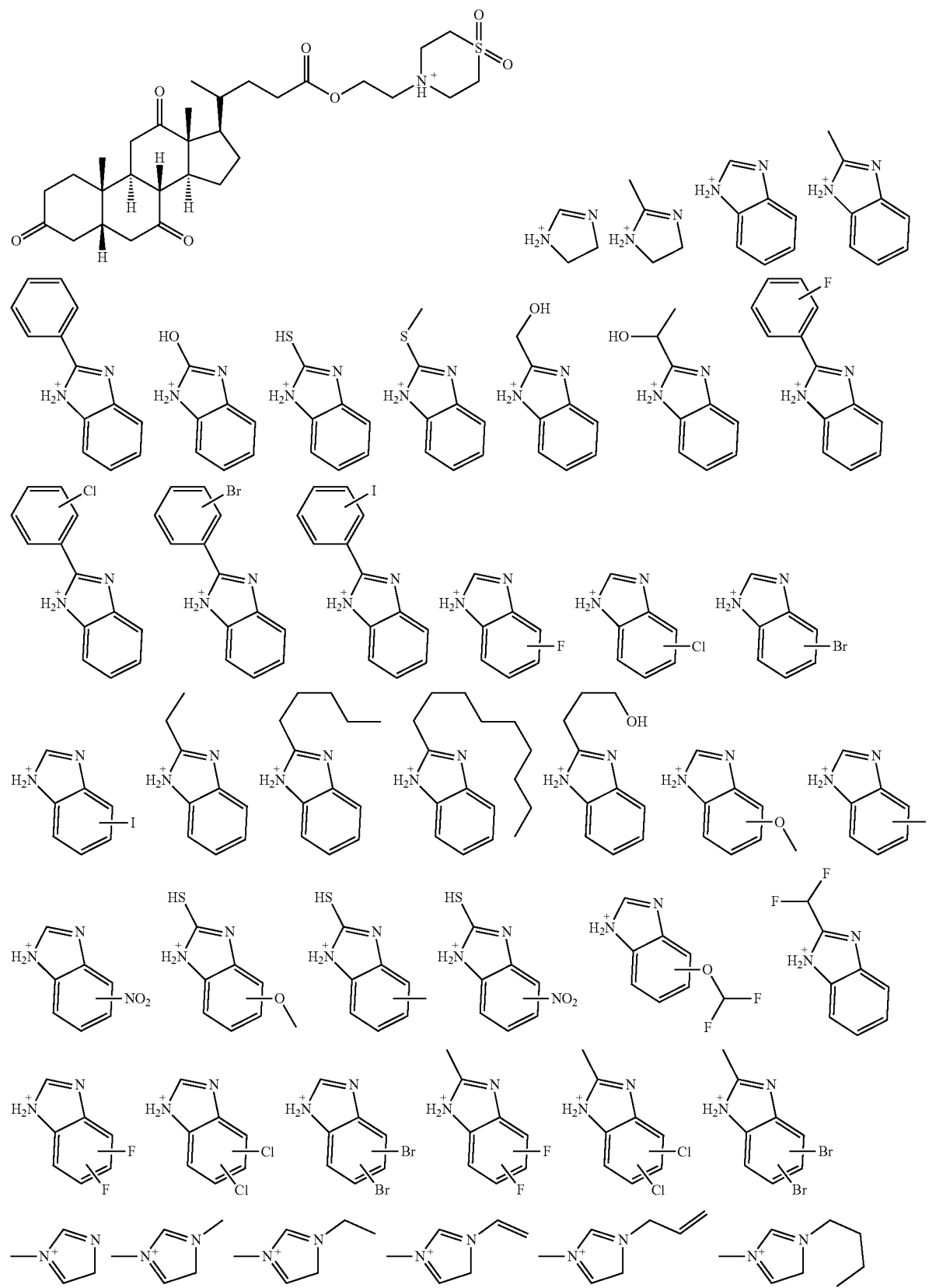

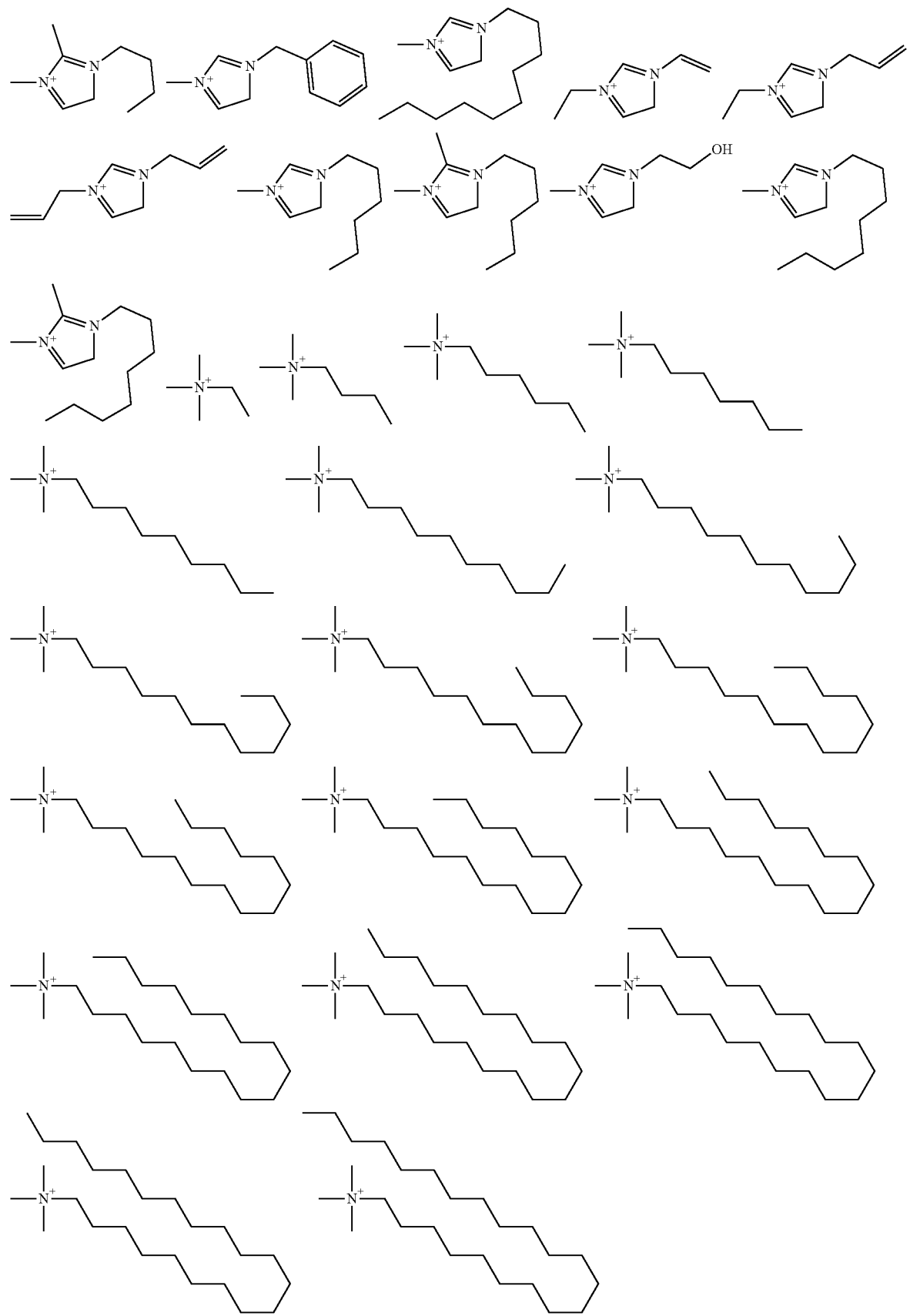
-continued

-continued
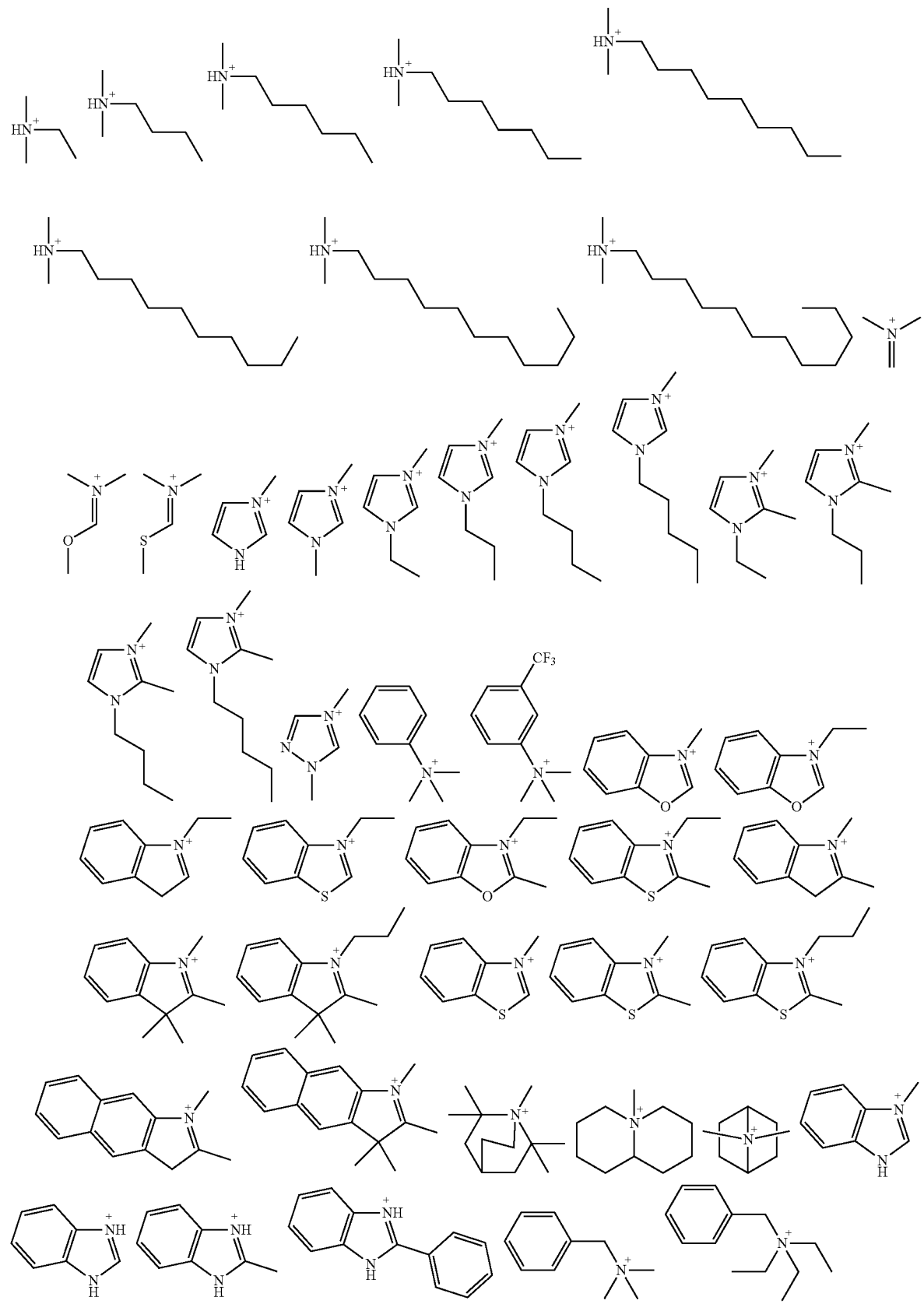

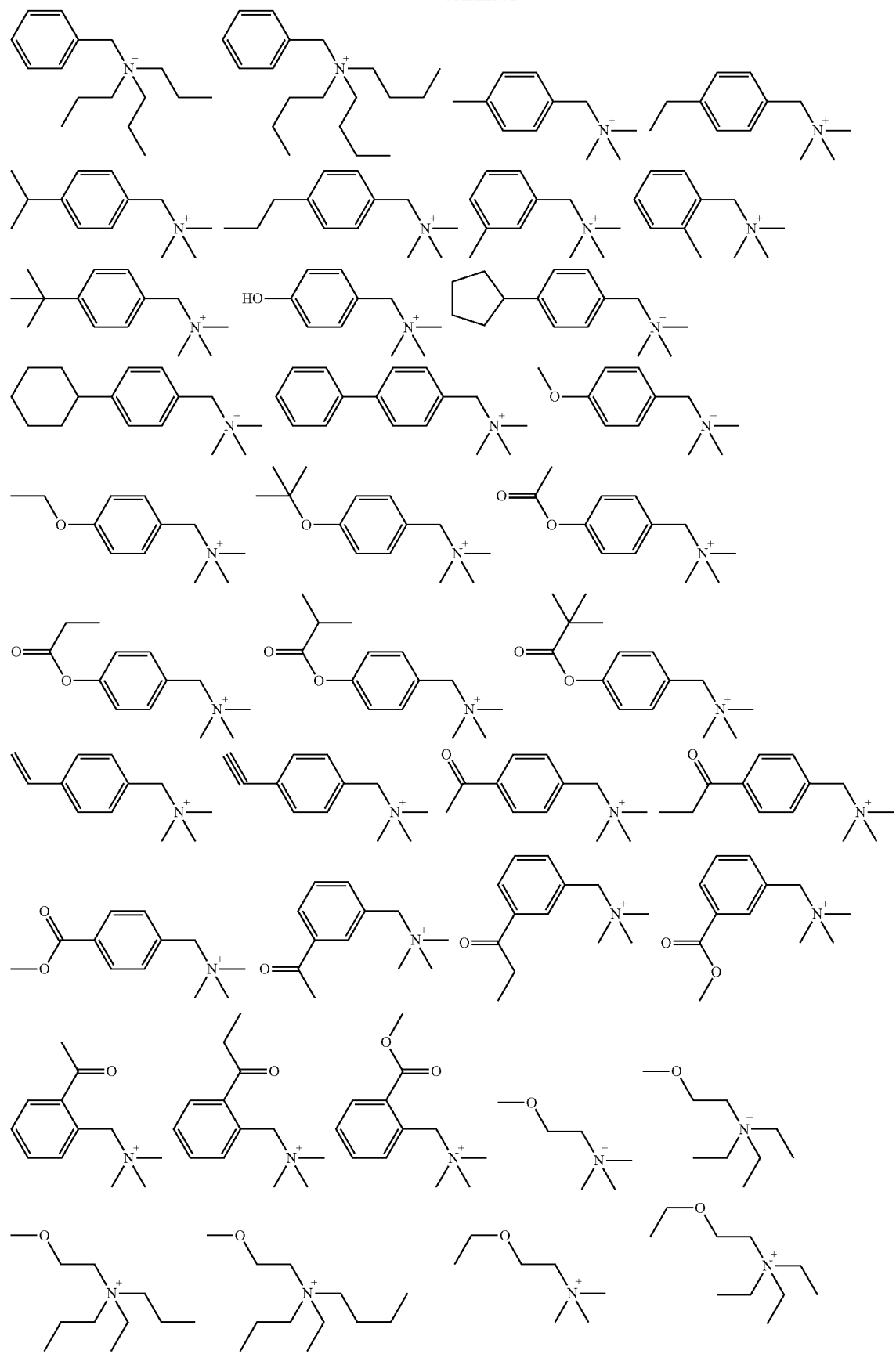

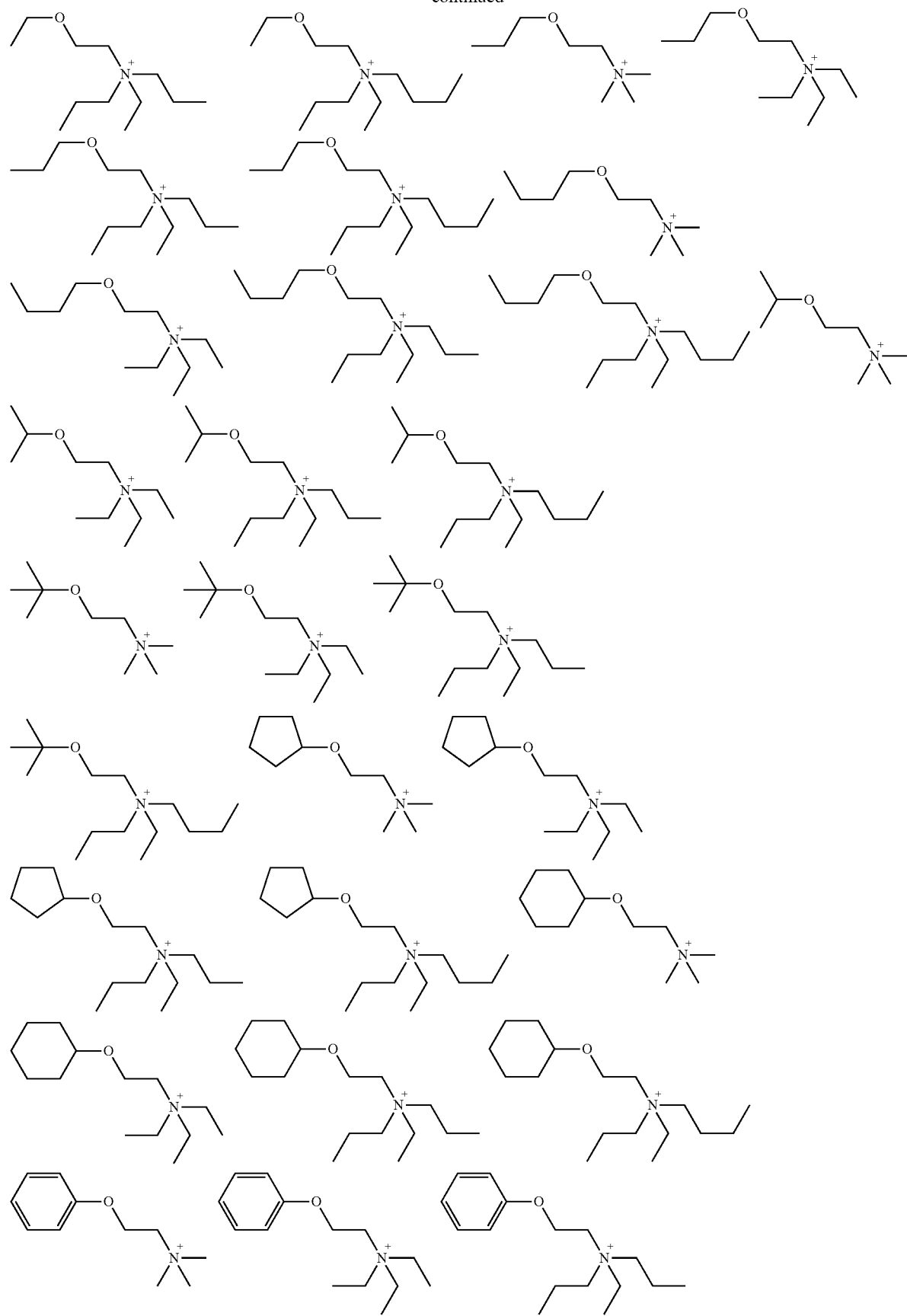

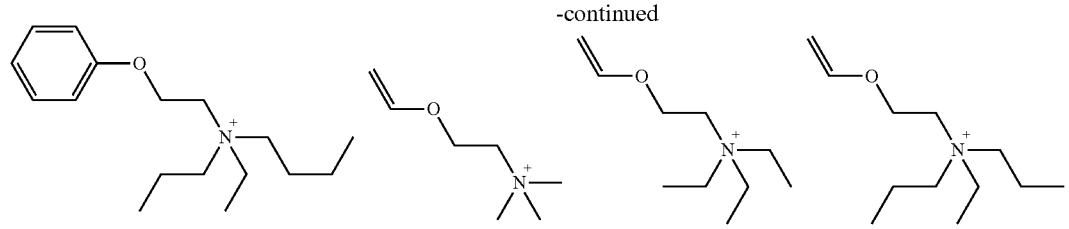
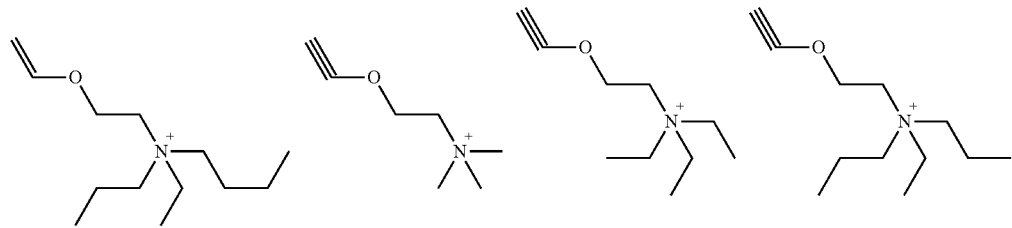
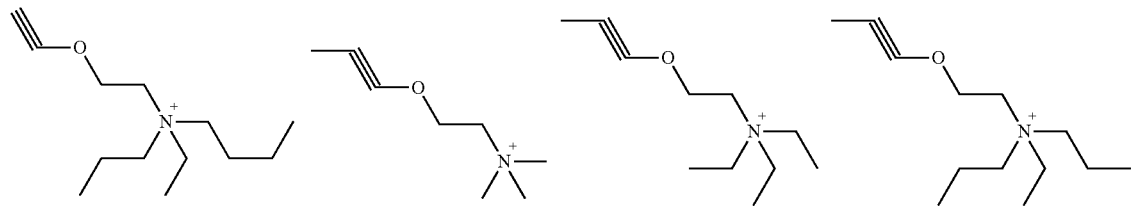
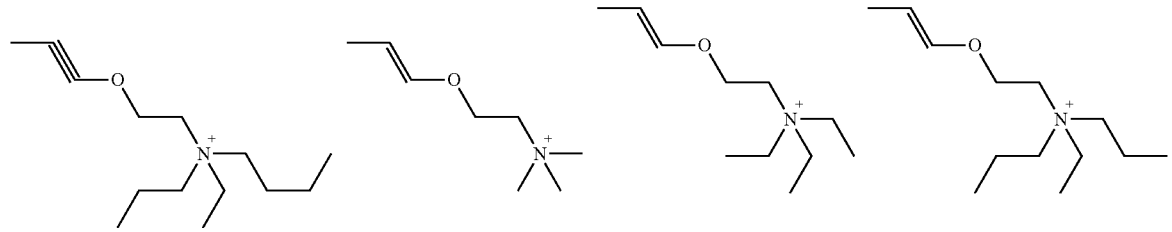
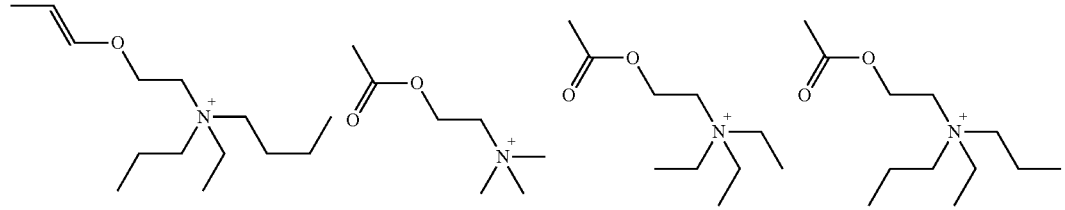
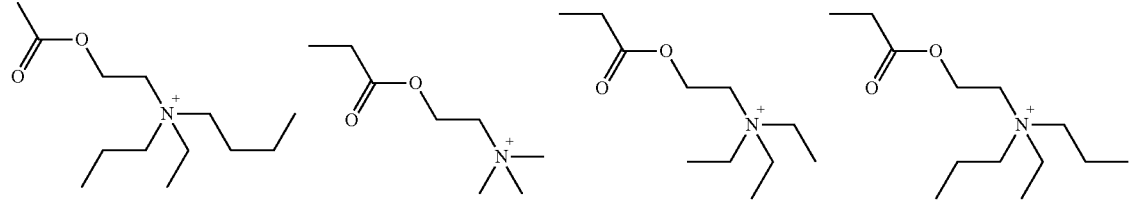
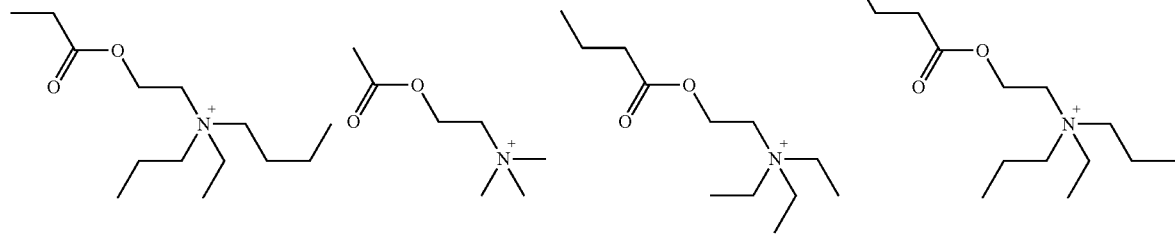

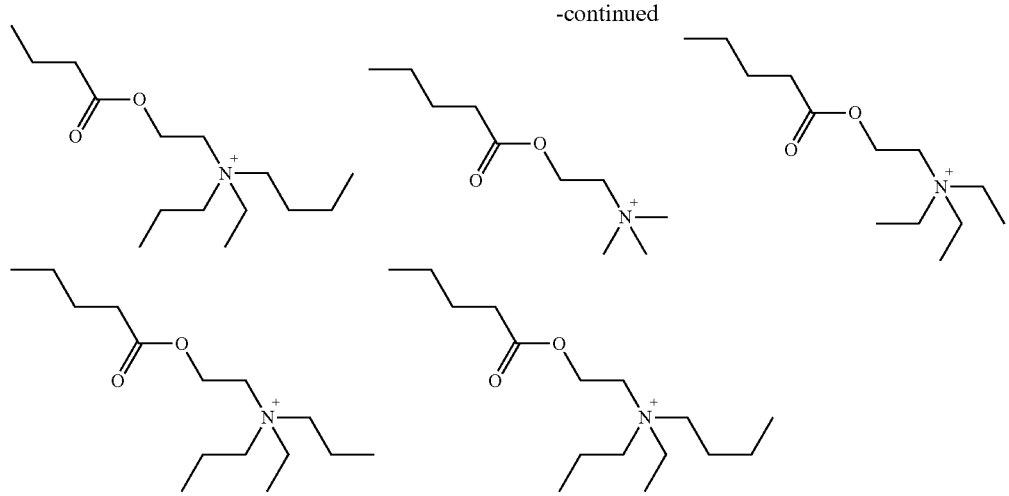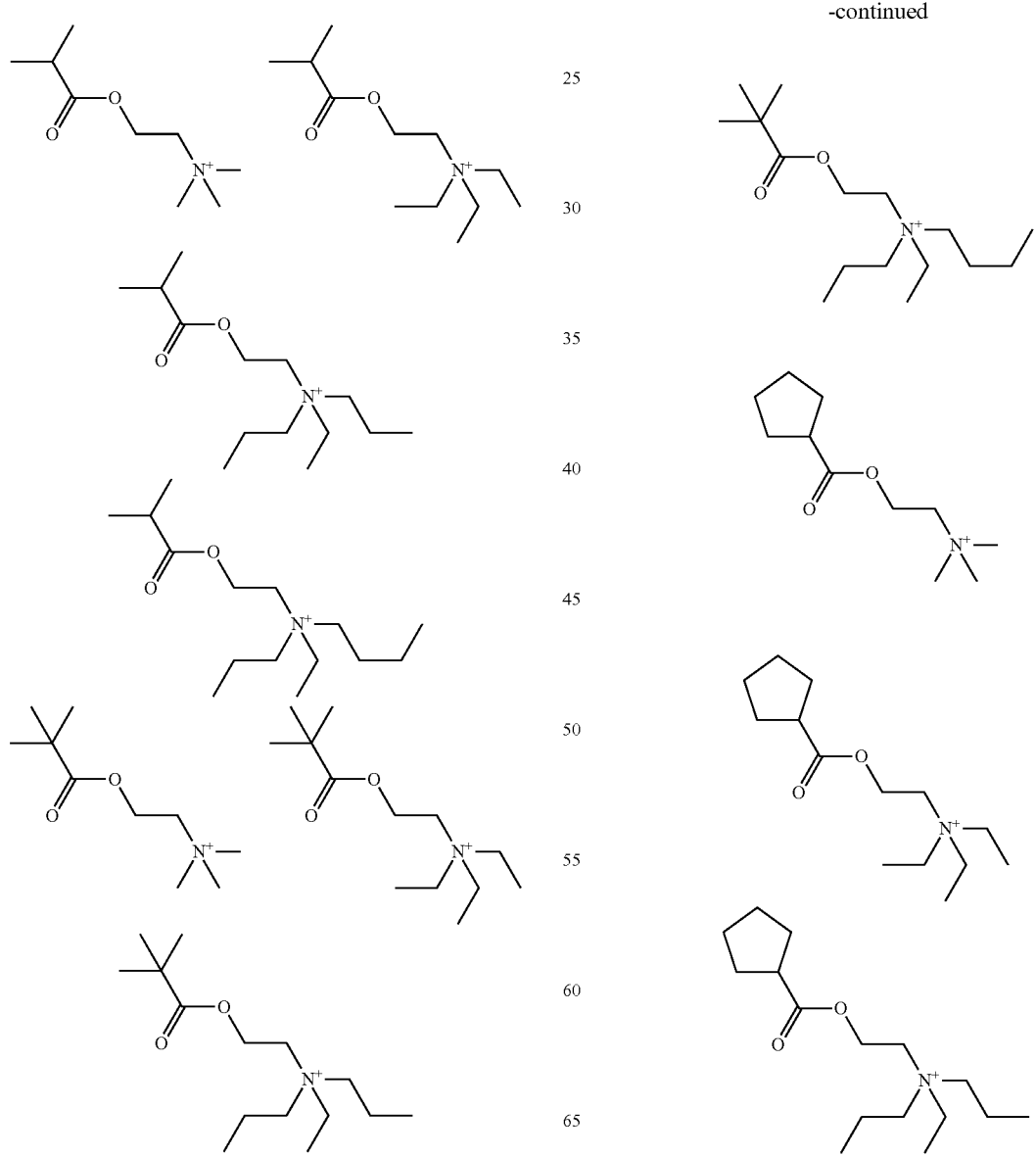

83
-continued
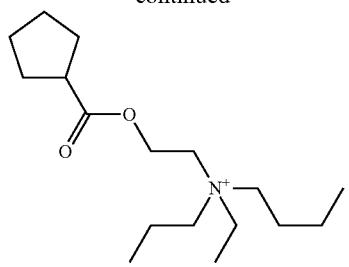
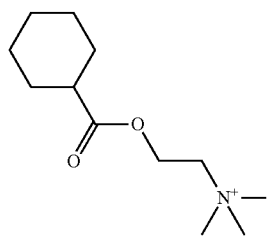
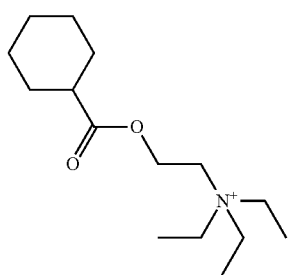
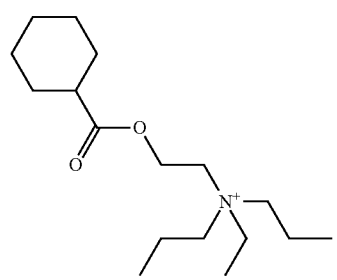
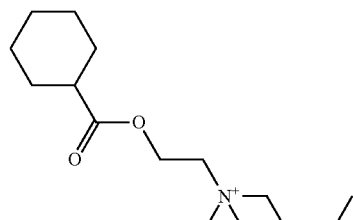
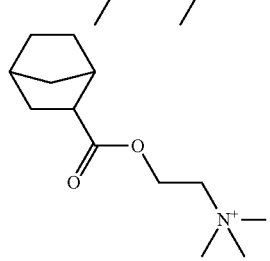
84
-continued
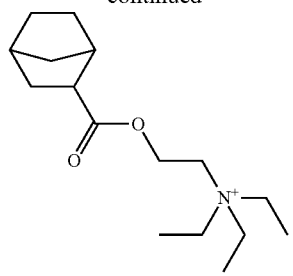
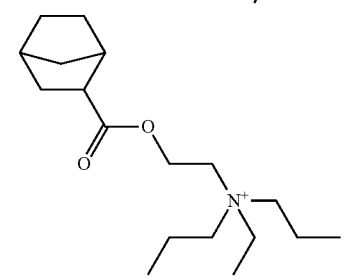
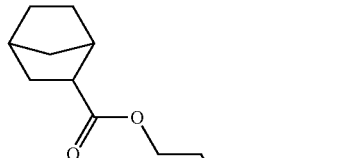
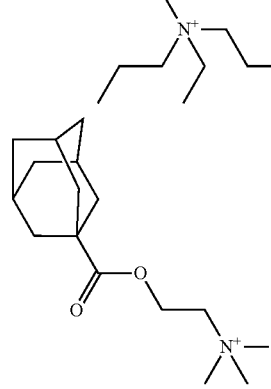
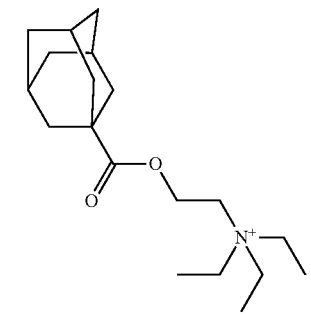
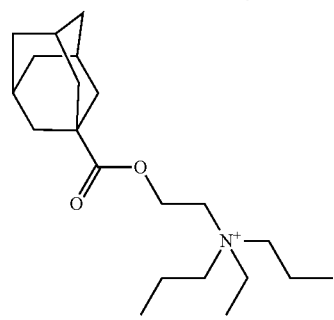

85
-continued
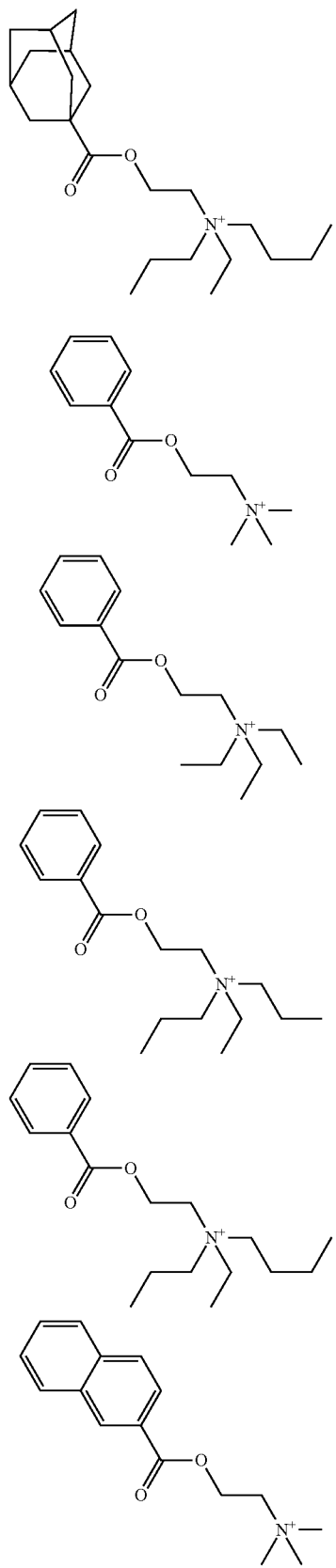
86
-continued
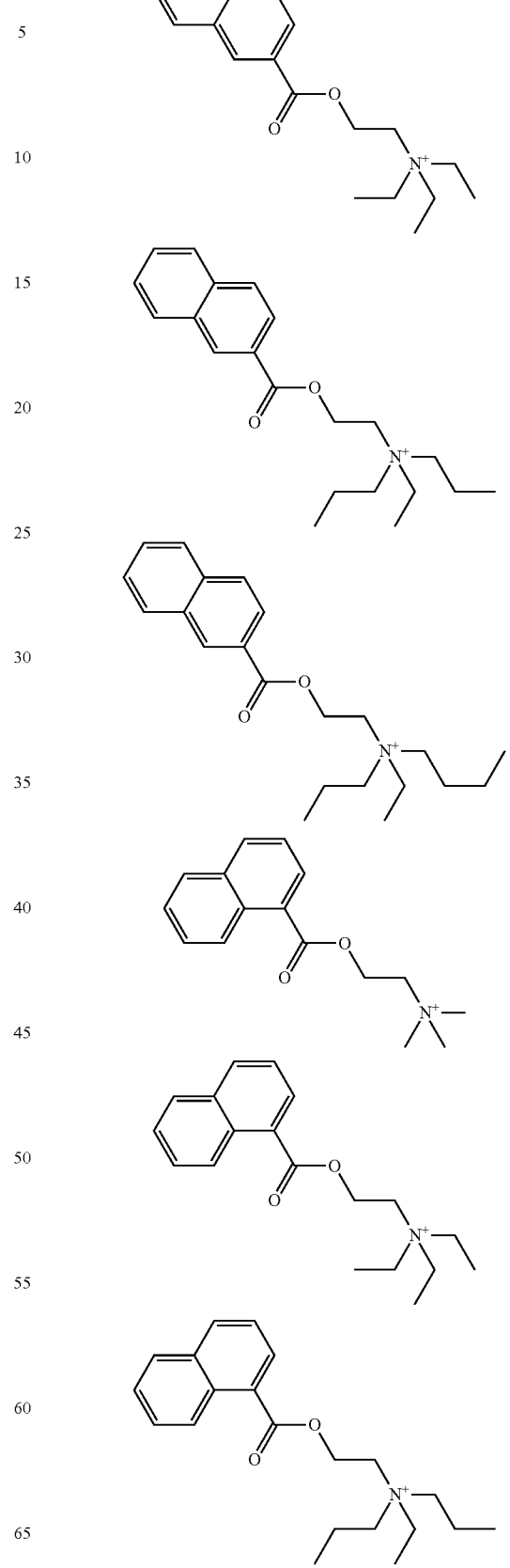

87
-continued
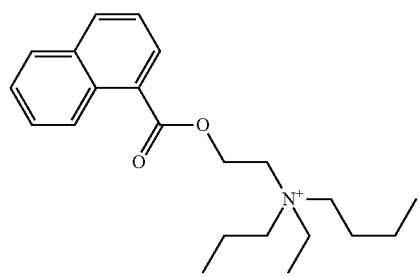
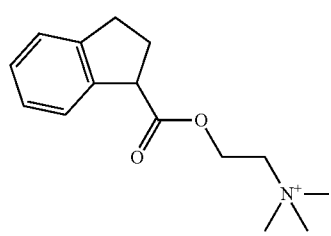
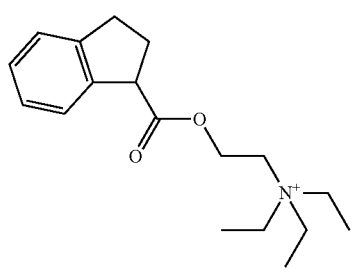
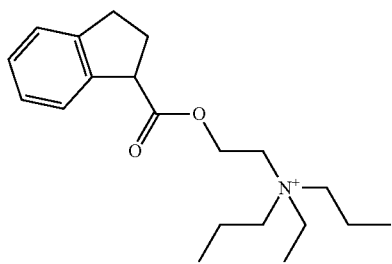
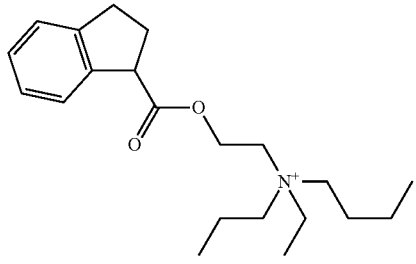
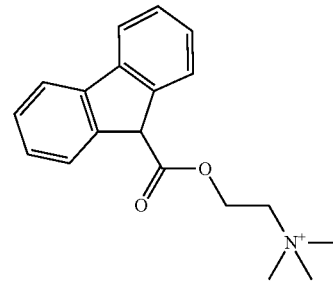
88
-continued
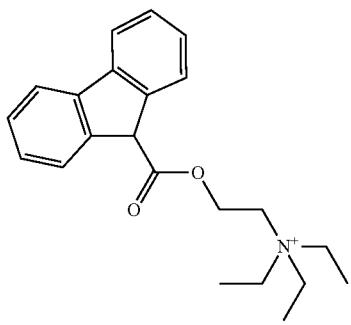
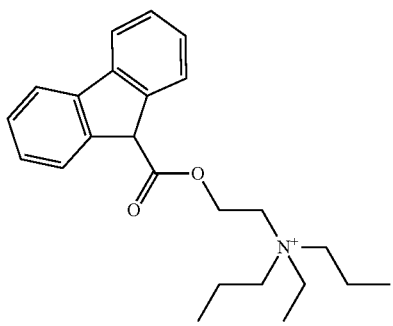
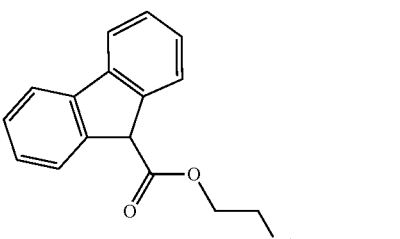
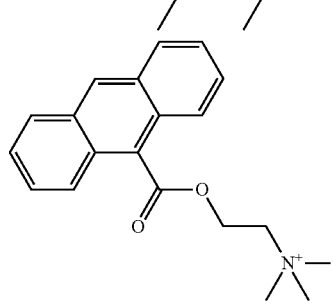
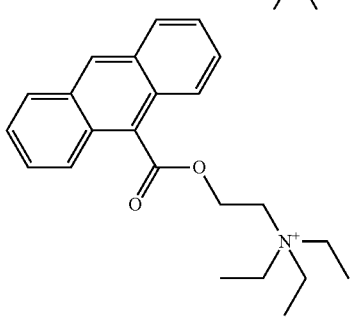

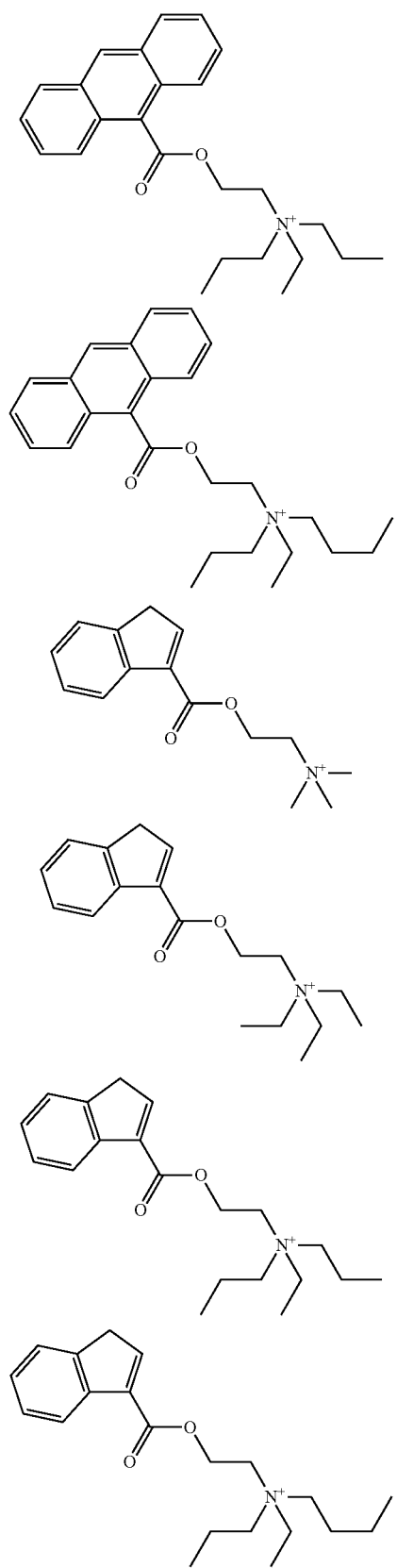
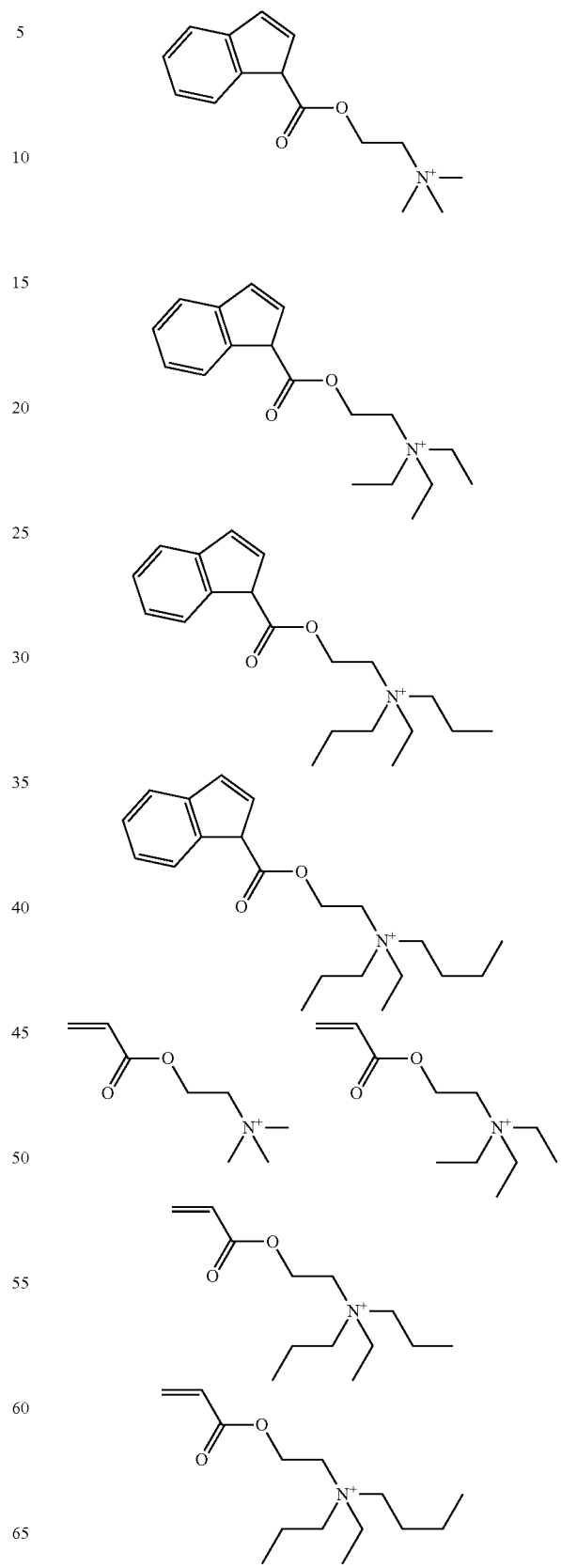

91
-continued
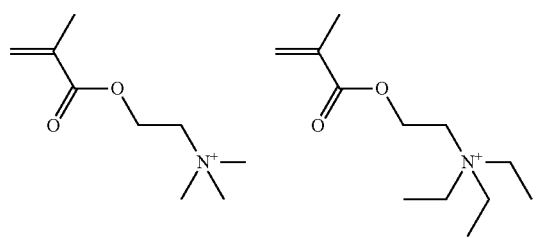
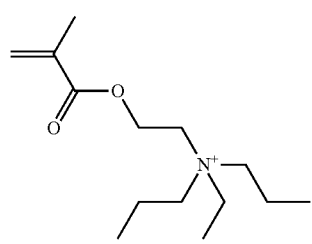
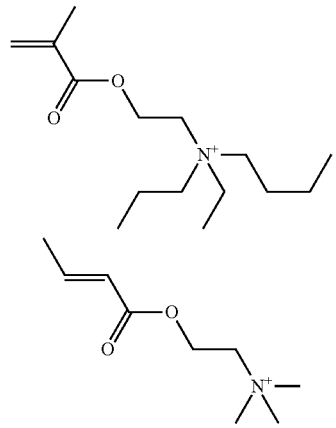
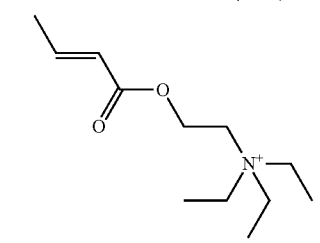
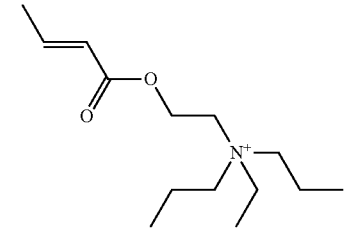
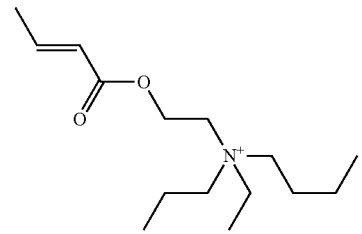
92
-continued
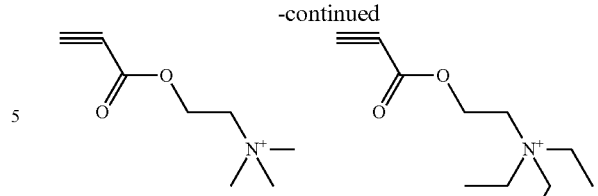
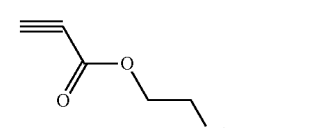
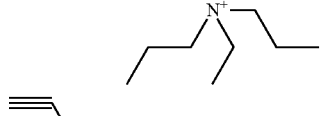
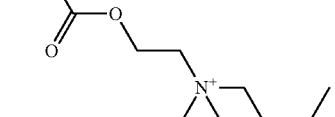
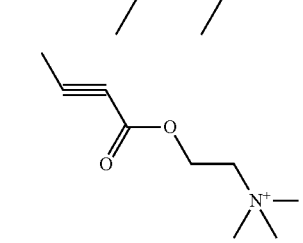
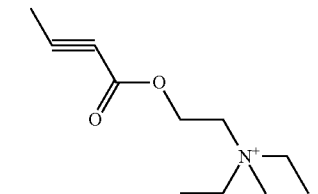
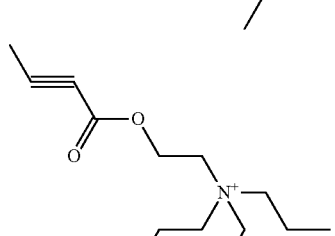
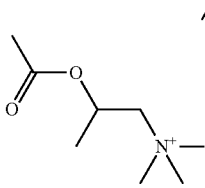
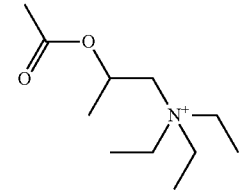

93
-continued
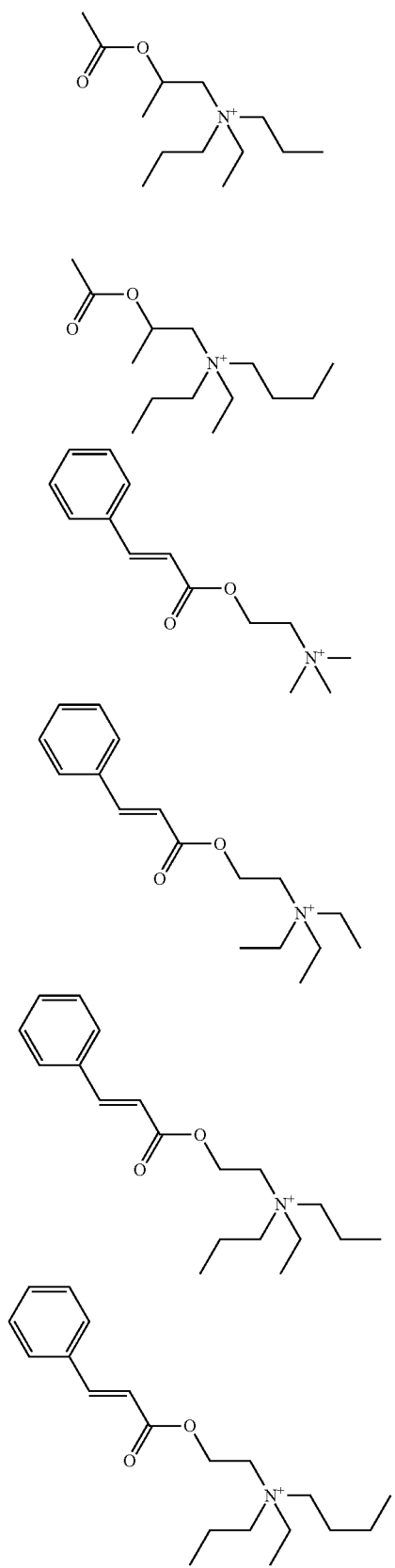
94
-continued
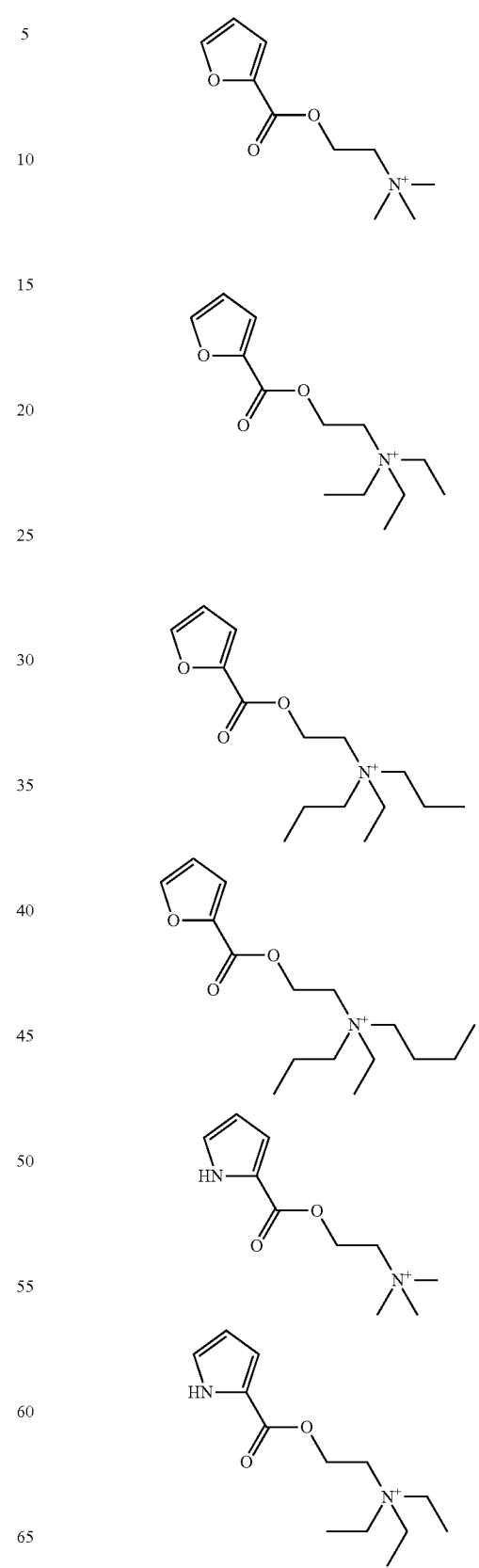

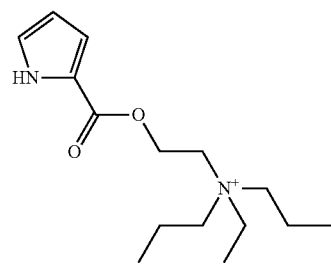
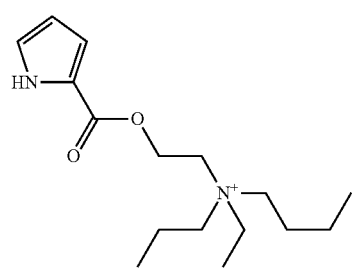
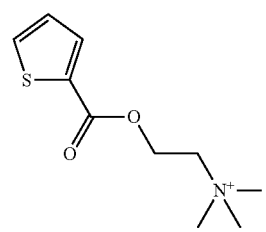
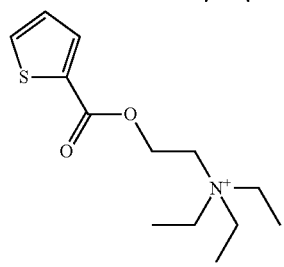
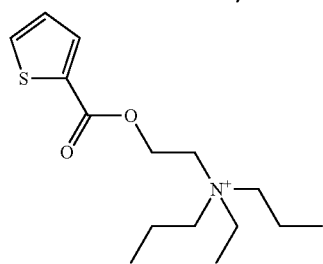
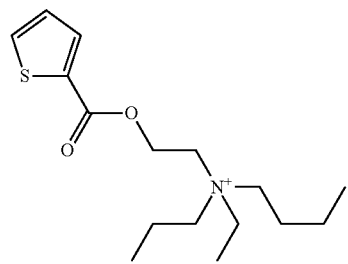
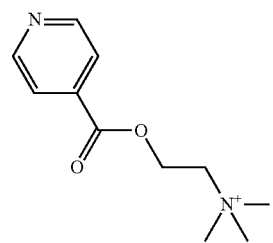
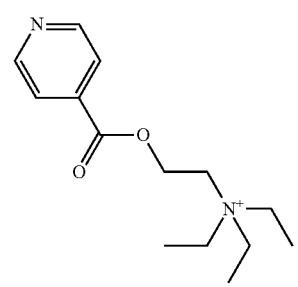
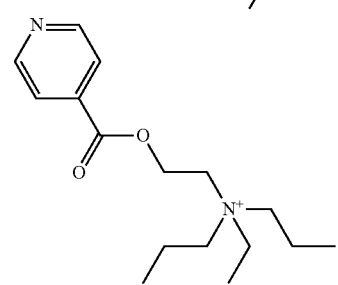
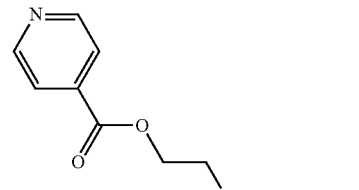
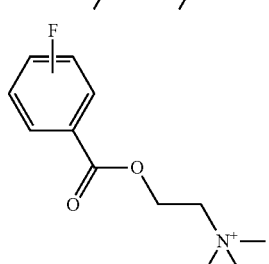
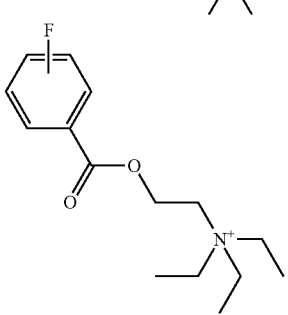

97
-continued
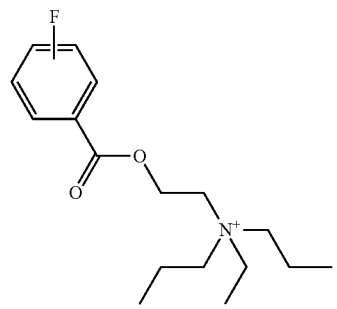
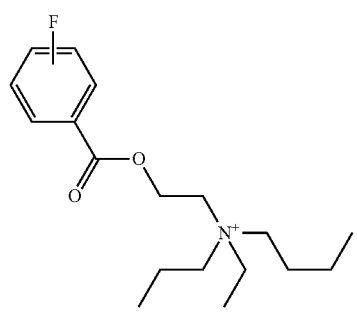
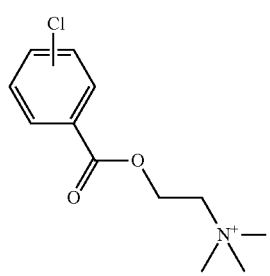
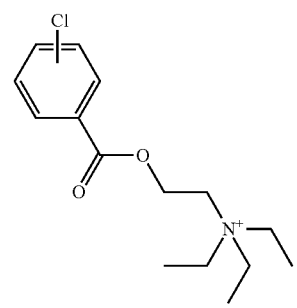
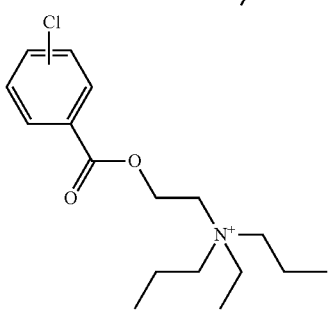
98
-continued
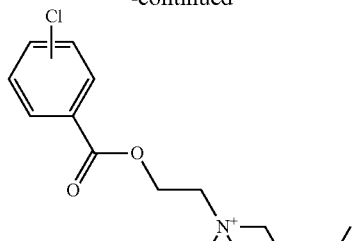
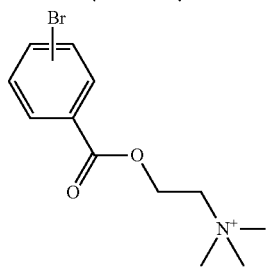
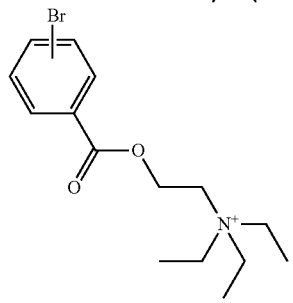
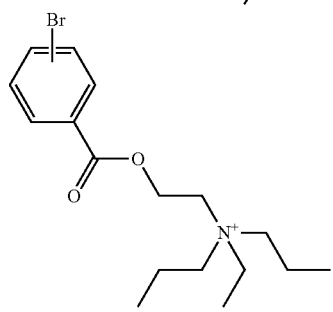
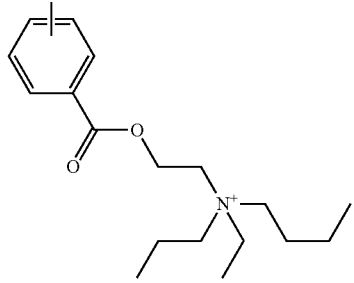
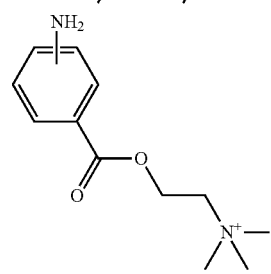

| 99 | 100 |
|---|---|
| 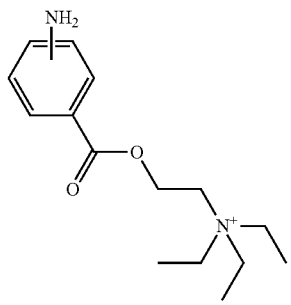 | 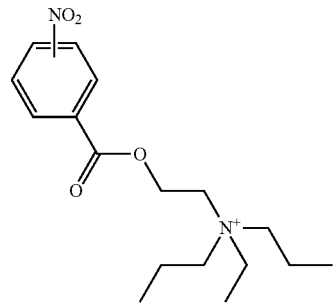 |
| 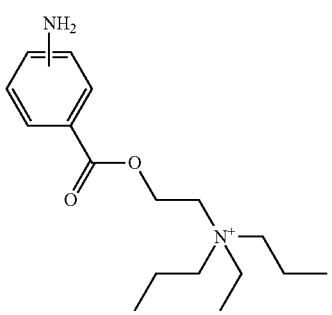 | 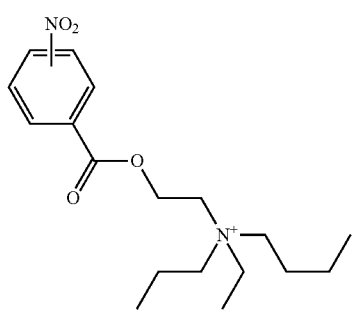 |
| 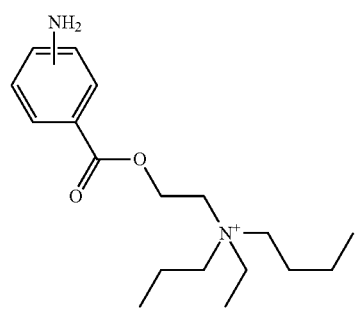 | 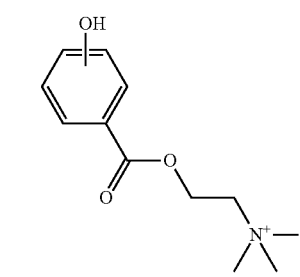 |
| 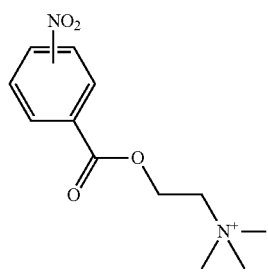 | 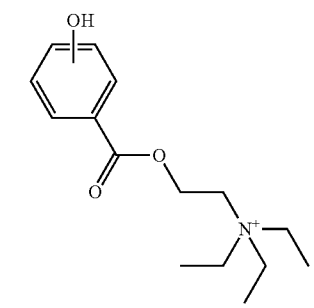 |
| 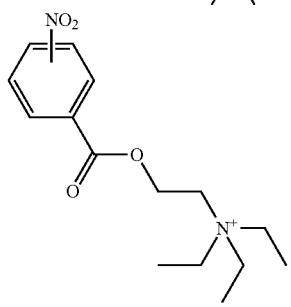 | 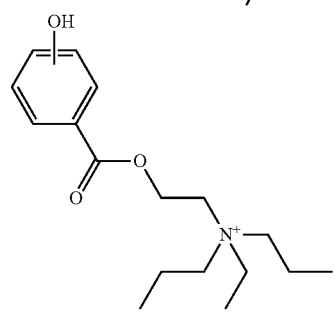 |

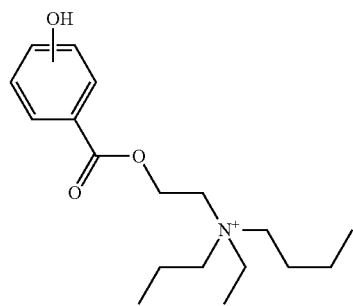
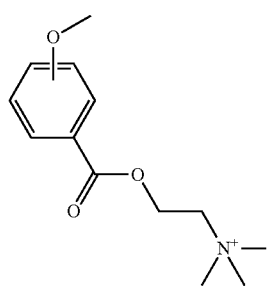
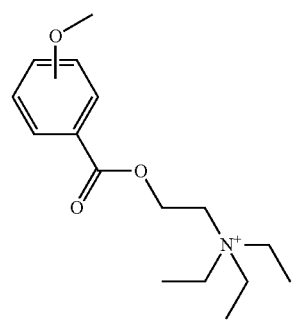
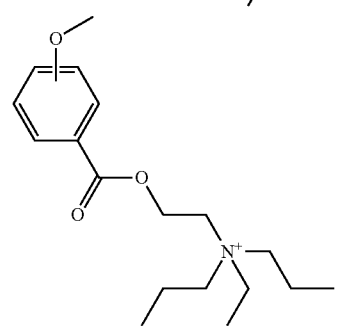
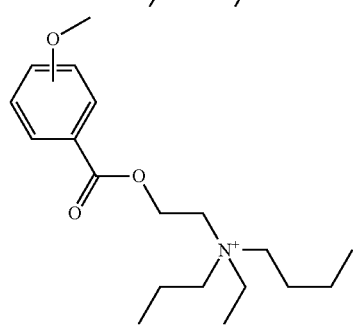
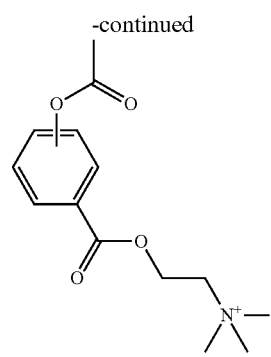
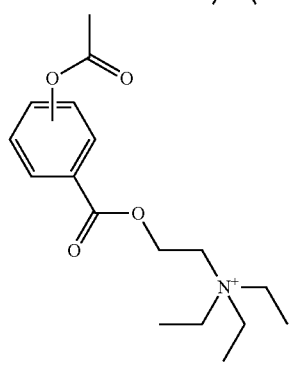
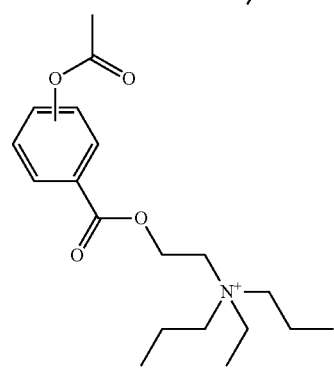
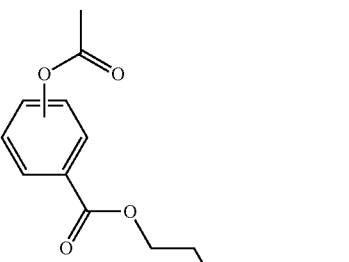
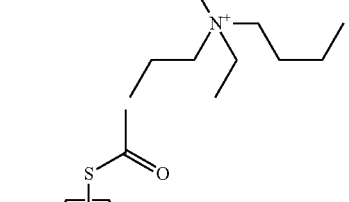
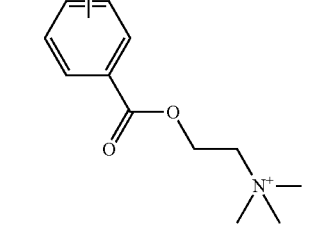

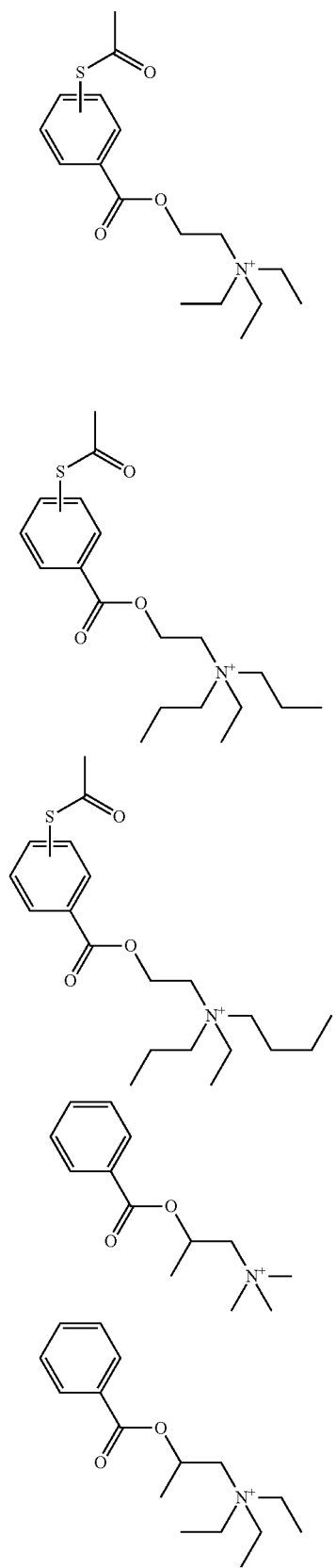

105
-continued
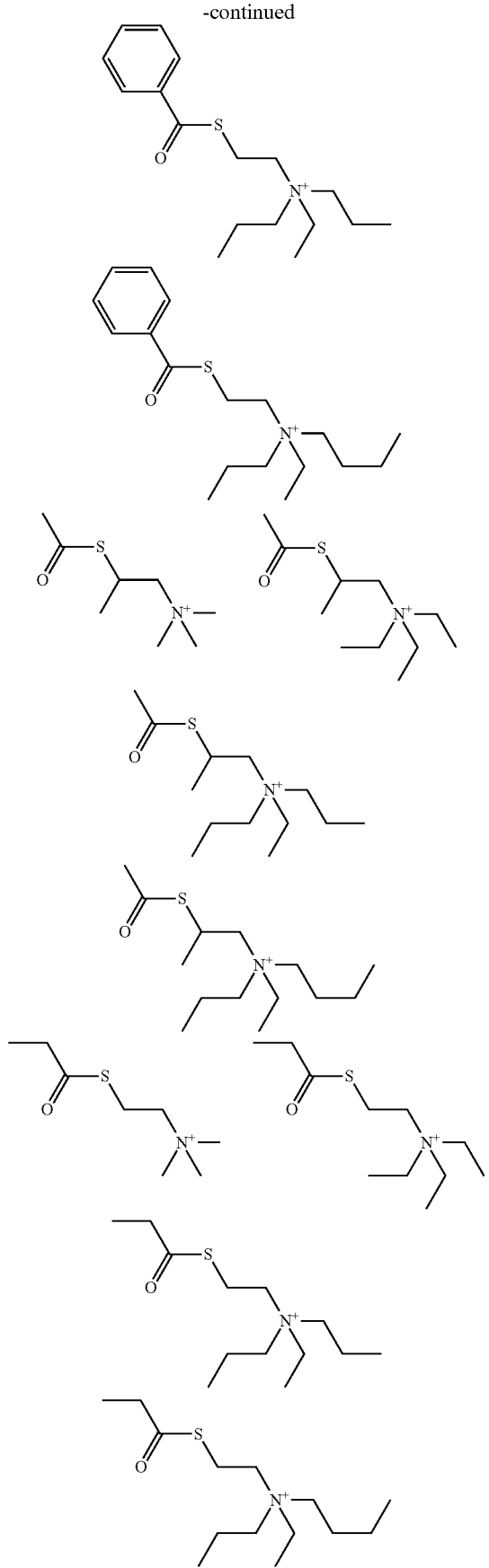
106
-continued
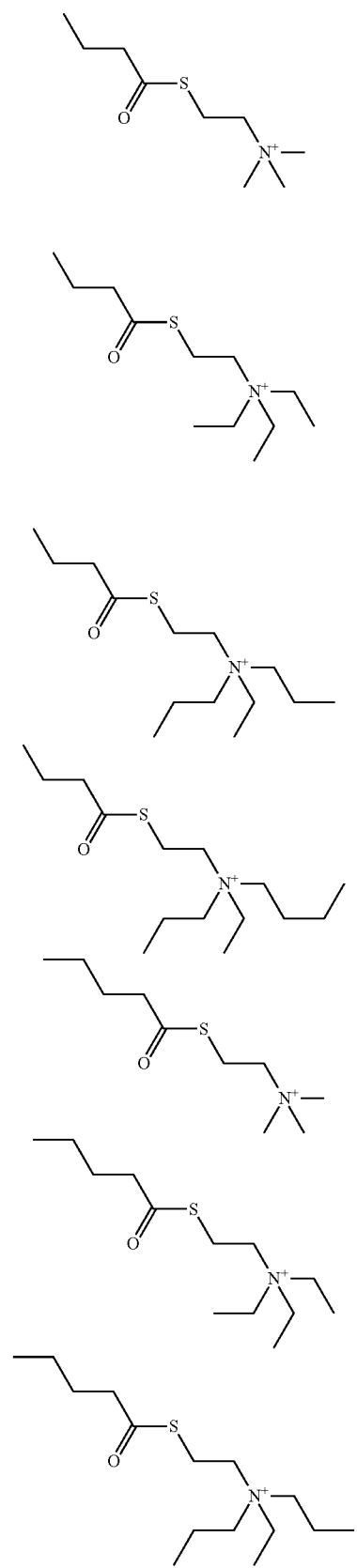

107
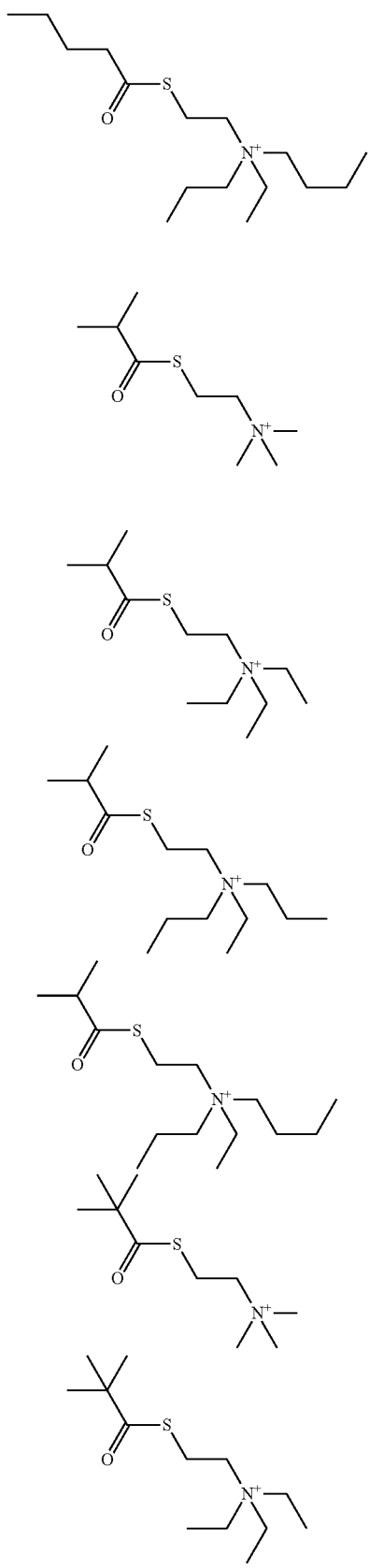
108
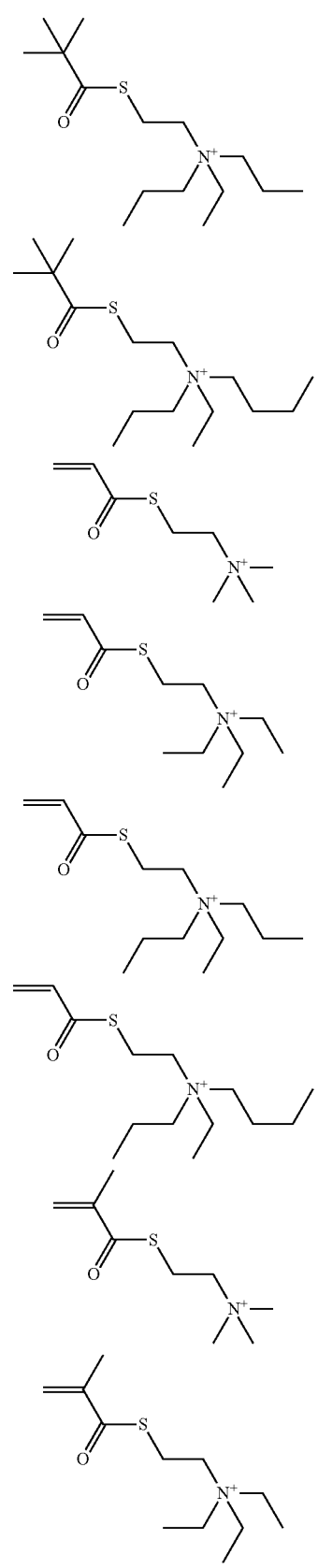

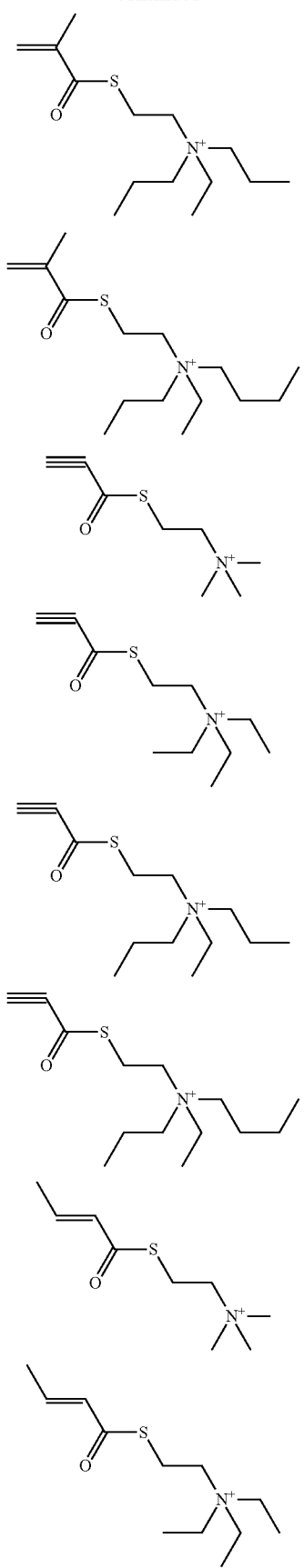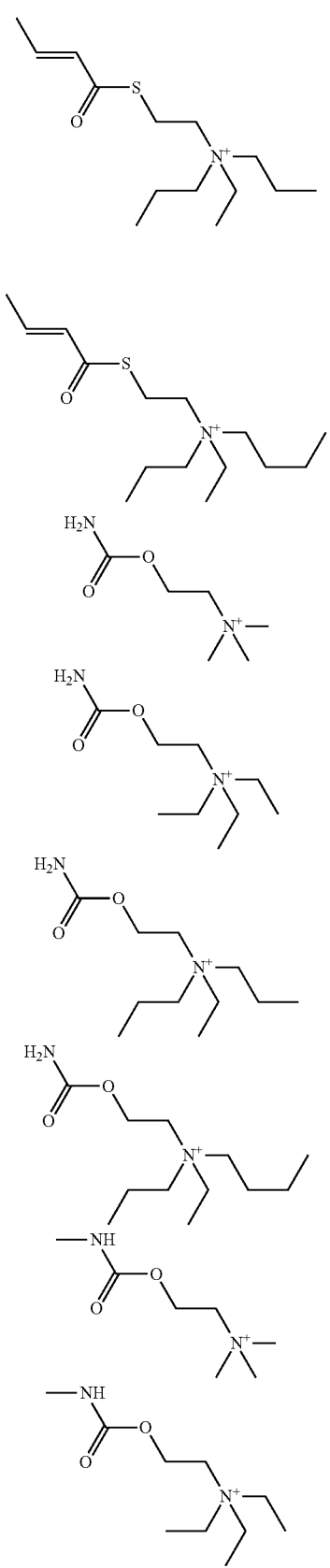

111
-continued
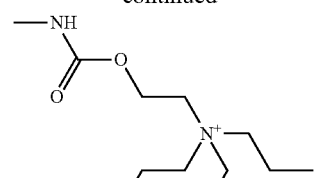
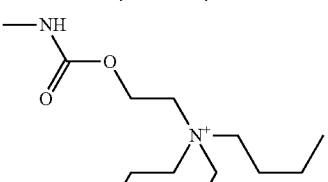
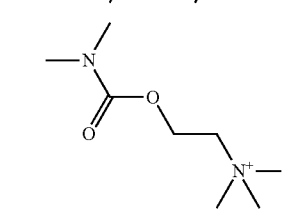
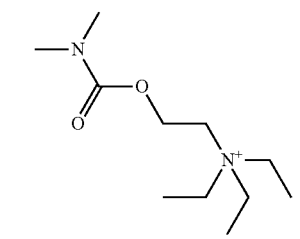
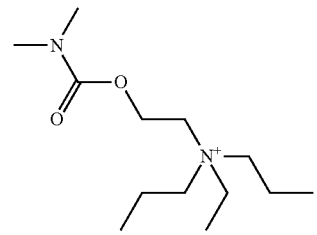
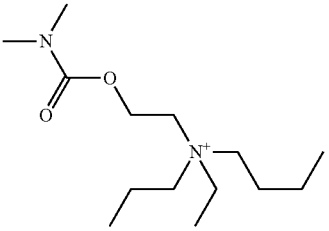
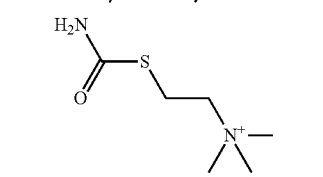
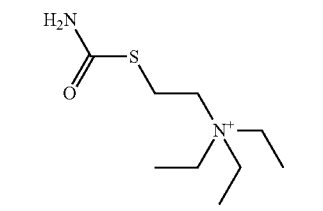
112
-continued
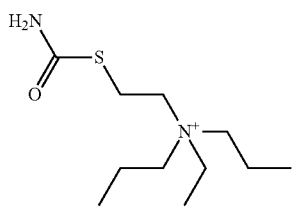
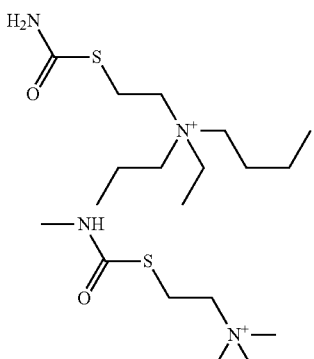
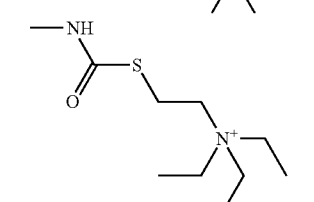
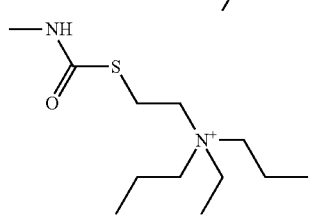
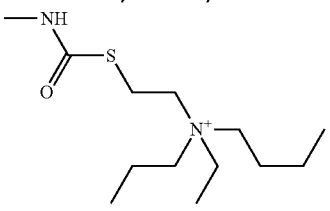
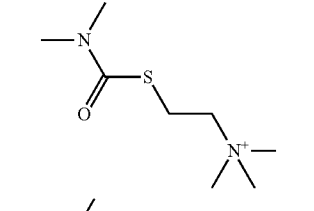
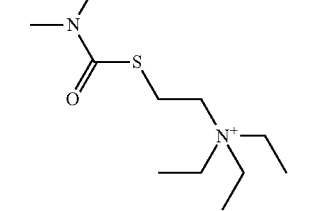

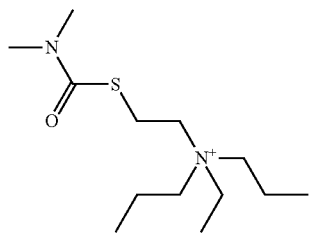
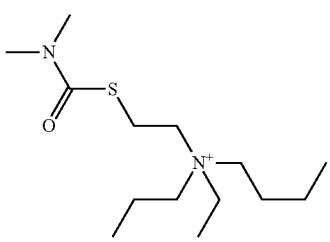
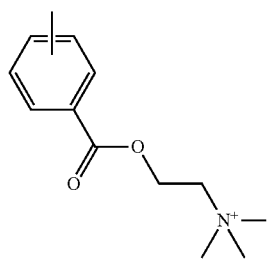
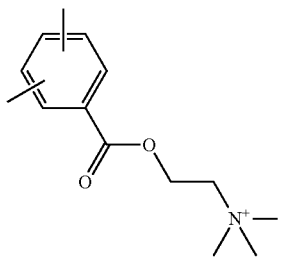
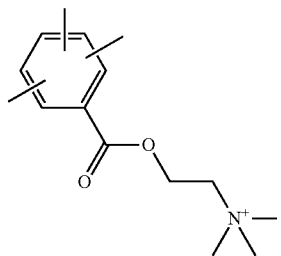
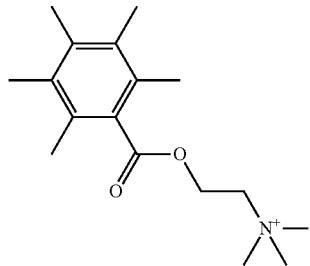
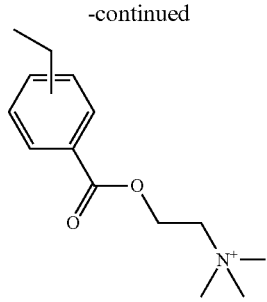
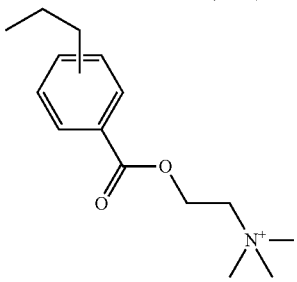
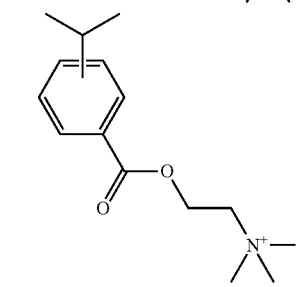
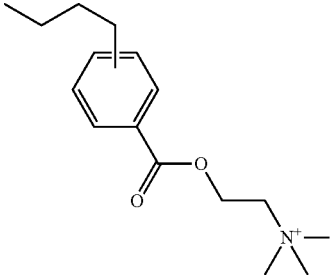
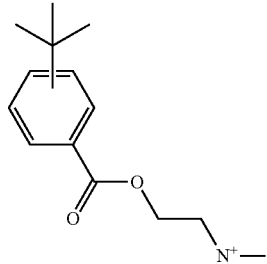
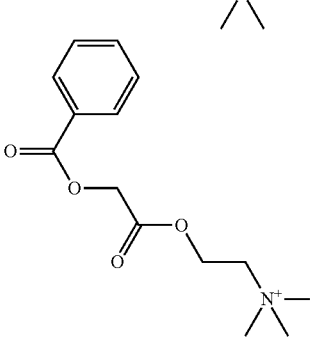

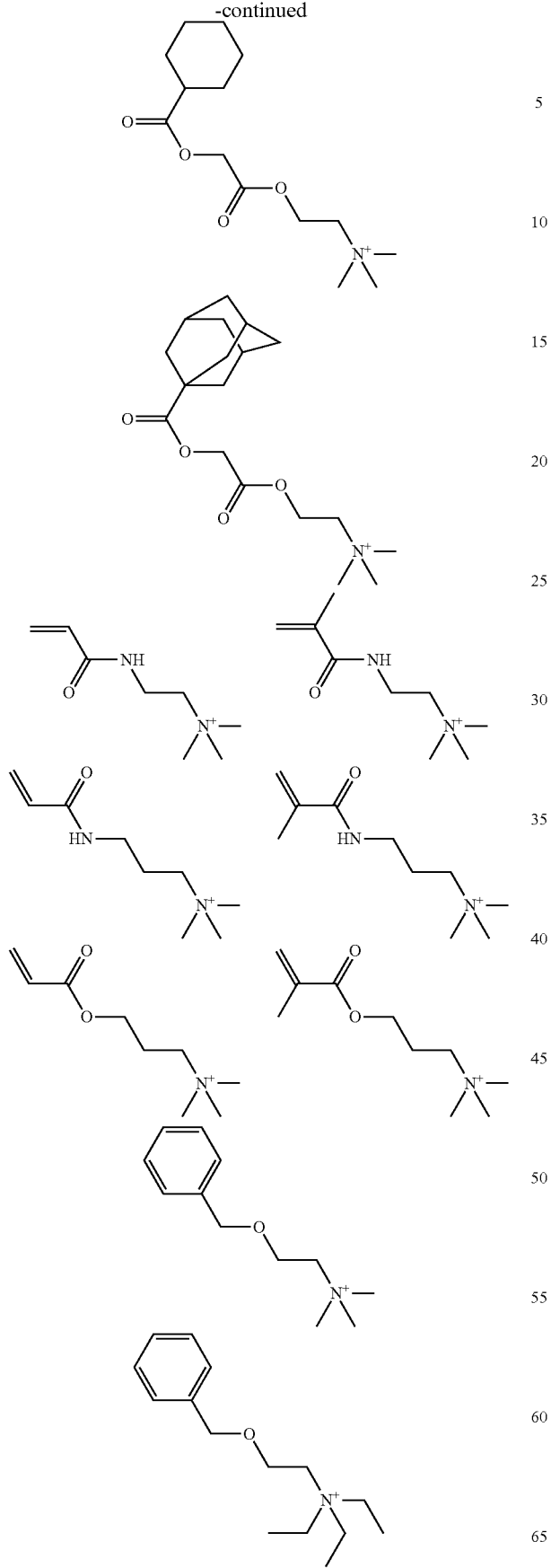
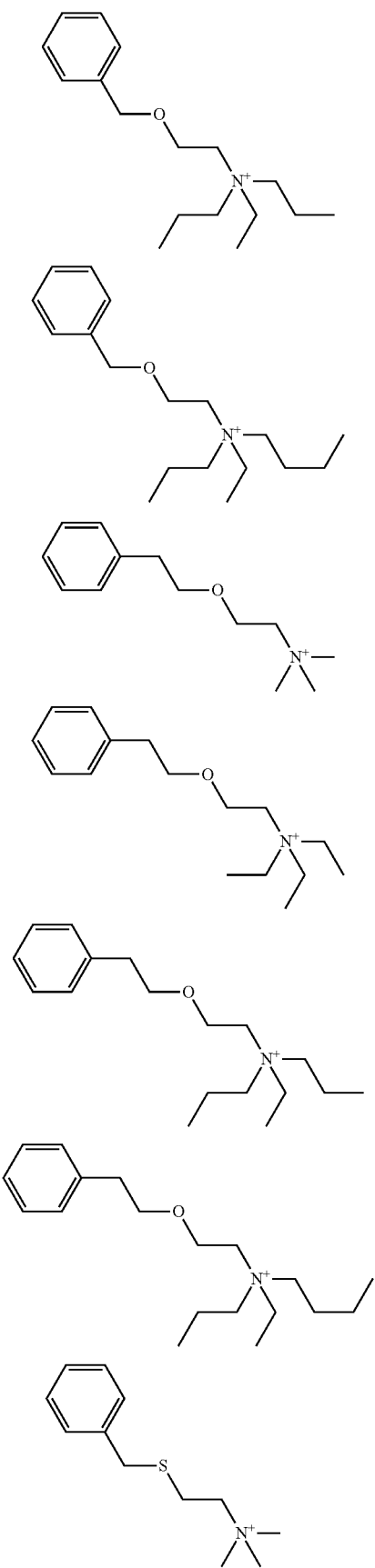

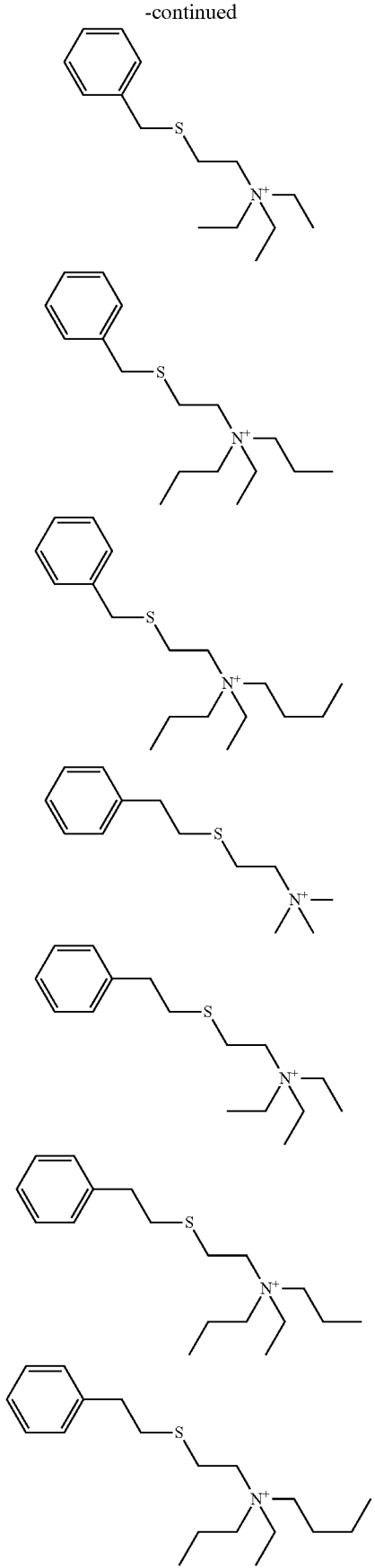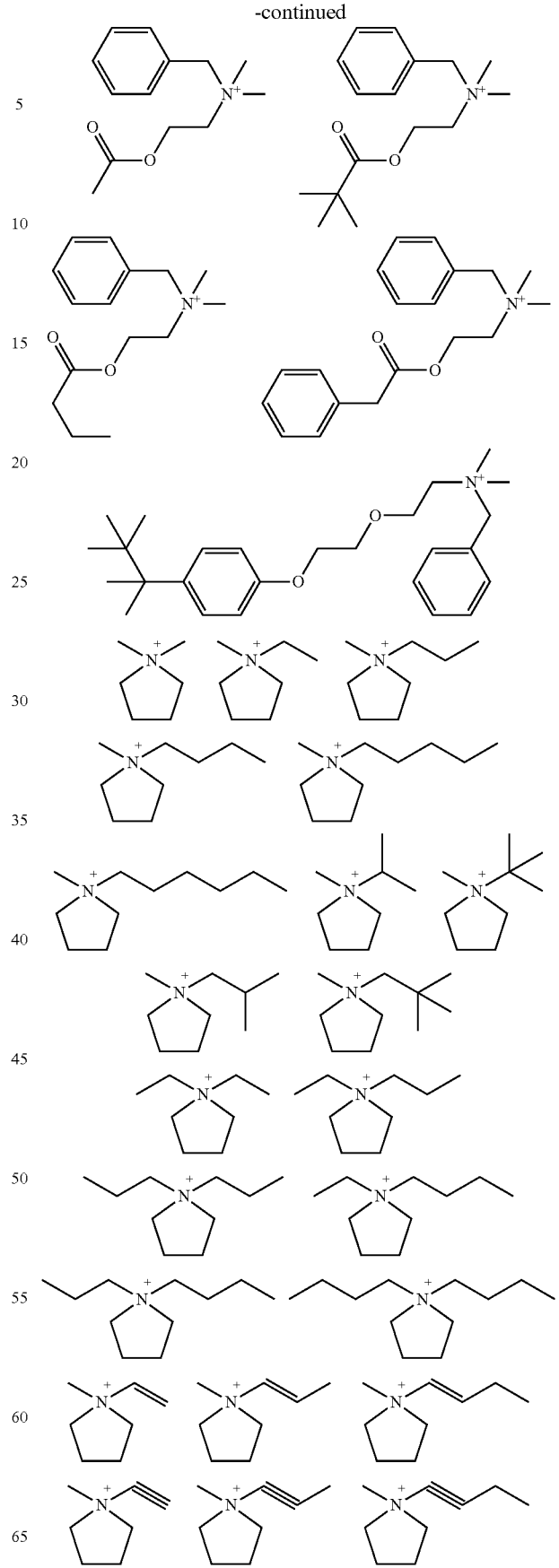

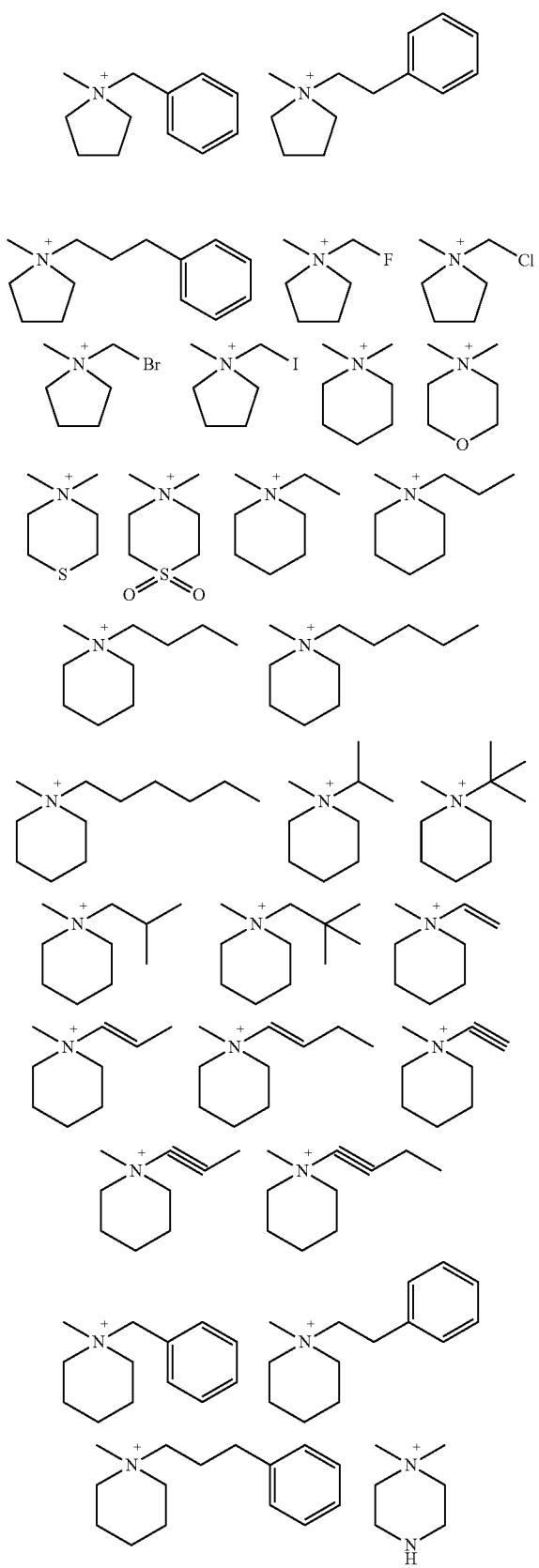

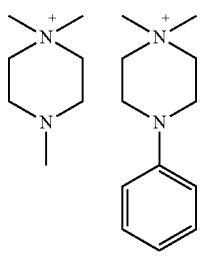

The onium salt having formula (A) may be synthesized, for example, by ion exchange with an onium salt of weaker acid than the iodized benzene ring-containing sulfonamide. Examples of the weaker acid than the iodized benzene ring-containing sulfonamide include hydrochloric acid, carbolic acid, carboxylic acids and fluorine-free sulfonic acids. Alternatively, the onium salt may be synthesized by ion exchange of a sodium salt of iodized benzene ring-containing sulfonamide with an onium chloride.

In the resist composition, the onium salt having formula (A) is preferably used in an amount of 0.001 to 50 parts, more preferably 0.01 to 20 parts by weight per 100 parts by weight of the base polymer, as viewed from sensitivity and acid diffusion suppressing effect Base Polymer Where the resist composition is of positive tone, the base polymer comprises recurring units containing an acid labile group, preferably recurring units having the formula (a1) or recurring units having the formula (a2). These units are simply referred to as recurring units (a1) and (a2).

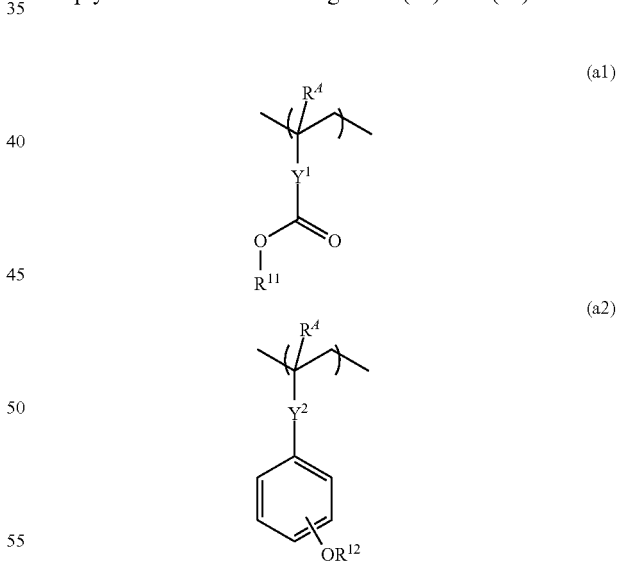

Herein $R^A$ is each independently hydrogen or methyl. $Y^1$ is a single bond, phenylene or naphthylene group, or $C_1$-$C_{12}$ linking group containing an ester bond or lactone ring. $Y^2$ is a single bond or ester bond. $R^{11}$ and $R^{12}$ each are an acid labile group. When the base polymer contains both recurring units (a1) and (a2), $R^{11}$ and $R^{12}$ may be the same or different.

Examples of the monomer from which the recurring units (a1) are derived are shown below, but not limited thereto. $R^A$ and $R^{11}$ are as defined above.

121

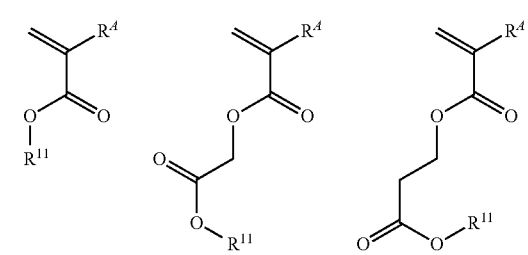

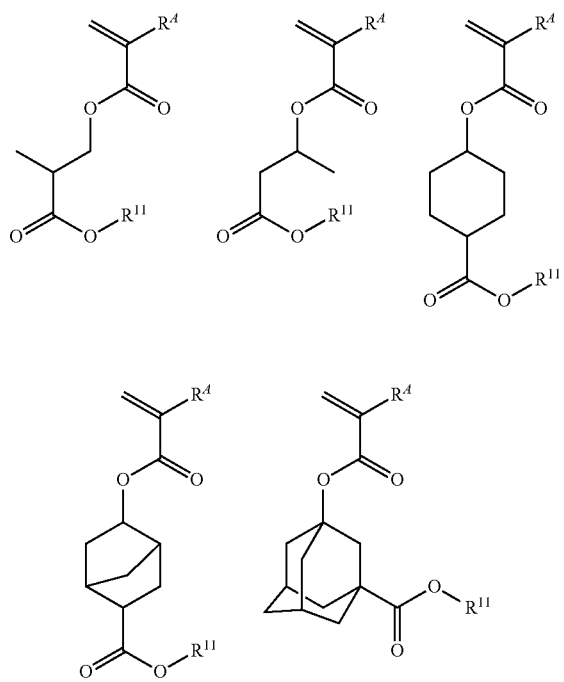

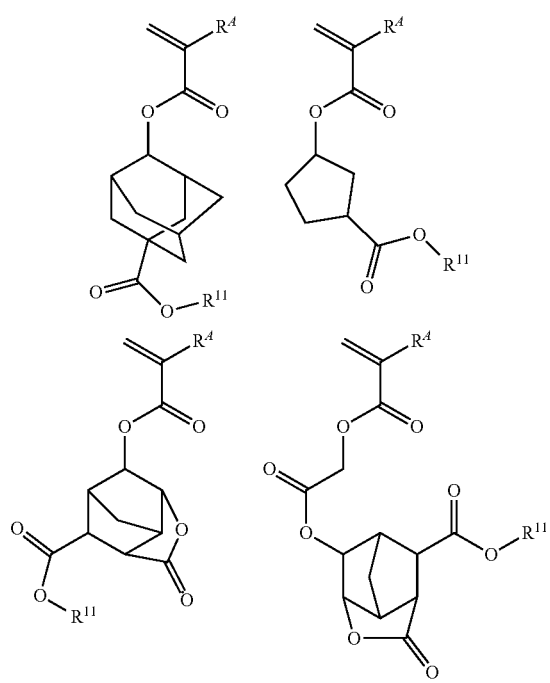

122

-continued

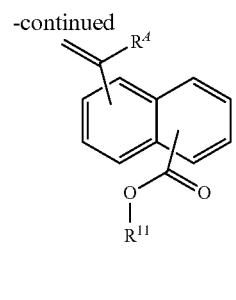

Examples of the monomer from which the recurring units (a2) are derived are shown below, but not limited thereto. $R^A$ and $R^{12}$ are as defined above.

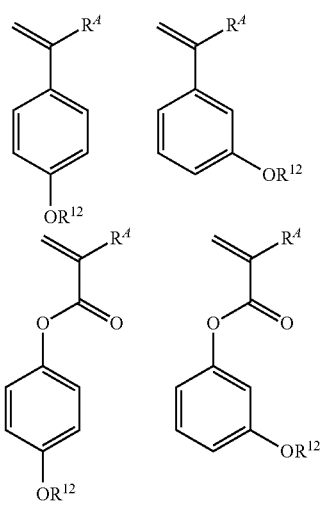

The acid labile groups represented by $R^{11}$ and $R^{12}$ in the recurring units (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

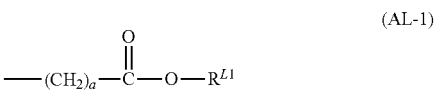 (AL-1)

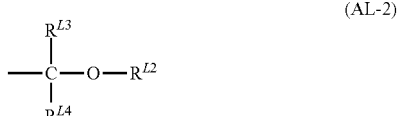 (AL-2)

 (AL-3)

In formulae (AL-1) and (AL-2), $R^{L1}$ and $R^{L2}$ are each independently a $C_1$-$C_{40}$ monovalent hydrocarbon group which may contain a heteroatom such as oxygen, sulfur, nitrogen or fluorine. The monovalent hydrocarbon groups may be straight, branched or cyclic while $C_1$-$C_{40}$ alkyl groups are preferred, and $C_1$-$C_{20}$ alkyl groups are more preferred. In formula (AL-1), a is an integer of 0 to 10, preferably 1 to 5.

In formula (AL-2), $R^{L3}$ and $R^{L4}$ are each independently hydrogen or a $C_1$-$C_{20}$ monovalent hydrocarbon group which may contain a heteroatom such as oxygen, sulfur, nitrogen or fluorine. The monovalent hydrocarbon groups may be straight, branched or cyclic while $C_1$-$C_{20}$ alkyl groups are preferred. Any two of $R^{L2}$, $R^{L3}$ and $R^{L4}$ may bond together to form a ring, typically alicyclic, with the carbon atom or carbon and oxygen atoms to which they are attached, the ring containing 3 to 20 carbon atoms, preferably 4 to 16 carbon atoms.

In formula (AL-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon groups may be straight, branched or cyclic while $C_1$-$C_{20}$ alkyl groups are preferred. Any two of $R^{L5}$, $R^{L6}$ and $R^{L7}$ may bond together to form a ring, typically alicyclic, with the carbon atom to which they are attached, the ring containing 3 to 20 carbon atoms, preferably 4 to 16 carbon atoms.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

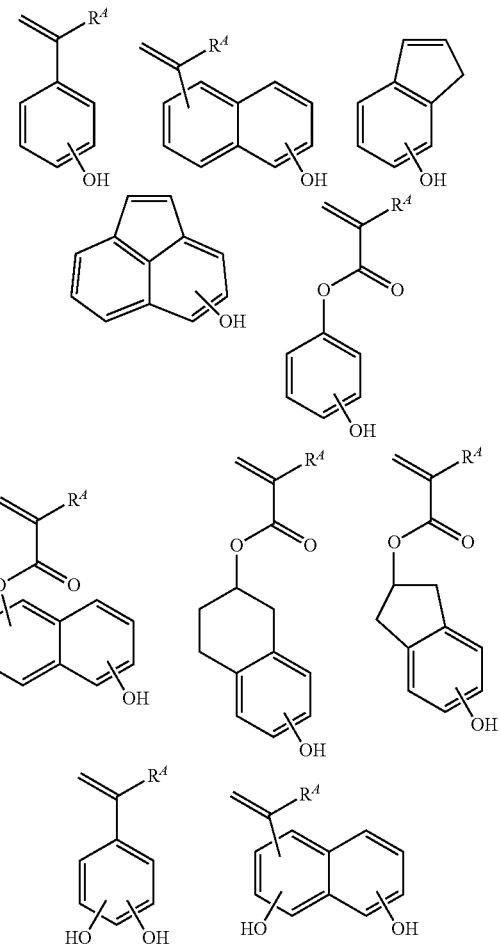

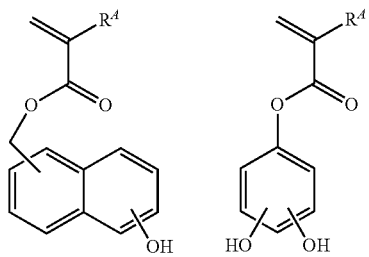

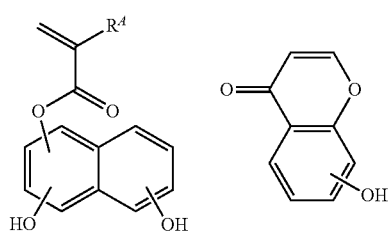

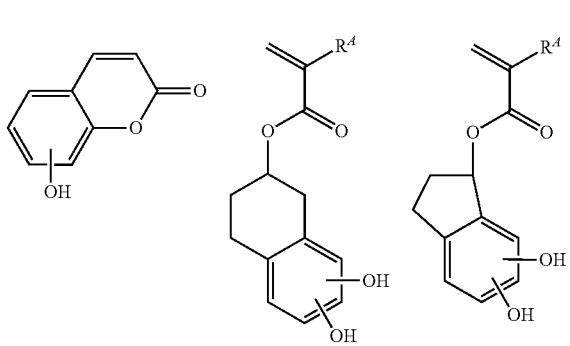

Further, recurring units (c) having another adhesive group selected from hydroxyl(other than the foregoing phenolic hydroxyl), carbonyl, lactone ring, ether bond, ester bond, carbonyl and cyano groups may also be incorporated in the base polymer. Examples of suitable monomers from which recurring units (c) are derived are given below, but not limited thereto. Herein $R^A$ is as defined above.

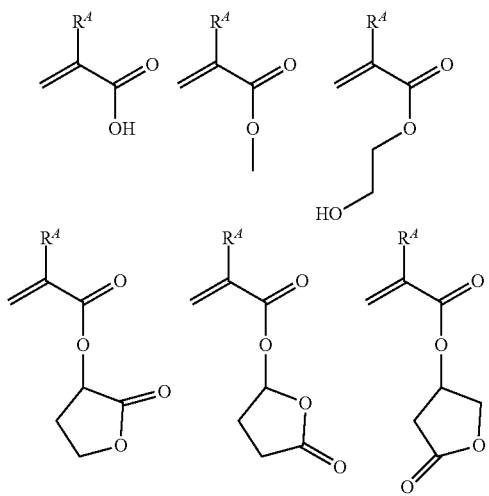

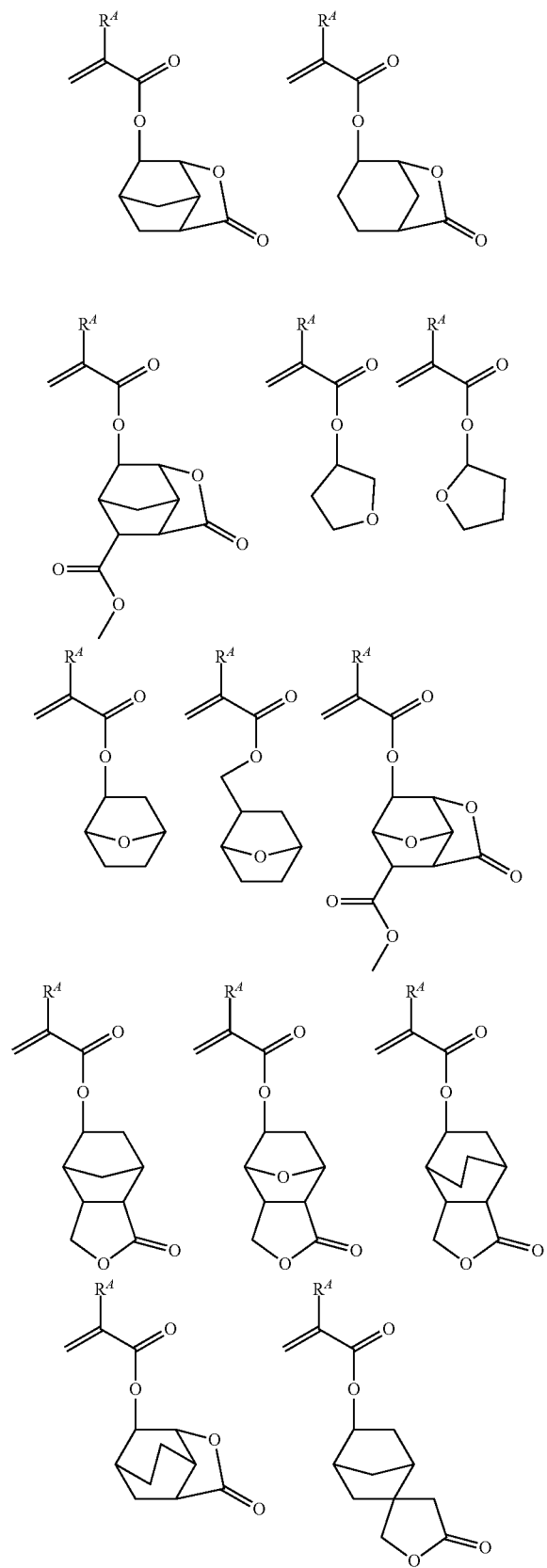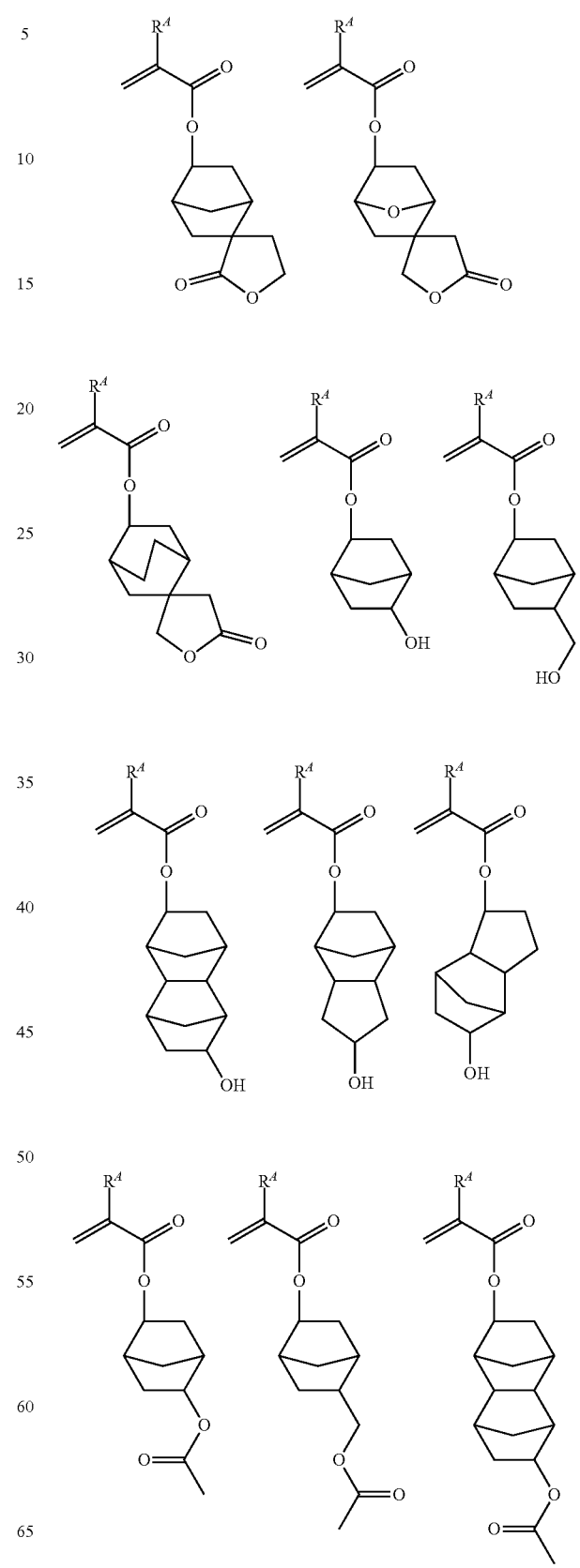

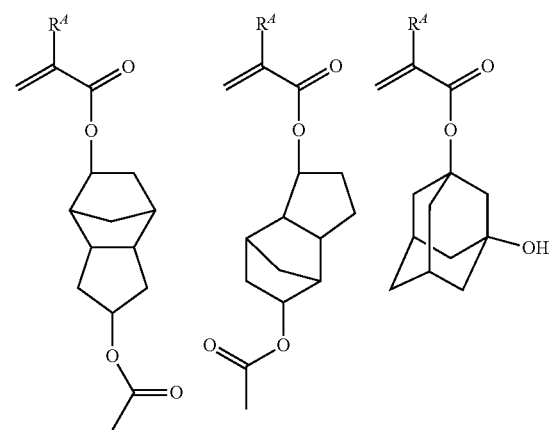
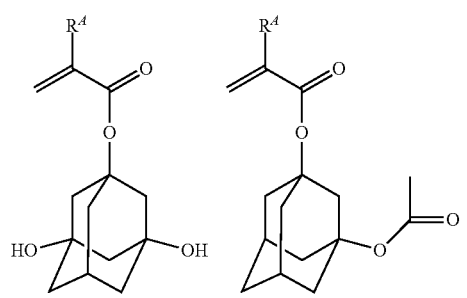
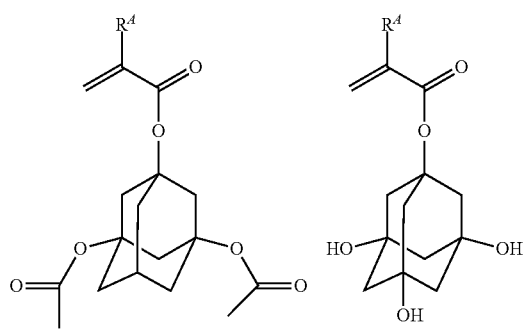
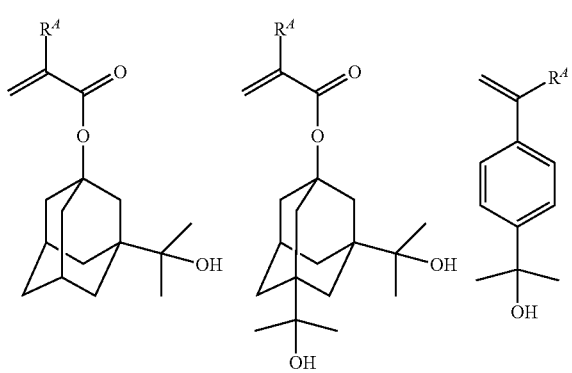
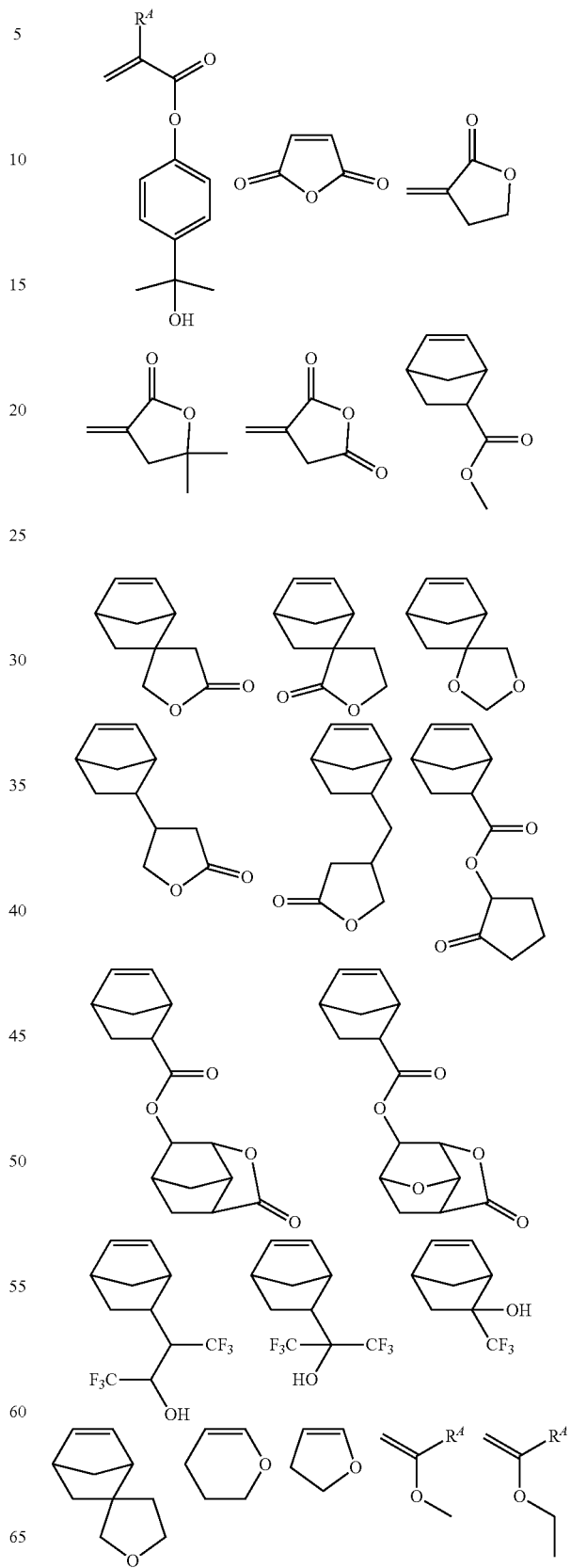

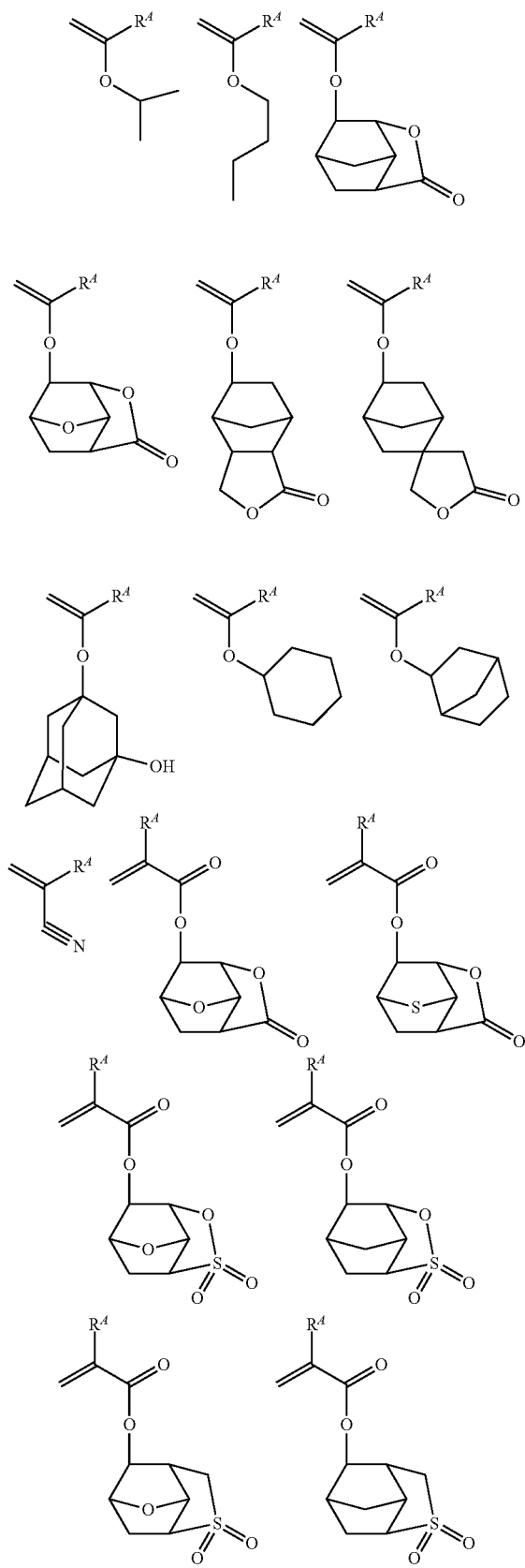
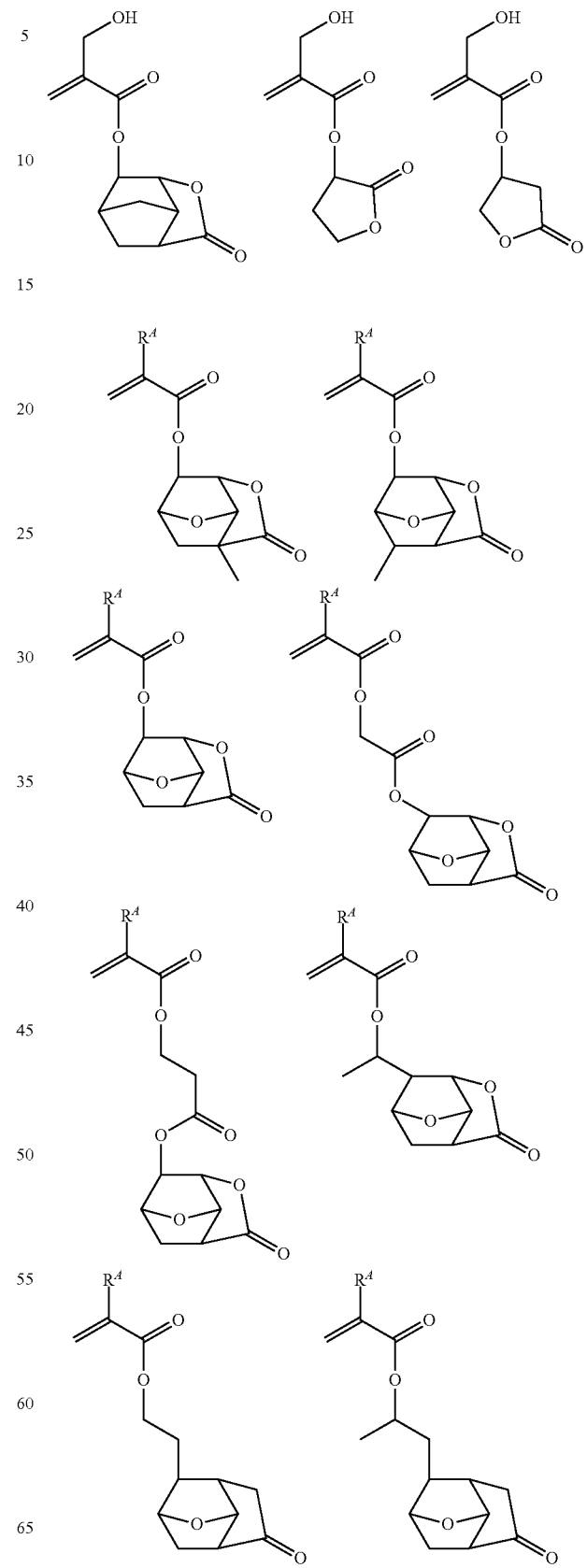

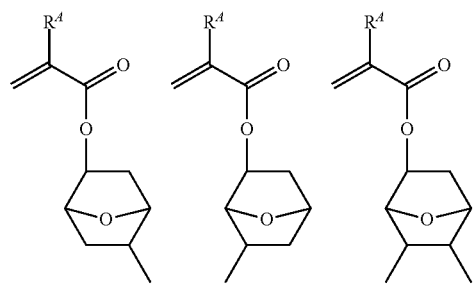
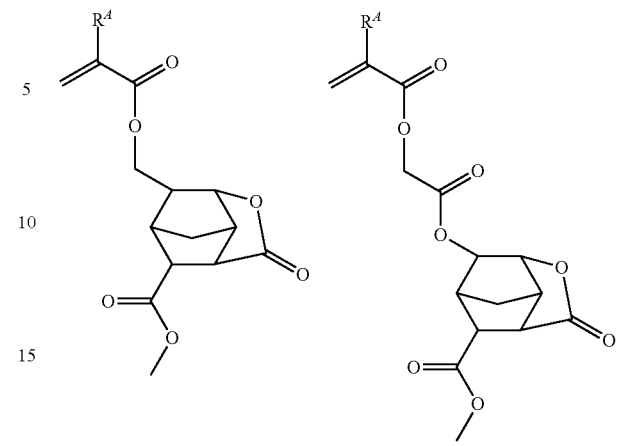
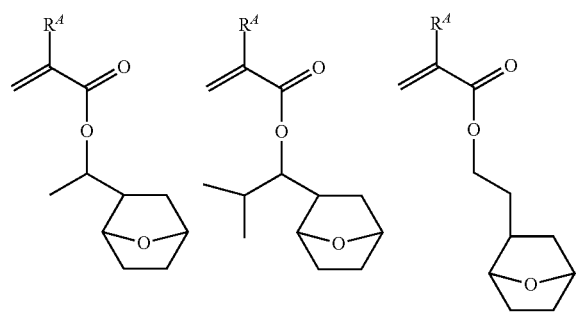
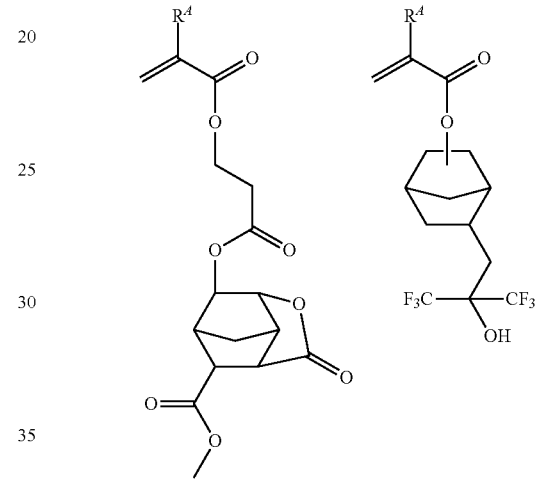
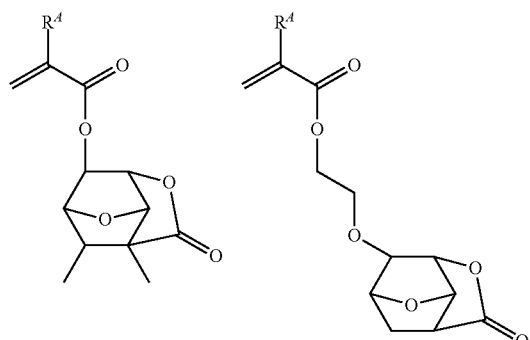
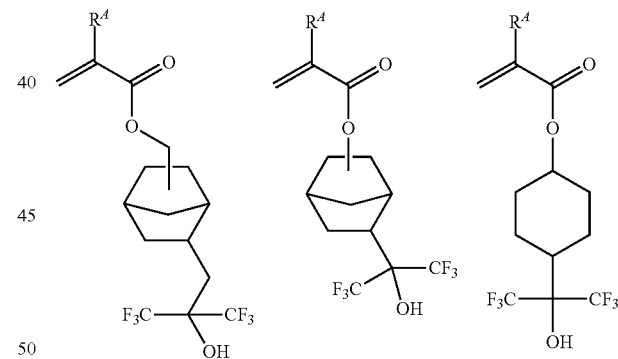
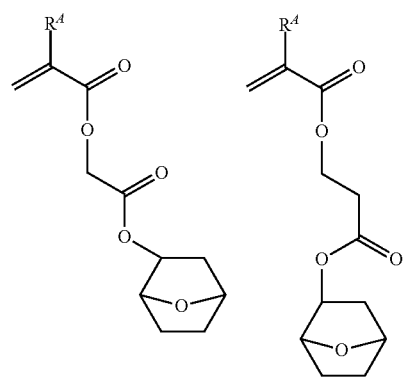
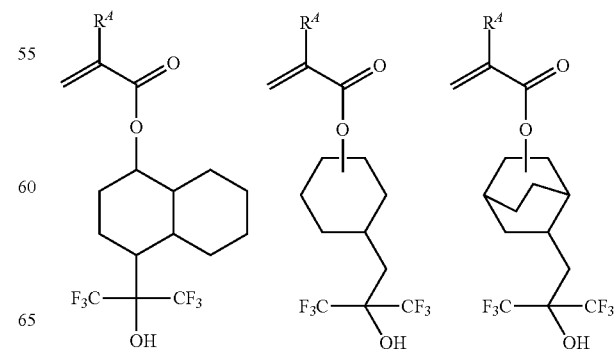

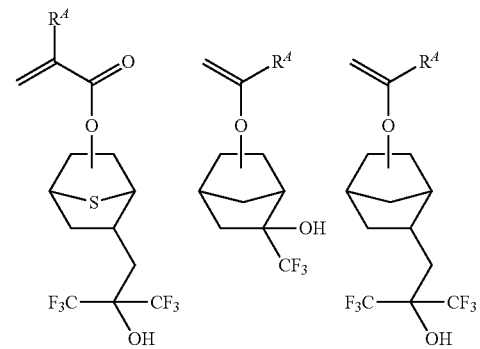
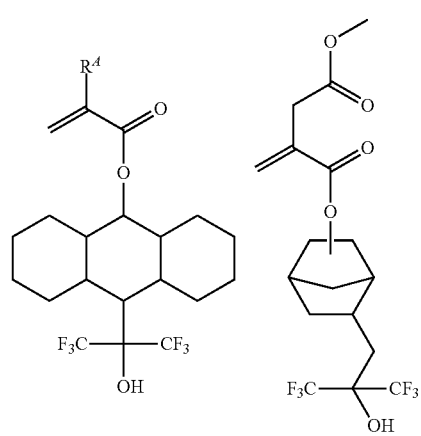
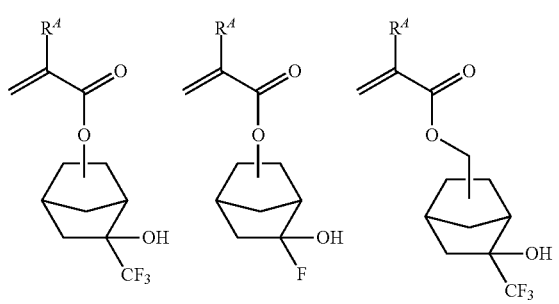
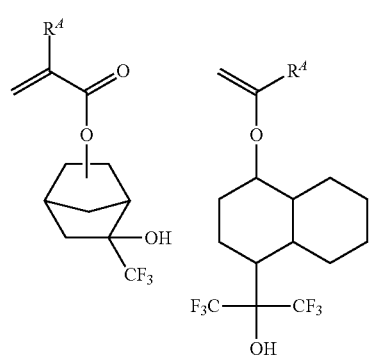
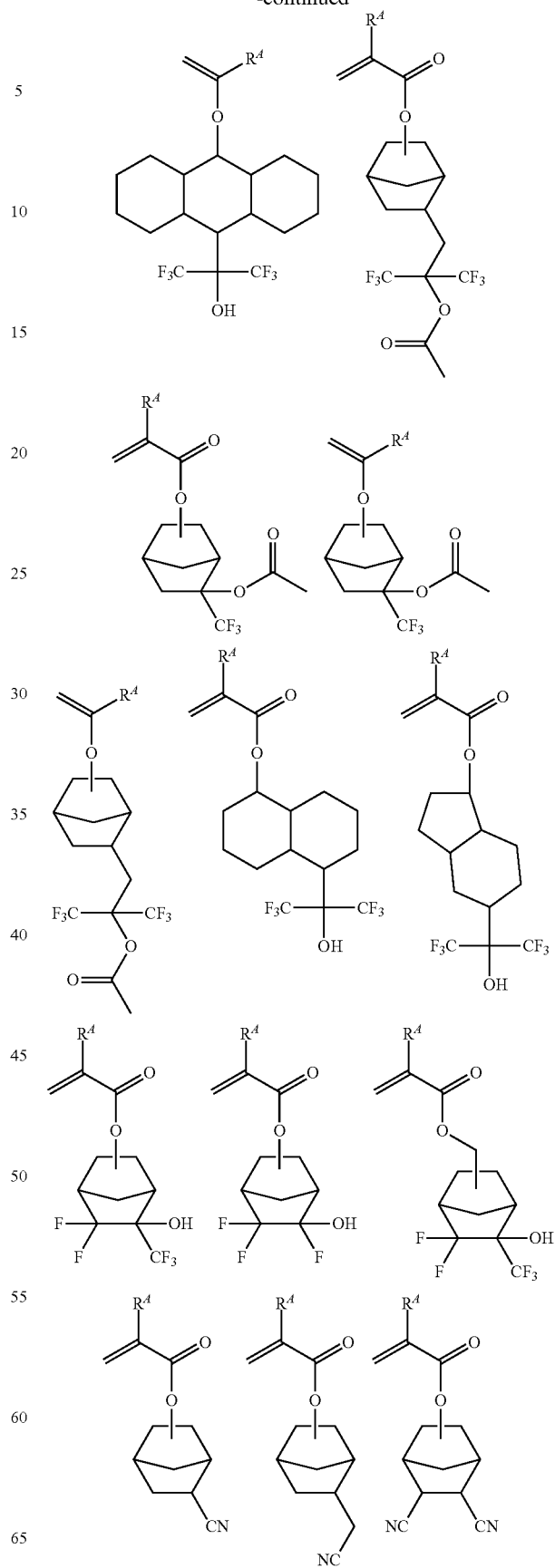

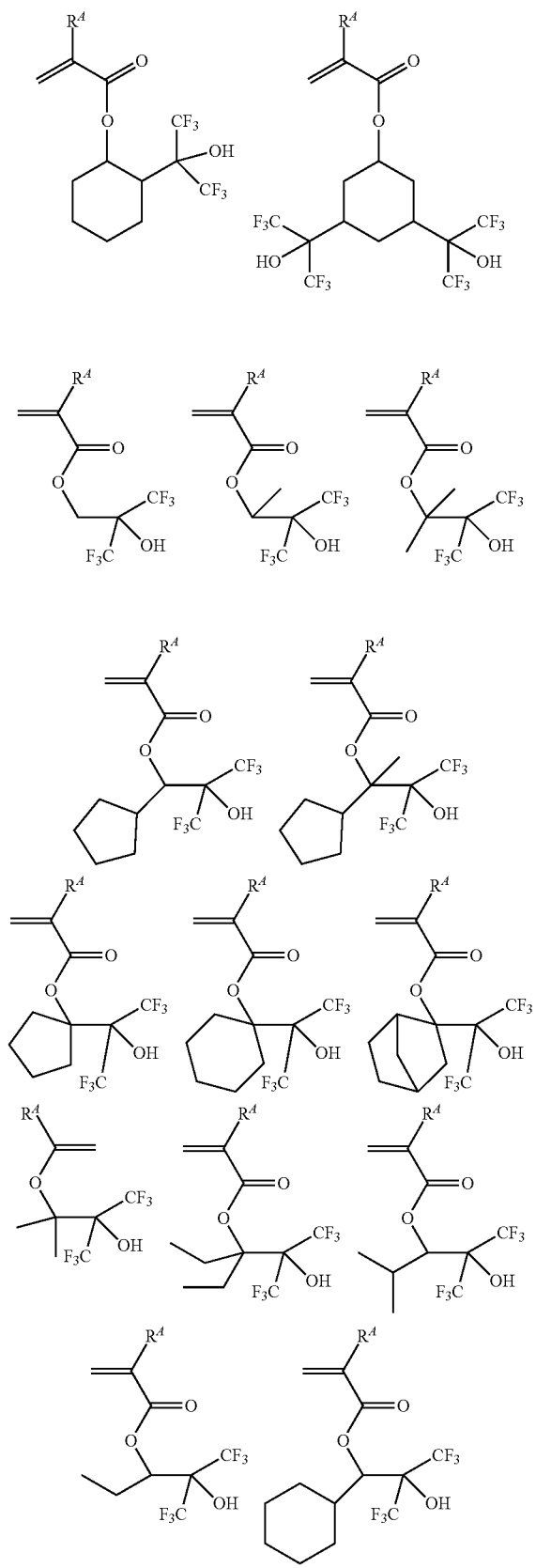
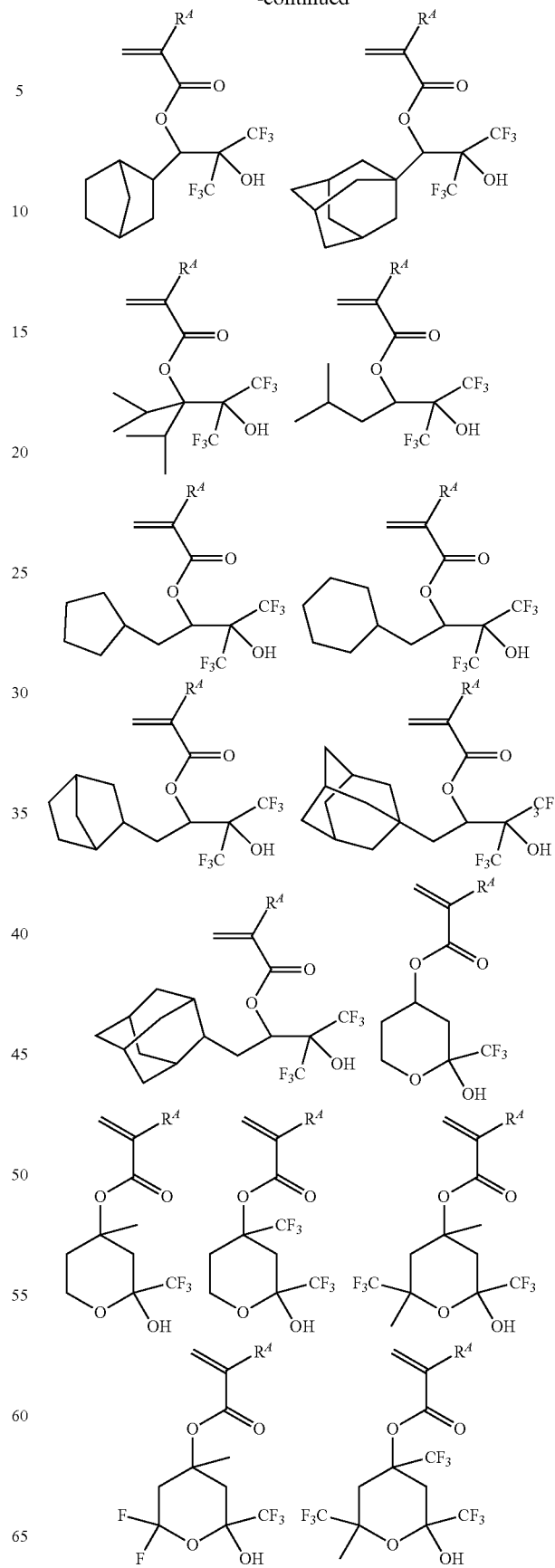

137
-continued
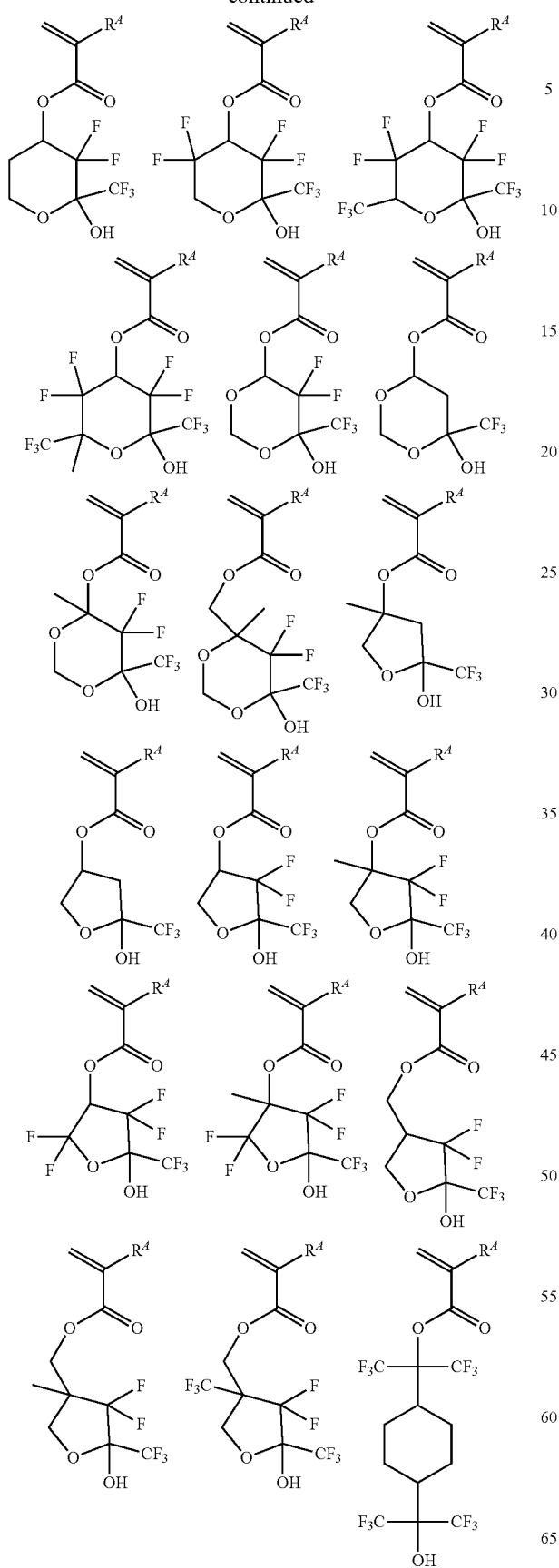
138
-continued
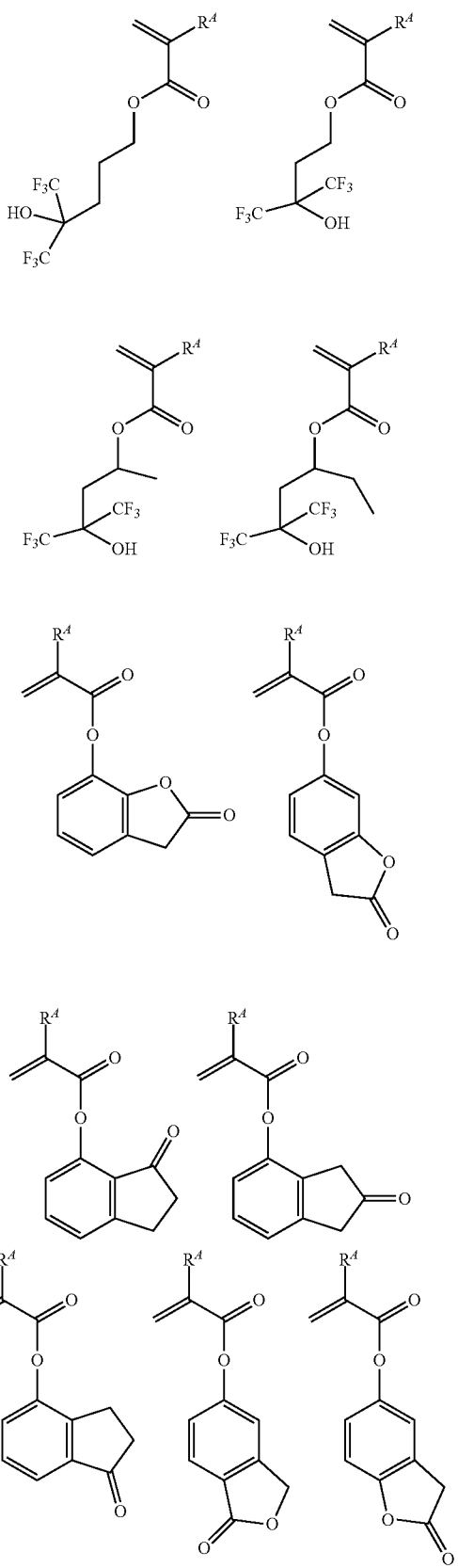

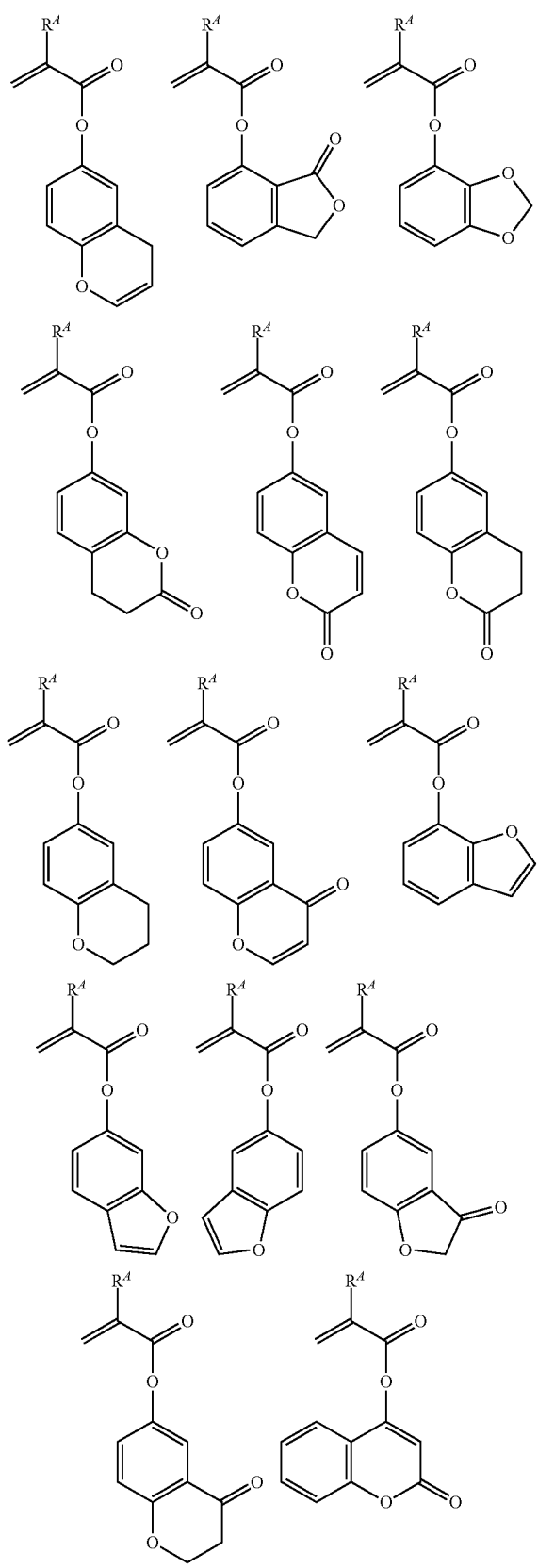
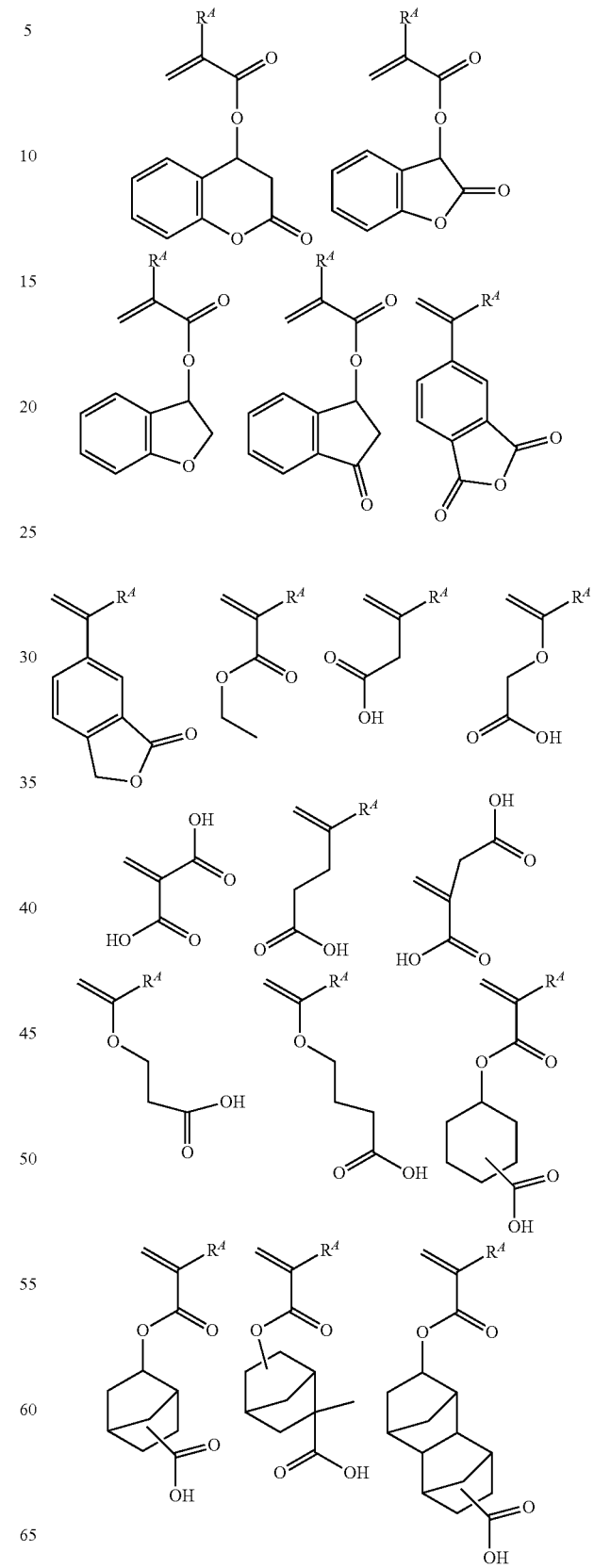

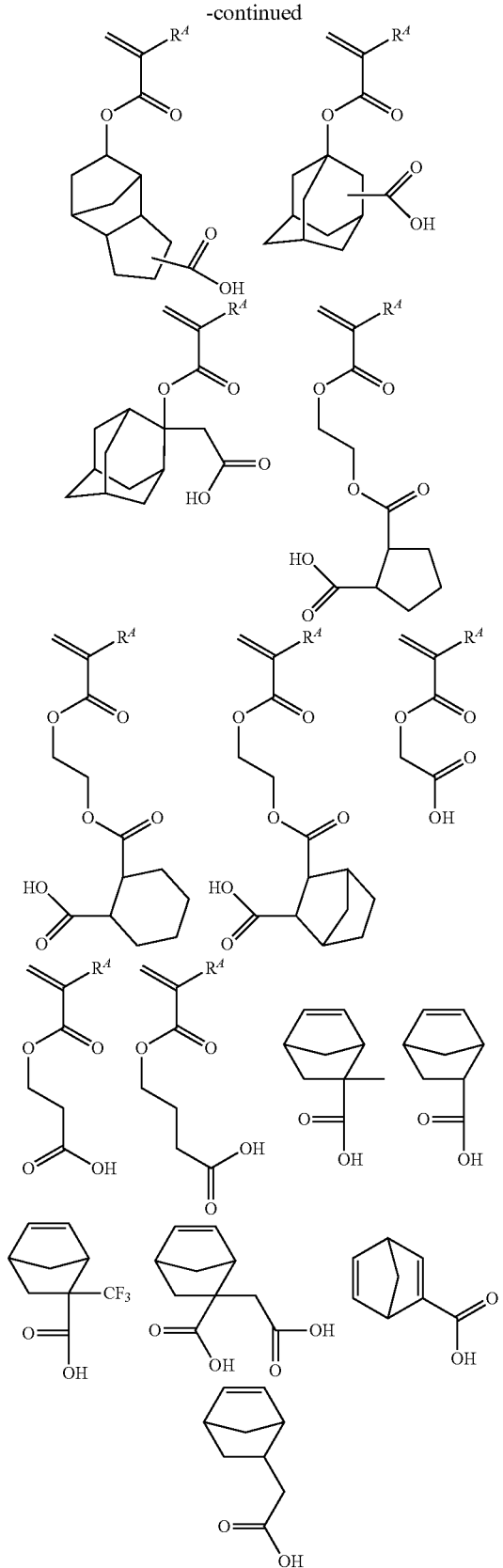

In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

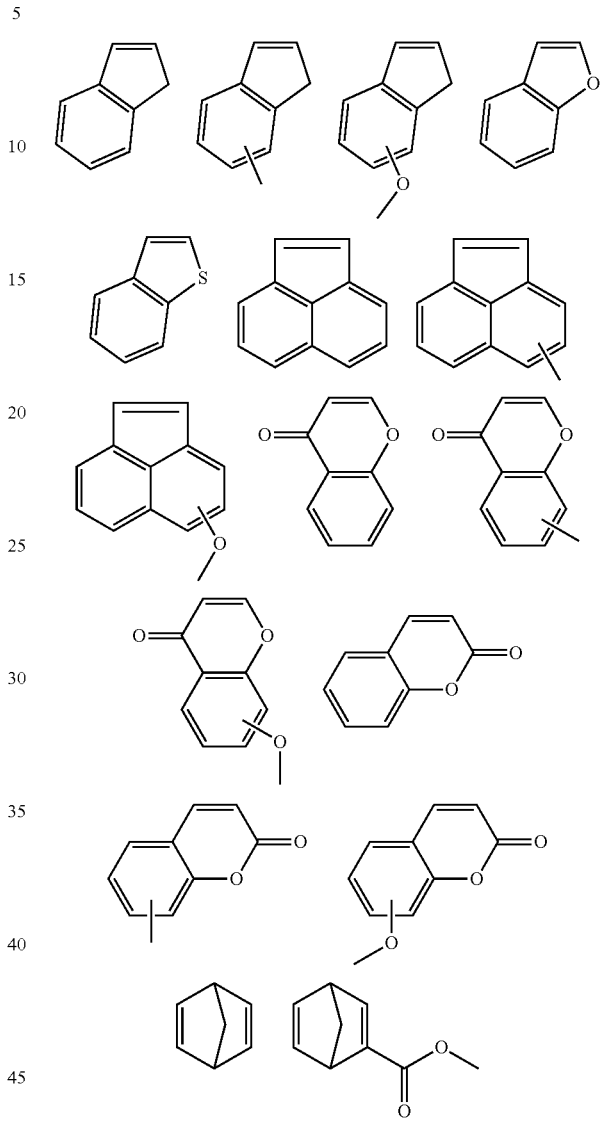

Besides the recurring units described above, further recurring units (e) may be incorporated in the base polymer, examples of which include styrene, vinylnaphthalene, vinylanthracene, vinylpyrene, methyleneindene, vinylpyridine, and vinylcarbazole.

In a further embodiment, recurring units (f) derived from an onium salt having a polymerizable unsaturated bond may be incorporated in the base polymer. JP-A 2005-084365 discloses sulfonium and iodonium salts having a polymerizable unsaturated bond capable of generating a sulfonic acid. JP-A 2006-178317 discloses a sulfonium salt having sulfonic acid directly attached to the main chain.

In a preferred embodiment, the base polymer may further comprise recurring units of at least one type selected from formulae (f1), (f2) and (f3). These units are simply referred to as recurring units (f1), (f2) and (f3), which may be used alone or in combination of two or more types.

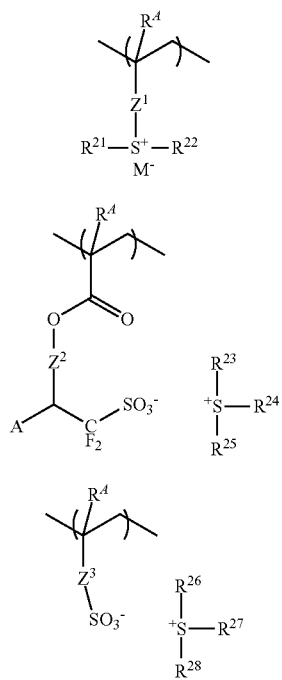

(f1)

(f2)

(f3)

In formulae (f1) to (f3), $R^A$ is as defined above. $Z^1$ is a single bond, phenylene group, —O—$Z^{11}$—, —C(=O)—O—$Z^{11}$—, or —C(=O)—NH—$Z^{11}$—, wherein $Z^{11}$ is a $C_1$-$C_6$ alkanediyl group, $C_2$-$C_6$ alkenediyl group, or phenylene group, which may contain a carbonyl, ester bond, ether bond or hydroxyl moiety. $Z^2$ is a single bond, —$Z^{21}$—C(=O)—O—, —$Z^{21}$—O— or —$Z^{21}$—O—C(=O)—, wherein $Z^{21}$ is a $C_1$-$C_{12}$ alkanediyl group which may contain a carbonyl moiety, ester bond or ether bond. $Z^3$ is a single bond, methylene, ethylene, phenylene, fluorinated phenylene, —C(=O)—O—$Z^{31}$—, or —C(=O)—NH—$Z^{31}$—, wherein $Z^{31}$ is a $C_1$-$C_6$ alkanediyl group, phenylene group, fluorinated phenylene group, trifluoromethyl-substituted phenylene group, or $C_2$-$C_6$ alkenediyl group, which may contain a carbonyl moiety, ester bond, ether bond or hydroxyl moiety. A is hydrogen or trifluoromethyl.

In formulae (f1) to (f3), $R^{21}$ to $R^{28}$ are each independently a $C_1$-$C_{20}$ monovalent hydrocarbon group which may contain a heteroatom. Any two of $R^{23}$, $R^{24}$ and $R^{25}$ or any two of $R^{26}$, $R^{27}$ and $R^{28}$ may bond together to form a ring with the sulfur atom to which they are attached.

The monovalent hydrocarbon groups may be straight, branched or cyclic, and examples thereof include those as exemplified above for $R^{a1}$ to $R^{a3}$ in formula (Aa). Examples of the sulfonium cation in formulae (f2) and (f3) include the same as exemplified above for the sulfonium cation having formula (Aa).

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (K-1) and sulfonate ions having fluorine substituted at α- and β-positions as represented by the formula (K-2).

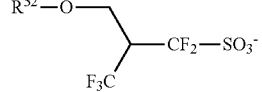

In formula (K-1), $R^{51}$ is hydrogen, or a $C_1$-$C_{20}$ alkyl group, $C_2$-$C_{20}$ alkenyl group, or $C_6$-$C_{20}$ aryl group, which may contain an ether bond, ester bond, carbonyl moiety, lactone ring, or fluorine atom. The alkyl and alkenyl groups may be straight, branched or cyclic.

In formula (K-2), $R^{52}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl and alkenyl groups may be straight, branched or cyclic.

Examples of the monomer from which recurring unit (f1) is derived are shown below, but not limited thereto. $R^A$ and $M^-$ are as defined above.

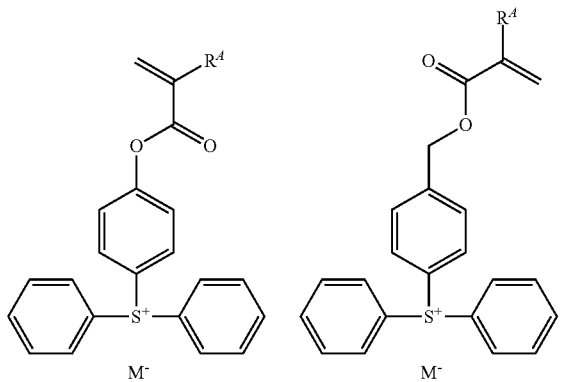

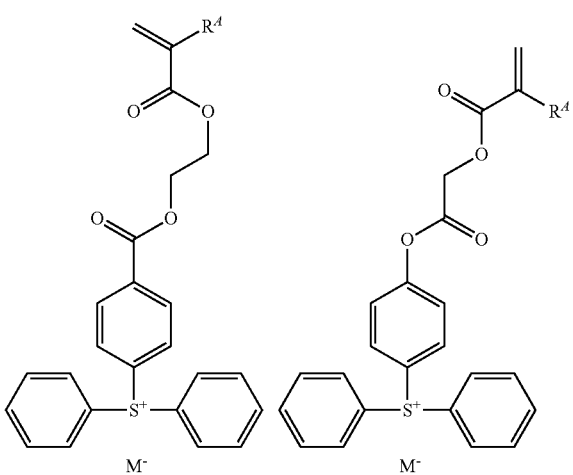

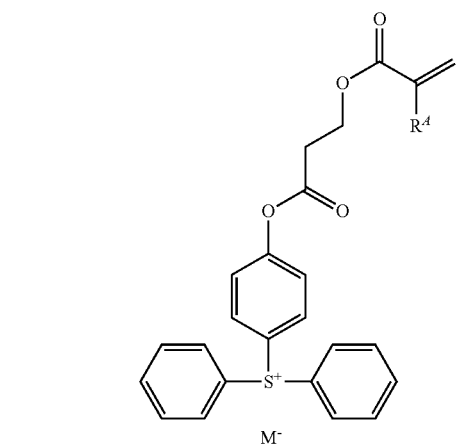
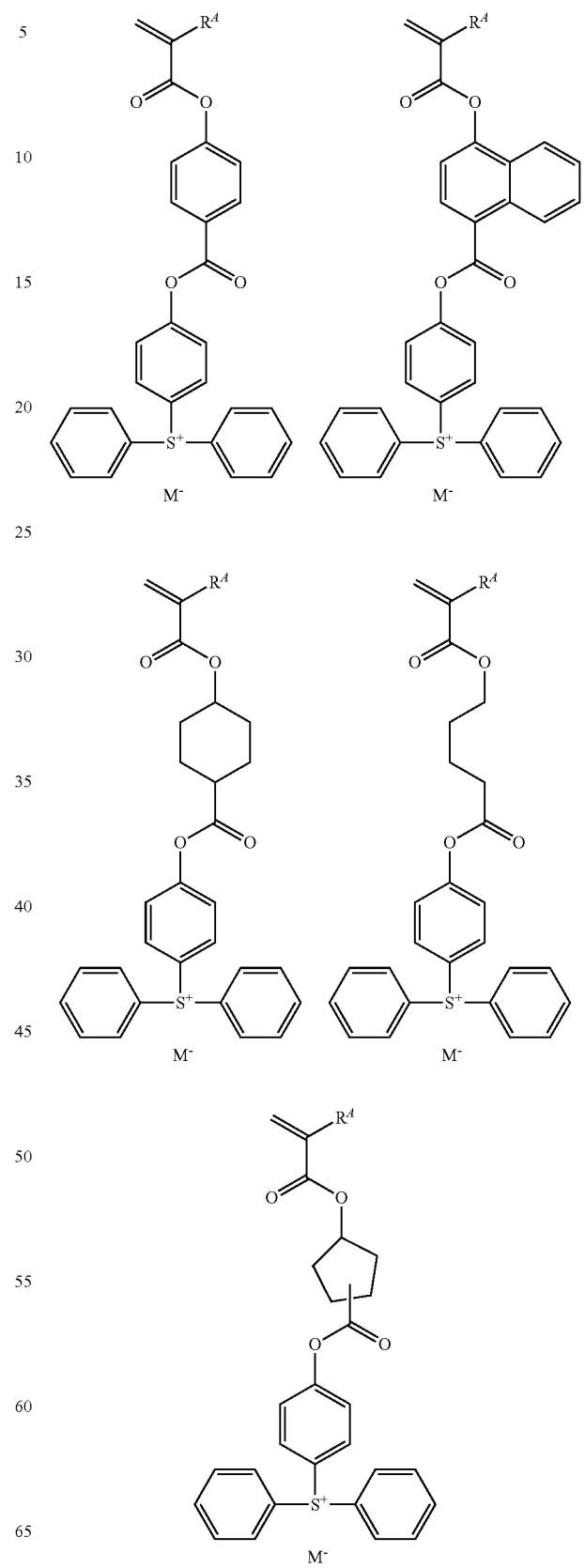

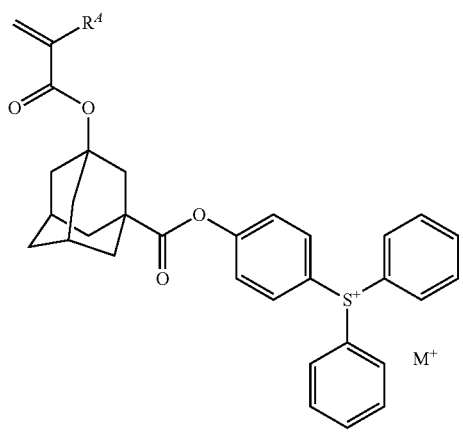
Examples of the monomer from which recurring unit (f2) is derived are shown below, but not limited thereto. $R^A$ is as defined above.
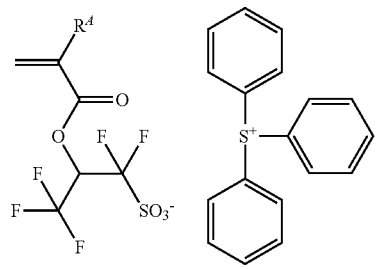
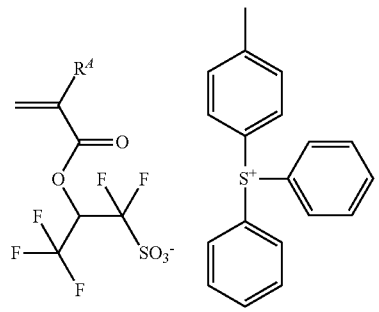
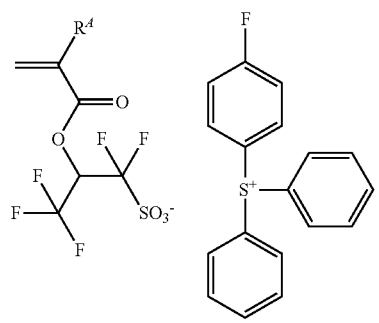
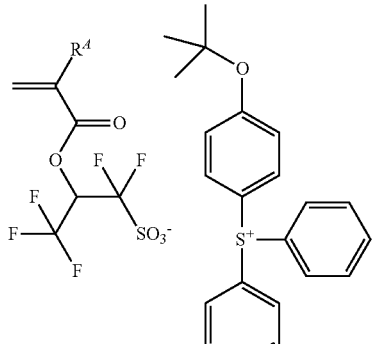
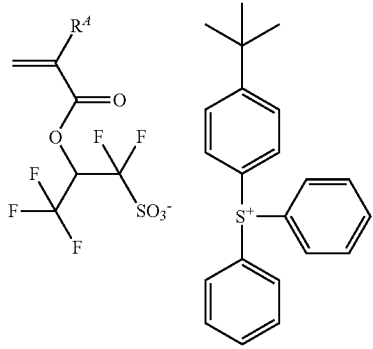
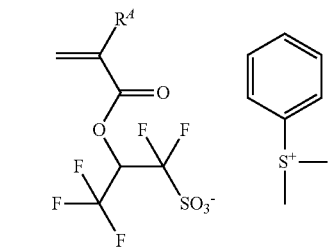
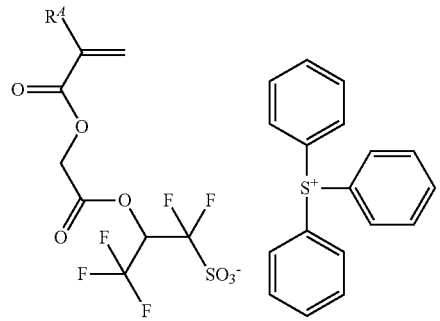
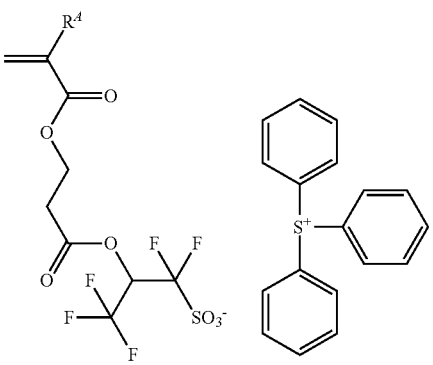

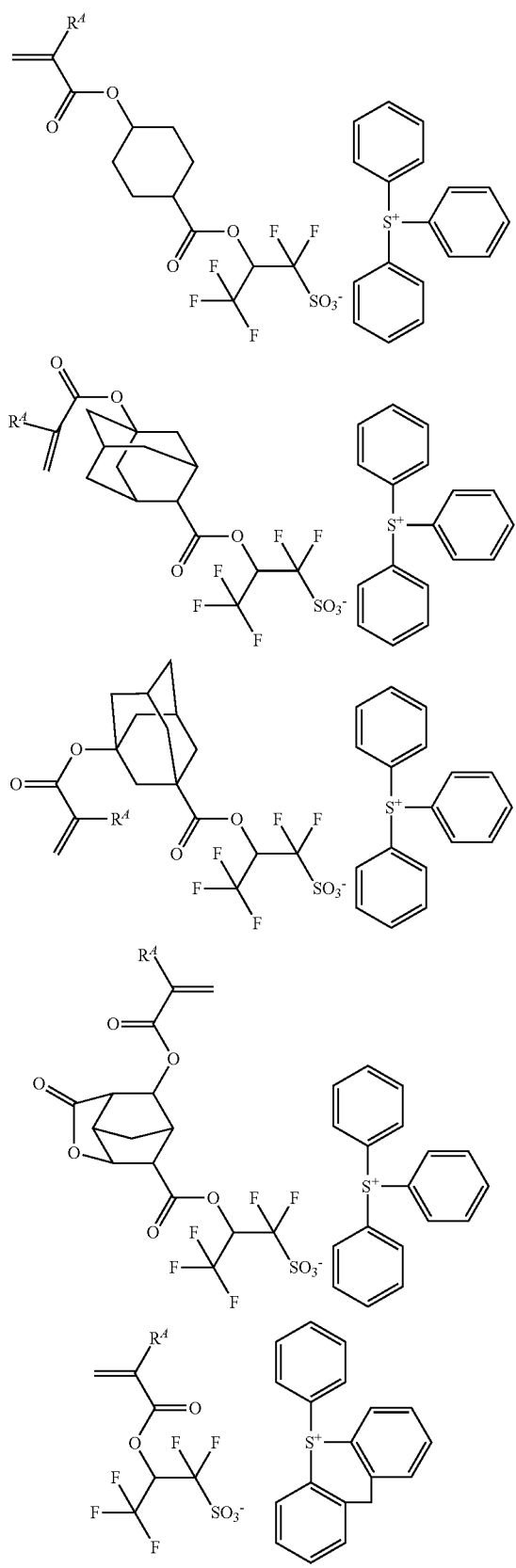
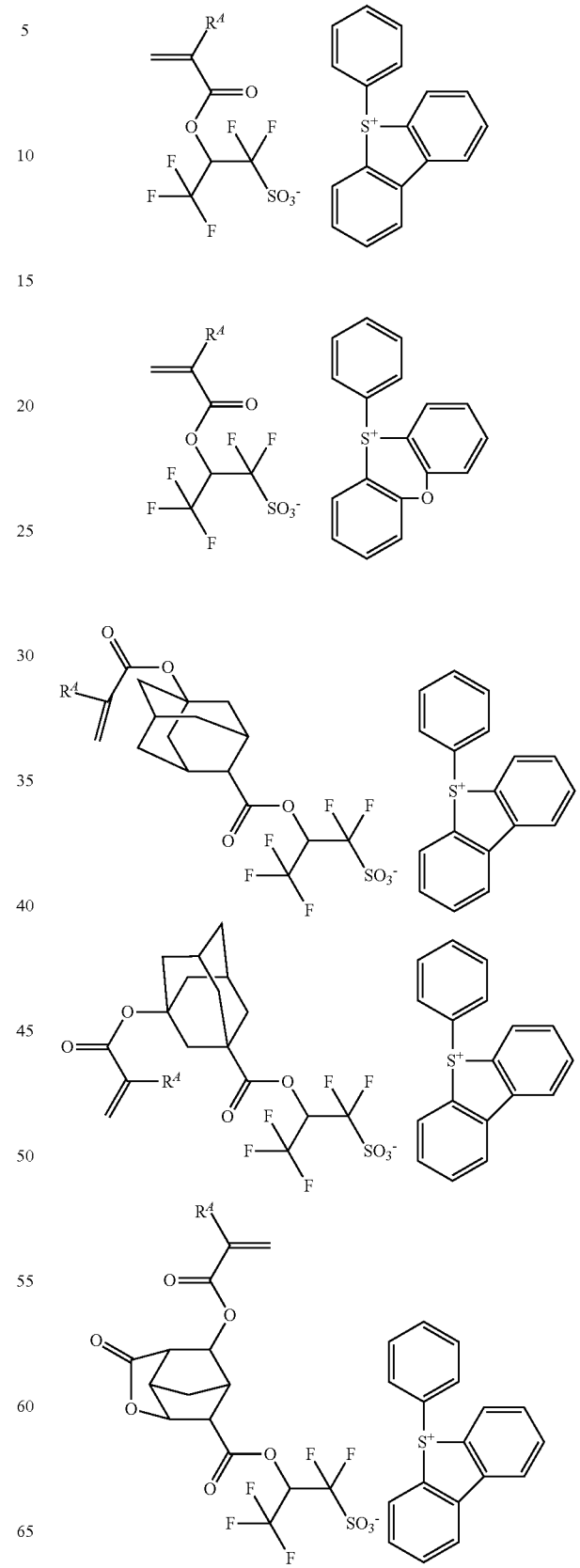

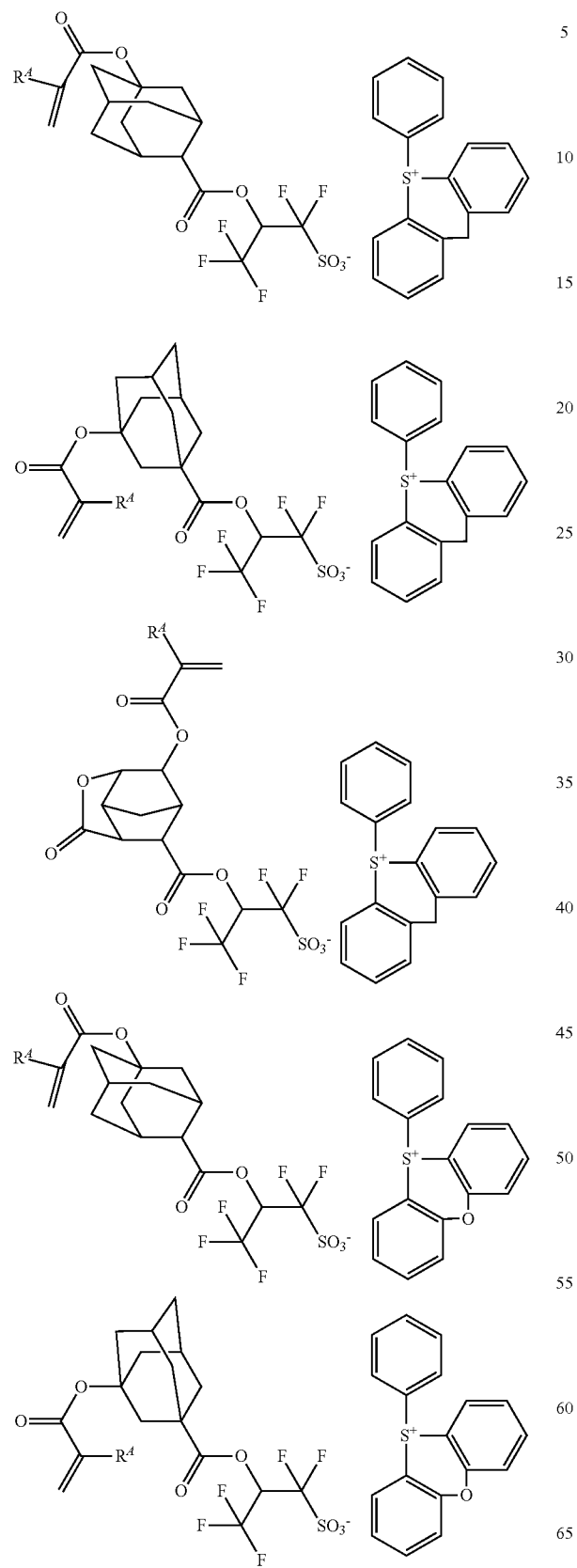
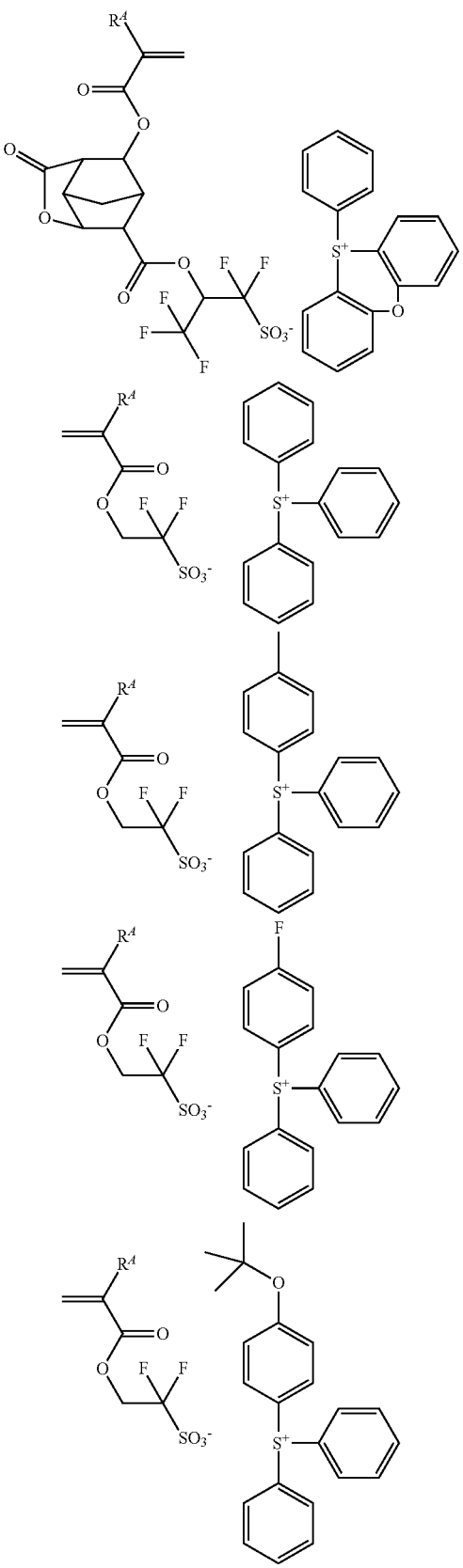

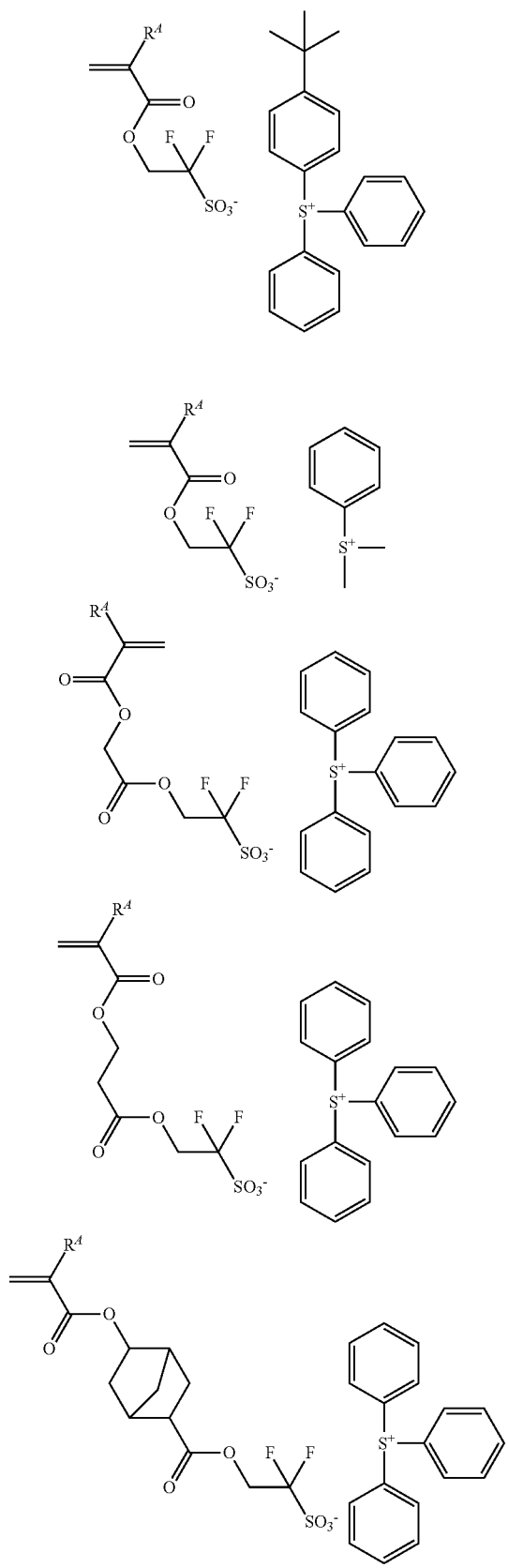
Examples of the monomer from which recurring unit (f3) is derived are shown below, but not limited thereto. $R^A$ is as defined above.

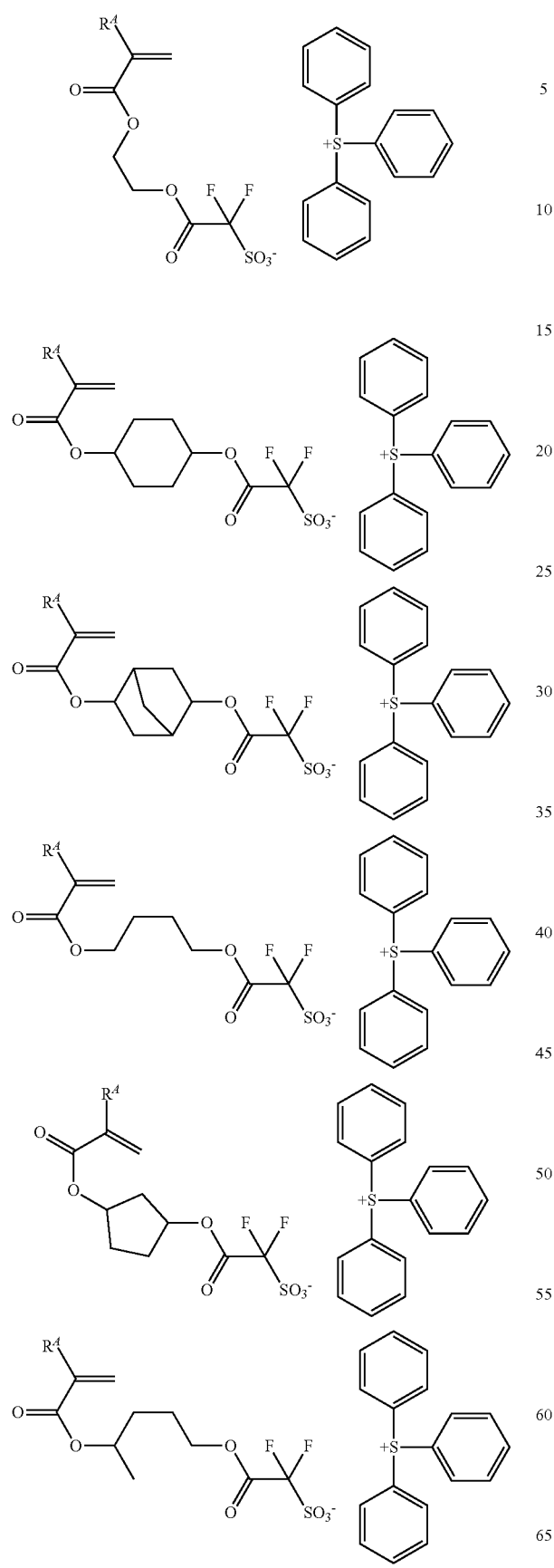
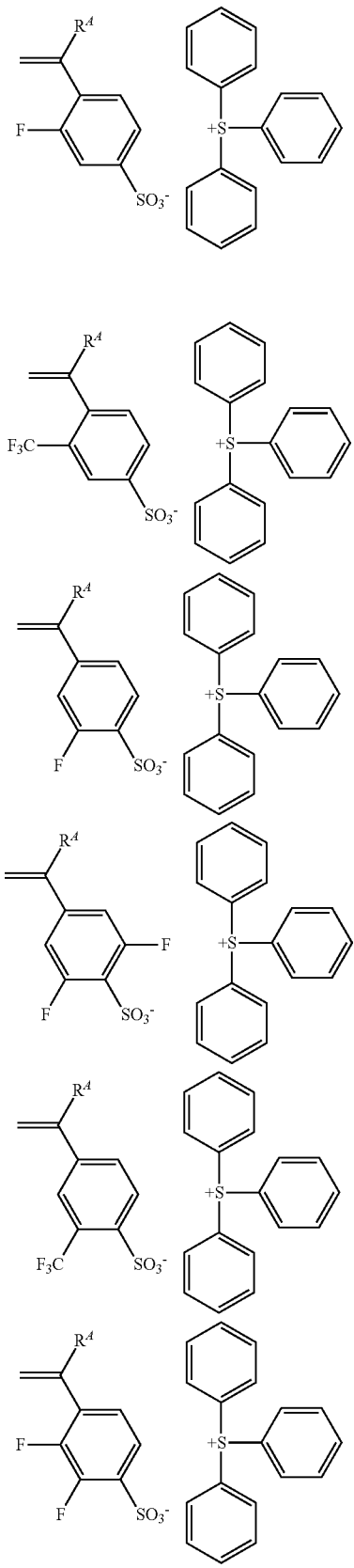

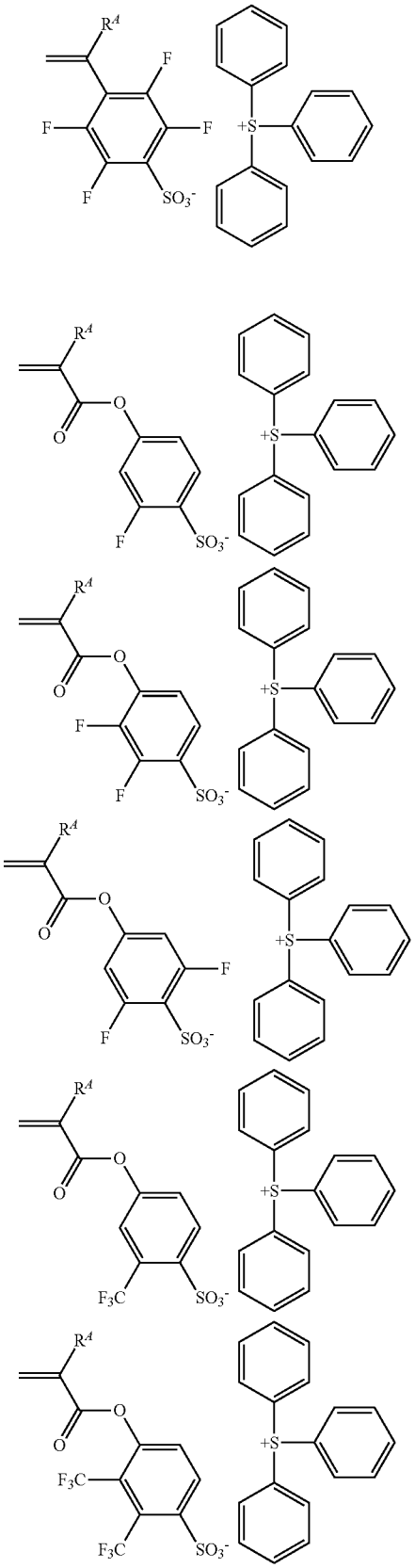
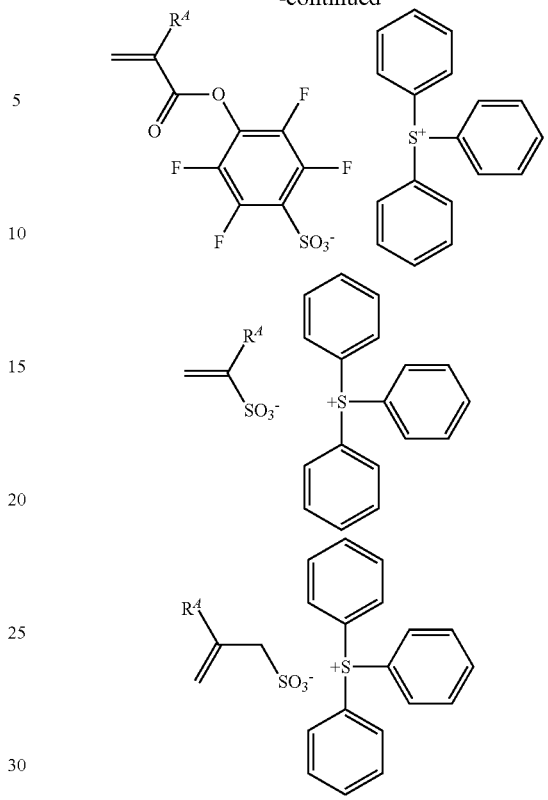

The attachment of an acid generator to the polymer main chain is effective in restraining acid diffusion, thereby preventing a reduction of resolution due to blur by acid diffusion. Also edge roughness is improved since the acid generator is uniformly distributed. Where a base polymer containing recurring units (f) is used, the addition of a separate acid generator may be omitted.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \le a1 < 1.0$, $0 \le a2 < 1.0$, $0 < a1+a2 < 1.0$, $0 \le b \le 0.9$, $0 \le c \le 0.9$, $0 \le d \le 0.8$, $0 \le e \le 0.8$, and $0 \le f \le 0.5$; more preferably $0 \le a1 \le 0.9$, $0 \le a2 \le 0.9$, $0.1 \le a1+a2 \le 0.9$, $0 \le b \le 0.8$, $0 \le c \le 0.8$, $0 \le d \le 0.7$, $0 \le e \le 0.7$, and $0 \le f \le 0.4$; and even more preferably $0 \le a1 \le 0.8$, $0 \le a2 \le 0.8$, $0.1 \le a1+a2 \le 0.8$, $0 \le b \le 0.75$, $0 \le c \le 0.75$, $0 \le d \le 0.6$, $0 \le e \le 0.6$, and $0 \le f \le 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \le 1.0$, $0 \le c \le 0.9$, $0 \le d \le 0.8$, $0 \le e \le 0.8$, and $0 \le f \le 0.5$; more preferably $0.2 \le b \le 1.0$, $0 \le c \le 0.8$, $0 \le d \le 0.7$, $0 \le e \le 0.7$, and $0 \le f \le 0.4$; and even more preferably $0.3 \le b \le 1.0$, $0 \le c \le 0.75$, $0 \le d \le 0.6$, $0 \le e \le 0.6$, and $0 \le f \le 0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

Where a monomer having a hydroxyl group is copolymerized, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxy vinylnaphthalene, and after polymerization, the acetoxy group is deprotected by alkaline hydrolysis, for thereby converting the polymer product to hydroxystyrene or hydroxy vinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenal after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable. The base polymer may contain a polymer different from the polymer defined above as long as the benefits of the invention are not impaired, although the absence of such an additional polymer is preferred.

Acid Generator

An acid generator (of addition type) may be added to the resist composition in order that the composition function as a chemically amplified positive or negative resist composition. Then the resist composition becomes more useful because it has a higher sensitivity and better properties. In the embodiment wherein the base polymer has recurring units (f) incorporated therein, that is, the acid generator is bound in the base polymer, an acid generator of addition type need not be added.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, those having the formula (1) are preferred.

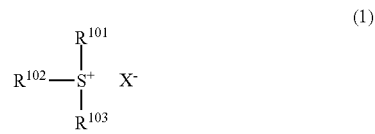

In formula (1), $R^{101}$, $R^{102}$ and $R^{103}$ are each independently a $C_1$-$C_{20}$ monovalent hydrocarbon group which may contain a heteroatom. Any two of $R^{101}$, $R^{102}$ and $R^{103}$ may bond together to form a ring with the sulfur atom to which they are attached. The monovalent hydrocarbon group may be straight, branched or cyclic, and examples thereof include those exemplified above for $R^{a1}$ to $R^{a3}$ in formula (Aa).

Examples of the cation in the sulfonium salt having formula (1) include those exemplified above as the sulfonium cation having formula (Aa).

In formula (1), $X^-$ is an anion of the following formula (1A), (1B), (1C) or (1D).

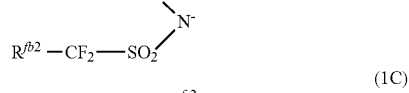

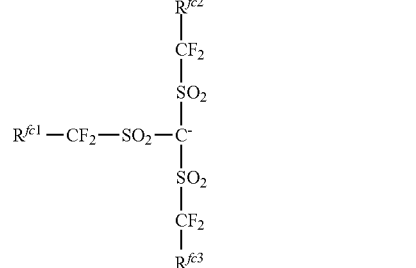

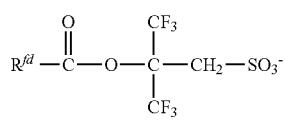

In formula (1A), $R^{fa}$ is fluorine or a $C_1$-$C_{40}$ monovalent hydrocarbon group which may contain a heteroatom. The monovalent hydrocarbon group may be straight, branched or cyclic, and examples thereof include those exemplified later for $R^{105}$.

Of the anions of formula (1A), an anion having the formula (1A') is preferred.

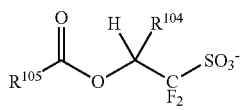

(1A')

In formula (1A'), $R^{104}$ is hydrogen or trifluoromethyl, preferably trifluoromethyl. $R^{105}$ is a $C_1$-$C_{38}$ monovalent hydrocarbon group which may contain a heteroatom. As the heteroatom, oxygen, nitrogen, sulfur and halogen atoms are preferred, with oxygen being most preferred. Of the monovalent hydrocarbon groups represented by $R^{105}$, those groups of 6 to 30 carbon atoms are preferred from the aspect of achieving a high resolution in forming patterns of fine feature size. The monovalent hydrocarbon groups may be straight, branched or cyclic. Examples thereof include, but are not limited to, straight or branched alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, eicosanyl, monovalent saturated alicyclic hydrocarbon groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; monovalent unsaturated aliphatic hydrocarbon groups such as allyl and 3-cyclohexenyl; and aralkyl groups such as benzyl and diphenylmethyl. Examples of the monovalent hydrocarbon group having a heteroatom include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

With respect to the synthesis of the sulfonium salt having an anion of formula (1A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

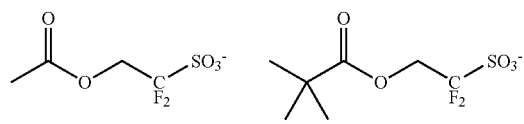

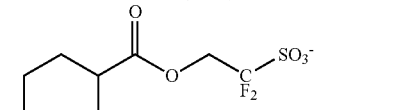

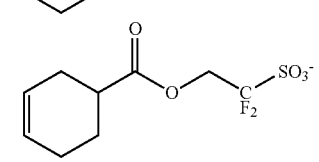

-continued

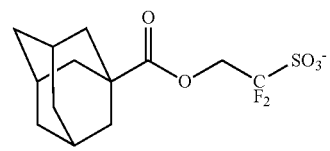

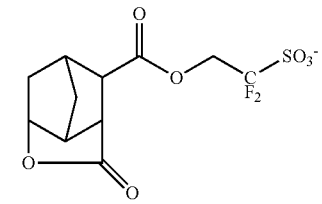

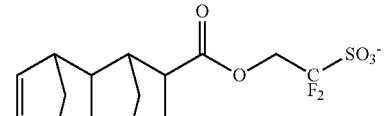

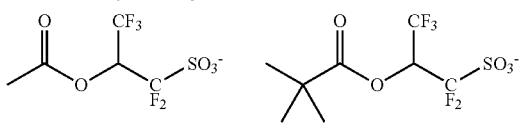

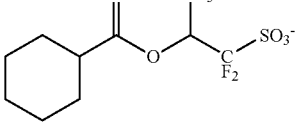

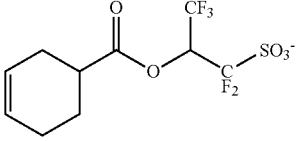

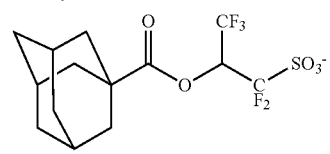

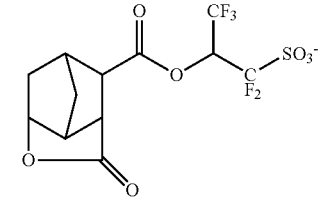

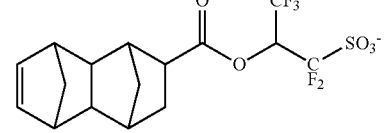

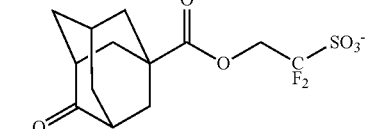

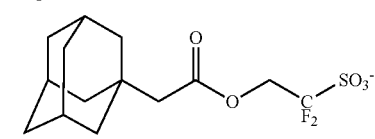

-continued

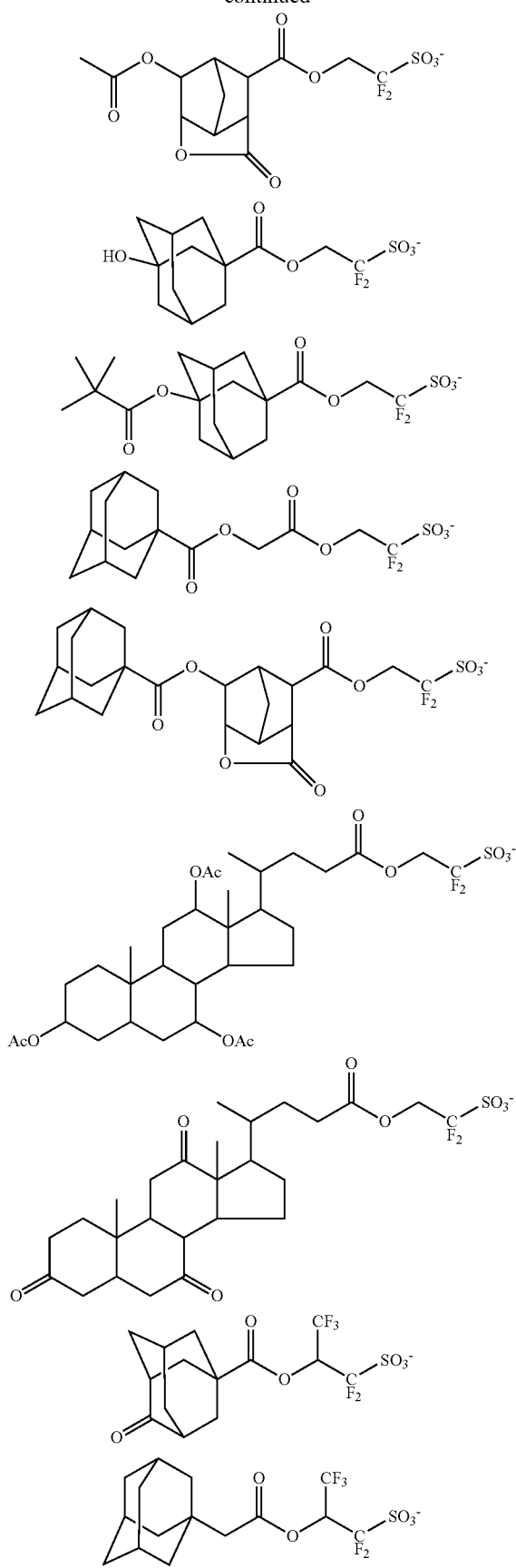

-continued

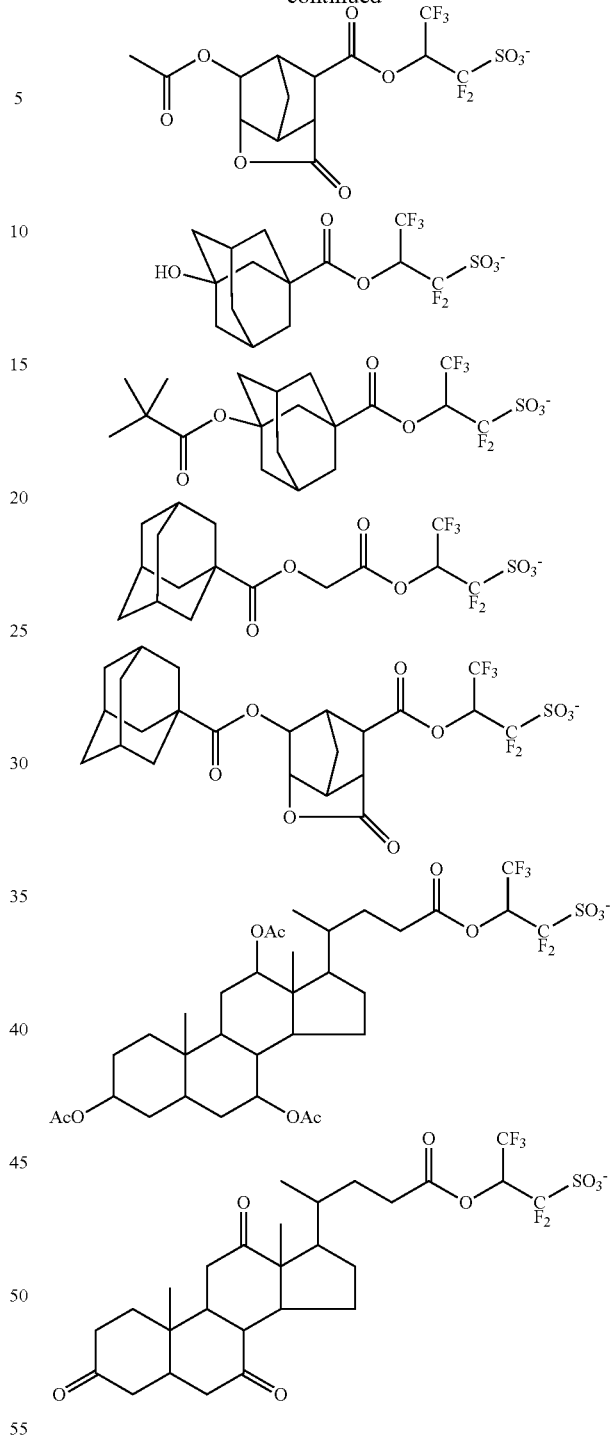

In formula (1B), $R^{fb1}$ and $R^{fb2}$ are each independently fluorine or a $C_1$-$C_{40}$ monovalent hydrocarbon group which may contain a heteroatom. The monovalent hydrocarbon group may be straight, branched or cyclic, and examples thereof are as exemplified for $R^{105}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. It is preferred that a combination of $R^{fb1}$ and $R^{fb2}$ be a fluorinated ethylene or fluorinated propylene group.

In formula (1C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon group may be straight, branched or cyclic, and examples thereof are as exemplified for $R^{105}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. It is preferred that a combination of $R^{fc1}$ and $R^{fc2}$ be a fluorinated ethylene or fluorinated propylene group.

In formula (1D), $R^{fd}$ is a $C_1$-$C_{40}$ monovalent hydrocarbon group which may contain a heteroatom. The monovalent hydrocarbon group may be straight, branched or cyclic, and examples thereof are as exemplified above for $R^{105}$.

With respect to the synthesis of the sulfonium salt having an anion of formula (1D), reference may be made to JP-A 2010-215608 and JP-A 2014-133723.

Examples of the anion having formula (1D) are shown below, but not limited thereto.

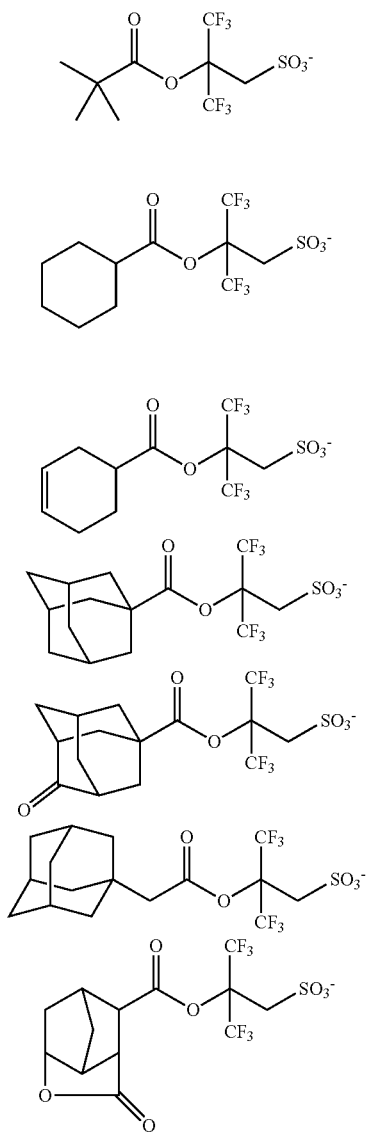
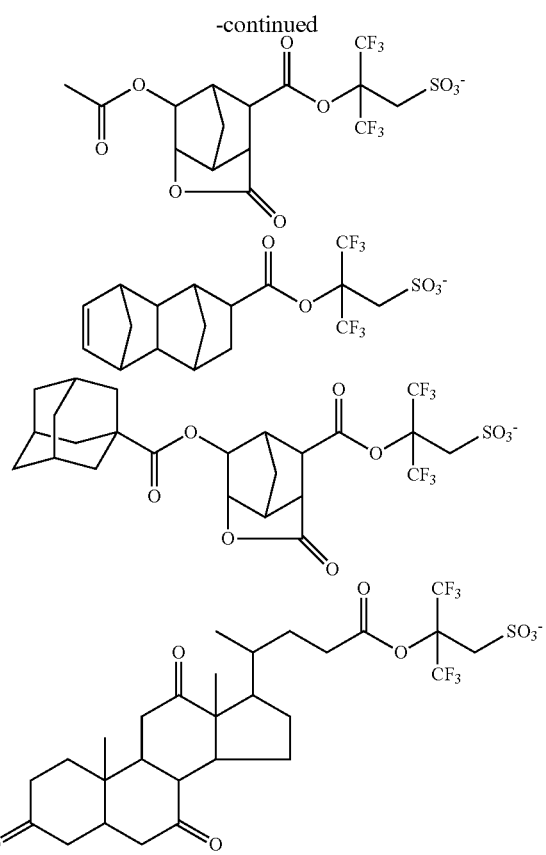

Notably, the compound having the anion of formula (1D) does not have fluorine at the α-position relative to the sulfo group, but two trifluoromethyl groups at the β-position. For this reason, it has a sufficient acidity to sever the acid labile groups in the resist polymer. Thus the compound is an effective PAG.

Another preferred PAG is a compound having the formula (2).

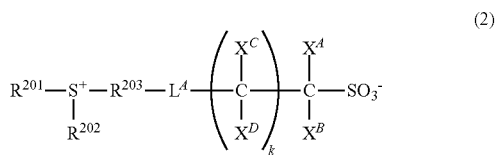

(2)

In formula (2), $R^{201}$ and $R^{202}$ are each independently a $C_1$-$C_{30}$ monovalent hydrocarbon group which may contain a heteroatom $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^A$ is a single bond, ether bond or a $C_1$-$C_{20}$ divalent hydrocarbon group which may contain a heteroatom $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

The monovalent hydrocarbon groups may be straight, branched or cyclic. Examples thereof include, but are not limited to, straight or branched alkyl groups such as methyl, ethyl, propyl, isopropyl, n-butyl, sec-butyl, tert-butyl, n-pentyl, tert-pentyl, n-hexyl, n-octyl, n-nonyl, n-decyl, and 2-ethylhexyl; monovalent saturated cyclic hydrocarbon groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; and aryl groups such as phenyl, naphthyl and anthracenyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

The divalent hydrocarbon groups may be straight, branched or cyclic. Examples thereof include straight or branched alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; divalent saturated cyclic hydrocarbon groups such as cyclopentanediyl, cyclohexanediyl, norbornanediyl and adamantanediyl; and divalent unsaturated cyclic hydrocarbon groups such as phenylene and naphthylene. Some hydrogen on these groups may be substituted by an alkyl moiety such as methyl, ethyl, propyl, n-butyl or t-butyl; some hydrogen may be substituted by a moiety containing a heteroatom such as oxygen, sulfur, nitrogen or halogen; or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety. Of the heteroatoms, oxygen is preferred.

Of the PAGs having formula (2), those having formula (2') are preferred.

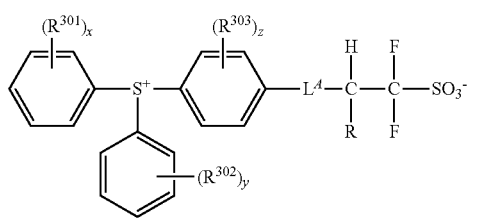

(2')

In formula (2'), $L^4$ is as defined above. R is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon groups may be straight, branched or cyclic, and examples thereof are as exemplified above for $R^{105}$. The subscripts x and y are each independently an integer of 0 to 5, and z is an integer of 0 to 4.

Examples of the PAG having formula (2) are shown below, but not limited thereto. Notably, R is as defined above.

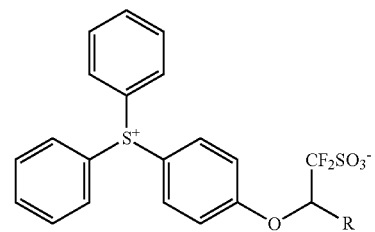

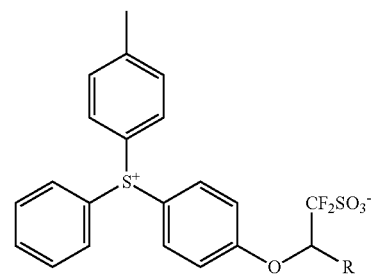

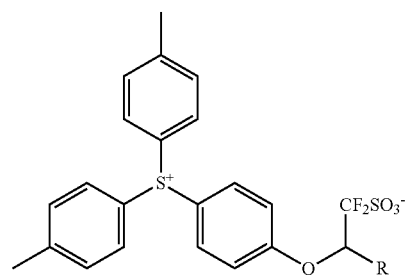

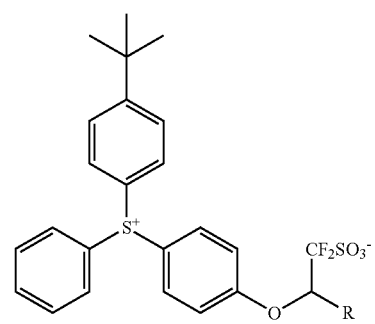

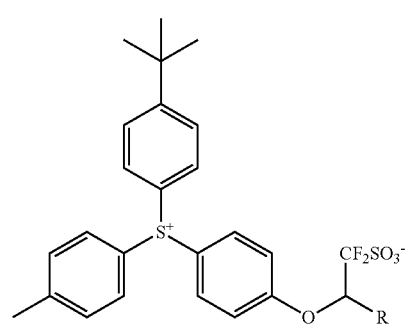

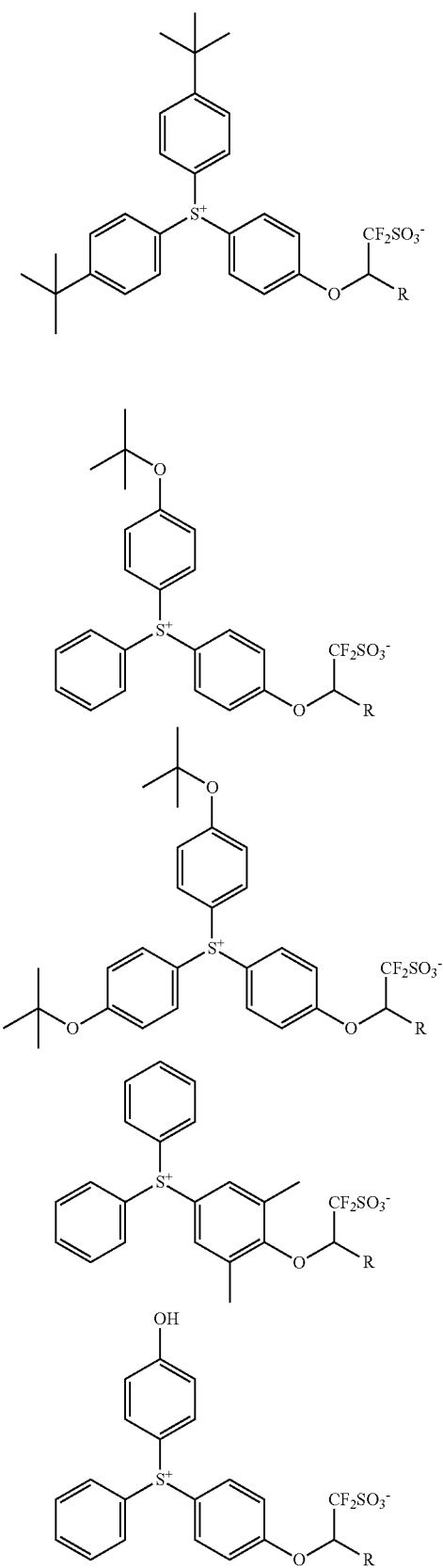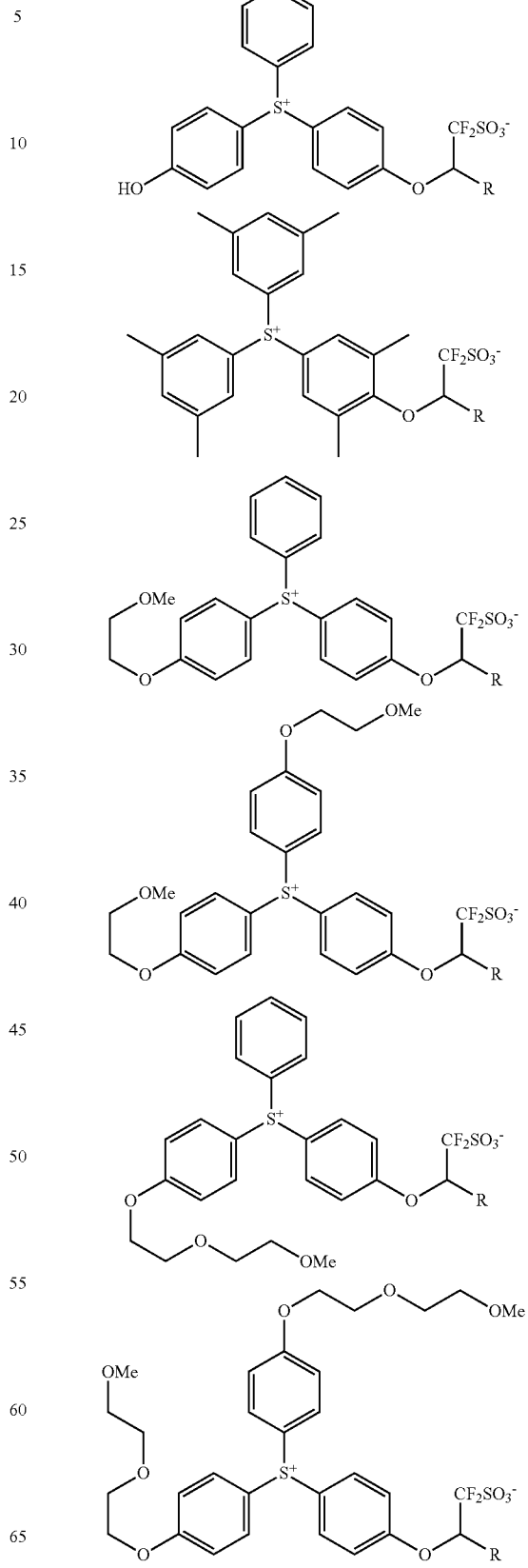

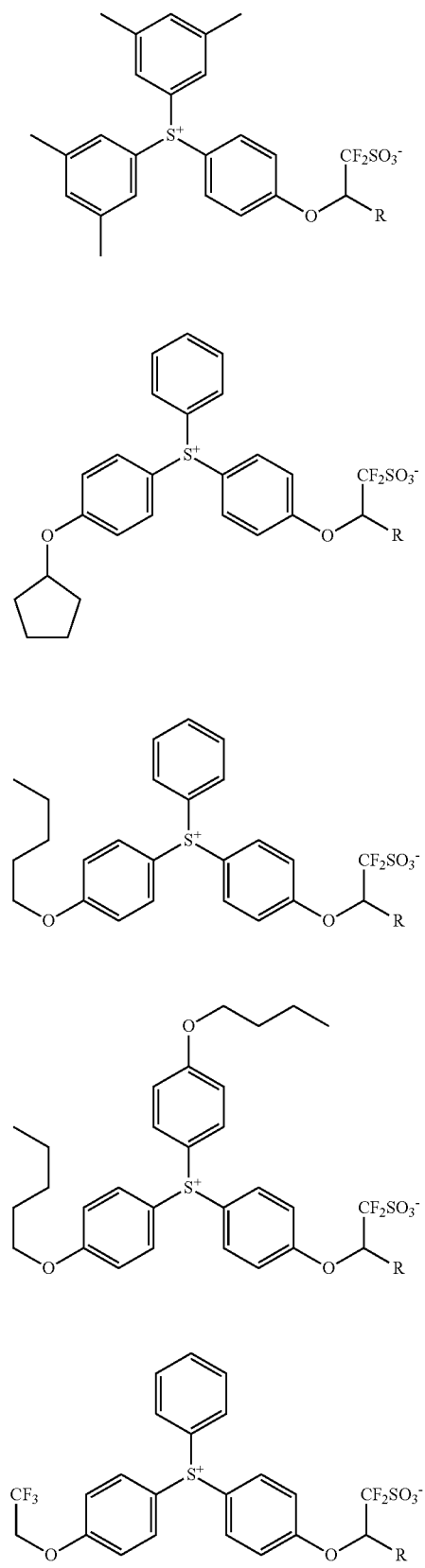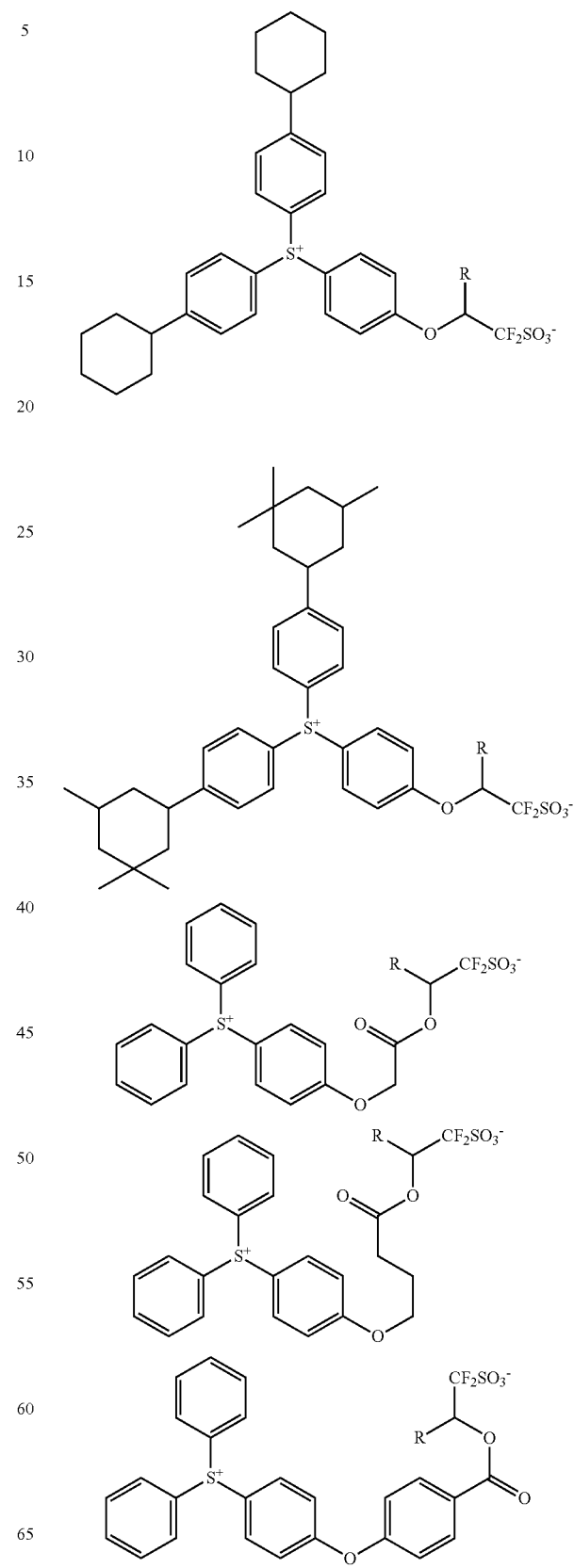

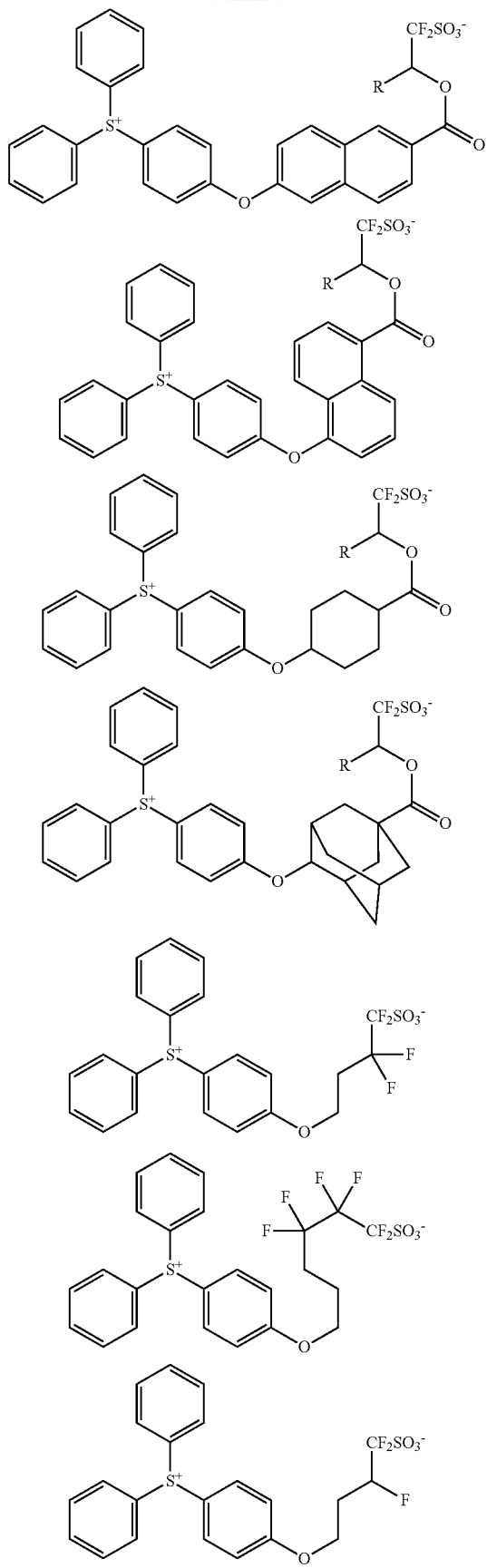

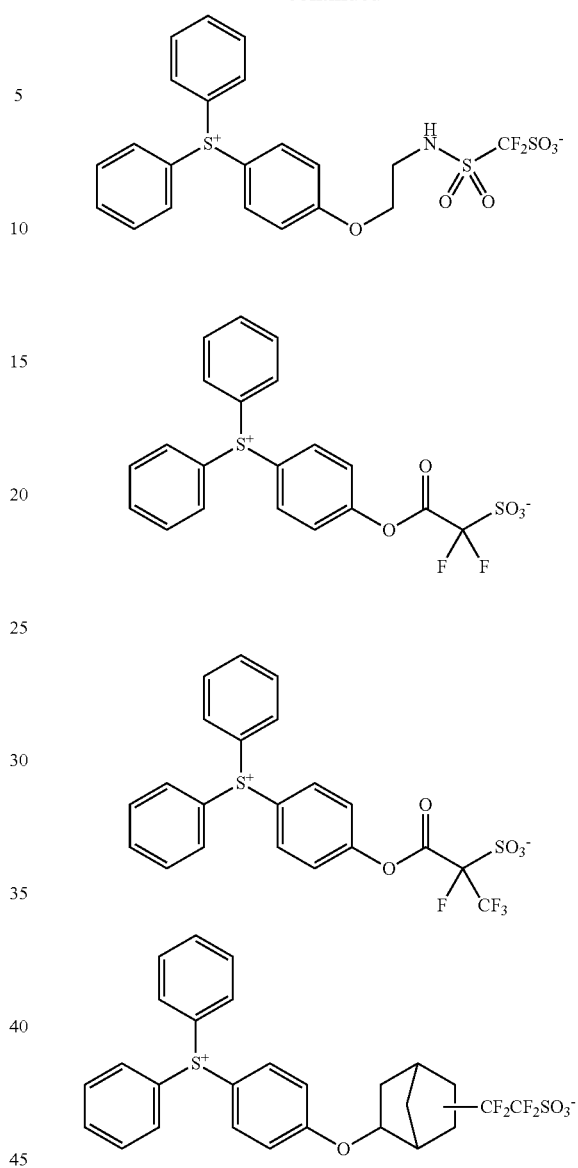

Of the foregoing PAGs, those having an anion of formula (1A') or (1D) are especially preferred because of reduced acid diffusion and high solubility in the resist solvent. Also those having an anion of formula (2') are especially preferred because of extremely reduced acid diffusion.

Also a sulfonium or iodonium salt having an iodized anion may be used as the PAG. Suitable are sulfonium and iodonium salts of iodized benzoyloxy-containing fluorinated sulfonic acid having the formulae (3-1) and (3-2).

(3-1)

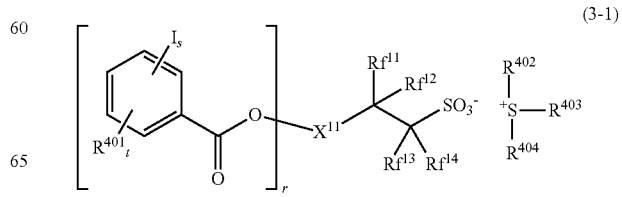

(3-2)

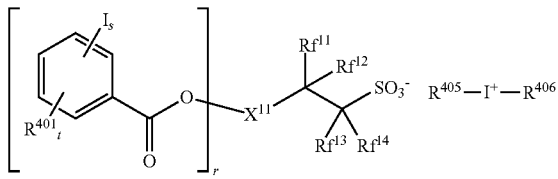

In formulae (3-1) and (3-2), $R^{401}$ is hydrogen, hydroxyl, carboxyl, nitro, cyano, fluorine, chlorine, bromine, amino group, or a $C_1$-$C_{20}$ alkyl, $C_1$-$C_{20}$ alkoxy, $C_2$-$C_{20}$ alkoxycarbonyl, $C_2$-$C_{20}$ acyloxy or $C_1$-$C_4$ alkylsulfonyloxy group, which may contain fluorine, chlorine, bromine, hydroxy, amino or alkoxy moiety, or $-NR^{407}-C(=O)-R^{408}$ or $-NR^{407}-C(=O)-O-R^{408}$, wherein $R^{407}$ is hydrogen, or a $C_1$-$C_6$ alkyl group which may contain halogen, hydroxy, alkoxy, acyl or acyloxy moiety, $R^{408}$ is a $C_1$-$C_{16}$ alkyl, $C_2$-$C_{16}$ alkenyl or $C_6$-$C_{12}$ aryl group, which may contain halogen, hydroxy, alkoxy, acyl or acyloxy moiety.

$X^{11}$ is a single bond or a $C_1$-$C_{20}$ divalent linking group when r=1, or a $C_1$-$C_{20}$ tri- or tetravalent linking group when r=2 or 3, the linking group optionally containing an oxygen, sulfur or nitrogen atom. $Rf^{11}$ to $Rf^{14}$ are each independently hydrogen, fluorine or trifluoromethyl, at least one of $Rf^{11}$ to $Rf^{14}$ is fluorine or trifluoromethyl, or $Rf^{11}$ and $Rf^{12}$, taken together, may form a carbonyl group.

$R^{402}$, $R^{403}$, $R^{404}$, $R^{405}$ and $R^{406}$ are each independently a $C_1$-$C_{20}$ monovalent hydrocarbon group which may contain a heteroatom. Any two of $R^{402}$, $R^{403}$ and $R^{404}$ may bond together to form a ring with the sulfur atom to which they are attached. The monovalent hydrocarbon group may be straight, branched or cyclic, and examples thereof are as exemplified above for $R^{a1}$ to $R^{a3}$ in formula (Aa).

In formulae (3-1) and (3-2), r is an integer of 1 to 3, s is an integer of 1 to 5, and t is an integer of 0 to 3.

The alkyl, alkoxy, alkoxycarbonyl, acyloxy, alkylsulfonyloxy, alkenyl and acyl groups may be straight, branched or cyclic.

Another example of the sulfonium or iodonium salt having an iodized anion is a sulfonium or iodonium salt of iodized benzene ring-containing fluorosulfonic acid have the formula (3-3) or (3-4).

(3-3)

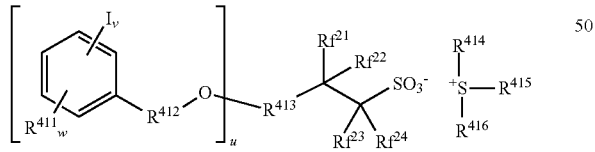

(3-4)

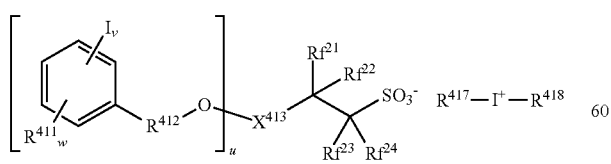

In formulae (3-3) and (3-4), $R^{411}$ is a hydroxyl group, $C_1$-$C_{20}$ alkyl or alkoxy group, $C_2$-$C_{20}$ acyl or acyloxy group, fluorine, chlorine, bromine, amino group or alkoxy carbonyl-substituted amino group.

$R^{412}$ is each independently a single bond or a $C_1$-$C_4$ alkylene group. $R^{413}$ is a single bond or a $C_1$-$C_{20}$ divalent linking group in case of u=1, or a $C_1$-$C_{20}$ tri or tetra-valent linking group in case of u=2 or 3. The linking group may contain an oxygen, sulfur or nitrogen atom.

$Rf^{21}$ to $Rf^{24}$ are each independently hydrogen, fluorine, or trifluoromethyl, at least one of $Rf^{21}$ to $Rf^{24}$ is fluorine or trifluoromethyl. $Rf^{21}$ and $Rf^{22}$, taken together, may form a carbonyl group.

$R^{414}$, $R^{415}$, $R^{416}$, $R^{417}$ and $R^{418}$ are each independently a $C_1$-$C_{20}$ monovalent hydrocarbon group which may contain a heteroatom. Any two of $R^{414}$, $R^{415}$, and $R^{416}$ may bond together to form a ring with the sulfur atom to which they are attached. The monovalent hydrocarbon group may be straight, branched or cyclic, and examples thereof are as exemplified above for $R^{a1}$ to $R^{a3}$ in formula (Aa).

The subscript u is an integer of 1 to 3, v is an integer of 1 to 5, and w is an integer of 0 to 3.

The alkyl, alkoxy, acyl, acyloxy, and alkenyl groups may be straight, branched or cyclic.

Examples of the cation in the sulfonium salt having formula (3-1) or (3-3) are as exemplified above as the sulfonium cation having formula (Aa). Examples of the cation in the iodonium salt having formula (3-2) or (3-4) are as exemplified above as the iodonium cation having formula (Ab).

Examples of the anion in the onium salts having formulae (3-1) to (3-4) are shown below, but not limited thereto.

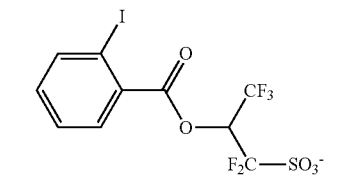

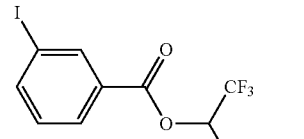

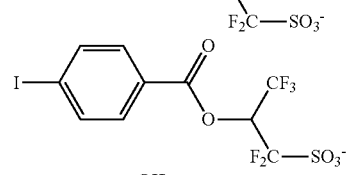

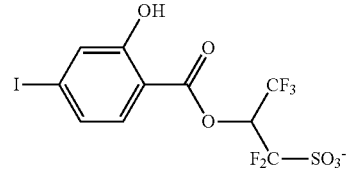

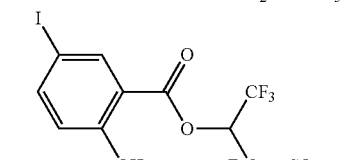

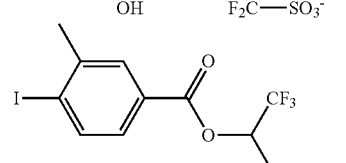

177
-continued
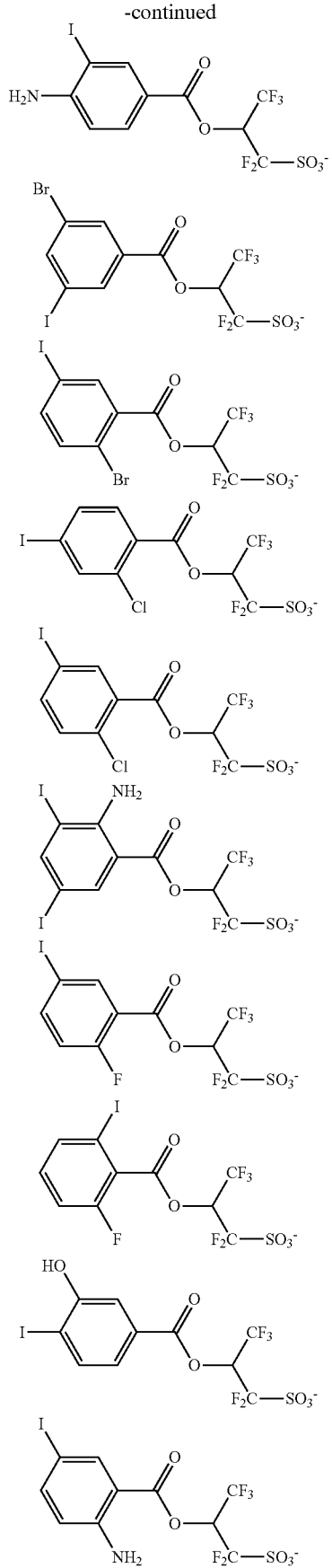
178
-continued
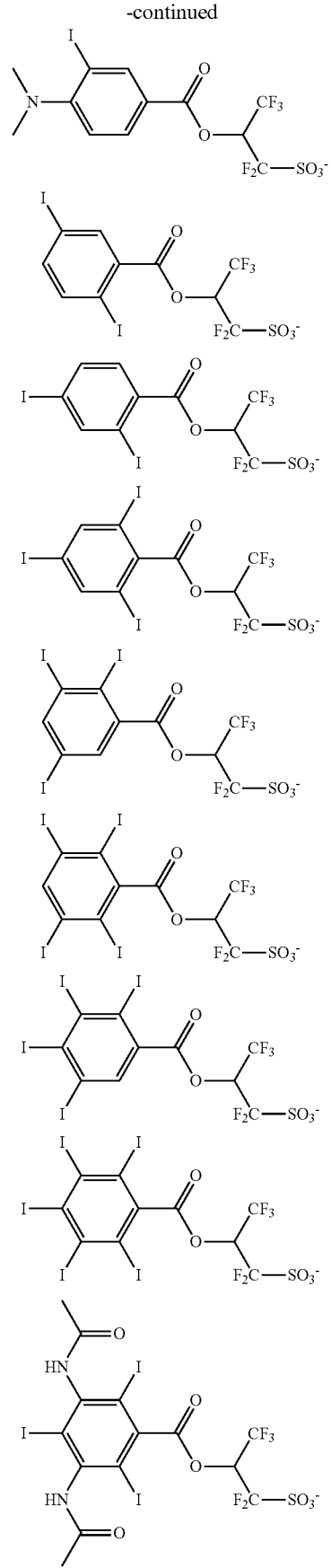

179
-continued
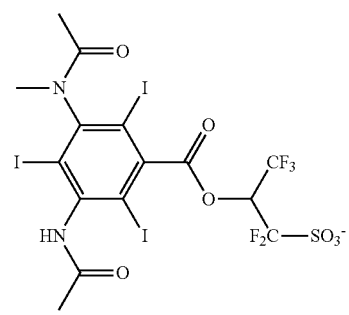
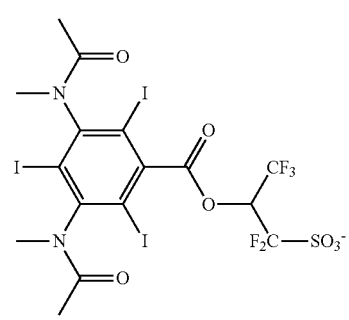
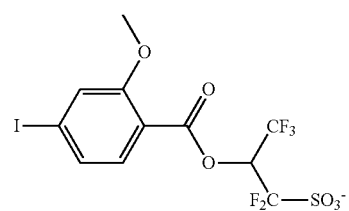
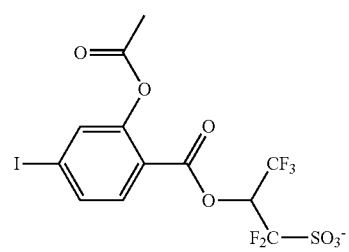
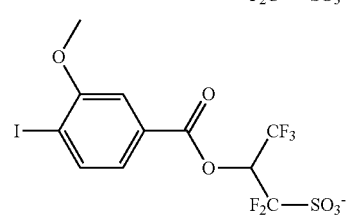
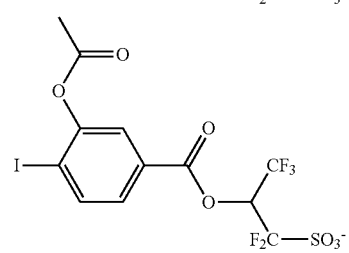
180
-continued
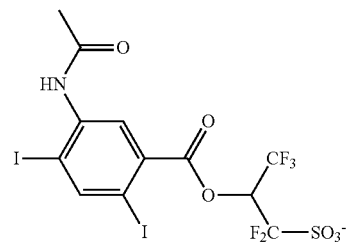
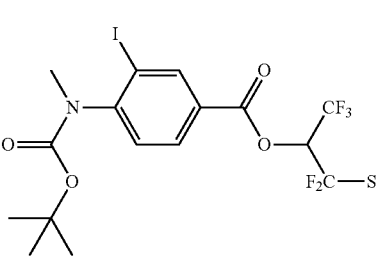
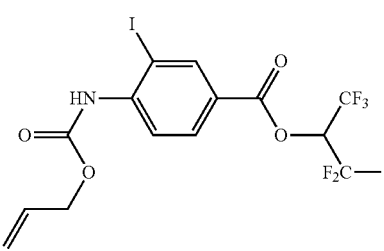
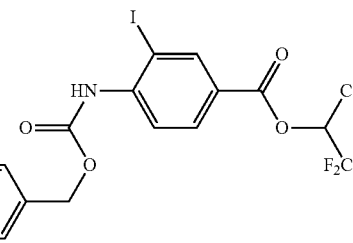
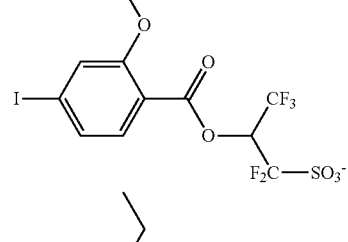
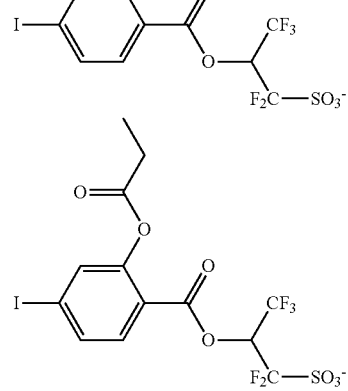

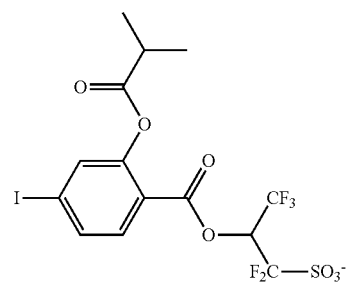
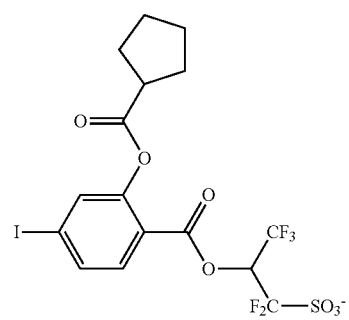
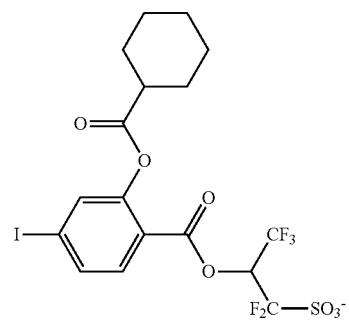
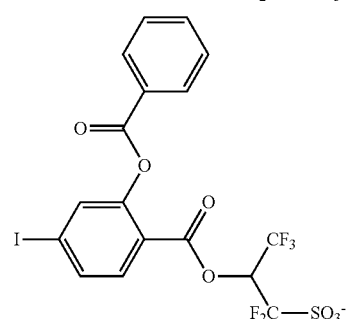
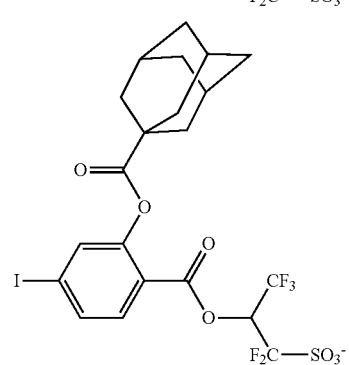
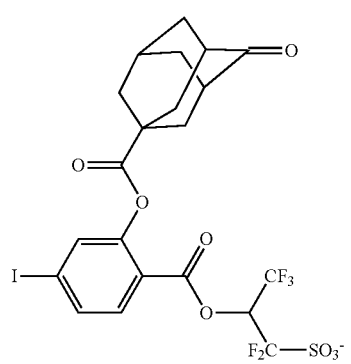
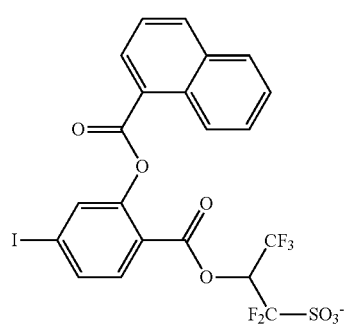
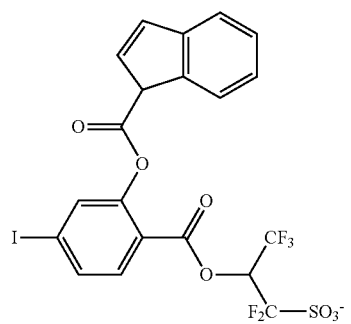
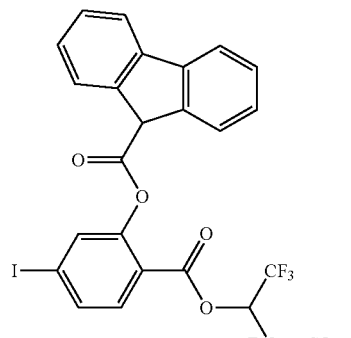
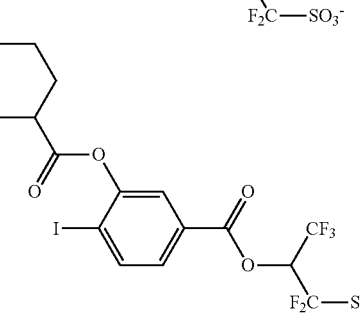

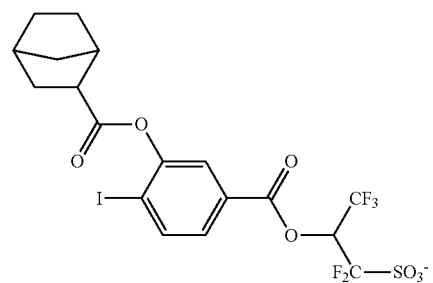
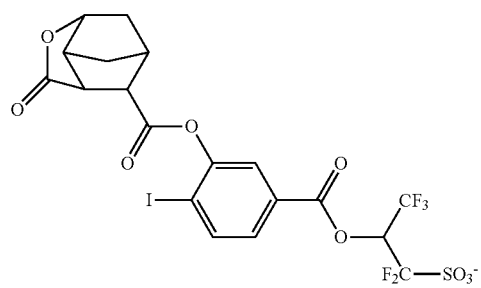
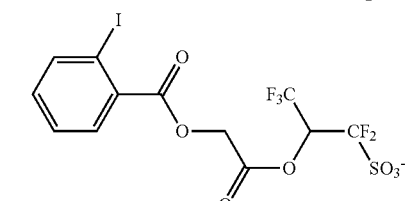
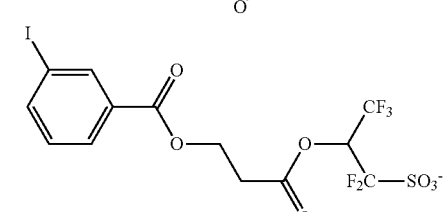
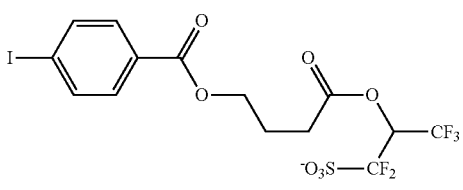
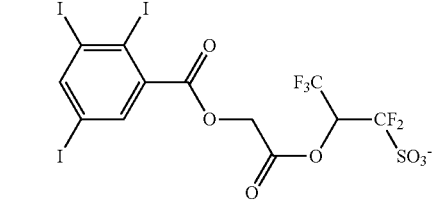
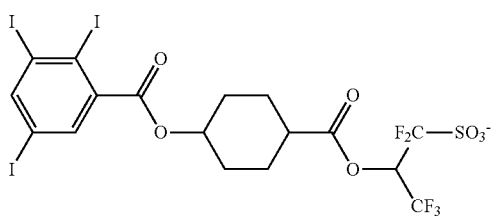
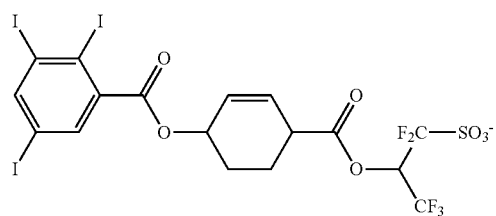
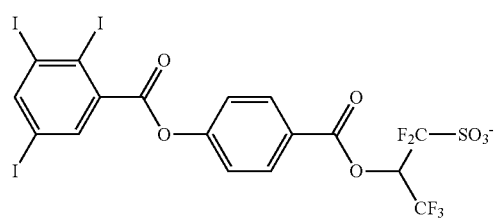
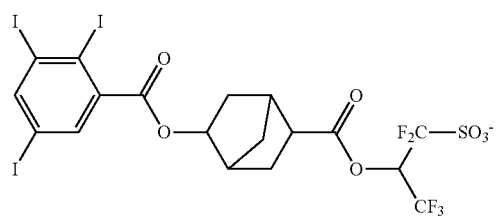
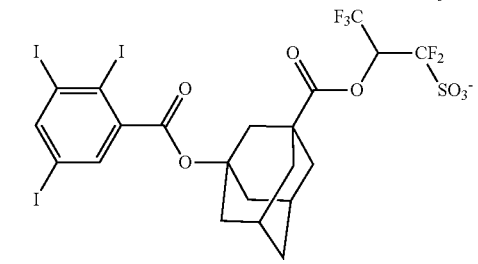
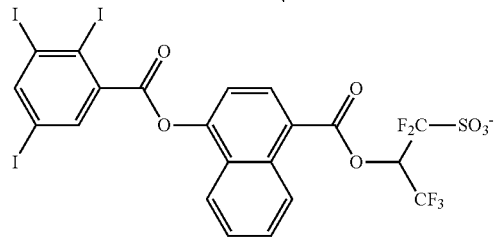
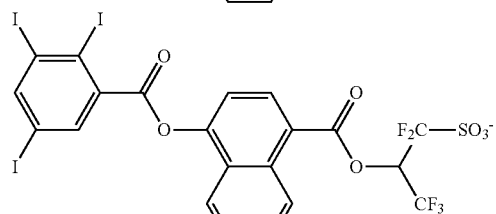
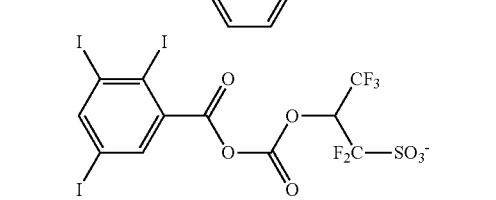

185
-continued
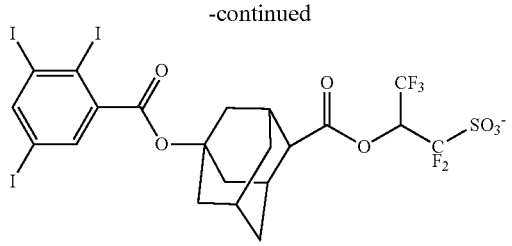
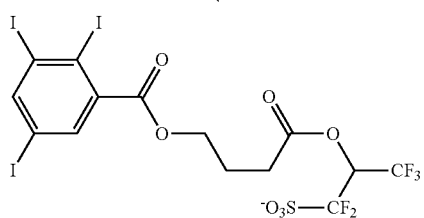
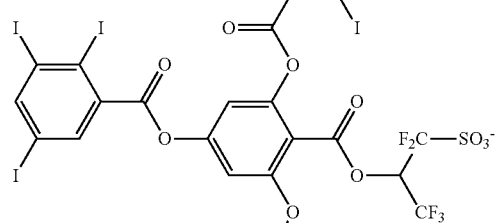
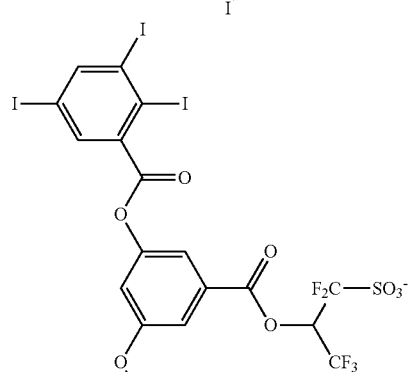
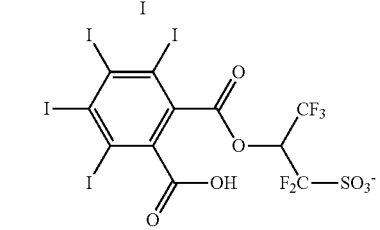
186
-continued
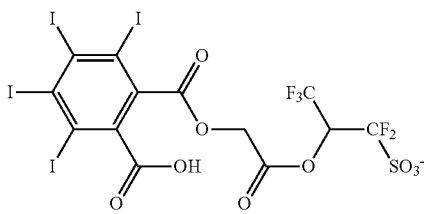
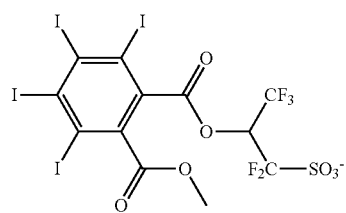
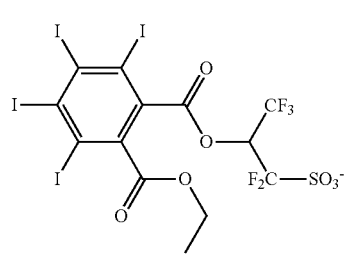
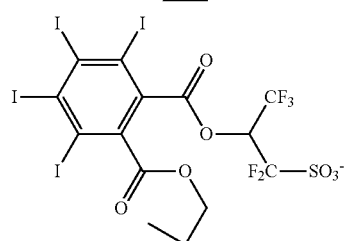

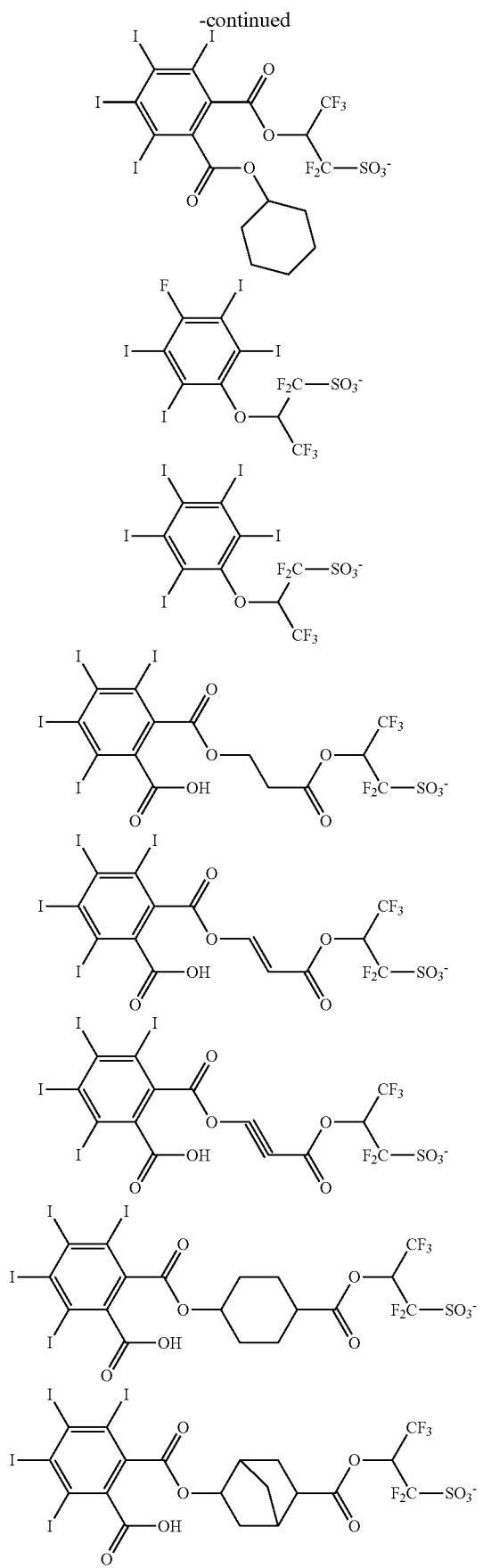
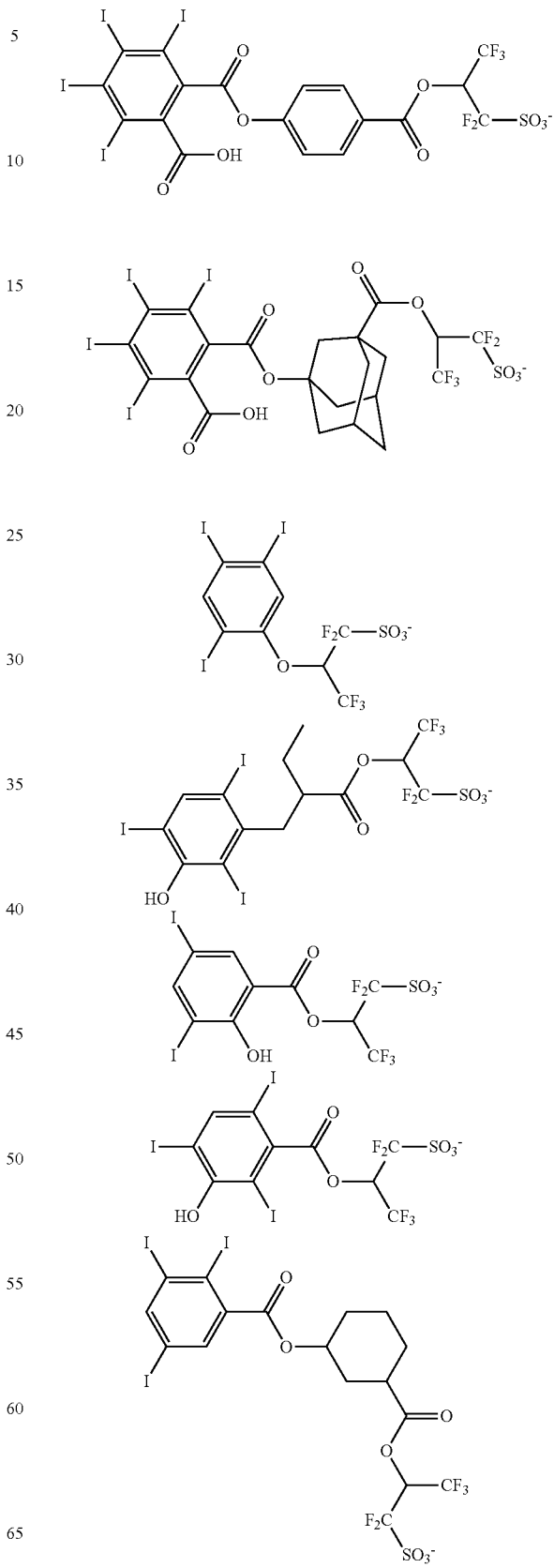

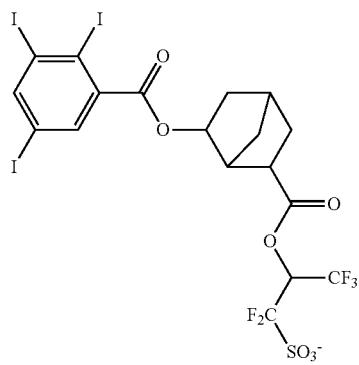
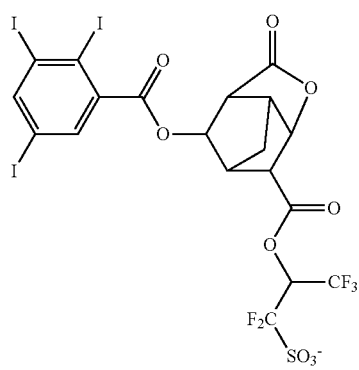
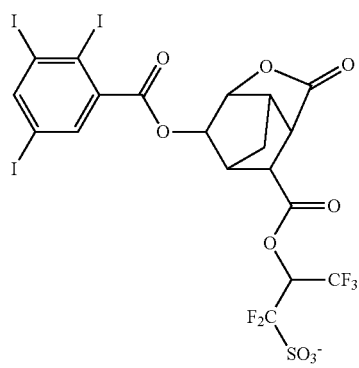
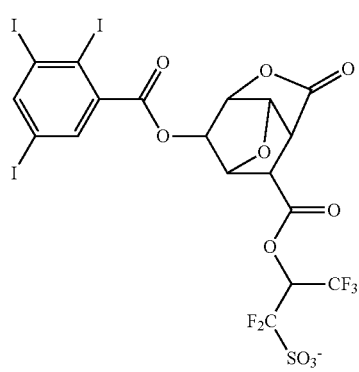
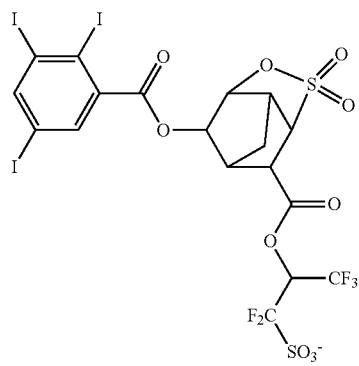
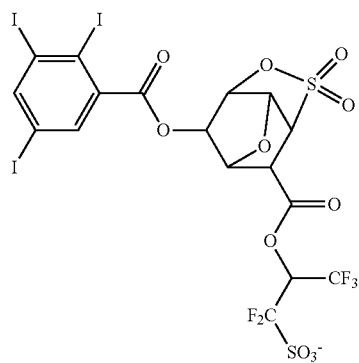
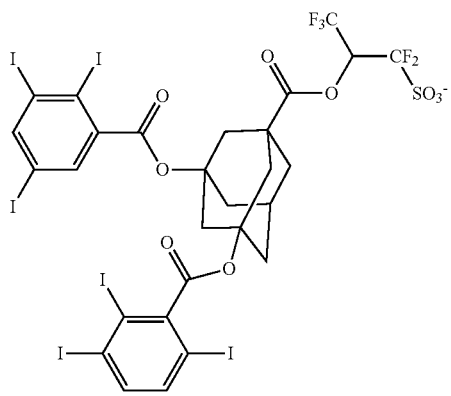
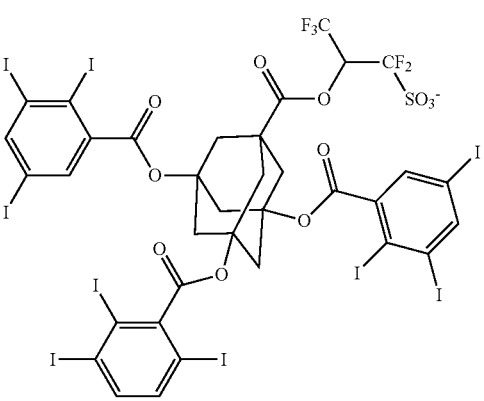

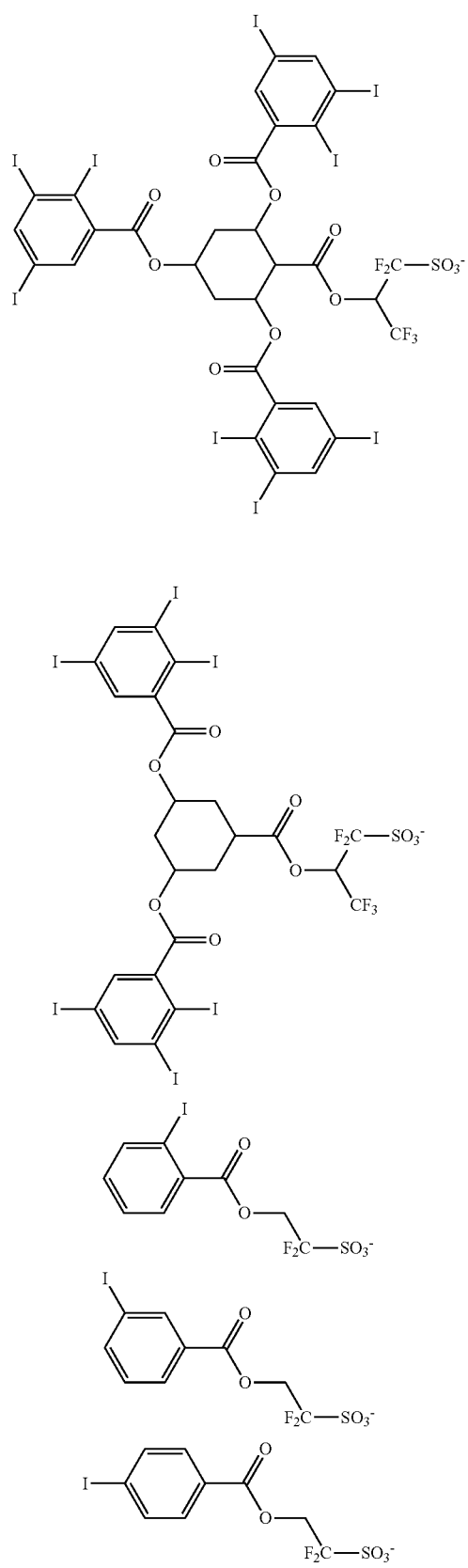
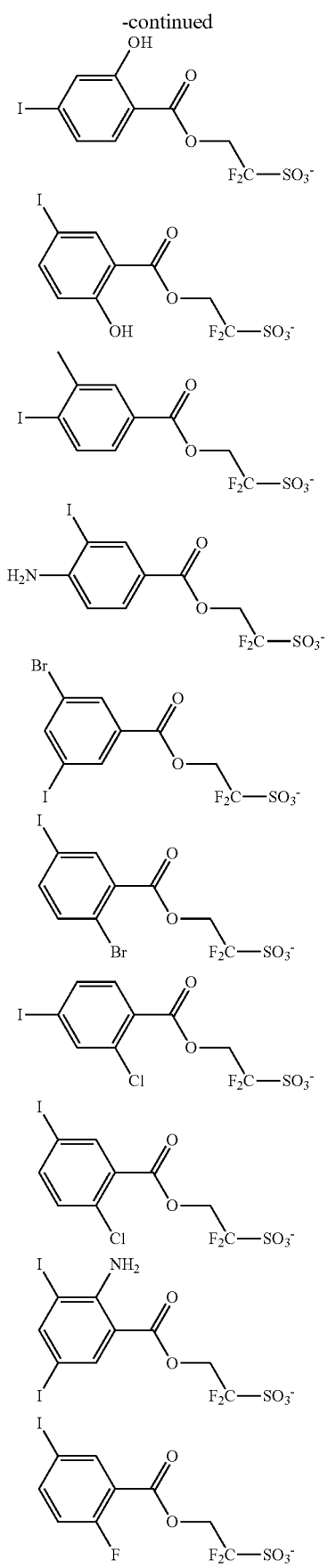

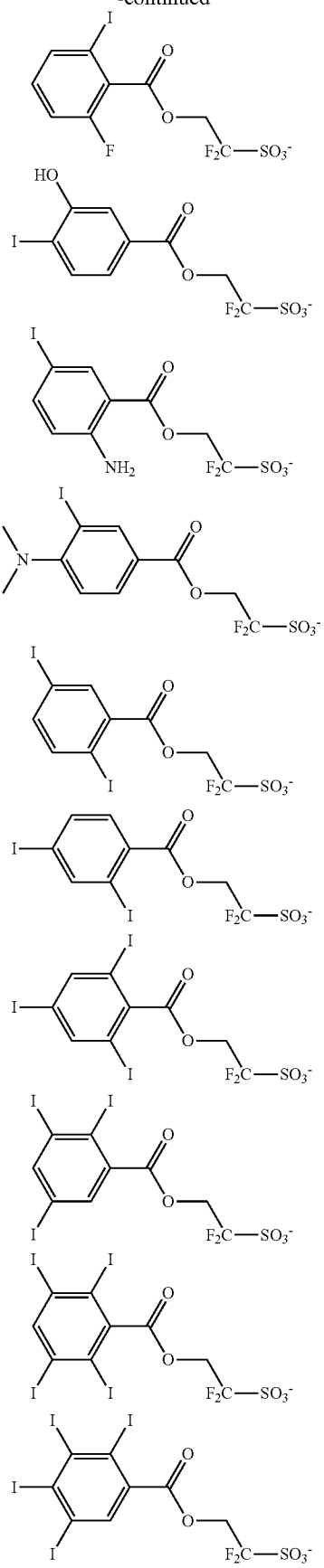
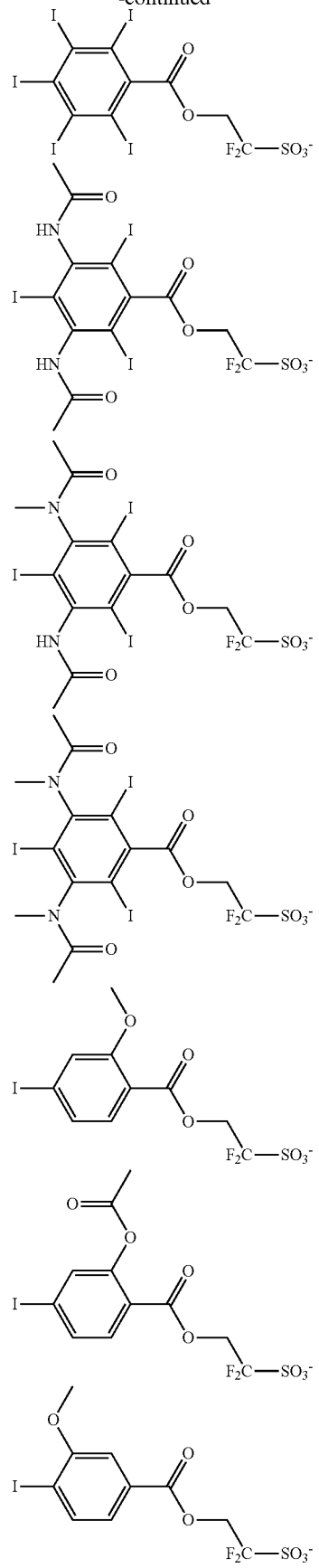

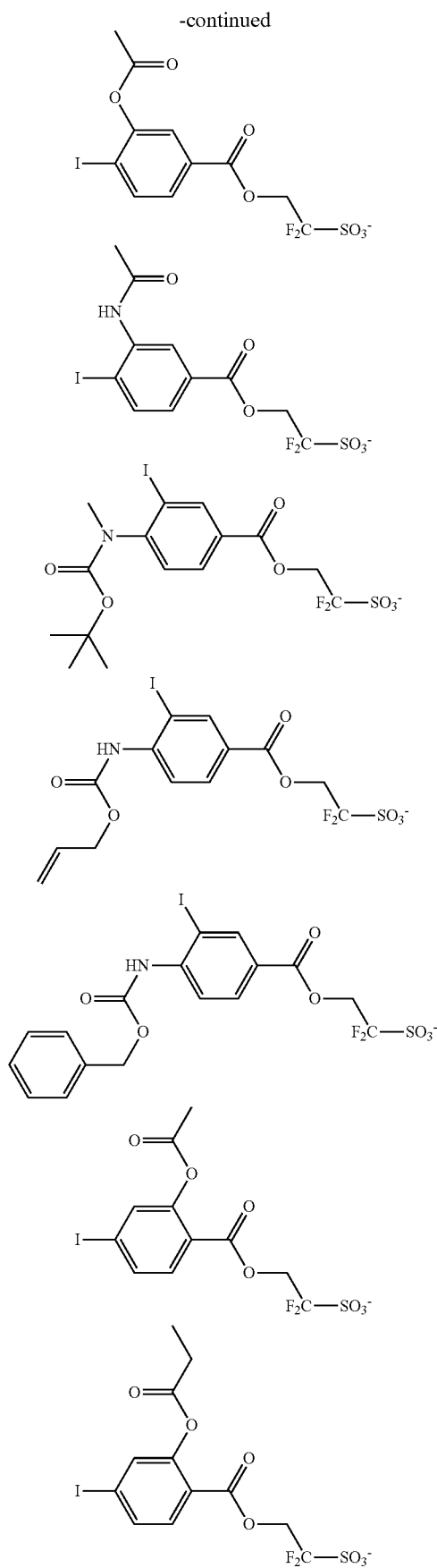
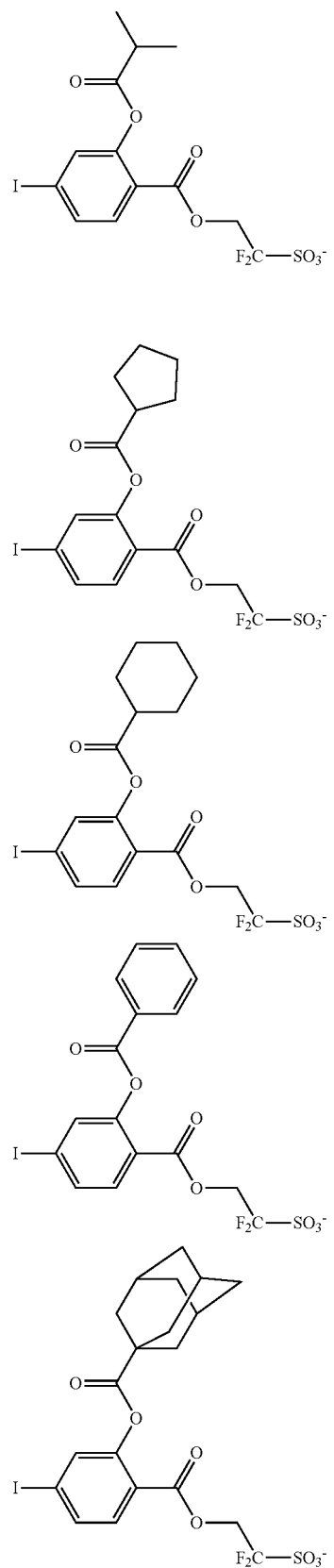

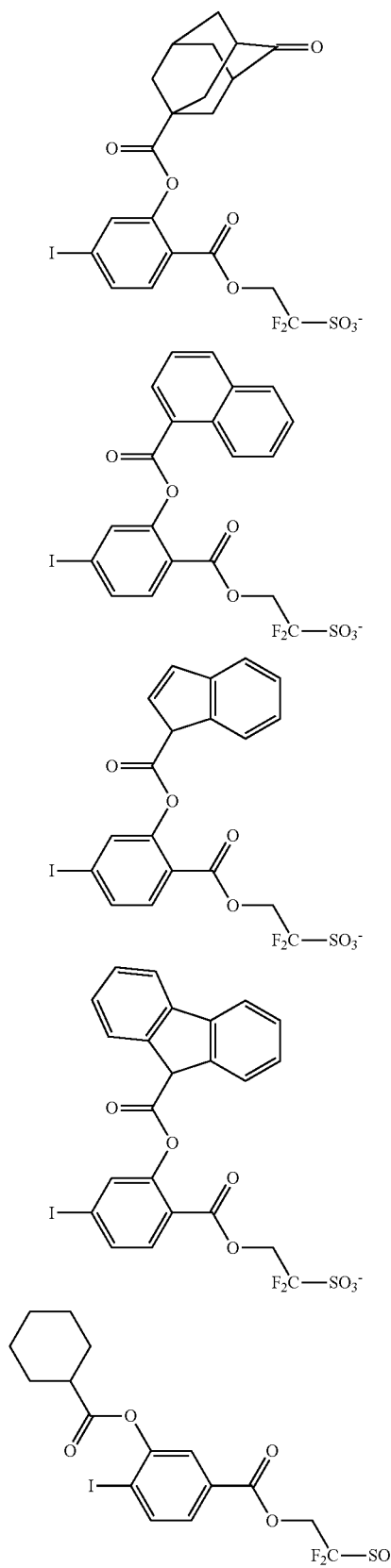
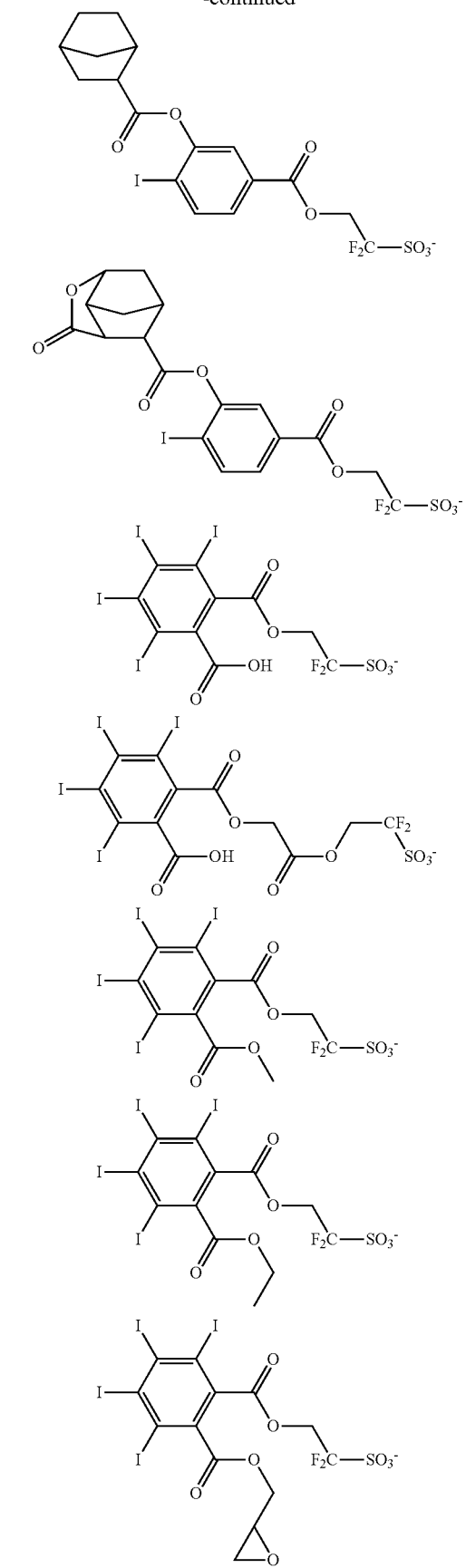

199
-continued
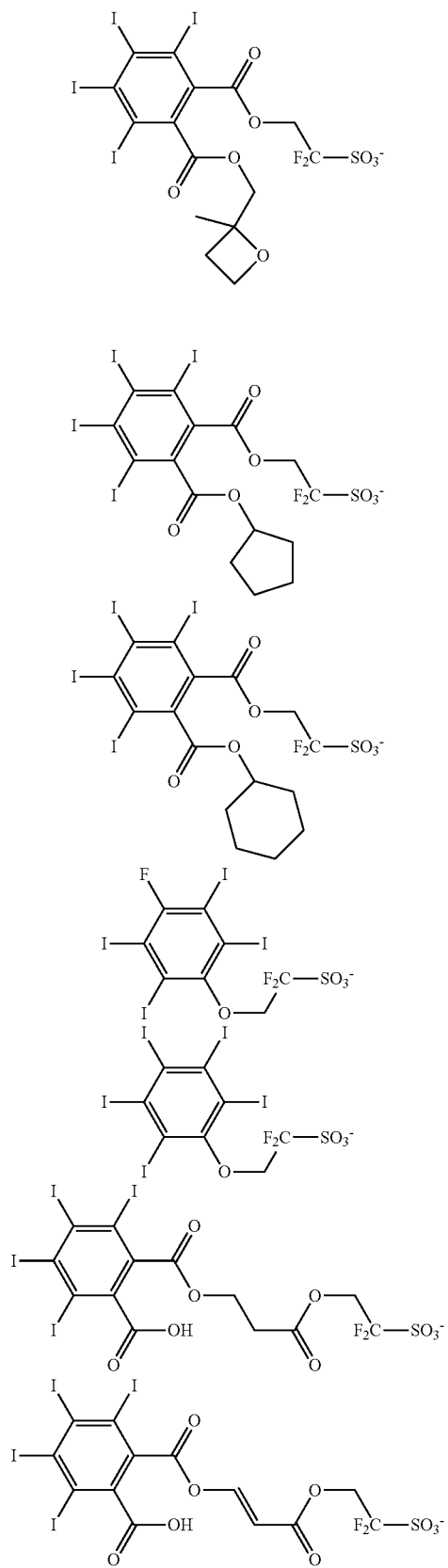
200
-continued
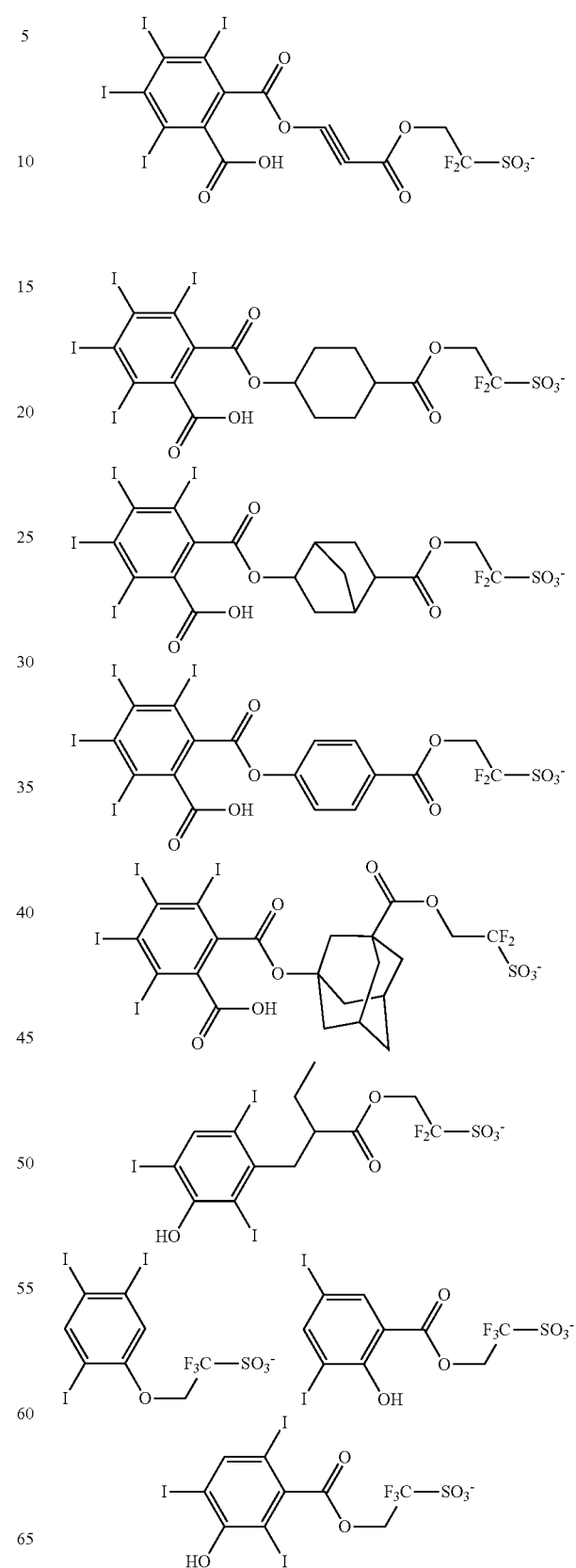

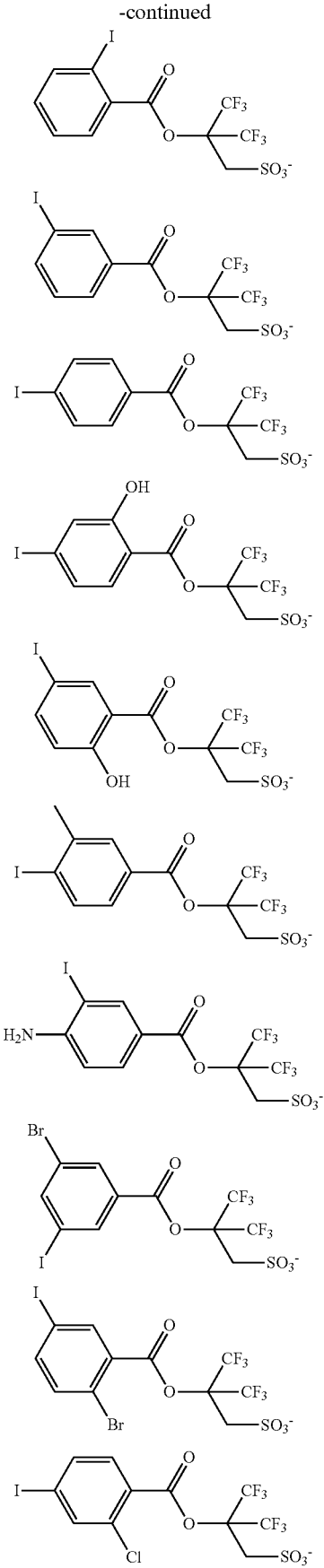
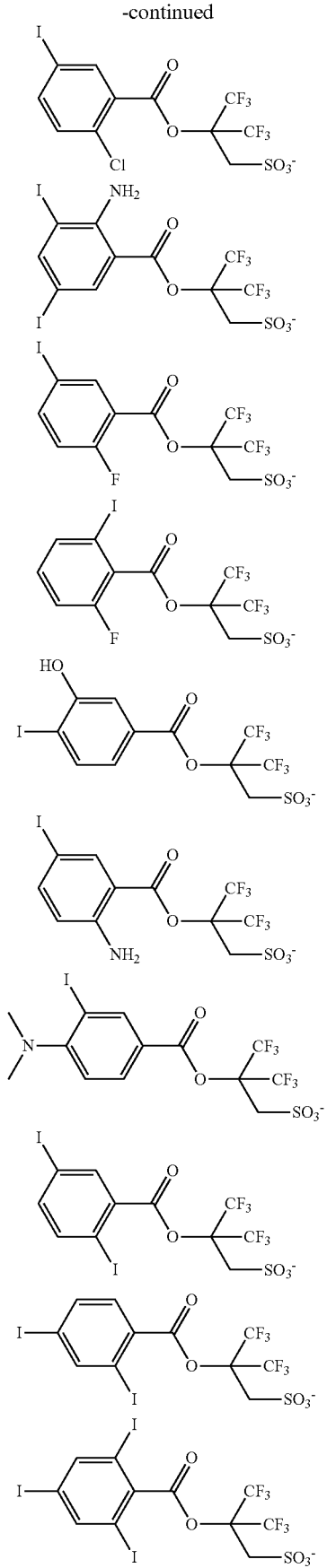

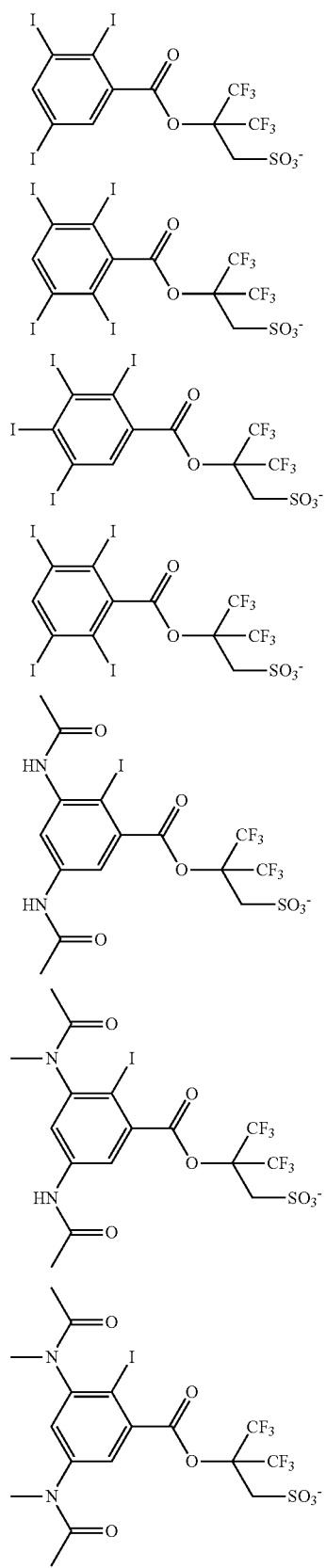
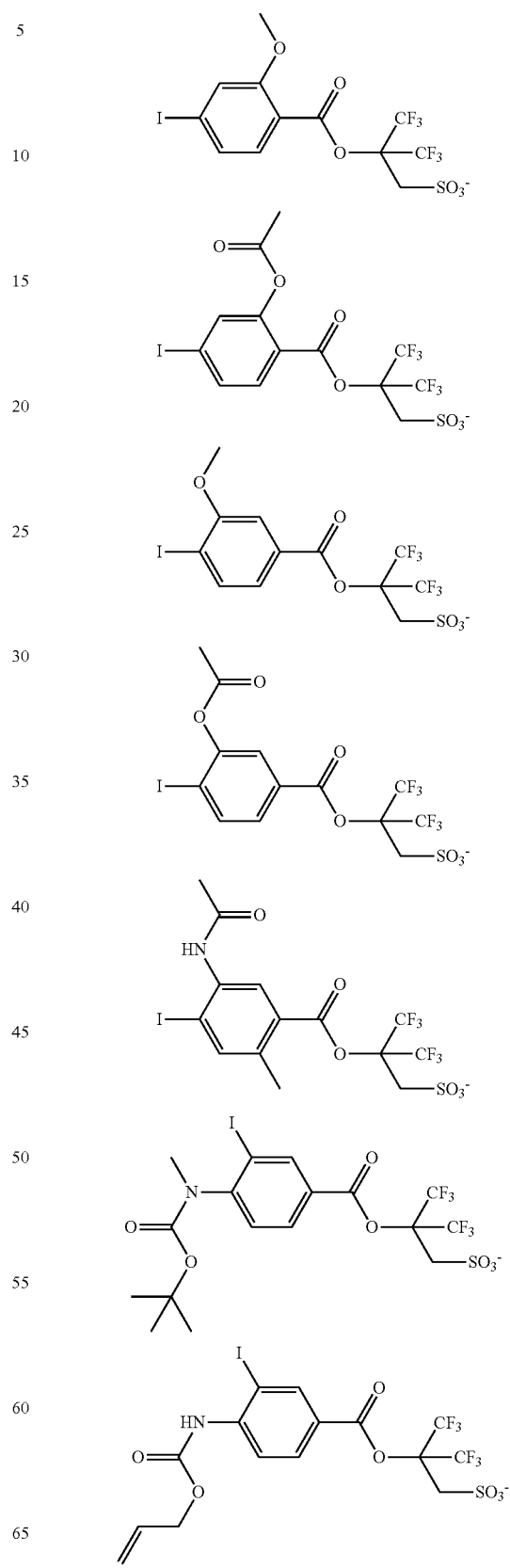

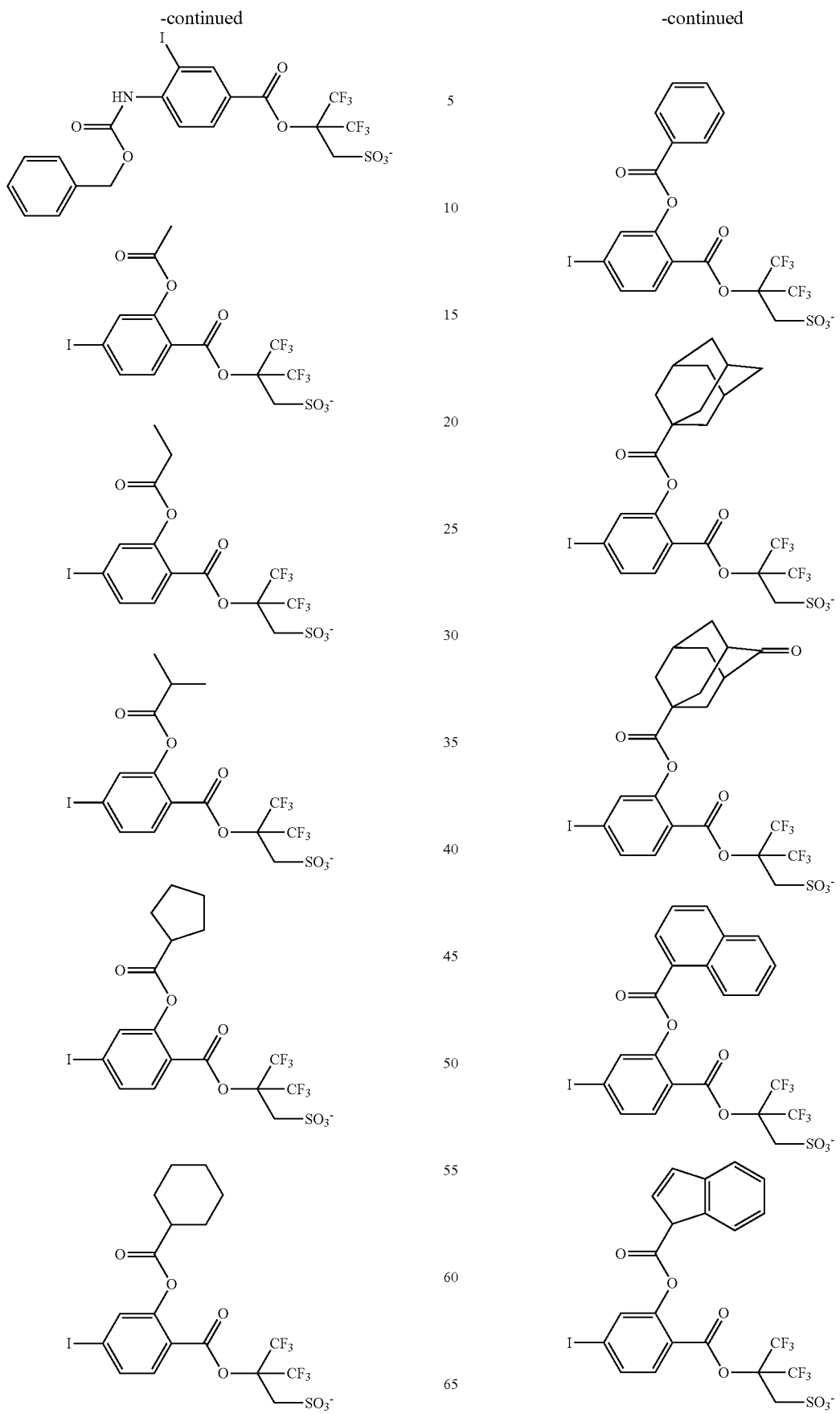

207
-continued
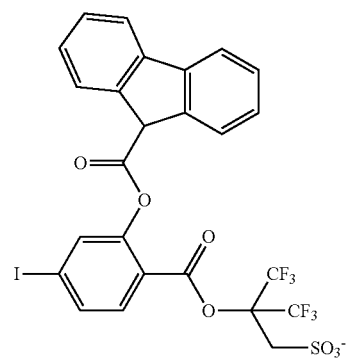
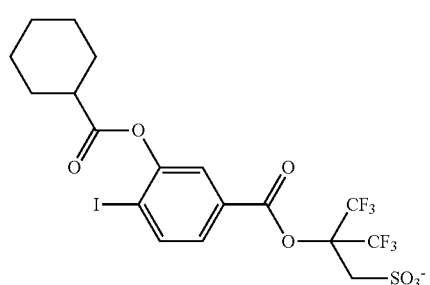
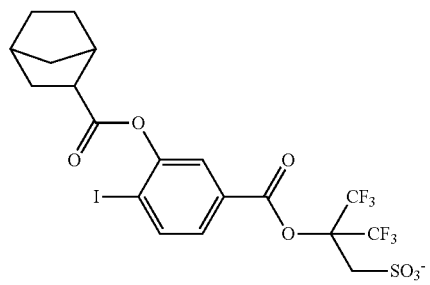
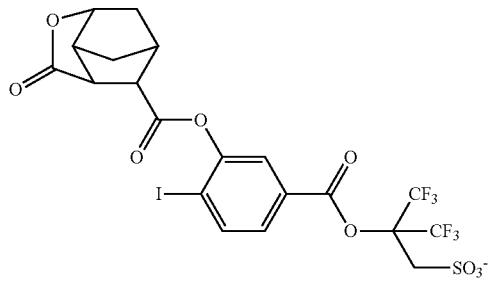
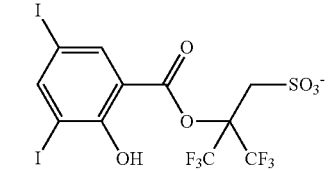
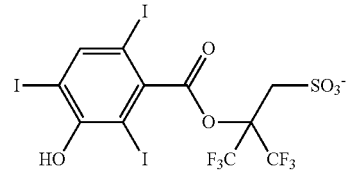
208
-continued
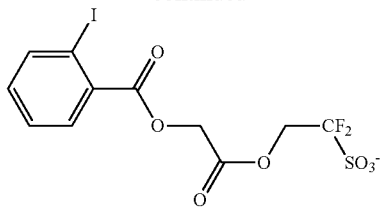
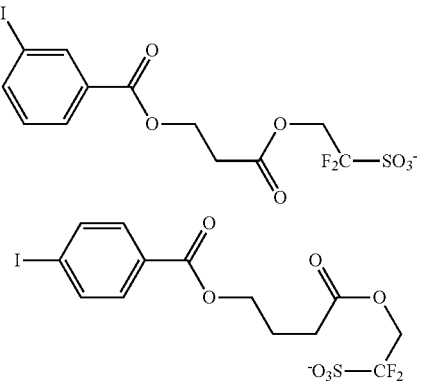
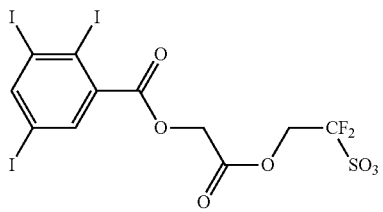
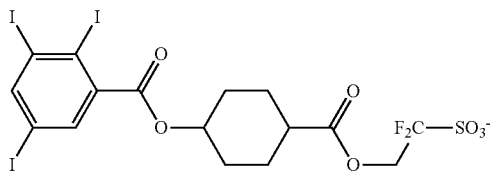
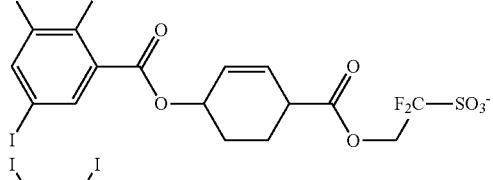
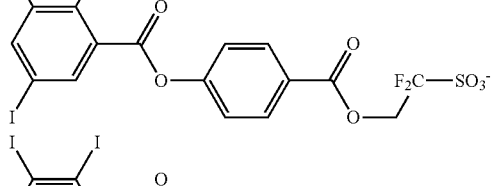
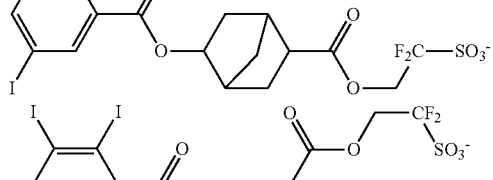
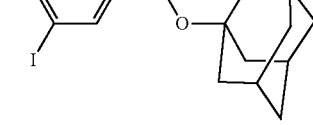

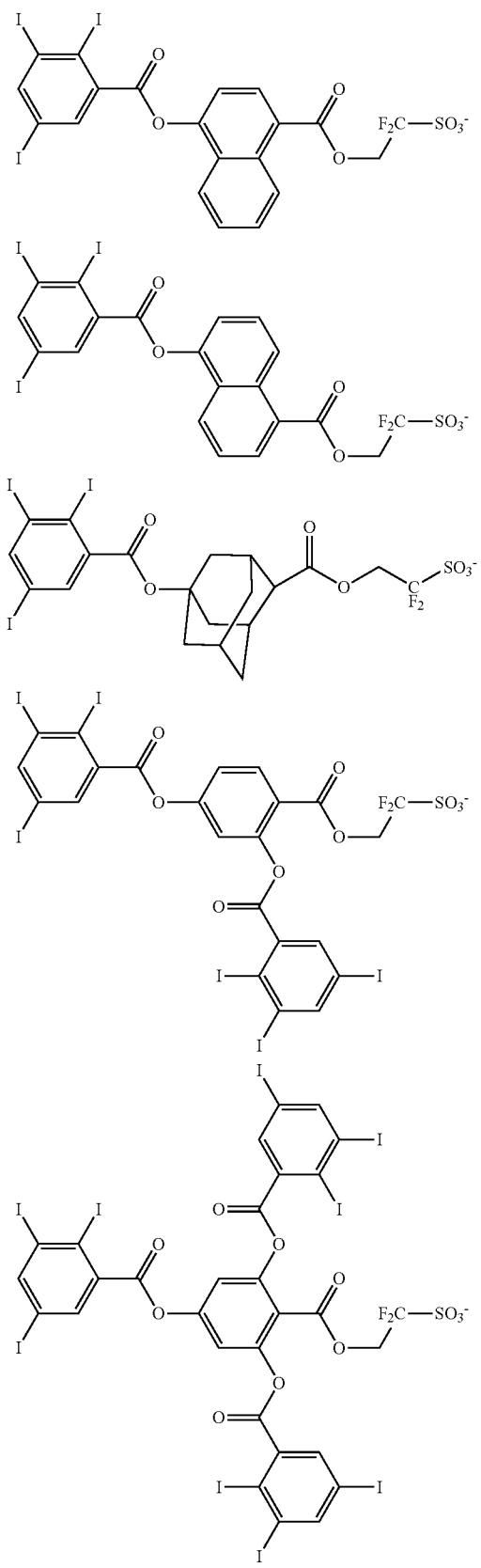
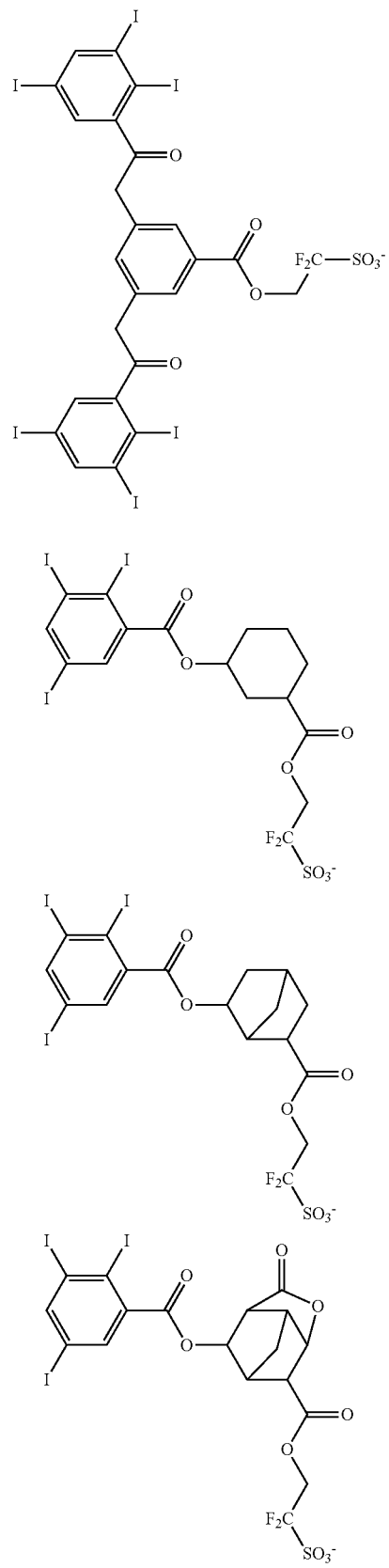

211
-continued
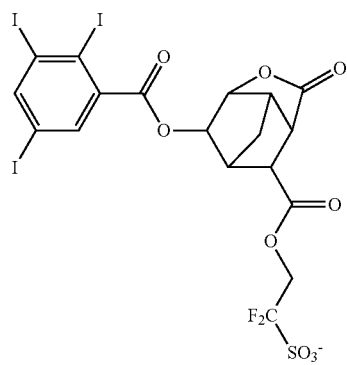
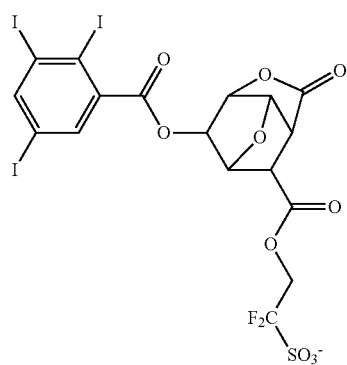
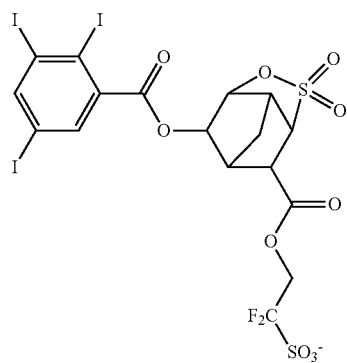
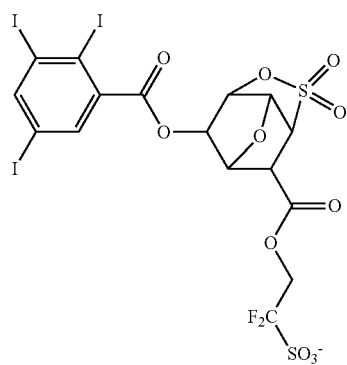
212
-continued
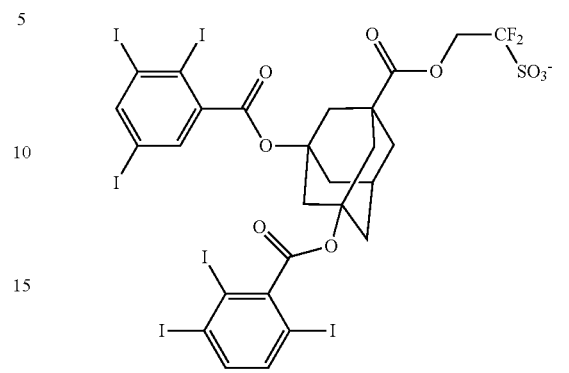
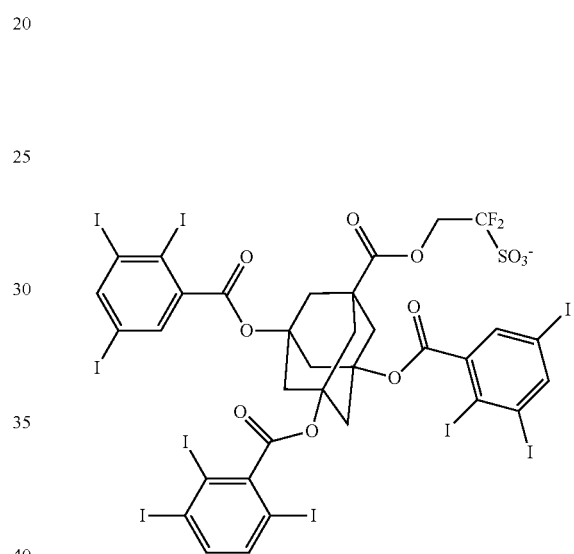
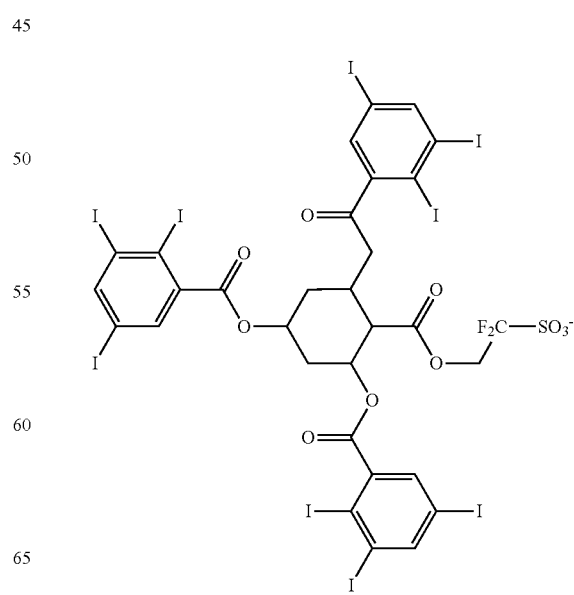

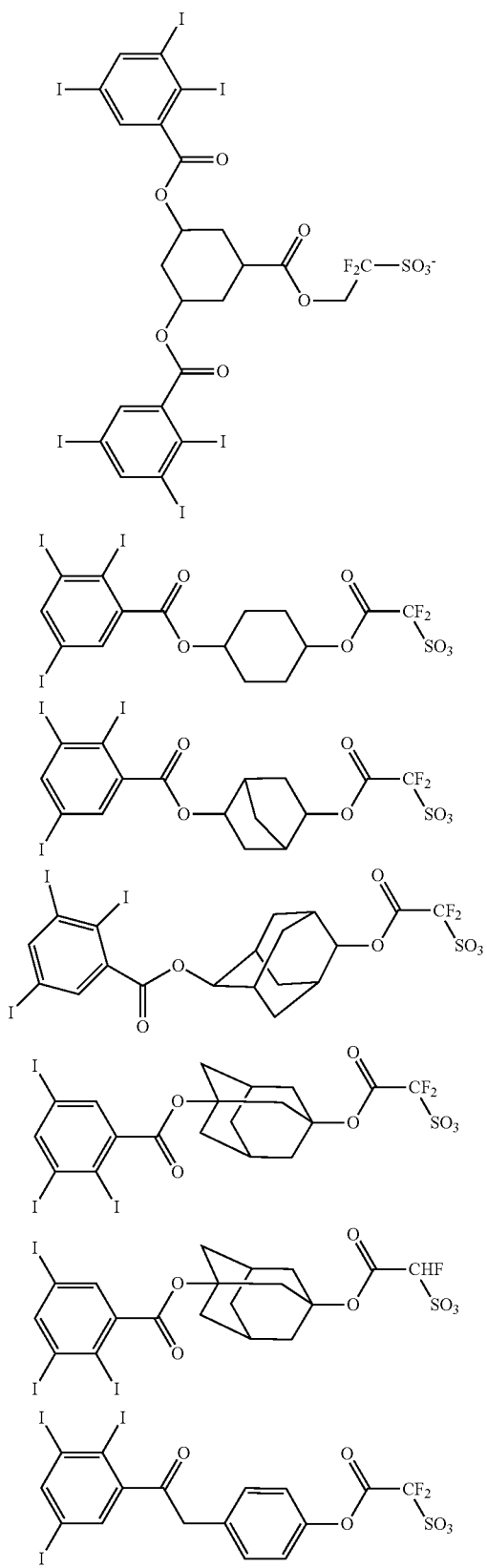
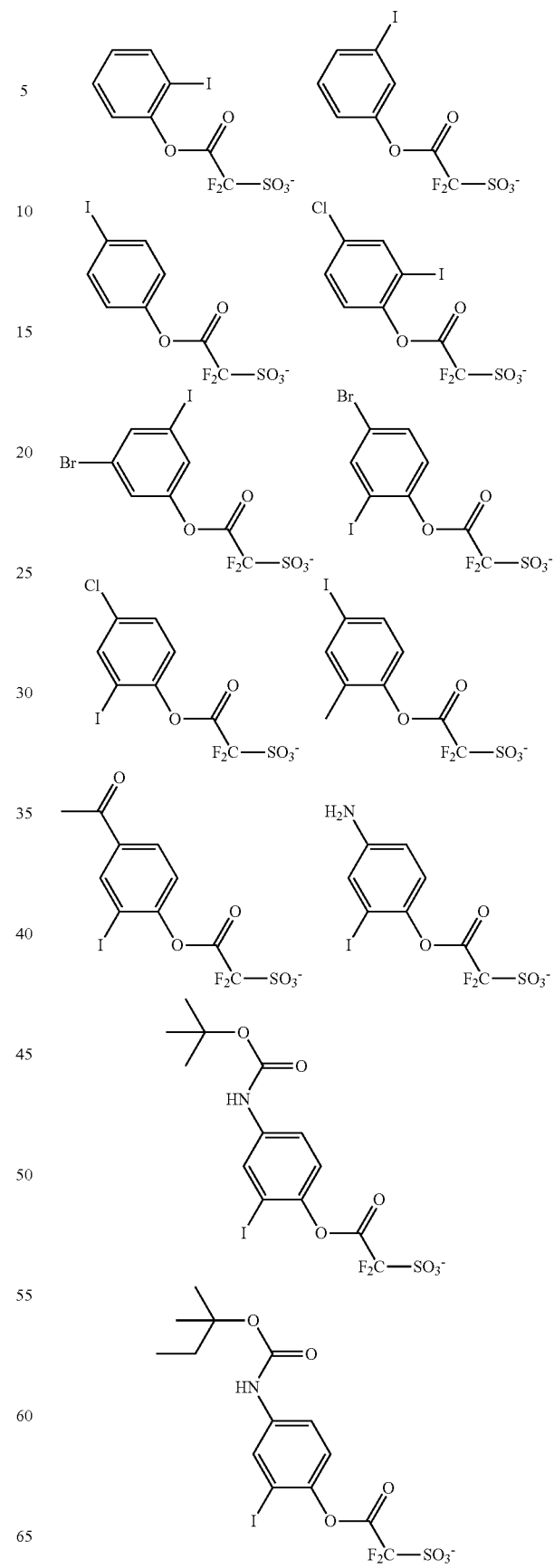

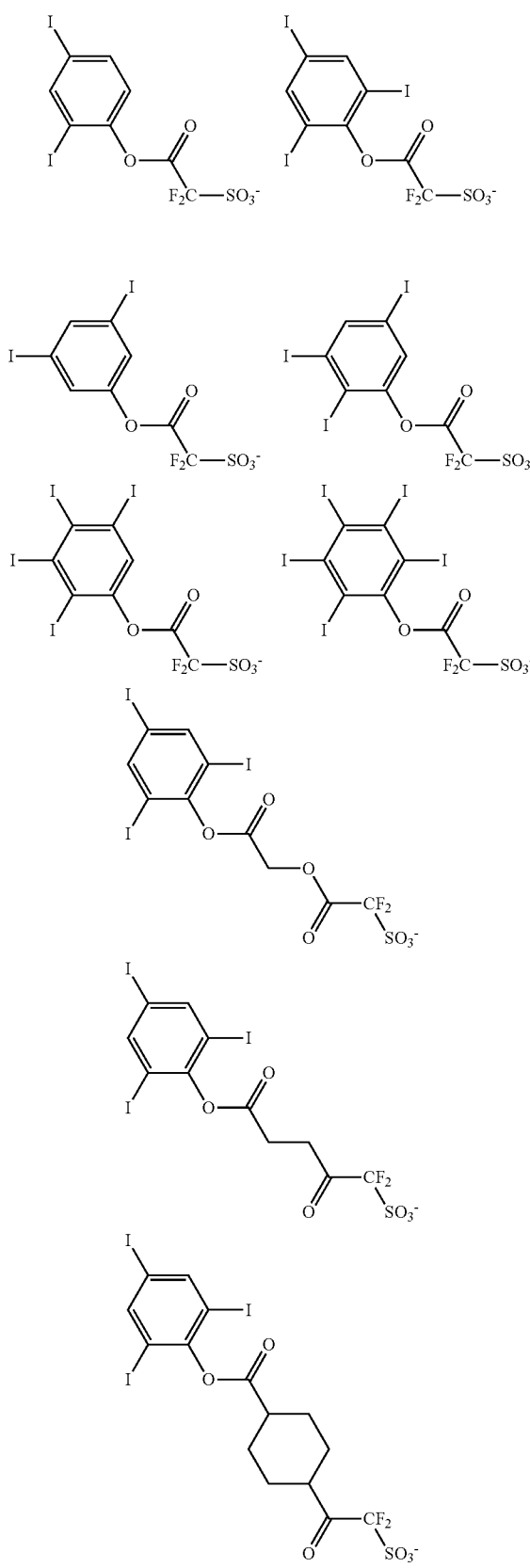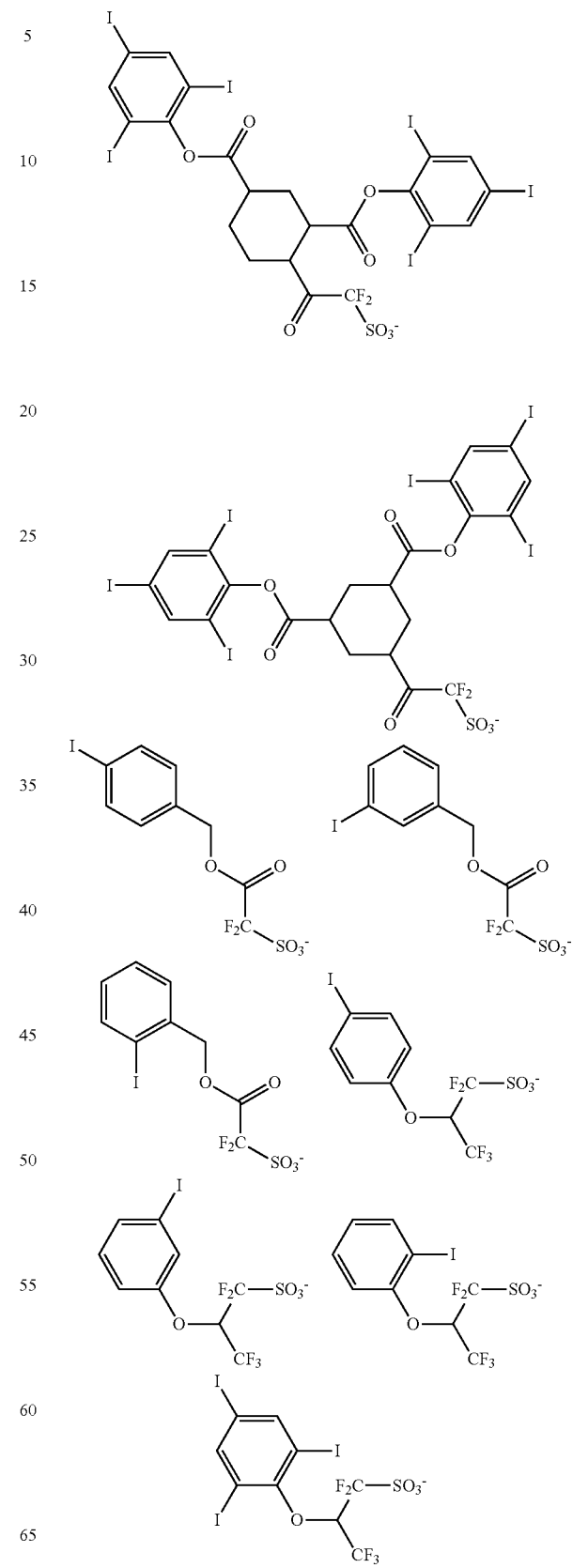

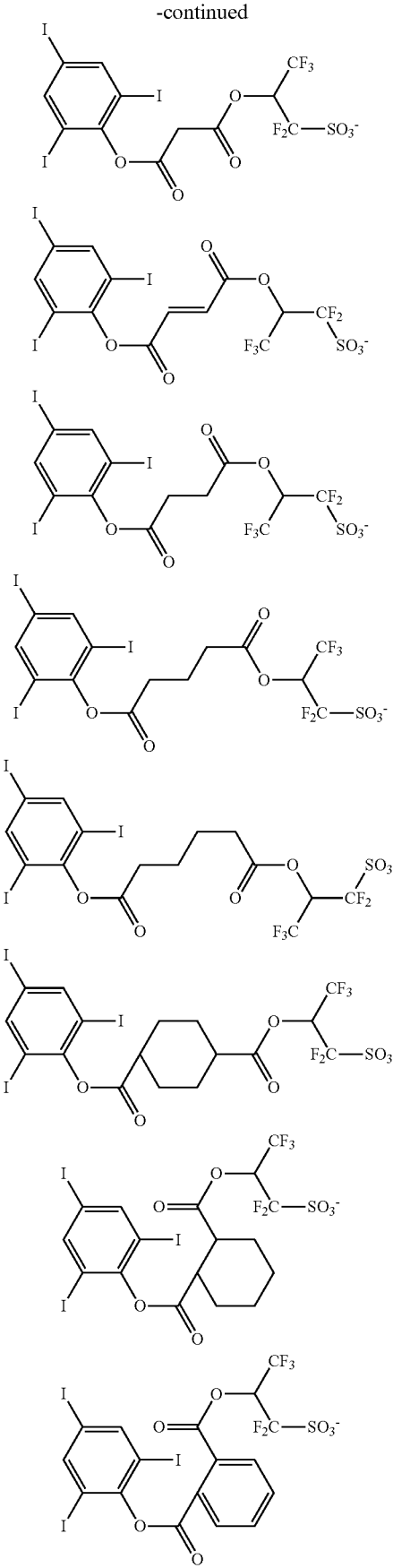
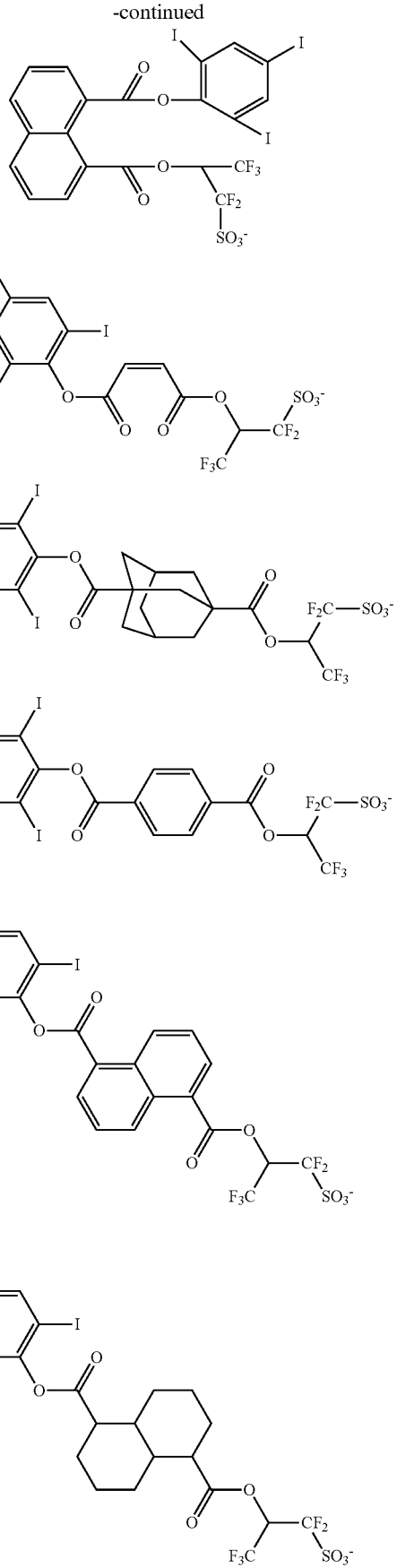

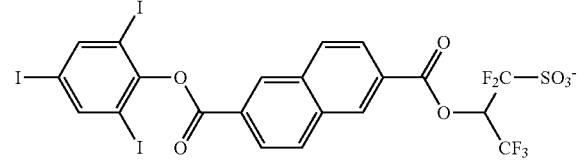
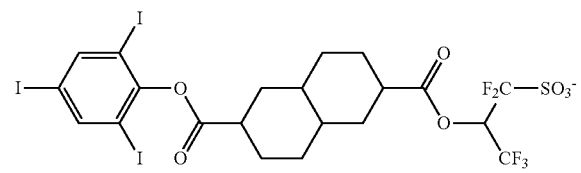
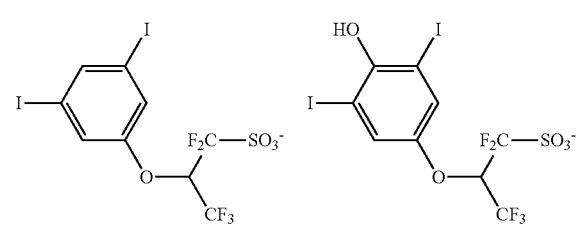
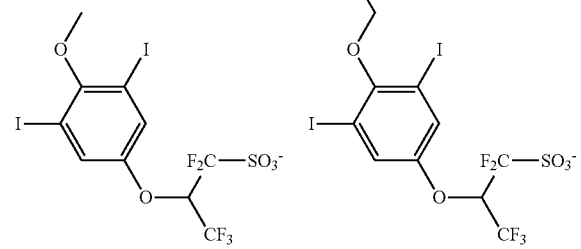
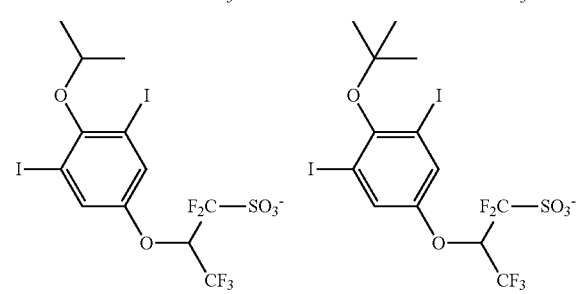
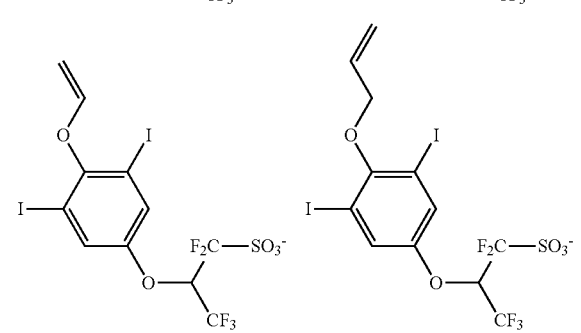
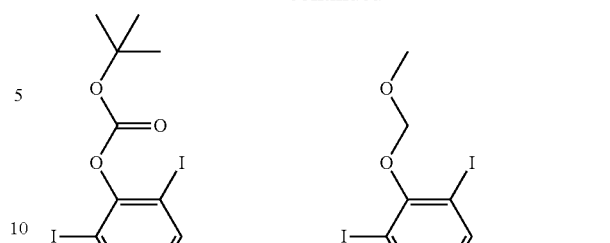
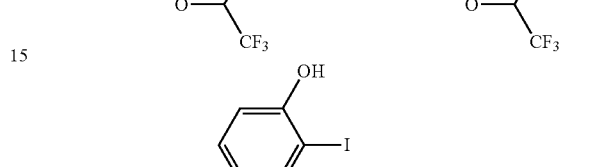
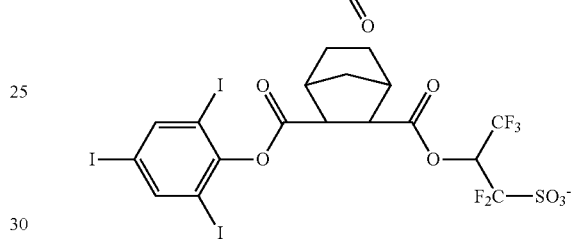
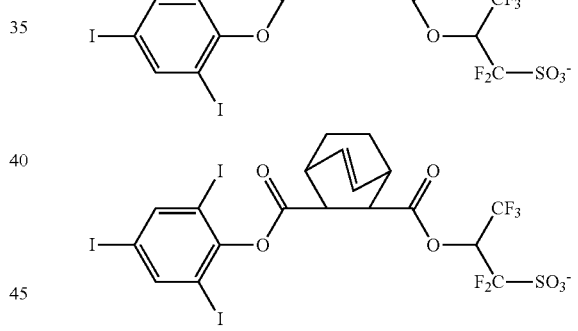
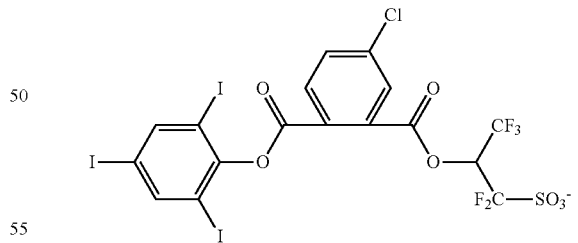
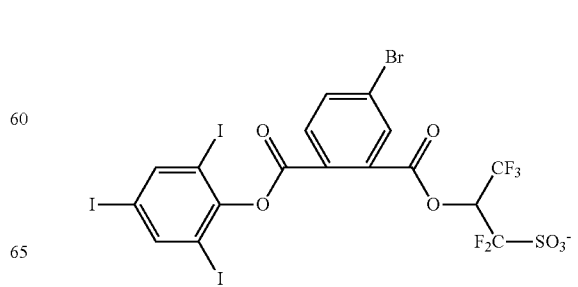

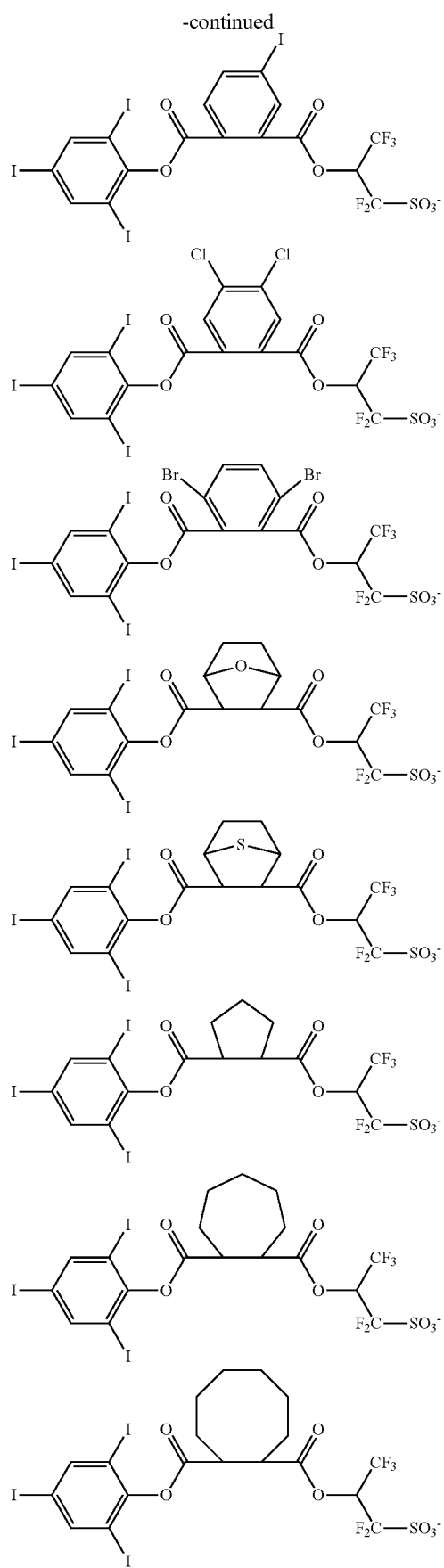
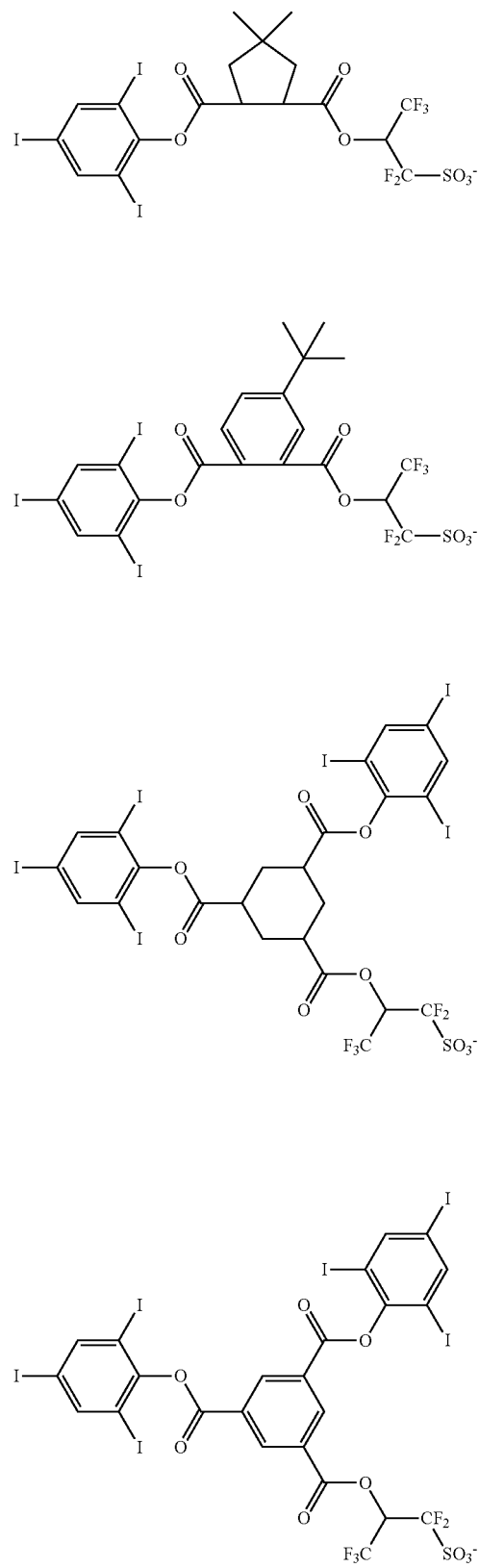

223
-continued
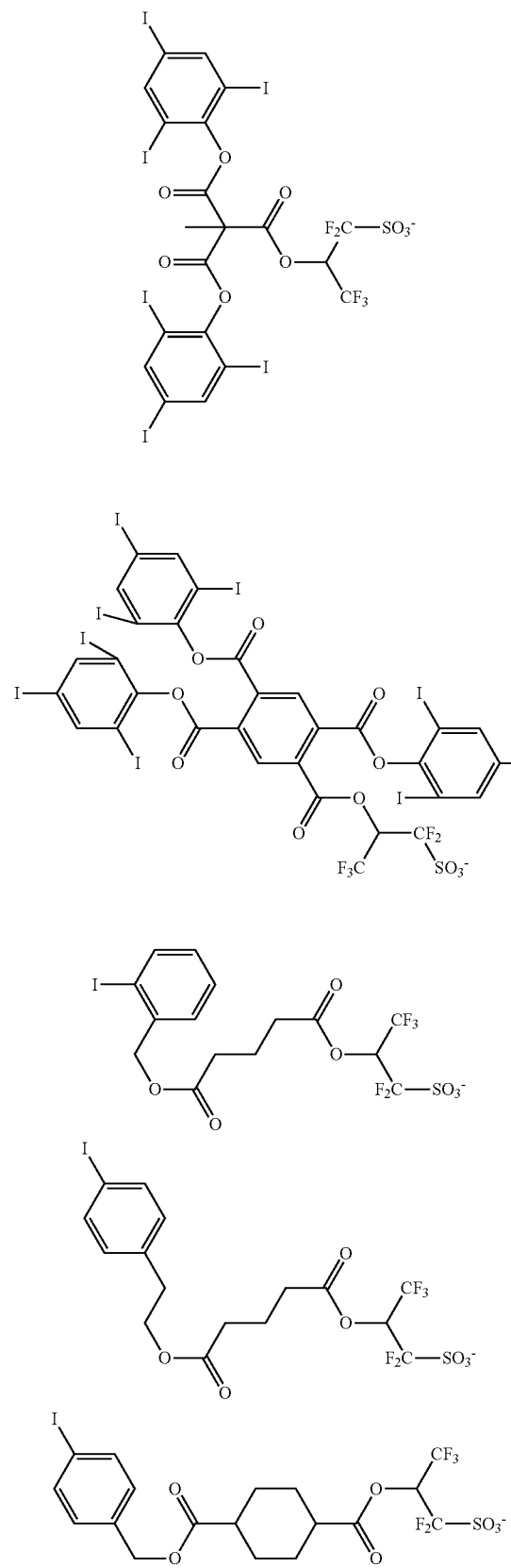
224
-continued
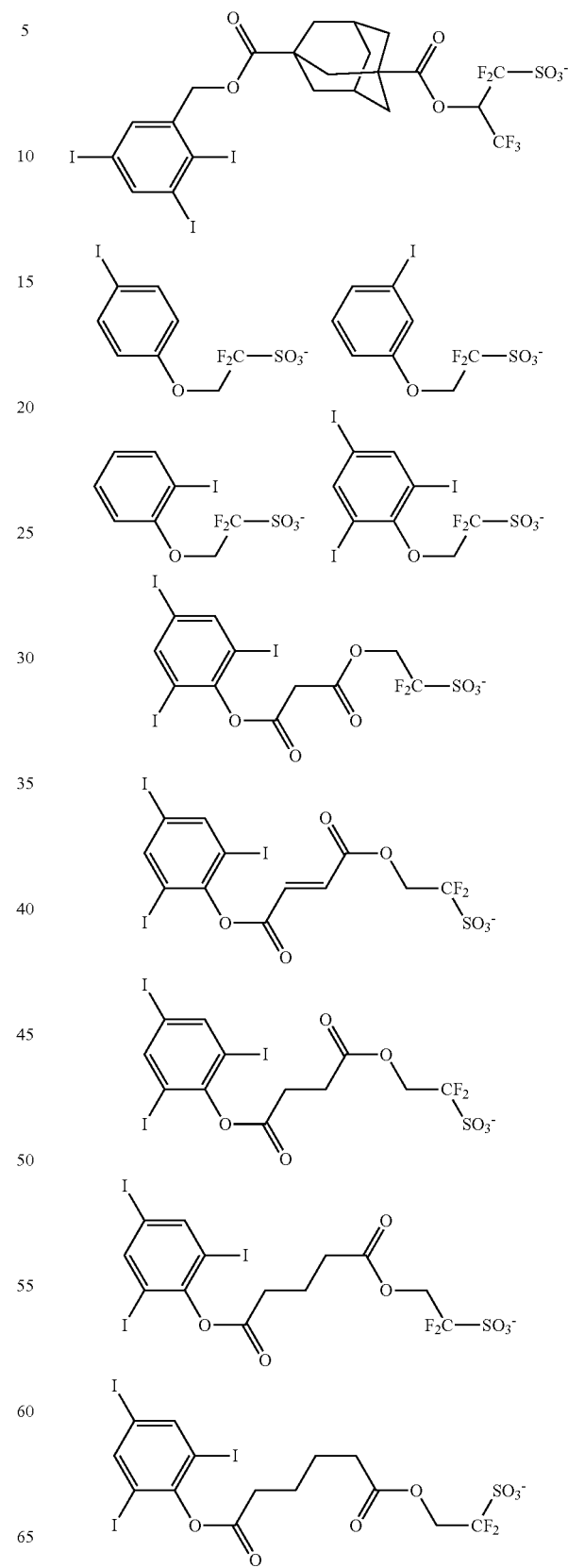

-continued
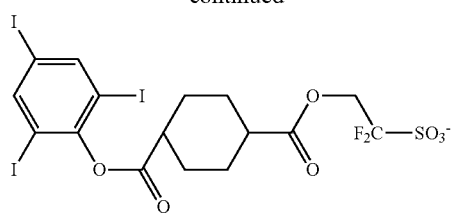
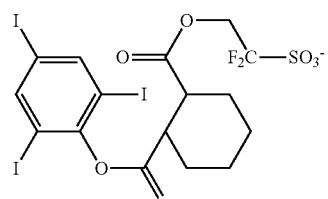
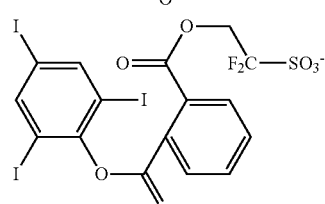
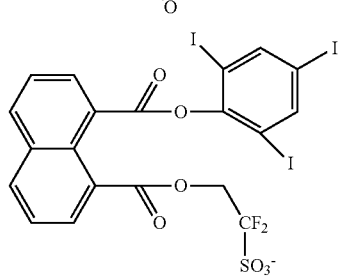
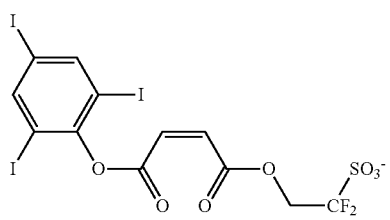
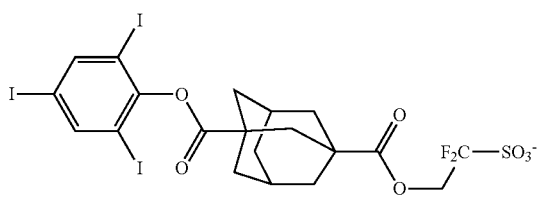
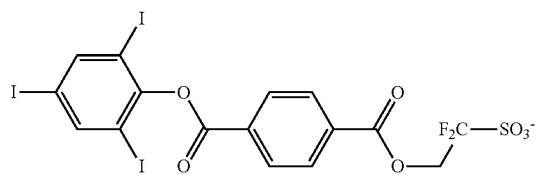
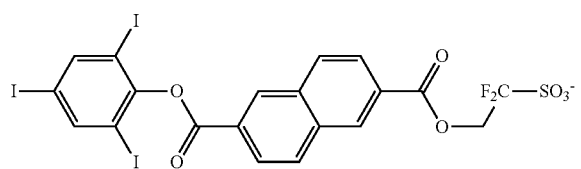
-continued
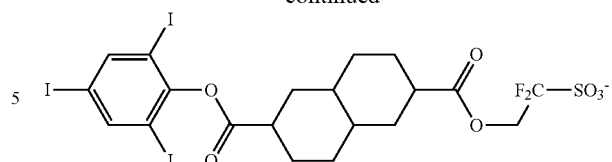
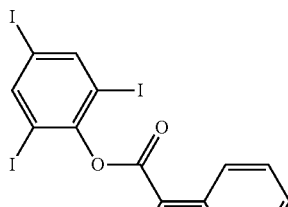
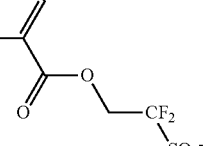
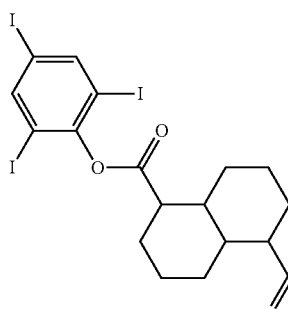
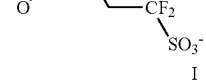
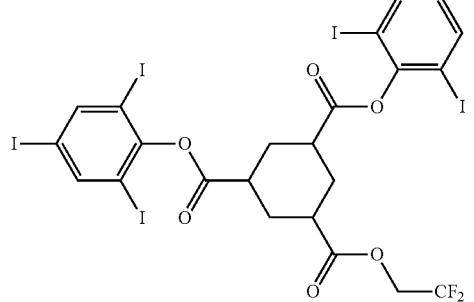
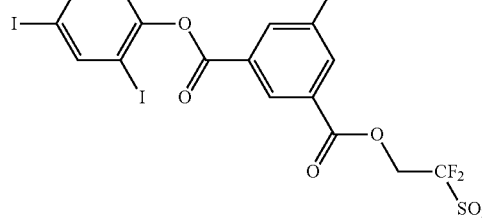

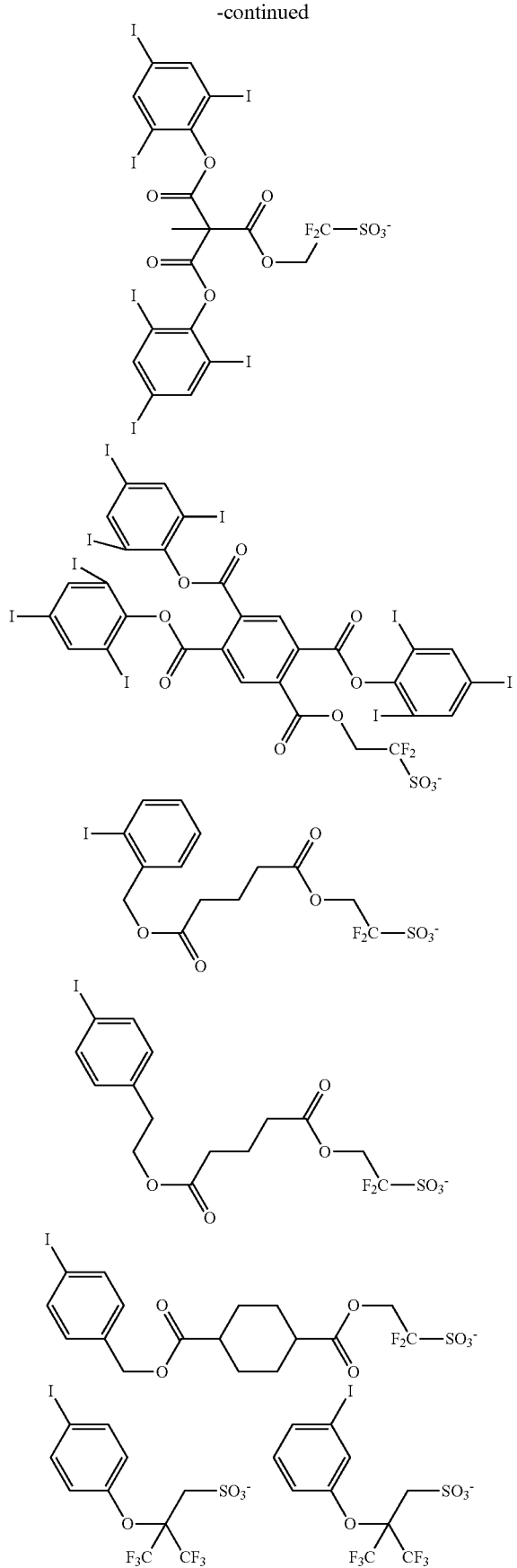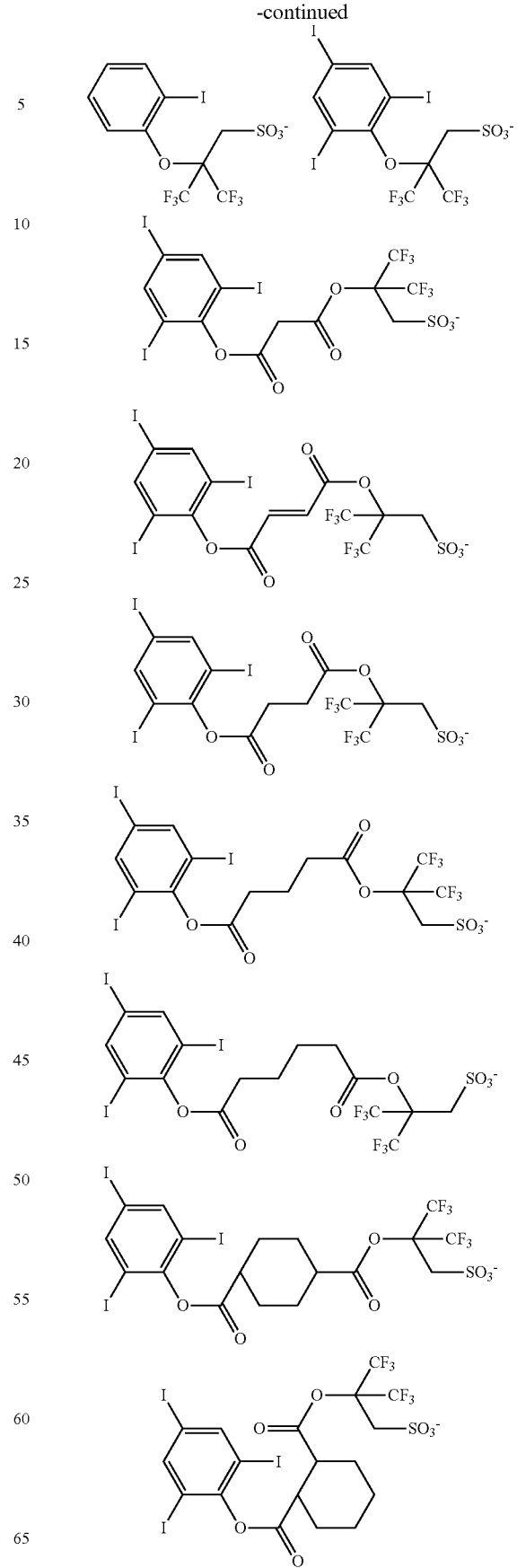

229
-continued
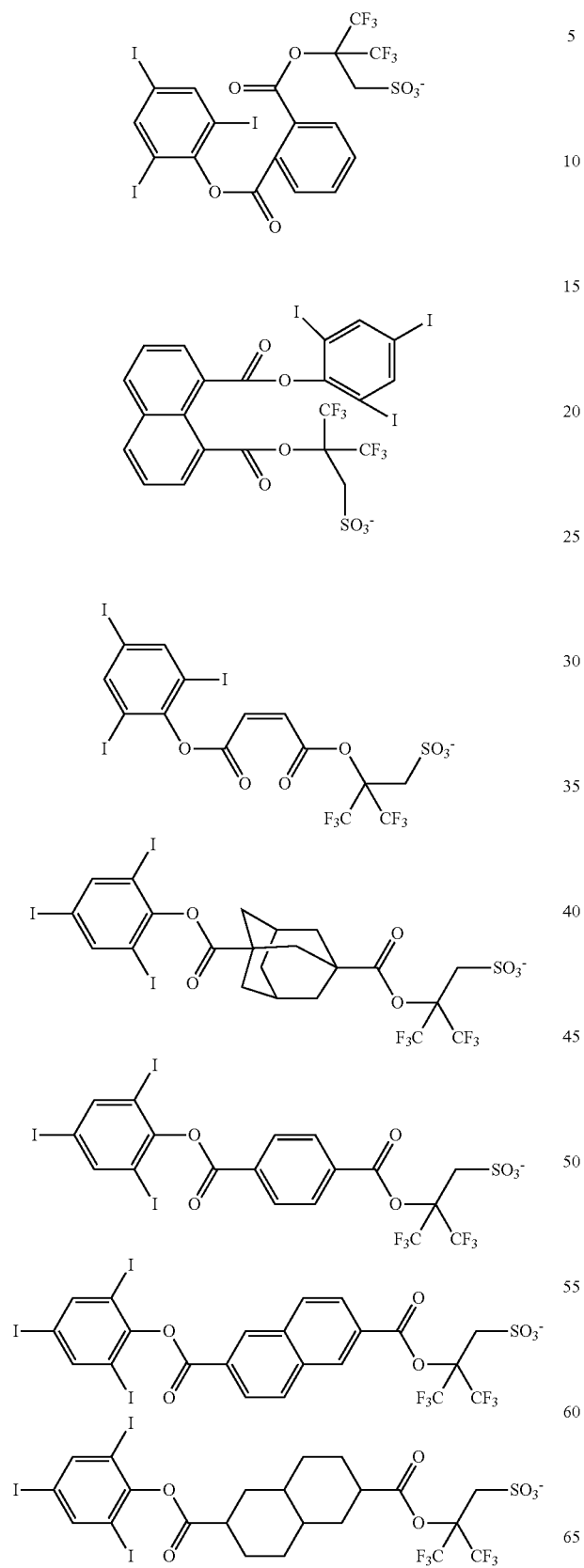
230
-continued
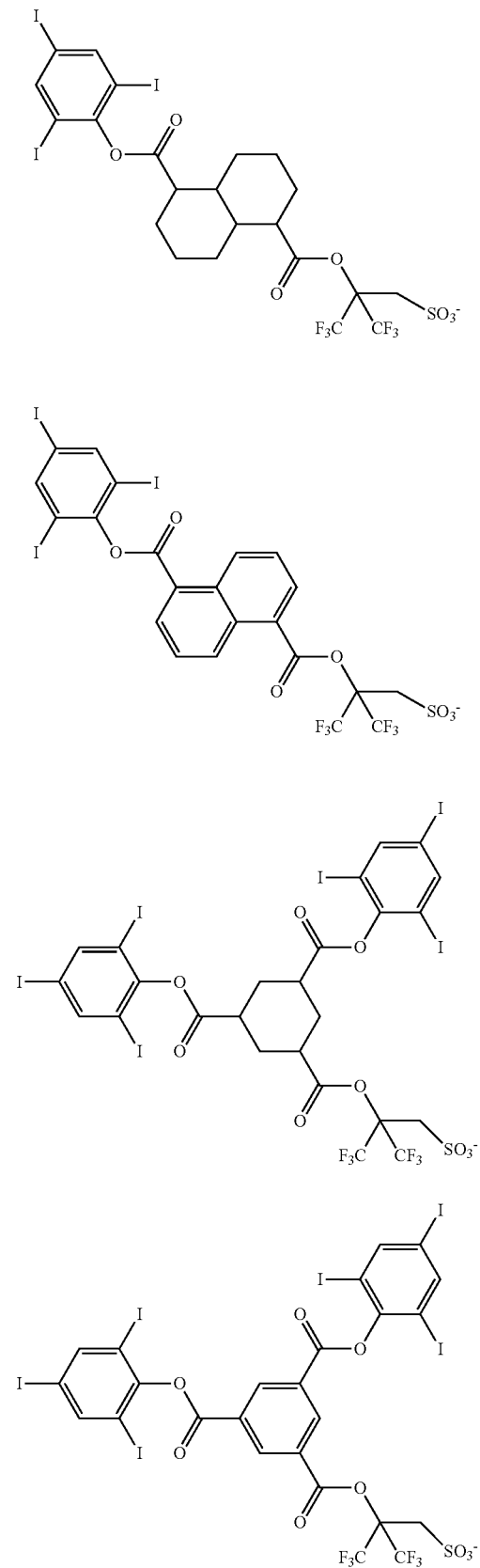

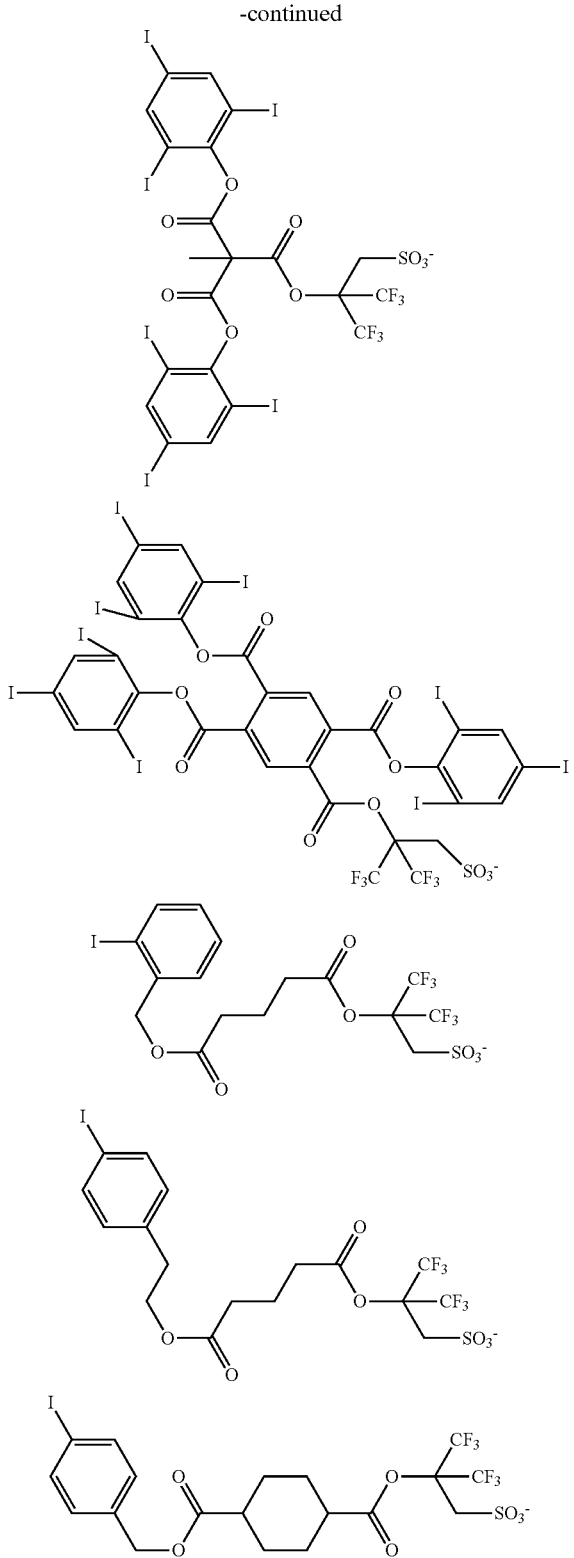

Further, a sulfonium or iodonium salt having a brominated anion may be used as the PAG. The brominated anions include those anions having formulae (3-1) to (3-4), provided that iodine is replaced by bromine. Examples include those examples of the iodized anion, provided that iodine is replaced by bromine.

When used, the acid generator of addition type is preferably added in an amount of 0.1 to 50 parts, and more preferably 1 to 40 parts by weight per 100 parts by weight of the base polymer.

Other Components

With the onium salt, base polymer, and acid generator, all defined above, other components such as an organic solvent, surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Examples of the organic solvent used herein are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, 1-ethoxy-2-propanol and diacetone alcohol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of a resist film in exposed area.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker. The crosslinker may be used alone or in admixture.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethoxymethyl urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

In the resist composition of the invention, a quencher other than the sulfonium salt of iodized benzene ring-containing sulfonamide may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxy phenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer.

To the resist composition, a polymeric additive (or water repellency improver) may also be added for improving the water repellency on surface of a resist film as spin coated. The water repellency improver may be used in the topcoat-less immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. The water repellency improver may be used alone or in admixture. An appropriate amount of the water repellency improver is 0 to 20 parts, more preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Pattern Forming Process

The resist composition is used in the fabrication of various integrated circuits. Pattern formation using the resist composition may be performed by well-known lithography processes. The process generally involves coating, prebaking, exposure, and development. If necessary, any additional steps may be added.

For example, the resist composition is first applied onto a substrate on which an integrated circuit is to be formed (e.g., Si, $SiO_2$, SiN, SiON, TiN, WSi, BPSG, SOG, or organic anti reflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2.0 μm thick.

The resist film is then exposed to a desired pattern of high-energy radiation such as UV, deep-UV, EB, EUV, x-ray, soft x-ray, excimer laser light, γ-ray or synchrotron radiation, directly or through a mask. The exposure dose is preferably about 1 to 200 $mJ/cm^2$, more preferably about 10 to 100 $mJ/cm^2$, or about 0.1 to 100 $\mu C/cm^2$, more preferably about 0.5 to 50 $\mu C/cm^2$. The resist film is further baked (PEB) on a hot plate at 60 to 150° C. for 10 seconds to 30 minutes, preferably at 80 to 120° C. for 30 seconds to 20 minutes.

The PEB may or may not be involved. In the embodiment wherein the polymer is an anion-bound PAG polymer comprising recurring units (f2) or (f3), a sulfonic acid is generated upon exposure whereby alkaline solubility is improved. Then the exposed region of the resist film is dissolvable in alkaline solution without PEB. When PEB is omitted, the image blur by acid diffusion is eliminated, and so, the formation of a pattern of finer size than the pattern formation via PEB is expected.

When PEB is omitted, the resist material is a non-chemically amplified resist material because deprotection reaction with the aid of acid does not take place. In this case, the dissolution contrast is so low that after development, a pattern film thickness loss can occur or some residual film be left in the space region. For the non-chemically amplified resist material, the key is how to improve dissolution contrast.

In the embodiment wherein the polymer is an anion-bound PAG polymer comprising recurring units (f2) or (f3), an α-fluorosulfonic acid is generated upon exposure whereby the solubility in alkaline developer is improved. When an onium salt of α-non-fluorinated sulfonic acid or carboxylic acid is added, the generation of an α-fluorosulfonic acid is controlled by a salt exchange therewith. Further, as the exposure dose is increased, the onium salt of α-non-fluorinated sulfonic acid or carboxylic acid is decomposed, whereby alkaline solubility is improved. Namely, contrast is enhanced by the mechanism that dissolution inhibition is improved in the under-exposure dose region whereas dissolution promotion is improved in the over-exposure dose region. Since the ion exchange reaction proceeds rapidly at room temperature, the PEB may be omitted. Since the onium salt having formula (A) is also a salt of weaker acid than α-fluorosulfonic acid, a similar ion exchange takes place. This ensures a contrast improvement even when PEB is omitted.

Thereafter, the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer. It is appreciated that the resist composition of the invention is best suited for micro-patterning using such high-energy radiation as KrF and ArF excimer laser, EB, EUV, x-ray, soft x-ray, γ-ray and synchrotron radiation.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight.

Synthesis Example 1-1

Synthesis of triphenylsulfonium N-[(trifluoromethyl)sulfonyl]-2,3,5-triiodobenzamide (Sulfonium Salt 1)

A mixture of 100 g of 2,3,5-triiodobenzoic acid, 0.73 g of dimethyl formamide, and 700 g of chloroform was heated at 60° C., after which 47.6 g of thionyl chloride was added dropwise thereto. The solution was stirred at 60° C. for 21 hours and concentrated under reduced pressure to remove the chloroform and unreacted thionyl chloride. The concentrate was combined with 500 g of hexane and stirred for 1 hour, whereupon a solid precipitated. The solid was filtered and washed mice with hexane, obtaining 97 g of 2,3,5-triiodobenzoyl chloride as solid.

A portion (10.1 g) of the 2,3,5-triiodobenzoyl chloride was added to a mixture of 2.24 g of trifluoromethanesulfonylamide, 3.73 g of potassium carbonate, and 40 g of acetonitrile, which was stirred at room temperature for 15 hours. Then 120 g of deionized water was added dropwise to the reaction solution to quench the reaction, after which 6.74 g of triphenylsulfonium methylsulfate and 80 g of methylene chloride were added thereto with stirring. After the insoluble was removed by filtration, the organic layer was taken out. The organic layer was sequentially washed with 40 g of deionized water, 40 g of 2.5 wt % hydrochloric acid, 40 g of deionized water, 60 g of sodium hydrogencarbonate aqueous solution, and 40 g of deionized water. The organic layer after washing was concentrated under reduced pressure. To the concentrate, 60 g of tert-butyl methyl ether was added and stirred. After a supernatant was removed, the residue was concentrated under reduced pressure, obtaining 10.5 g of the target compound, triphenylsulfonium N-[(trifluoromethyl)sulfonyl]-2,3,5-triiodobenzamide (designated Sulfonium Salt 1) as an oily matter (yield 78%).

Sulfonium Salt 1 was analyzed by spectroscopy. The IR spectroscopy data are shown below. The NMR spectra,

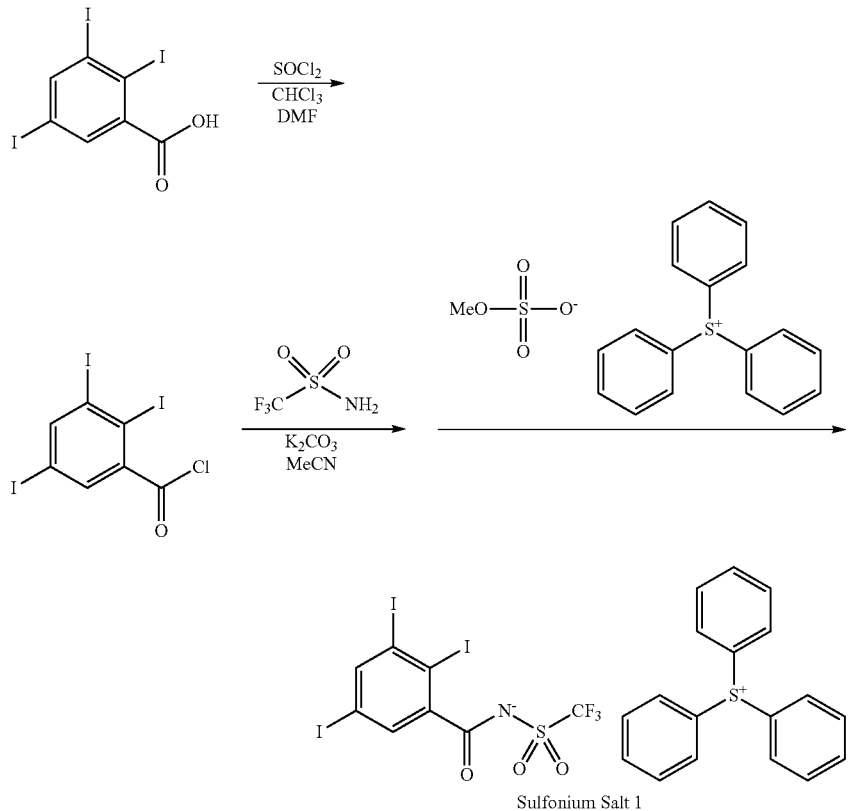

Sulfonium Salt 1

Figure 2:
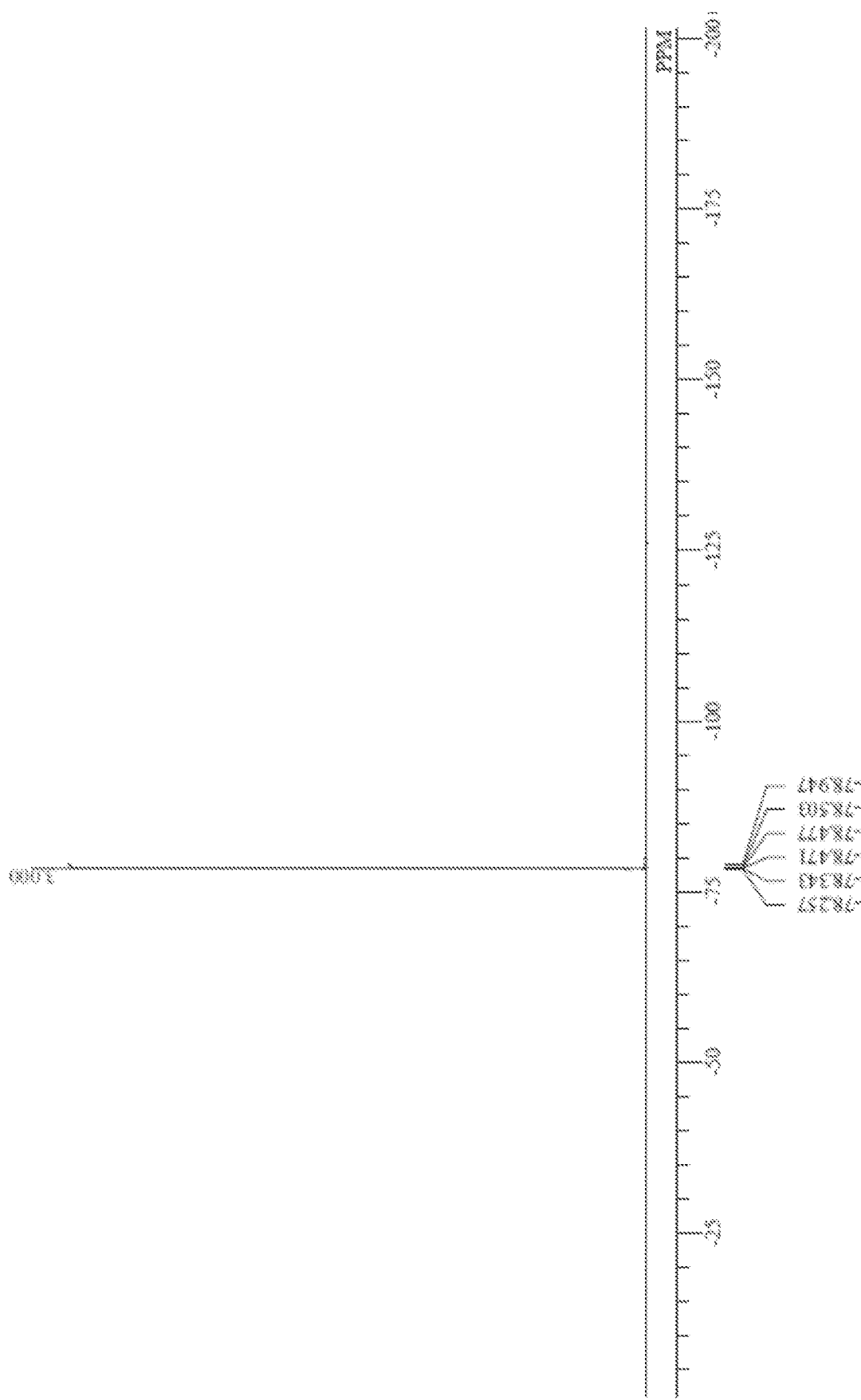
FIG. 2 is a diagram showing the $^{19}$F-NMR spectrum of Sulfonium Salt 1 in Synthesis Example 1-1.

$^1$H-NMR and $^{19}$F-NMR in DMSO-$d_6$ are shown in FIGS. 1 and 2. In $^1$H-NMR analysis, minute amounts of residual solvents (tert-butyl methyl ether and water) were observed.

IR (D-ATR): ν=3520, 3061, 2972, 1628, 1518, 1476, 1447, 1387, 1363, 1304, 1238, 1196, 1117, 1078, 1021, 998, 925, 865, 821, 748, 711, 684, 614, 581, 502 cm$^{-1}$

Synthesis Examples 1-2 to 1-24

Synthesis of Sulfonium Salts 2 to 15, Iodonium Salts 1 to 3, and Ammonium Salts 1 to 6

The structure of Sulfonium Salts 1 to 15, Iodonium Salts 1 to 3, and Ammonium Salts 1 to 6 of iodized benzene ring-containing sulfonamide used in resist compositions is summarized below.

Sulfonium Salts 2 to 15 and Iodonium Salts 1 to 3 were synthesized as in Synthesis Example 1-1 by ion exchange between an iodized benzene ring-containing sulfonamide providing the anion shown below and a sulfonium methanesulfonate providing the cation shown below. Ammonium Salts 1 and 2 were synthesized by neutralizing reaction of an iodized benzene ring-containing sulfonamide providing the anion shown below with a quaternary ammonium hydroxide, and Ammonium Salts 3 to 6 were synthesized by neutralizing reaction of an iodized benzene ring-containing sulfonamide providing the anion shown below with a tertiary amine compound.

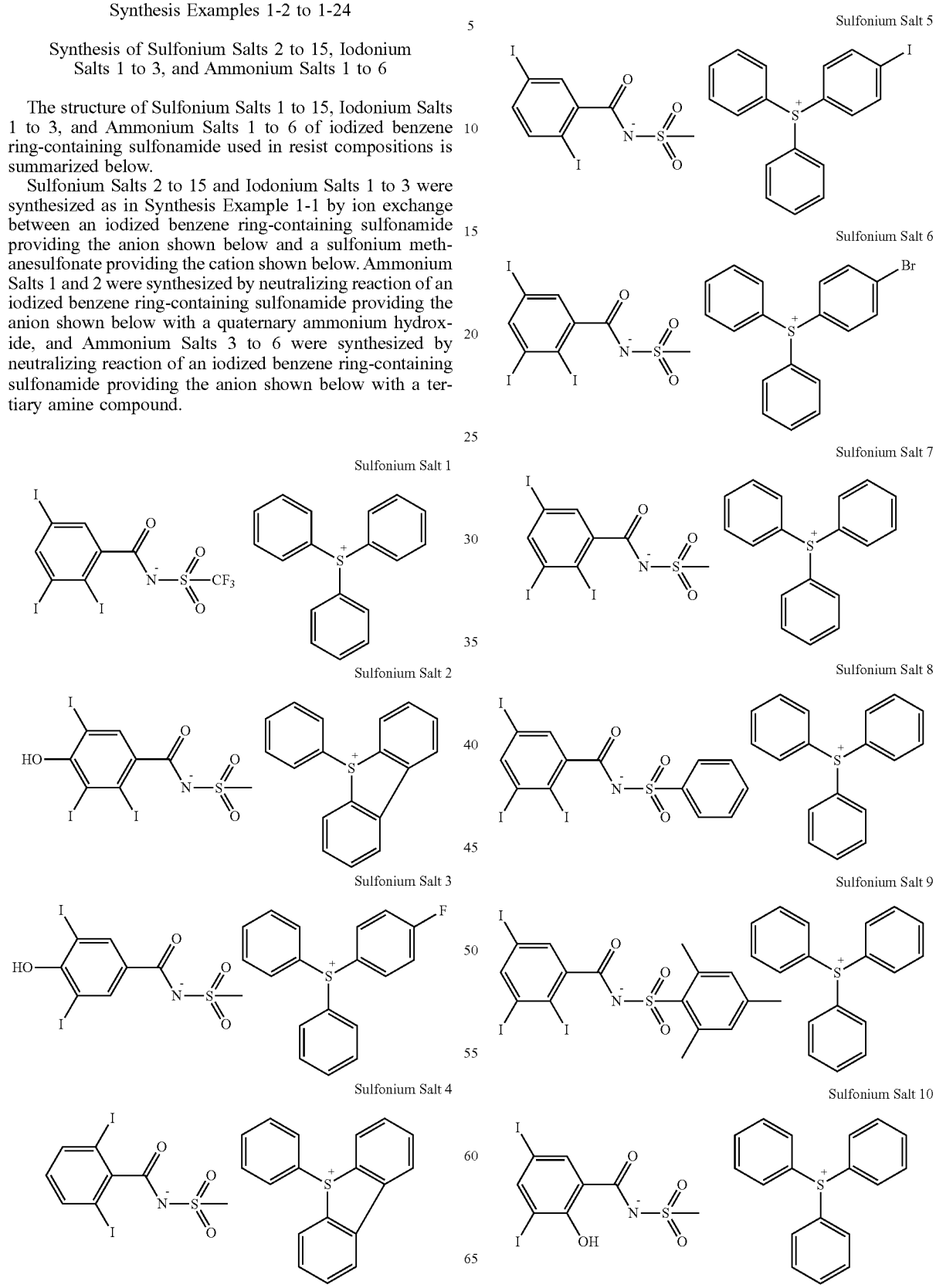

Sulfonium Salt 11
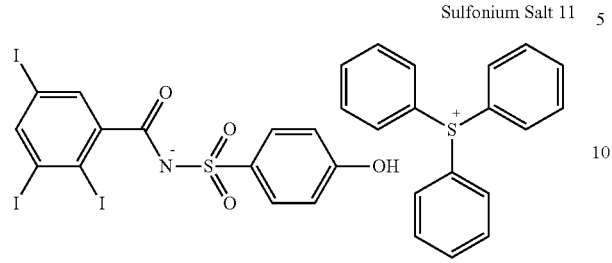
Sulfonium Salt 12
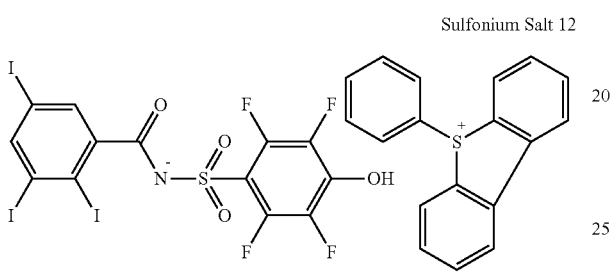
Sulfonium Salt 13
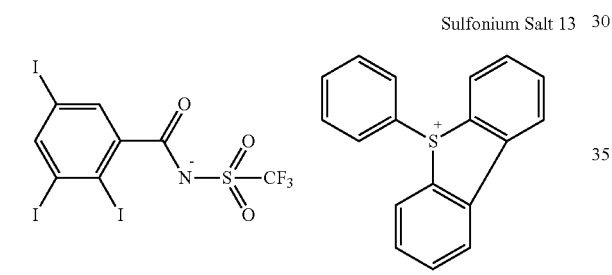
Sulfonium Salt 14
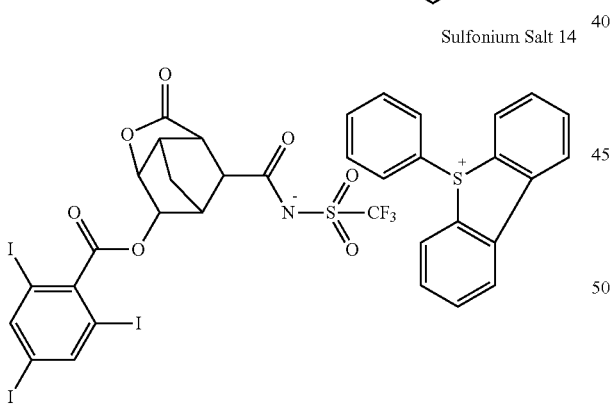
Sulfonium Salt 15
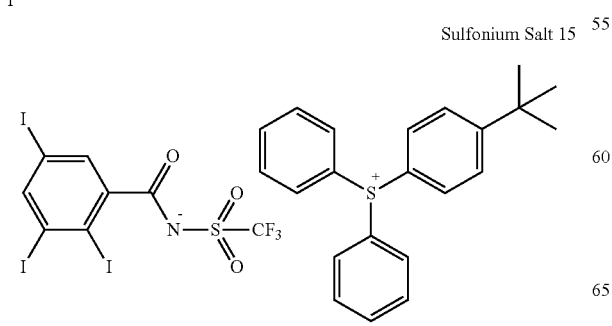
Iodonium Salt 1
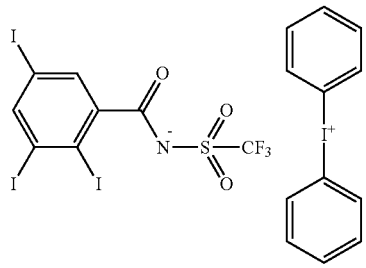
Iodonium Salt 2
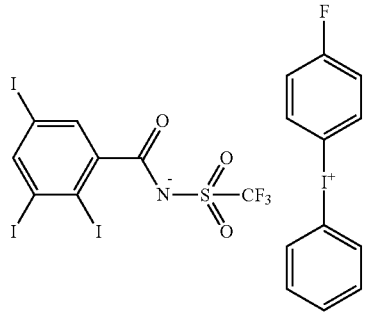
Iodonium Salt 3
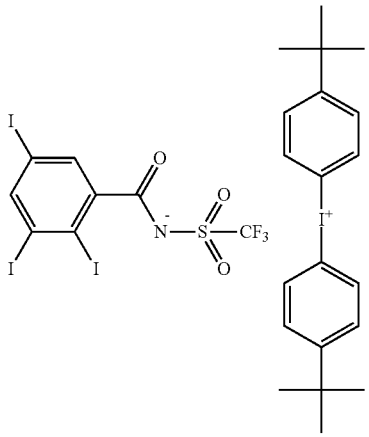
Ammonium Salt 1
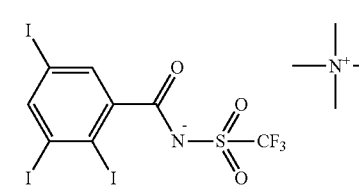
Ammonium Salt 2
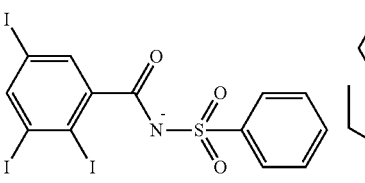
Ammonium Salt 3
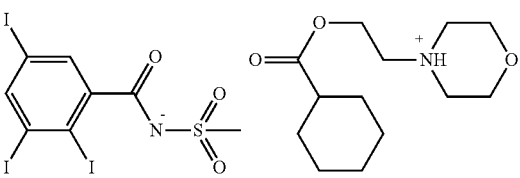

243

-continued

Ammonium Salt 4

Ammonium Salt 5

Ammonium Salt 6

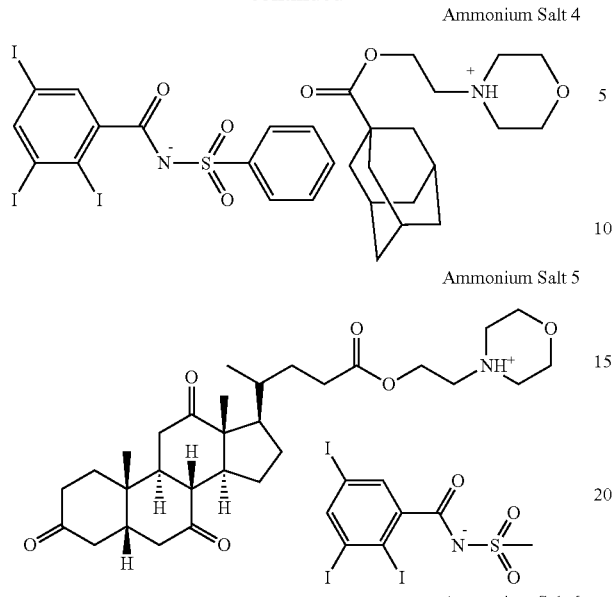

Synthesis Examples 2-1 to 2-5

Synthesis of base polymers (Polymers 1 to 5)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 5, were analyzed for composition by $^1$H-NMR spectroscopy, and for Mw and Mw/Mn by GPC versus polystyrene standards using THF solvent.

Polymer 1

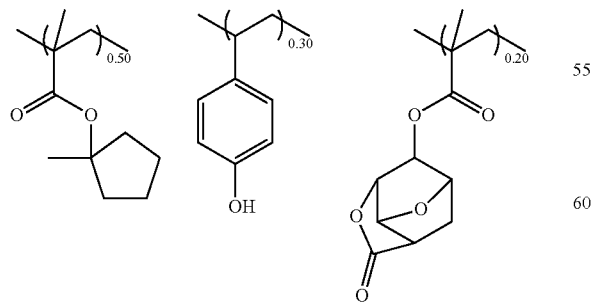

Mw = 8,600
Mw/Mn = 1.73

244

-continued

Polymer 2

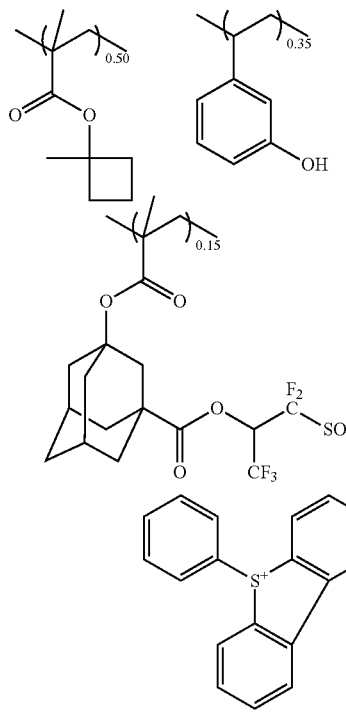

Mw = 8,900
Mw/Mn = 1.81

Polymer 3

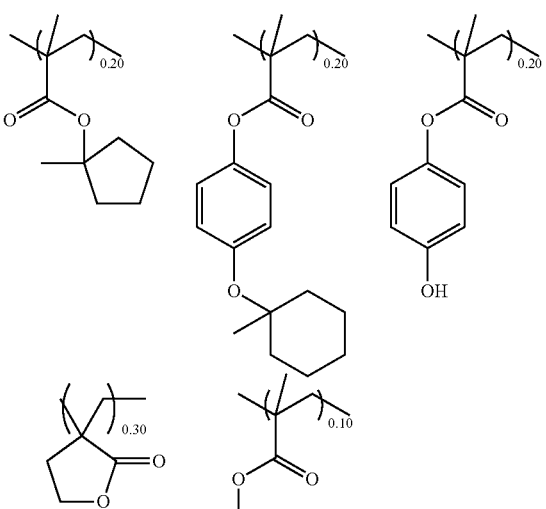

Mw = 7,600
Mw/Mn = 1.73

-continued

Polymer 4

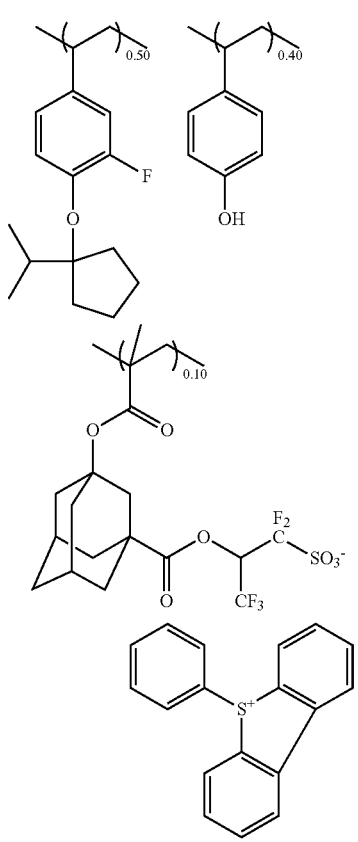

Mw = 8,800
Mw/Mn = 1.77

Polymer 5

Mw = 6,900
Mw/Mn = 1.62

Examples 1 to 30 and Comparative Examples 1 to 7

Resist compositions were prepared by dissolving the polymer and selected components in a solvent in accordance with the recipe shown in Tables 1 to 3, and filtering through a filter having a pore size of 0.2 μm. The solvent contained 100 ppm of surfactant FC-4430 (3M). The components in Tables 1 to 3 are as identified below.

Organic Solvents:
  PGMEA (propylene glycol monomethyl ether acetate)
  GBL (γ-butyrolactone)
  CyH (cyclohexanone)
  PGME (propylene glycol monomethyl ether)
  DAA (diacetone alcohol)

Acid generators: PAG 1 to PAG 7 of the following structural formulae

PAG 1

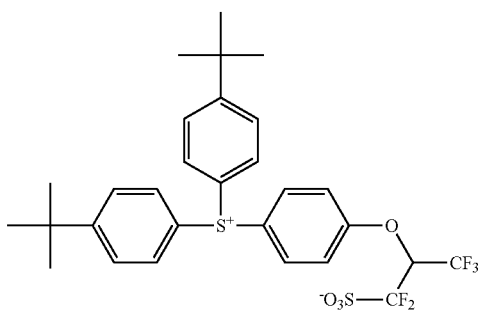

PAG 2

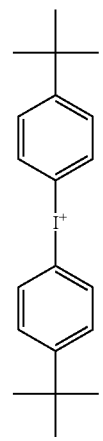

PAG 3

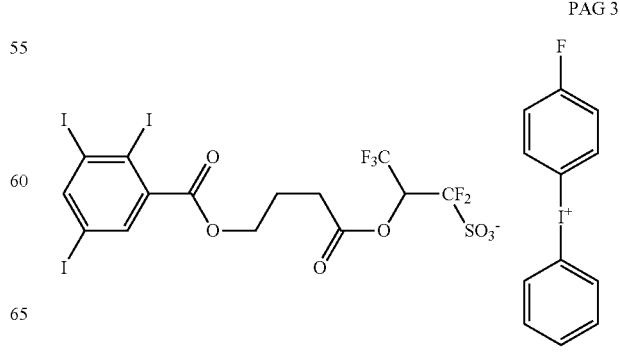

-continued

PAG 4

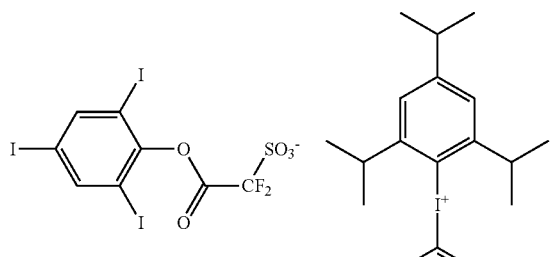

PAG 5

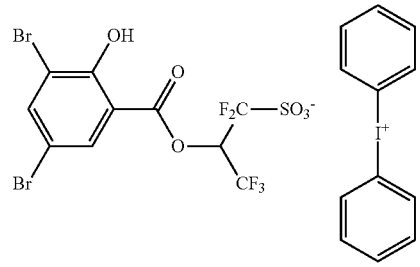

PAG 6

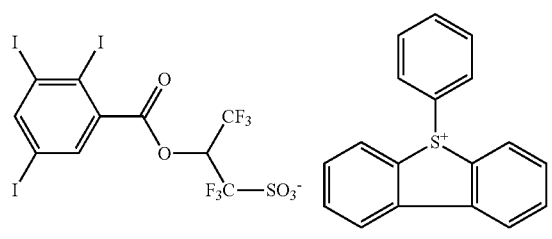

PAG 7

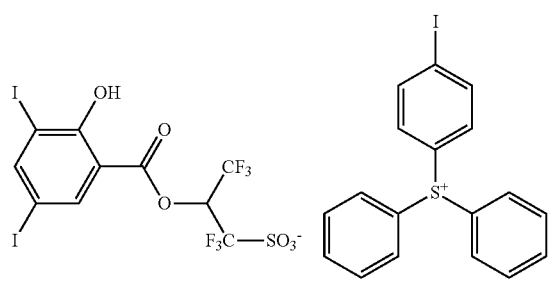

Comparative Quenchers 1 to 6 of the Following Structural Formulae

Comparative Quencher 1

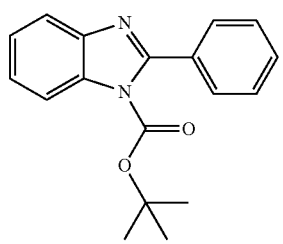

-continued

Comparative Quencher 2

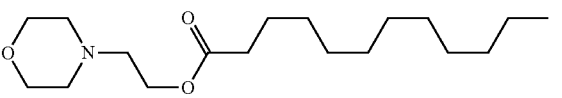

Comparative Quencher 3

Comparative Quencher 4

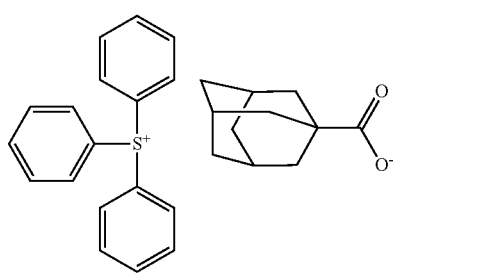

Comparative Quencher 5

Comparative Quencher 6

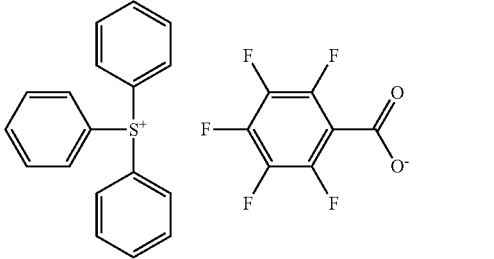

EB Lithography Test

A silicon substrate was coated with an antireflective coating of 60 nm thick (DUV-62, Nissan Chemical Corp.). Each of the resist compositions in Tables 1 to 3 was spin coated on the substrate and prebaked on a hotplate at 105° C. for 60 seconds to form a resist film of 50 nm thick. The resist film was exposed to electron beam using an EB lithography system ELS-F125 (Elionix Co., Ltd., accelerating voltage 125 kV), then baked (PEB) on a hotplate at the temperature shown in Tables 1 to 3 for 60 seconds, and developed with a 2.38 wt % TMAH aqueous solution for 30 seconds to form a pattern. In Examples 1 to 13, 15 to 30 and Comparative Examples 1 to 6, a positive resist pattern, i.e., hole pattern having a size of 24 nm was formed. In Example 14 and Comparative Example 7, a negative resist pattern, i.e., dot pattern having a size of 24 nm was formed.

The resist pattern was observed under CD-SEM (CG-5000, Hitachi High-Technologies Corp.). The exposure dose that provides a hole or dot pattern having a size of 24 nm is reported as sensitivity. The diameter of 50 holes or dots was measured, from which a size variation ($3\sigma$) was computed and reported as CDU.

The resist composition is shown in Tables 1 to 3 together with the sensitivity and CDU of EB lithography.

TABLE 1

|  |  | Polymer (pbw) | Acid generator (pbw) | Quencher (pbw) | Organic solvent (pbw) | PEB temp. | Sensitivity ($\mu C/cm^2$) | CDU (nm) |
|---|---|---|---|---|---|---|---|---|
| Example | 1 | Polymer 1 (100) | PAG 1 (30) | Sulfonium Salt 1 (2.94) | PGMEA (400) CyH (2,000) | 90 | 330 | 2.6 |
|  | 2 | Polymer 1 (100) | PAG 2 (30) | Sulfonium Salt 2 (3.60) | PGMEA (400) CyH (2,000) | 90 | 350 | 2.9 |
|  | 3 | Polymer 1 (100) | PAG 2 (30) | Sulfonium Salt 3 (3.73) | PGMEA (400) CyH (2,000) | 90 | 340 | 2.9 |
|  | 4 | Polymer 1 (100) | PAG 2 (30) | Sulfonium Salt 4 (3.55) | PGMEA (400) CyH (2,000) | 90 | 340 | 2.8 |
|  | 5 | Polymer 1 (100) | PAG 2 (30) | Sulfonium Salt 5 (4.19) | PGMEA (400) CyH (2,000) | 90 | 340 | 2.9 |
|  | 6 | Polymer 1 (100) | PAG 2 (30) | Sulfonium Salt 6 (4.59) | PGMEA (400) CyH (2,000) | 90 | 320 | 2.9 |
|  | 7 | Polymer 1 (100) | PAG 2 (30) | Sulfonium Salt 7 (4.20) | PGMEA (400) CyH (2,000) | 90 | 320 | 2.8 |
|  | 8 | Polymer 1 (100) | PAG 2 (30) | Sulfonium Salt 8 (4.50) | PGMEA (2,200) GBL (400) | 90 | 330 | 2.9 |
|  | 9 | Polymer 2 (100) | — | Sulfonium Salt 9 (4.71) | PGMEA (400) CyH (2,000) | 100 | 330 | 2.2 |
|  | 10 | Polymer 3 (100) | — | Sulfonium Salt 10 (3.65) | PGMEA (400) CyH (2,000) | 90 | 340 | 1.9 |
|  | 11 | Polymer 3 (100) | PAG 3 (12) | Sulfonium Salt 11 (4.59) | PGMEA (400) CyH (2,000) | 90 | 220 | 2.2 |
|  | 12 | Polymer 3 (100) | PAG 4 (12) | Sulfonium Salt 4 (3.55) | PGMEA (400) CyH (2,000) | 90 | 240 | 2.3 |
|  | 13 | Polymer 4 (100) | — | Sulfonium Salt 4 (3.55) | PGMEA (400) CyH (2,000) | 110 | 340 | 2.2 |
|  | 14 | Polymer 5 (100) | PAG 5 (15) | Sulfonium Salt 4 (3.55) | PGMEA (400) CyH (2,000) | 130 | 370 | 3.5 |

TABLE 2

|  |  | Polymer (pbw) | Acid generator (pbw) | Quencher (pbw) | Organic solvent (pbw) | PEB temp. | Sensitivity ($\mu C/cm^2$) | CDU (nm) |
|---|---|---|---|---|---|---|---|---|
| Example | 15 | Polymer 1 (100) | Sulfonium Salt 12 (30) | Comparative Quencher 5 | PGMEA (2,200) GBL (400) | 115 | 340 | 2.9 |
|  | 16 | Polymer 1 (100) | Sulfonium Salt 13 (30) | Sulfonium Salt 1 (2.94) | PGMEA (2,200) GBL (400) | 115 | 330 | 2.8 |
|  | 17 | Polymer 1 (100) | Sulfonium Salt 14 (30) | Sulfonium Salt 1 (2.94) | PGMEA (2,200) GBL (400) | 115 | 320 | 2.8 |
|  | 18 | Polymer 3 (100) | — | Sulfonium Salt 12 (4.93) | PGMEA (2,000) DAA (500) | 90 | 380 | 2.5 |
|  | 19 | Polymer 3 (100) | — | Sulfonium Salt 13 (4.45) | PGMEA (2,000) DAA (500) | 90 | 310 | 2.9 |
|  | 20 | Polymer 3 (100) | — | Sulfonium Salt 14 (5.35) | PGMEA (2,000) DAA (500) | 90 | 340 | 2.8 |
|  | 21 | Polymer 3 (100) | — | Sulfonium Salt 15 (5.20) | PGMEA (2,000) DAA (500) | 90 | 340 | 2.8 |
|  | 22 | Polymer 3 (100) | — | Iodonium Salt 1 (4.55) | PGMEA (2,000) DAA (500) | 90 | 310 | 2.8 |
|  | 23 | Polymer 3 (100) | — | Iodonium Salt 2 (4.64) | PGMEA (2,000) DAA (500) | 90 | 300 | 3.0 |
|  | 24 | Polymer 3 (100) | — | Iodonium Salt 3 (5.11) | PGMEA (2,000) DAA (500) | 90 | 350 | 2.7 |
|  | 25 | Polymer 3 (100) | — | Ammonium Salt 1 (3.63) | PGMEA (2,000) DAA (500) | 90 | 380 | 2.7 |
|  | 26 | Polymer 3 (100) | — | Ammonium Salt 2 (4.40) | PGMEA (2,000) DAA (500) | 90 | 370 | 2.6 |
|  | 27 | Polymer 3 (100) | — | Ammonium Salt 3 (4.09) | PGMEA (2,000) DAA (500) | 90 | 380 | 2.6 |
|  | 28 | Polymer 3 (100) | — | Ammonium Salt 4 (4.66) | PGMEA (2,000) DAA (500) | 90 | 390 | 2.5 |

TABLE 2-continued

| | Polymer (pbw) | Acid generator (pbw) | Quencher (pbw) | Organic solvent (pbw) | PEB temp. | Sensitivity ($\mu C/cm^2$) | CDU (nm) |
|---|---|---|---|---|---|---|---|
| 29 | Polymer 3 (100) | PAG 6 (6) | Ammonium Salt 5 (5.46) | PGMEA (2,000) DAA (500) | 90 | 310 | 2.4 |
| 30 | Polymer 3 (100) | PAG 7 (6) | Ammonium Salt 6 (5.70) | PGMEA (2,000) DAA (500) | 90 | 320 | 2.4 |

TABLE 3

| | | Polymer (pbw) | Acid generator (pbw) | Quencher (pbw) | Organic solvent (pbw) | PEB temp. | Sensitivity ($\mu C/cm^2$) | CDU (nm) |
|---|---|---|---|---|---|---|---|---|
| Comparative Example | 1 | Polymer 1 (100) | PAG 2 (30) | Comparative Quencher 1 | PGMEA (400) CyH (2,000) | 90 | 390 | 4.1 |
| | 2 | Polymer 1 (100) | PAG 2 (30) | Comparative Quencher 2 | PGMEA (400) CyH (2,000) | 90 | 420 | 3.8 |
| | 3 | Polymer 1 (100) | PAG 2 (30) | Comparative Quencher 3 | PGMEA (400) CyH (2,000) | 90 | 380 | 3.9 |
| | 4 | Polymer 1 (100) | PAG 2 (30) | Comparative Quencher 4 | PGMEA (400) CyH (2,000) | 90 | 410 | 3.6 |
| | 5 | Polymer 1 (100) | PAG 2 (30) | Comparative Quencher 5 | PGMEA (400) CyH (2,000) | 90 | 380 | 3.6 |
| | 6 | Polymer 1 (100) | PAG 2 (30) | Comparative Quencher 6 | PGMEA (400) CyH (2,000) | 90 | 390 | 3.9 |
| | 7 | Polymer 5 (100) | PAG 5 (15) | Comparative Quencher 6 | PGMEA (400) CyH (2,000) | 130 | 470 | 5.9 |

It is demonstrated in Tables 1 to 3 that resist compositions comprising an onium salt of formula (A) offer a high sensitivity and improved CDU.

Japanese Patent Application Nos. 2018-104855 and 2019-028583 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and an onium salt having the formula (A):

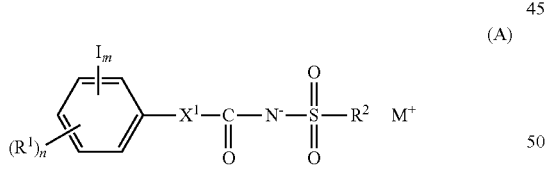

(A)

wherein $R^1$ is hydrogen, hydroxyl, $C_1$-$C_6$ alkyl group, $C_1$-$C_6$ alkoxy group, $C_2$-$C_7$ acyloxy group, $C_2$-$C_7$ alkoxycarbonyl group, $C_1$-$C_4$ alkylsulfonyloxy group, fluorine, chlorine, bromine, amino, nitro, cyano, —NR$^{1A}$—C(=O)—R$^{1B}$, or —NR$^{1A}$—C(=O)—O—R$^{1B}$, some or all of the hydrogen atoms on the alkyl, alkoxy, acyloxy, alkoxycarbonyl and alkylsulfonyloxy groups may be substituted by halogen, R$^{1A}$ is hydrogen or a $C_1$-$C_6$ alkyl group, R$^{1B}$ is a $C_1$-$C_6$ alkyl group or $C_2$-$C_8$ alkenyl group, $R^2$ is a $C_1$-$C_{10}$ alkyl or $C_6$-$C_{10}$ aryl group in which some or all hydrogen may be substituted by amino, nitro, cyano, $C_1$-$C_{12}$ alkyl, $C_1$-$C_{12}$ alkoxy, $C_2$-$C_{12}$ alkoxycarbonyl, $C_2$-$C_{12}$ acyl, $C_2$-$C_{12}$ alkylcarbonyloxy, hydroxyl, or halogen, $X^1$ is a single bond, m and n are integers satisfying $2 \le m \le 3$, $0 \le n \le 3$, and $2 \le m+n \le 5$, $M^+$ is a sulfonium cation having the formula (Aa), an iodonium cation having the formula (Ab), or an ammonium cation having the formula (Ac):

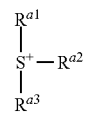

(Aa)

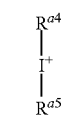

(Ab)

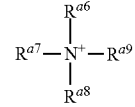

(Ac)

wherein $R^{a1}$ to $R^{a3}$ are each independently halogen or a $C_1$-$C_{20}$ monovalent hydrocarbon group which may contain a heteroatom, or any two of $R^{a1}$, $R^{a2}$ and $R^{a3}$ may bond together to form a ring with the sulfur atom to which they are attached, $R^{a4}$ and $R^{a5}$ are each independently halogen or a $C_1$-$C_{20}$ monovalent hydrocarbon group which may contain a heteroatom, $R^{a6}$ to $R^{a9}$ are each independently hydrogen or a $C_1$-$C_{24}$ monovalent hydrocarbon group which may contain halogen, hydroxyl, carboxyl, ether bond, ester bond, thiol, thioester bond, thionoester bond, dithioester bond, amino moiety, nitro moiety, sulfone moiety, or ferrocenyl moiety, $R^{a6}$ and $R^{a7}$ may bond together to form a ring with the nitrogen atom to which they are attached, a pair of $R^{a6}$ and $R^{a7}$ and a pair of $R^{a8}$ and $R^{a9}$ may bond together to form a spiro-ring with the nitrogen atom to which they are attached, $R^{a8}$ and $R^{a9}$, taken together, may form $=C(R^{a10})(R^{a11})$, $R^{a10}$ and $R^{a11}$ are each independently hydrogen or a $C_1$-$C_{16}$ monovalent hydrocarbon group, $R^{a10}$ and $R^{a11}$ may bond together to form a ring with the carbon and nitrogen atoms to which they are attached, the ring may contain a double bond, oxygen, sulfur or nitrogen atom therein.

2. The resist composition of claim 1, further comprising an acid generator capable of generating a sulfonic acid, imide acid or methide acid.

3. The resist composition of claim 1, further comprising an organic solvent.

4. The resist composition of claim 1 wherein the base polymer comprises recurring units having the formula (a1) or recurring units having the formula (a2):

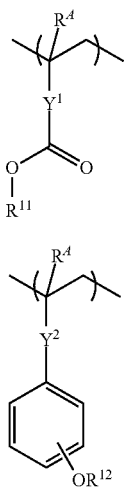

(a1)

(a2)

wherein $R^A$ is each independently hydrogen or methyl, $Y^1$ is a single bond, phenylene group, naphthylene group, or $C_1$-$C_{12}$ linking group containing ester bond or lactone ring, $Y^2$ is a single bond or ester bond, $R^{11}$ and $R^{12}$ each are an acid labile group.

5. The resist composition of claim 4 which is a chemically amplified positive resist composition.

6. The resist composition of claim 1 wherein the base polymer is free of an acid labile group.

7. The resist composition of claim 6, further comprising a crosslinker.

8. The resist composition of claim 6 which is a chemically amplified negative resist composition.

9. The resist composition of claim 1 wherein the base polymer further comprises recurring units of at least one type selected from recurring units having the formulae (f1) to (f3):

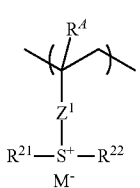

(f1)

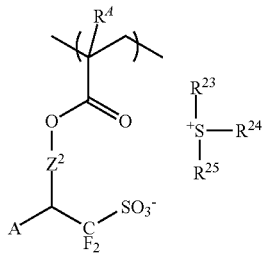

(f2)

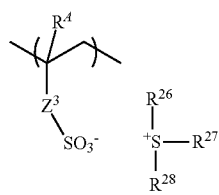

(f3)

wherein $R^A$ is each independently hydrogen or methyl,
$Z^1$ is a single bond, phenylene group, $-O-Z^{11}-$, $-C(=O)-O-Z^{11}-$ or $-C(=O)-NH-Z^{11}-$, $Z^{11}$ is a $C_1$-$C_6$ alkanediyl group, $C_2$-$C_6$ alkenediyl group, or phenylene group, which may contain a carbonyl, ester bond, ether bond or hydroxyl moiety,
$Z^2$ is a single bond, $-Z^{21}-C(=O)-O-$, $-Z^{21}-O-$ or $-Z^{21}-O-C(=O)-$, $Z^{21}$ is a $C_1$-$C_{12}$ alkanediyl group which may contain a carbonyl moiety, ester bond or ether bond,
$Z^3$ is a single bond, methylene, ethylene, phenylene, fluorinated phenylene, $-C(=O)-O-Z^{31}-$, or $-C(=O)-NH-Z^{31}-$, $Z^{31}$ is a $C_1$-$C_6$ alkanediyl group, phenylene group, fluorinated phenylene group, trifluoromethyl-substituted phenylene group, or $C_2$-$C_6$ alkenediyl group, which may contain a carbonyl moiety, ester bond, ether bond or hydroxy moiety,
A is hydrogen or trifluoromethyl,
$R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, and
$M^-$ is a non-nucleophilic counter ion.

10. The resist composition of claim 1, further comprising a surfactant.

11. A process for forming a pattern comprising the steps of applying the resist composition of claim 1 onto a substrate, baking to form a resist film, exposing the resist film to high-energy radiation, and developing the exposed resist film in a developer.

12. The process of claim 11 wherein the high-energy radiation is ArF excimer laser radiation of wavelength 193 nm or KrF excimer laser radiation of wavelength 248 nm.

13. The process of claim 11 wherein the high-energy radiation is EB or EUV of wavelength 3 to 15 nm.

14. A sulfonium salt having the formula (B):

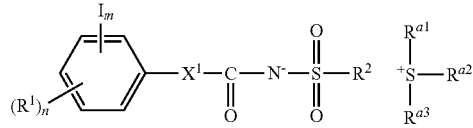

(B)

wherein $R^1$ is hydrogen, hydroxyl, $C_1$-$C_6$ alkyl group, $C_1$-$C_6$ alkoxy group, $C_2$-$C_7$ acyloxy group, $C_2$-$C_7$ alkoxycarbonyl group, $C_1$-$C_4$ alkylsulfonyloxy group, fluorine, chlorine, bromine, amino, nitro, cyano, —$NR^{1A}$—C(=O)—$R^{1B}$, or —$NR^{1A}$—C(=O)—O—$R^{1B}$, some or all of the hydrogen atoms on the alkyl, alkoxy, acyloxy, alkoxycarbonyl and alkylsulfonyloxy groups may be substituted by halogen, $R^{1A}$ is hydrogen or a $C_1$-$C_6$ alkyl group, $R^{1B}$ is a $C_1$-$C_6$ alkyl group or $C_2$-$C_8$ alkenyl group, $R^2$ is a $C_1$-$C_{10}$ alkyl or $C_6$-$C_{10}$ aryl group in which some or all hydrogen may be substituted by amino, nitro, cyano, $C_1$-$C_{12}$ alkyl, $C_1$-$C_{12}$ alkoxy, $C_2$-$C_{12}$ alkoxycarbonyl, $C_2$-$C_{12}$ acyl, $C_2$-$C_{12}$ alkylcarbonyloxy, hydroxyl, or halogen, $X^1$ is a single bond, m and n are integers satisfying $2 \leq m \leq 3$, $0 \leq n \leq 3$, and $2 \leq m+n \leq 5$, $R^{a1}$ to $R^{a3}$ are each independently halogen or a $C_1$-$C_{20}$ monovalent hydrocarbon group which may contain a heteroatom, or any two of $R^{a1}$, $R^{a2}$ and $R^{a3}$ may bond together to form a ring with the sulfur atom to which they are attached.

* * * * *